(12) United States Patent
de Juan, Jr. et al.

(10) Patent No.: US 9,033,911 B2
(45) Date of Patent: May 19, 2015

(54) INJECTOR APPARATUS AND METHOD FOR DRUG DELIVERY

(75) Inventors: Eugene de Juan, Jr., Menlo Park, CA (US); Yair Alster, Menlo Park, CA (US); Kathleen Cogan Farinas, Menlo Park, CA (US); K. Angela MacFarlane, Menlo Park, CA (US); Cary J. Reich, Menlo Park, CA (US); Randolph E. Campbell, Menlo Park, CA (US); Darren Doud, Menlo Park, CA (US); Signe Erickson, Menlo Park, CA (US); Mike Barrett, Menlo Park, CA (US); David Batten, Menlo Park, CA (US); Christina Skieller, Menlo Park, CA (US); Greg Stine, Menlo Park, CA (US)

(73) Assignee: ForSight Vision4, Inc., Menlo Park, CA (US)

( * ) Notice: Subject to any disclaimer, the term of this patent is extended or adjusted under 35 U.S.C. 154(b) by 17 days.

(21) Appl. No.: 13/814,461

(22) PCT Filed: Aug. 5, 2011

(86) PCT No.: PCT/US2011/046812
§ 371 (c)(1),
(2), (4) Date: Aug. 14, 2013

(87) PCT Pub. No.: WO2012/019136
PCT Pub. Date: Feb. 9, 2012

(65) Prior Publication Data
US 2013/0324918 A1 Dec. 5, 2013

Related U.S. Application Data

(60) Provisional application No. 61/371,154, filed on Aug. 5, 2010, provisional application No. 61/371,169, filed (Continued)

(51) Int. Cl.
*A61F 9/00* (2006.01)
*A61M 5/142* (2006.01)
(Continued)

(52) U.S. Cl.
CPC ............. *A61F 9/0008* (2013.01); *A61F 9/0017* (2013.01); *A61M 5/14276* (2013.01);
(Continued)

(58) Field of Classification Search
CPC ............ A61M 5/31596; A61M 5/284; A61M 5/2448; A61M 2005/3128; A61M 5/2033; A61M 5/3202; A61M 2005/287
USPC ................... 604/27, 36, 38, 43–44, 264, 272; 606/107
See application file for complete search history.

(56) References Cited

U.S. PATENT DOCUMENTS

| | | |
|---|---|---|
| 2,564,977 A | 8/1951 | Hu et al. |
| 2,585,815 A | 2/1952 | McLintock |

(Continued)

FOREIGN PATENT DOCUMENTS

| | | |
|---|---|---|
| EP | 0033042 B1 | 8/1984 |
| EP | 0228185 B1 | 7/1990 |

(Continued)

OTHER PUBLICATIONS

Andrews, "Effect of nonsteroidal anti-inflammatory drugs on LFA-1 and ICAM-1 expression in gastric mucosa," Am J Physiol. Apr. 1994;266(4 Pt 1):G657-664.

(Continued)

*Primary Examiner* — Nicholas Lucchesi
*Assistant Examiner* — Melissa A Snyder
(74) *Attorney, Agent, or Firm* — Fred C. Hernandez; Mintz Levin Cohn Ferris Glovsky and Popeo, P.C.

(57) ABSTRACT

Methods and apparatus provide a therapeutic fluid to devices implanted in the body, for example to containers of devices implanted in the eye of a patient. The methods and apparatus may comprise an injector to increase an amount of therapeutic agent injected into the device implanted in the eye, or a structure to receive the therapeutic fluid within the device implanted in the eye, or combinations thereof. The device implanted in the eye may comprise a reservoir chamber having a fluid with a density different than the therapeutic fluid, and the apparatus can be adapted to at least partially separate the implanted device fluid from therapeutic fluid within the reservoir chamber to increase and amount of therapeutic fluid placed in the reservoir chamber.

16 Claims, 71 Drawing Sheets

Related U.S. Application Data on Aug. 5, 2010, provisional application No. 61/495,251, filed on Jun. 9, 2011, provisional application No. 61/495,718, filed on Jun. 10, 2011, provisional application No. 61/499,095, filed on Jun. 20, 2011, provisional application No. 61/501,021, filed on Jun. 24, 2011, provisional application No. 61/504,038, filed on Jul. 1, 2011.

(51) Int. Cl.
*A61M 5/178* (2006.01)
*A61M 5/31* (2006.01)
*A61M 39/02* (2006.01)

(52) U.S. Cl.
CPC ............ *A61M5/178* (2013.01); *A61M 5/31* (2013.01); *A61M 39/0208* (2013.01); *A61M 39/0247* (2013.01); *A61M 2039/027* (2013.01); *A61M 2039/0276* (2013.01)

(56) References Cited

U.S. PATENT DOCUMENTS

| | | |
|---|---|---|
| 2,886,497 A | 5/1959 | Butler |
| 3,232,117 A | 2/1966 | Gilmont |
| 3,416,530 A | 12/1968 | Ness |
| 3,618,604 A | 11/1971 | Ness |
| 3,641,237 A | 2/1972 | Gould et al. |
| 3,734,095 A * | 5/1973 | Santomieri ............ 604/168.01 |
| 3,828,777 A | 8/1974 | Ness |
| 3,831,583 A | 8/1974 | Edmunds, Jr. et al. |
| 3,845,201 A | 10/1974 | Haddad et al. |
| 3,902,495 A | 9/1975 | Weiss et al. |
| 3,914,402 A | 10/1975 | Shell |
| 3,916,899 A | 11/1975 | Theeuwes et al. |
| 3,926,188 A | 12/1975 | Baker et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,238,687 A | 8/1993 | Magruder et al. |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,511 A | 12/1995 | Gwon et al. |
| 5,554,132 A | 9/1996 | Straits et al. |
| 5,562,915 A | 10/1996 | Lowe et al. |
| 5,578,042 A | 11/1996 | Cumming |
| 5,674,193 A | 10/1997 | Hayes |
| 5,681,572 A | 10/1997 | Seare, Jr. |
| 5,725,493 A | 3/1998 | Avery et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 6,001,386 A | 12/1999 | Ashton et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |

(56) References Cited

U.S. PATENT DOCUMENTS

| | | |
|---|---|---|
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,222 B1 | 8/2006 | Siekas et al. |
| 7,094,226 B2 | 8/2006 | Yaacobi |
| 7,117,870 B2 | 10/2006 | Prescott |
| 7,141,023 B2 * | 11/2006 | Diermann et al. ............ 600/573 |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,276,050 B2 | 10/2007 | Franklin |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,709,049 B2 | 5/2010 | Chappa |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0047011 A1 | 3/2003 | Diermann et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0171997 A1 | 9/2004 | Wilson et al. |
| 2004/0209359 A1 | 10/2004 | Yayon et al. |
| 2004/0230183 A1 | 11/2004 | Breegi et al. |
| 2004/0247487 A1 | 12/2004 | Commercon et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0255144 A1 | 11/2005 | Schultz |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0233037 A1 | 10/2007 | Gifford et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0265599 A1 | 11/2007 | Castillejos |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |

(56) References Cited

U.S. PATENT DOCUMENTS

| | | |
|---|---|---|
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0286338 A1 | 11/2008 | Rosenthal et al. |
| 2008/0292679 A1 | 11/2008 | Lyons et al. |
| 2009/0005864 A1 | 1/2009 | Eggleston |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0074786 A1 | 3/2009 | Dor et al. |
| 2009/0081271 A1 | 3/2009 | Clarke et al. |
| 2009/0081272 A1 | 3/2009 | Clarke et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124997 A1 | 5/2009 | Pettis et al. |
| 2009/0192493 A1 | 7/2009 | Meng et al. |
| 2009/0196903 A1 | 8/2009 | Kliman |
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | De Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Sabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306025 A1 | 12/2009 | Lane |
| 2009/0306595 A1 | 12/2009 | Shih et al. |
| 2009/0318545 A1 | 12/2009 | Silver et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0015158 A1 | 1/2010 | Robinson et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0189765 A1 | 7/2010 | Erickson et al. |
| 2010/0191176 A1 | 7/2010 | Ho et al. |
| 2010/0197512 A1 | 8/2010 | Trinkle et al. |
| 2010/0211041 A1 | 8/2010 | Omori et al. |
| 2010/0216702 A1 | 8/2010 | Szkudlinski et al. |
| 2010/0221309 A1 | 9/2010 | Myers et al. |
| 2010/0223979 A1 | 9/2010 | Ploehn et al. |
| 2010/0227904 A1 | 9/2010 | Kabra et al. |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0190723 A1 | 8/2011 | Fangrow |
| 2011/0206646 A1 | 8/2011 | Alfonso et al. |
| 2012/0029445 A1 | 2/2012 | de Juan, Jr. et al. |
| 2012/0029470 A1 | 2/2012 | Juan, Jr. et al. |

FOREIGN PATENT DOCUMENTS

| | | |
|---|---|---|
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 A1 | 6/2006 |
| EP | 1385452 | 9/2006 |
| EP | 1409065 | 1/2007 |
| EP | 1337284 B1 | 12/2007 |
| EP | 1911481 | 4/2008 |
| EP | 1521572 B1 | 3/2009 |
| JP | 01-149716 | 6/1989 |
| JP | 01-197429 A | 8/1989 |
| WO | WO-8804573 | 6/1988 |
| WO | WO-9007545 | 7/1990 |
| WO | WO-9528984 | 11/1995 |
| WO | WO-9729850 | 8/1997 |
| WO | WO-9825982 | 6/1998 |
| WO | WO-9911244 | 3/1999 |
| WO | WO-0048660 | 8/2000 |
| WO | WO-0126714 | 4/2001 |
| WO | WO-0150943 | 7/2001 |
| WO | WO-0168016 | 9/2001 |
| WO | WO-02100318 | 12/2002 |
| WO | WO-03028765 | 4/2003 |
| WO | WO-03077972 | 9/2003 |
| WO | WO-03082188 | 10/2003 |
| WO | WO-2004000267 | 12/2003 |
| WO | WO-2004112653 | 12/2004 |
| WO | WO-2005016401 | 2/2005 |
| WO | WO-2005027906 | 3/2005 |
| WO | WO-2005028006 | 3/2005 |

(56) References Cited

FOREIGN PATENT DOCUMENTS

| | | |
|---|---|---|
| WO | WO-2005091922 | 10/2005 |
| WO | WO-2005107705 | 11/2005 |
| WO | WO-2005110362 | 11/2005 |
| WO | WO-2005110436 | 11/2005 |
| WO | WO-2005110473 | 11/2005 |
| WO | WO-2005117780 | 12/2005 |
| WO | WO-2006014484 | 2/2006 |
| WO | WO-2006015385 | 2/2006 |
| WO | WO-2006023530 | 3/2006 |
| WO | WO-2006031358 | 3/2006 |
| WO | WO-2006031388 | 3/2006 |
| WO | WO-2006044614 | 4/2006 |
| WO | WO-2006050221 | 5/2006 |
| WO | WO-2006068838 | 6/2006 |
| WO | WO-2006071554 | 7/2006 |
| WO | WO-2006082588 | 8/2006 |
| WO | WO-2006108054 | 10/2006 |
| WO | WO-2006127962 | 11/2006 |
| WO | WO-2006138609 | 12/2006 |
| WO | WO-2007012974 | 2/2007 |
| WO | WO-2007035473 | 3/2007 |
| WO | WO-2007035621 | 3/2007 |
| WO | WO-2007038453 | 4/2007 |
| WO | WO-2007044534 | 4/2007 |
| WO | WO-2007047744 | 4/2007 |
| WO | WO-2007066339 | 6/2007 |
| WO | WO-2007084582 | 7/2007 |
| WO | WO-2007084765 | 7/2007 |
| WO | WO-2007101204 | 9/2007 |
| WO | WO-2007115259 | 10/2007 |
| WO | WO-2007117394 | 10/2007 |
| WO | WO-2007131050 | 11/2007 |
| WO | WO-2007133761 | 11/2007 |
| WO | WO-2007133762 | 11/2007 |
| WO | WO-2008003043 | 1/2008 |
| WO | WO-2008005240 | 1/2008 |
| WO | WO-2008011125 | 1/2008 |
| WO | WO-2008019265 | 2/2008 |
| WO | WO-2008033924 | 3/2008 |
| WO | WO-2008040062 | 4/2008 |
| WO | WO-2008045272 | 4/2008 |
| WO | WO-2008052145 | 5/2008 |
| WO | WO-2008060359 | 5/2008 |
| WO | WO-2008061043 | 5/2008 |
| WO | WO-2008076544 | 6/2008 |
| WO | WO-2008094989 | 8/2008 |
| WO | WO-2008115290 | 9/2008 |
| WO | WO-2008116165 | 9/2008 |
| WO | WO-2008144340 | 11/2008 |
| WO | WO-2008144919 | 12/2008 |
| WO | WO-2009012075 | 1/2009 |
| WO | WO-2009023615 | 2/2009 |
| WO | WO-2009046164 | 4/2009 |
| WO | WO-2009055620 | 4/2009 |
| WO | WO-2009055671 | 4/2009 |
| WO | WO-2009055729 | 4/2009 |
| WO | WO-2009055824 | 4/2009 |
| WO | WO-2009061607 | 5/2009 |
| WO | WO-2009073192 | 6/2009 |
| WO | WO-2009086112 | 7/2009 |
| WO | WO-2009089409 | 7/2009 |
| WO | WO-2009094466 | 7/2009 |
| WO | WO-2009112878 | 9/2009 |
| WO | WO-2009117112 | 9/2009 |
| WO | WO-2009124096 | 10/2009 |
| WO | WO-2009128932 | 10/2009 |
| WO | WO-2009134929 | 11/2009 |
| WO | WO-2009137777 | 11/2009 |
| WO | WO-2010008424 | 1/2010 |
| WO | WO-2010021993 | 2/2010 |
| WO | WO-2010047753 | 4/2010 |
| WO | WO-2010062628 | 6/2010 |
| WO | WO-2010066714 | 6/2010 |
| WO | WO-2010075565 | 7/2010 |
| WO | WO-2010078063 | 7/2010 |
| WO | WO-2010088548 | 8/2010 |
| WO | WO-2010093945 | 8/2010 |
| WO | WO-2010095940 | 8/2010 |
| WO | WO-2010125416 | 11/2010 |
| WO | WO-2010126908 | 11/2010 |
| WO | WO-2010135369 | 11/2010 |
| WO | WO-2010141729 | 12/2010 |
| WO | WO-2010147661 | 12/2010 |
| WO | WO-2011008896 | 1/2011 |
| WO | WO-2011008897 | 1/2011 |
| WO | WO-2011028850 | 3/2011 |
| WO | WO-2011034627 | 3/2011 |
| WO | WO-2011079232 | 6/2011 |
| WO | WO-2012019047 | 2/2012 |
| WO | WO-2012019136 | 2/2012 |
| WO | WO-2013003620 | 1/2013 |
| WO | WO-2013022801 | 2/2013 |

OTHER PUBLICATIONS

Arvo, Agenda for the Summer Eye Research Conference, (Jul. 2009).
Avery et al., "Intravitreal bevacizumab (Avastin) in the treatment of proliferative diabetic retinopathy," Ophthalmology. Oct. 2006, 113(10):1695-1705.e6.
Bakri et al., "The effect of intravitreal triamcinolone acetonide on intraocular pressure," Ophthalmic Surgery, Lasers and Imaging, Sep./Oct. 2003; 34(5): 386-390.
Bird et al., Transport Phenomena, John Wiley & Sons, Inc., New York, 1960, pp. 196-201.
Block et al., "Solubility and dissolution of triamcinolone acetonide," Journal of Pharmaceutical Sciences, Apr. 1973; 62(4):617-621.
Breslin, C.W., et al., "Chapter 7. Slow Release Artificial Tears", *Symposium on Ocular Therapy* pp. 77-83, 1977.
Castro et al., "Effect of COX inhibitors on VEGF-induced retinal vascular leakage and experimental corneal and choroidal neovascularization," Exp Eye Res. Aug. 2004;79(2):275-285.
Chirila et al., "*The* Vitreous Humor" in *Handbook of Biomaterial Properties*, eds. Black & Hastings. Chapman & Hall, London, 1998; pp. 125-131.
Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010.
Deissler et al., "VEGF-induced effects on proliferation, migration and tight junctions are restored by ranibizumab (Lucentis) in microvascular retinal endothelial cells,"Br J Ophthalmol 2008;92:839-843.
Del Amo, et al., Current & future ophthalmic drug delivery systems . . . , *Drug Discovery Today*, vol. 13, Nos. 3/4, Feb. 2008.
Donoso et al., "The role of inflammation in the pathogenesis of age-related macular degeneration," Surv Ophthalmol. Mar.-Apr. 2006;51(2):137-52.
Duvvuri et al., Drug Delivery to the Retina: Challenges and Opportunities, *Expert Opinion on Biological Therapy*, 2003, vol. 3(1): 45-56.
European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.
Funatsu et al. "Association of vitreous inflammatory factors with diabetic macular edema," Ophthalmology 2009;116:73-79.
Gaudana et al., Recent Perspectives in Ocular Drug Delivery, *Pharmaceutical Research*, 2008.
Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.
Gillies et al., "Intravitreal triamcinolone for refractory diabetic macular edema: two-year results of a double-masked, placebo-controlled, randomized clinical trial," Ophthalmology. Sep. 2006;113(9):1533-1538.
Haller, An Overview of Sustained-release Drug Implants, Retinal Physician, Jan. 2008.

(56) References Cited

OTHER PUBLICATIONS

Hastedt & Wright, "Diffusion in porous materials above the percolation threshold," Pharm. Res. Sep. 1990; 7(9):893-901 (1990).
Heier et al, "Ketorolac versus prednisolone versus combination therapy in the treatment of acute pseudophakic cystoid macular edema," Ophthalmology. Nov. 2000;107(11):2034-2038 ;discussion 2039.
Janoria et al., Novel Approaches to Retinal Drug Delivery, *Expert Opinion Drug Delivery*, 2007.
Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.
"Juvederm", FDA, 2006, XP002670727, Retrieved from the Internet: URL:http://www.accessdata.fda.gov/cdrh_docs/pdf5/P050047b.pdf [retrieved on Mar. 1, 2012] p. 1, last paragraph.
Kang et al., "Inhibitory effects of anti-inflammatory drugs on interleukin-6 bioactivity," Biol Pharm Bull. Jun. 2001;24(6):701-703.
Katz, I.M., et al., "A Soluble Sustained-Release Ophthalmic Delivery Unit", 8:5 (May 1977) pp. 728-734.
Lamberts, D.W., M.D., et al., "A Clinical Study of Slow-Releasing Artificial Tears", *Ophthalmology* 85 (1978) pp. 794-800.
Lee, D.A., et al., "Glaucoma Filtration Surgery in Rabbits Using Bioerodible Polymers and 5-Fluorouracil", *Ophthalmology* 94:12 (1987) pp. 1523-1530.
Lee, D.A., et al., "The Use of Bioerodible Polymers and 5-Fluorouracil in Glaucoma Filtration Surgery", *Investigative Ophthalmology & Visual Science* 29-11 (1988) pp. 1692-1697.
Li, et al., An electrochemical introculardrug delivery device, *Science Direct, Sensors and Actuators*, www.sciencedirect.com,Jul. 4, 2007.
Lopez-Armada et al., "Modulation of cell recruitment by anti-inflammatory agents in antigen-induced arthritis," Ann Rheum Dis Nov. 2002;61(11):1027-1030.
Luncentis, INN-Ranibizumab, "Scientific Discussion," European Medicines Agency ; retrieved from the Internet:<http://www.ema.europa.eu/docs/en_GB/document_library/EPAR_-_Assessment_Report_-_Variation/human/000715/WC500101009.pdf>. Oct. 21, 2010.
MAbPac SCX-10 Column for Monoclonal Antibody Variant Analysis, http://www.dionex.com/en-us/webdocs/87008-DS-MAbPac-SCX-10-Column-20Aug2010-LPN2567-03.pdf.
Metal Powder Industries Federation, Porous Metal Design Guidebook, 2007, 24 pages total. Downloaded from the Internet: <<http://www.mpif.org/DesignCenter/porous.pdf>>.
Miller, DP, et al., *Thermophysical Properties of Trehalose and Its Concentrated Aqueous Solutions*,Pharmaceutical Research, vol. 14, No. 5, 1997, pp. 578-590.
Molokhia et al, "Transscleral iontophoretic and intravitreal delivery of a macromolecule: Study of ocular distribution in vivo and postmortem with MRI", Experimental Eye Research 88 (2009) 418-425.
Moritera, T., et al., "Microspheres of Biodegradable Polymers as a Drug-Delivery System in the Vitreous", *Investigative Ophthalmology & Visual Science* 32-6 (1991) pp. 1785-1790.
Mott Corporation, "Sintered Metal Powder Media," American Filtration & Separation Society 2007, 2 pages total. Downloaded from the Internet:<<http://www.afssociety.org/education/0907oneminute.htm>>.
Navarro, "The Optical Design of the Human Eye: a Critical Review," J Optom, Jan.-Mar. 2009 2(1): 3-18.
Nutan, Mth, et al., *General Principles of Suspensions, in Pharmaceutical Suspensions Fron Formulation Development to Manufacturing*, editors AK Kulshreshtha, et al., Spinger, 2010.
Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.org/cgi/reprint/44/6/2702>>.
Rosenfeld, "The Latest Research: Intravitreal Bevacizumab for Proliferative Diabetic Retinopathy," Review of Ophthalmology's Retina Online, Feb. 2006; retrieved from the Internet: http://www.revophth.com/archive/newsletter/0206_retina.htm.
Saline (medicine)—Wikipedia, the free encyclopedia. http://web.archive.org/web/20110205192937/http://en.wikipedia.org/wiki/Saline_(medicine). Apr. 27, 2012.
Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).
Sheardown and Saltzman, Novel Drug Delivery Systems for Posterior Segment Ocular Disease, *Opthalmology: Ocular Angiogenesis: Diseases, Mechanisms and Therapeutics*, 2007, pp. 393-408.
Smith et al., "Spectrophotometric determination of pKa values for fluorescein using activity coefficient corrections," WaterSA 2002; 28(4):395-402.
Smith, T.J., et al., "Intravitreal Sustained-Release Ganciclovir", *Arch. Ophthamol* 110 (1992) pp. 255-258.
Soheilian et al., "Pilot Study of Intravitreal Injection of Diclofenac for Treatment of Macular Edema of Various Etiologies," Retina, Mar. 2010; 30(3): 509-515.
Stay et al. Computer Simulation of Convective and Diffusive Transport of Controlled-Release Drugs in the vitreous Humor, *Pharm Res* 2003,20(1), pp. 96-102.
Theodossiadis et al., "Intravitreal administration of the anti-tumor necrosis factor agent infliximab for neovascular age-related macular degeneration," Am J Ophthalmol. May 2009;147(5):825-830.
Weiner, A.L., "Chapter 13: Polymeric Drug Delivery Systems for the Eye", *Polymeric Site-Specific Pharmacotherapy*, pp. 315-346, Edited by A.J. Domb (1994) John Wiley & Sons Ltd.
Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.
Wright, P., et al. "Slow-Release Artificial Tear Inserts in the Treatment of Dry Eyes Resulting from the Oculomucocutaneous Syndrome", *British Journal of Ophthalmology* 67 (1983) pp. 393-397.
Yao et al. (Prevention of Laser Photocoagulation Induced Choroidal Neovascularization Lesions by Intravitreal Doses of Ranibizumab in Cynomolgus Monkeys, ARVO 2009 abstract D906).
International Search Report dated Feb. 27, 2012 for PCT/US2011/046812.

\* cited by examiner

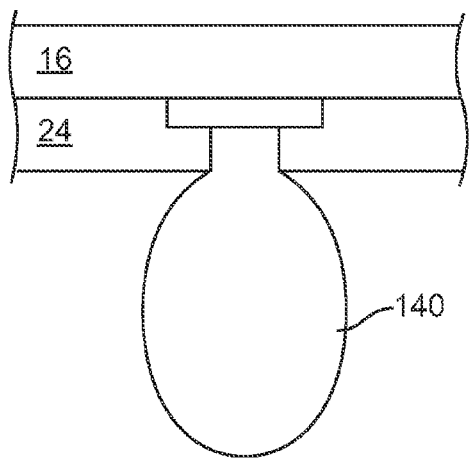
FIG. 1A-2-2
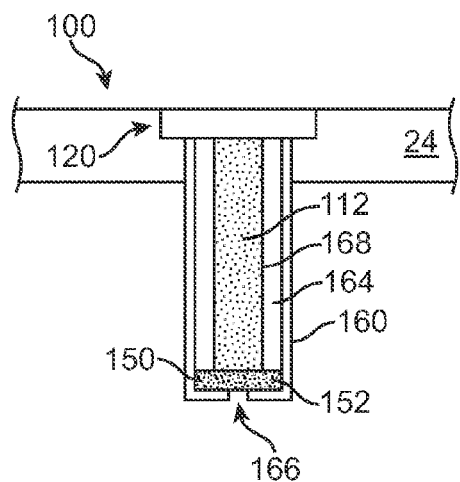
FIG. 1B
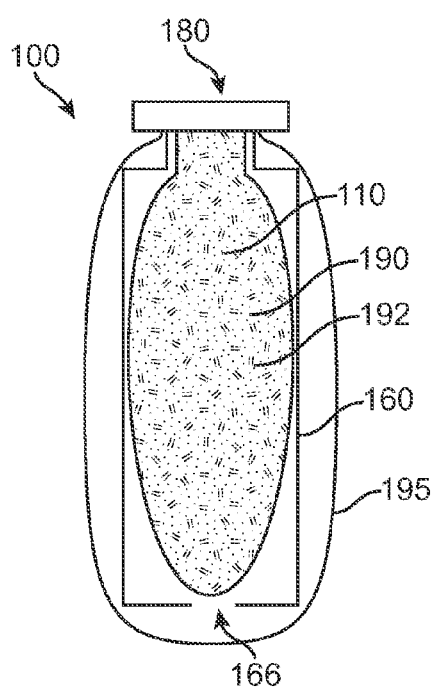
FIG. 1C
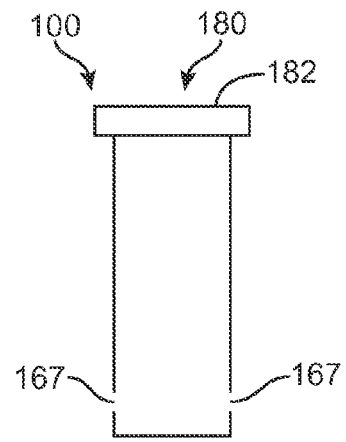
FIG. 1C-A

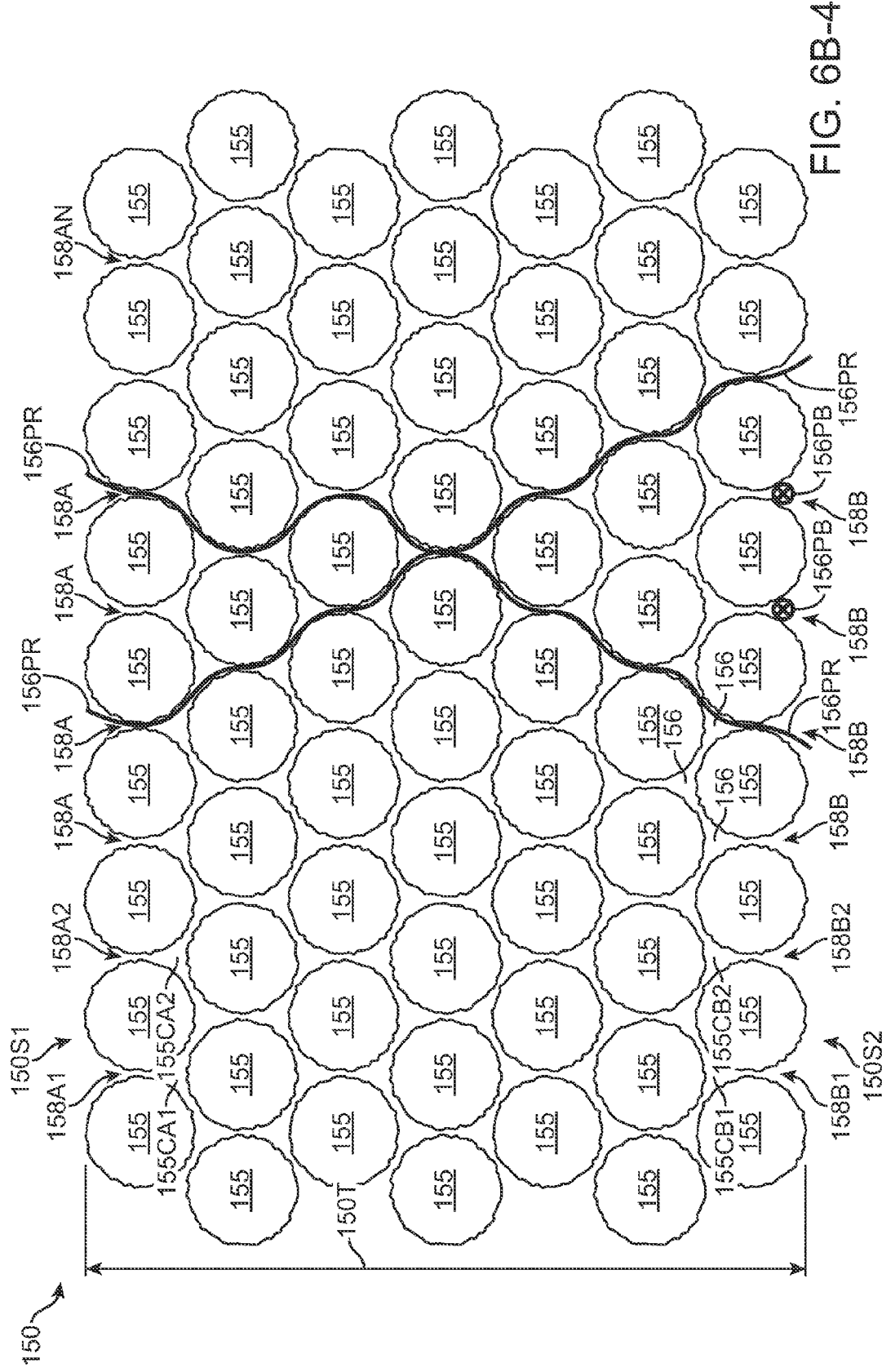

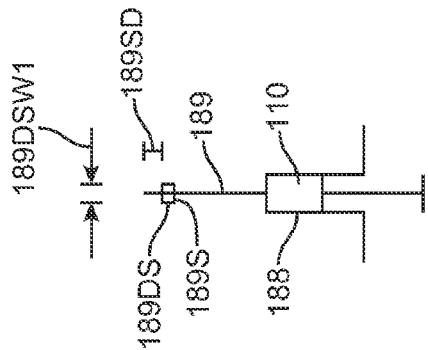
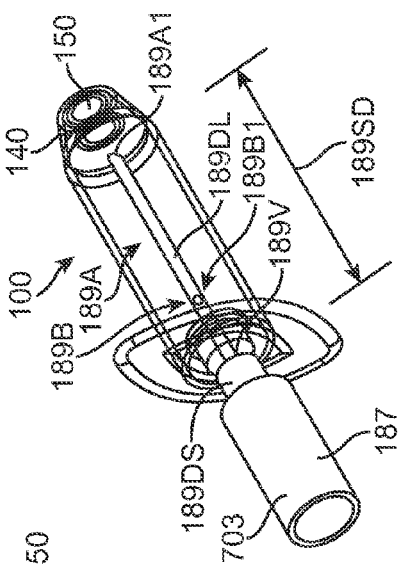
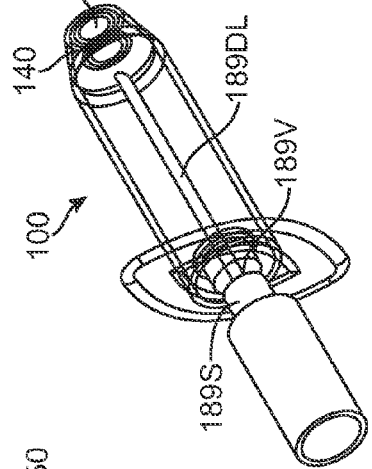
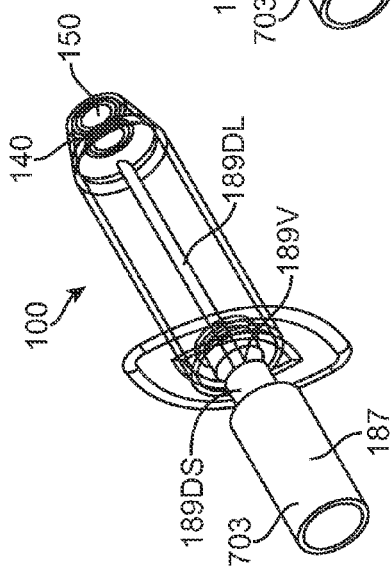
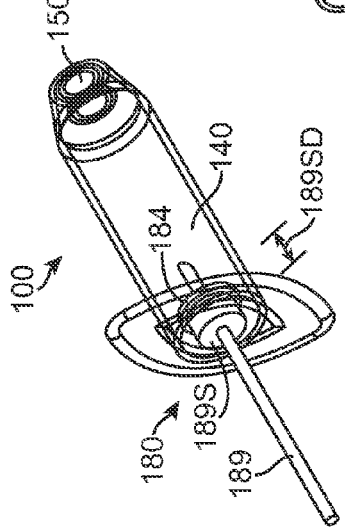
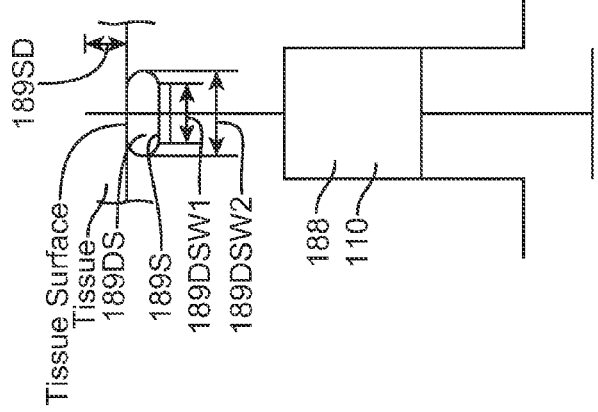

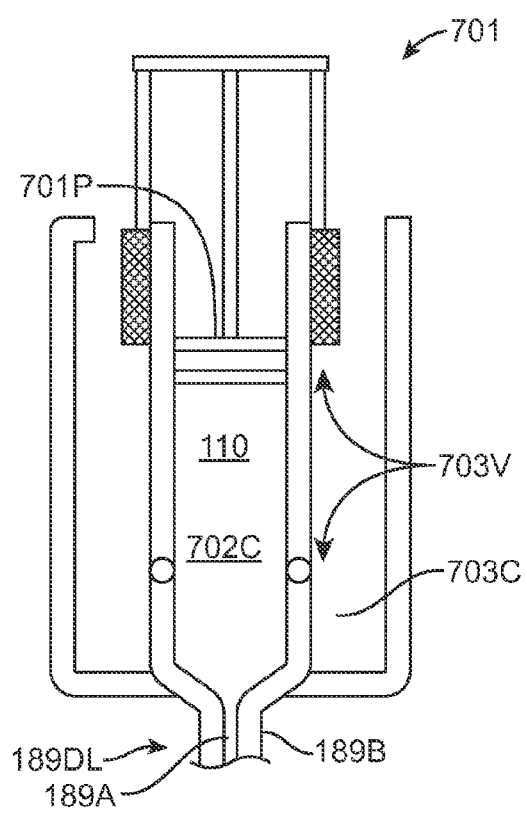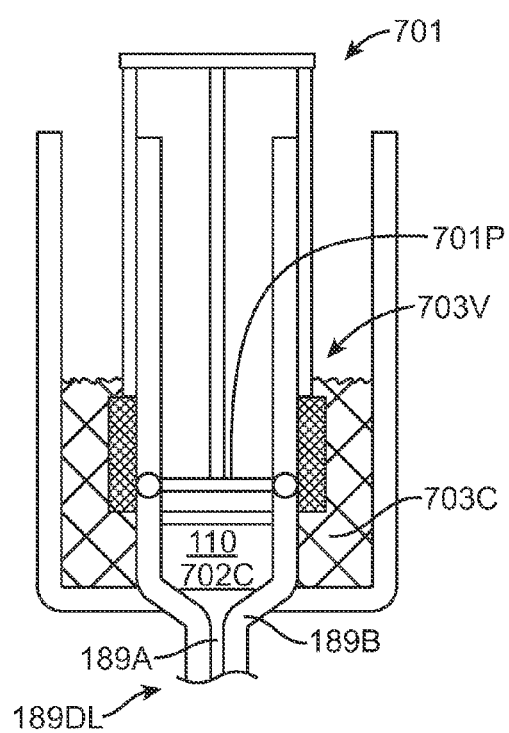
FIG. 7A-8A  FIG. 7A-8B

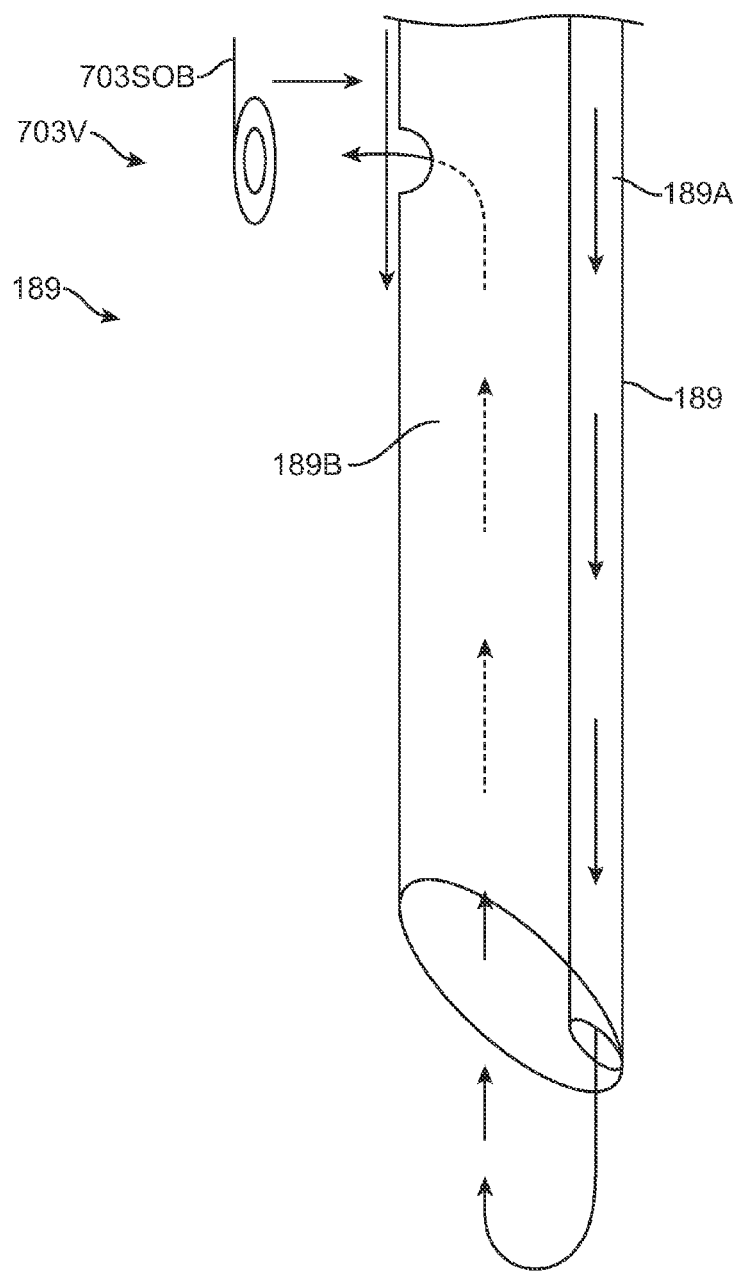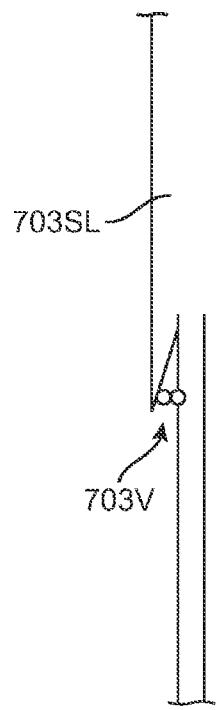
FIG. 7A-11A    FIG. 7A-11B

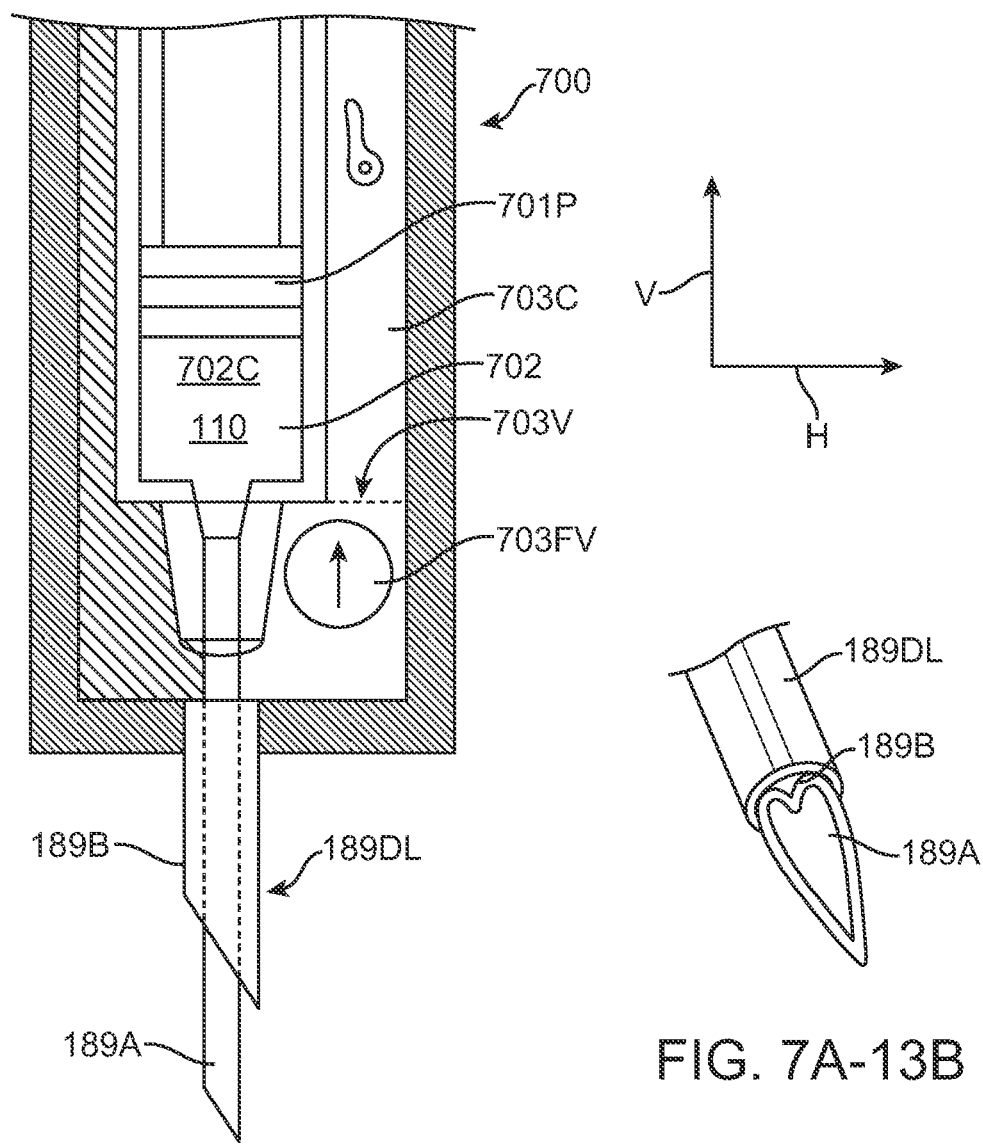
FIG. 7A-13A
FIG. 7A-13B
FIG. 7A-13C

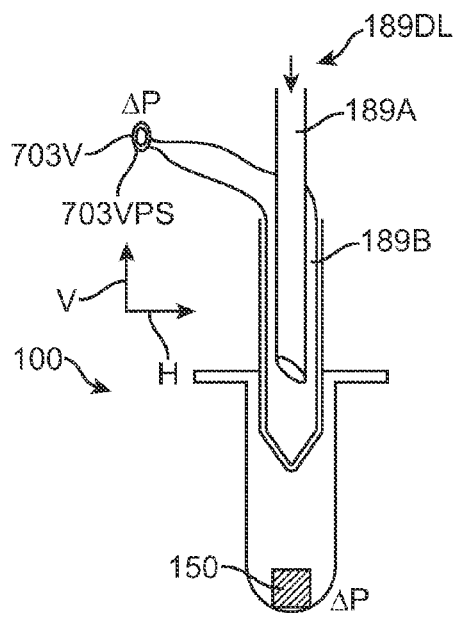
FIG. 7A-15A
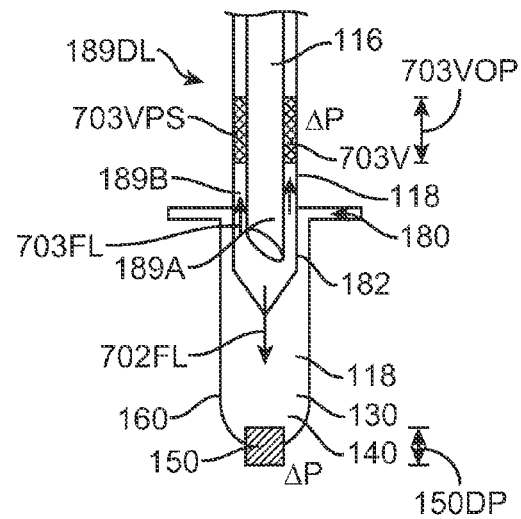
FIG. 7A-15B
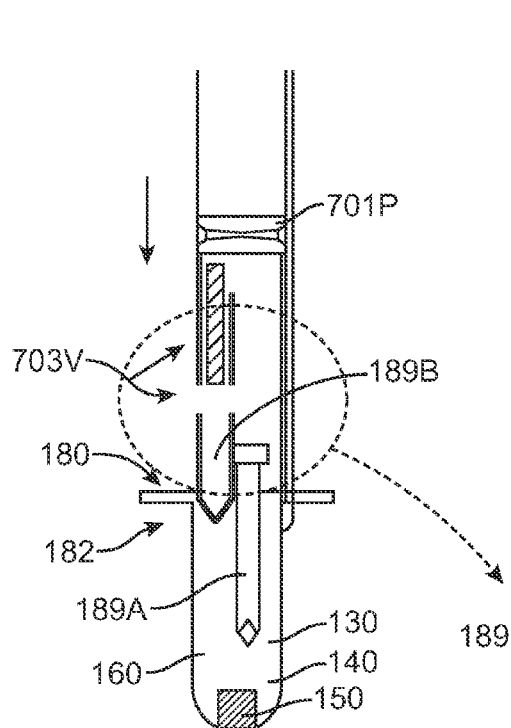
FIG. 7A-15C1
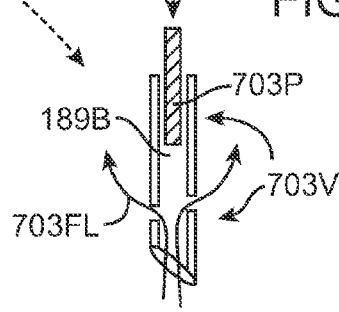
FIG. 7A-15C2
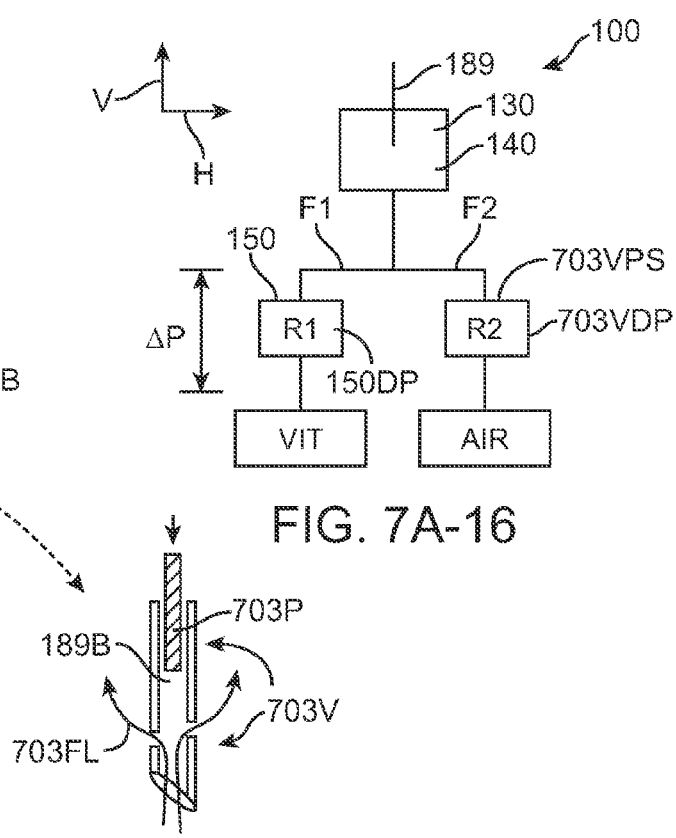
FIG. 7A-16

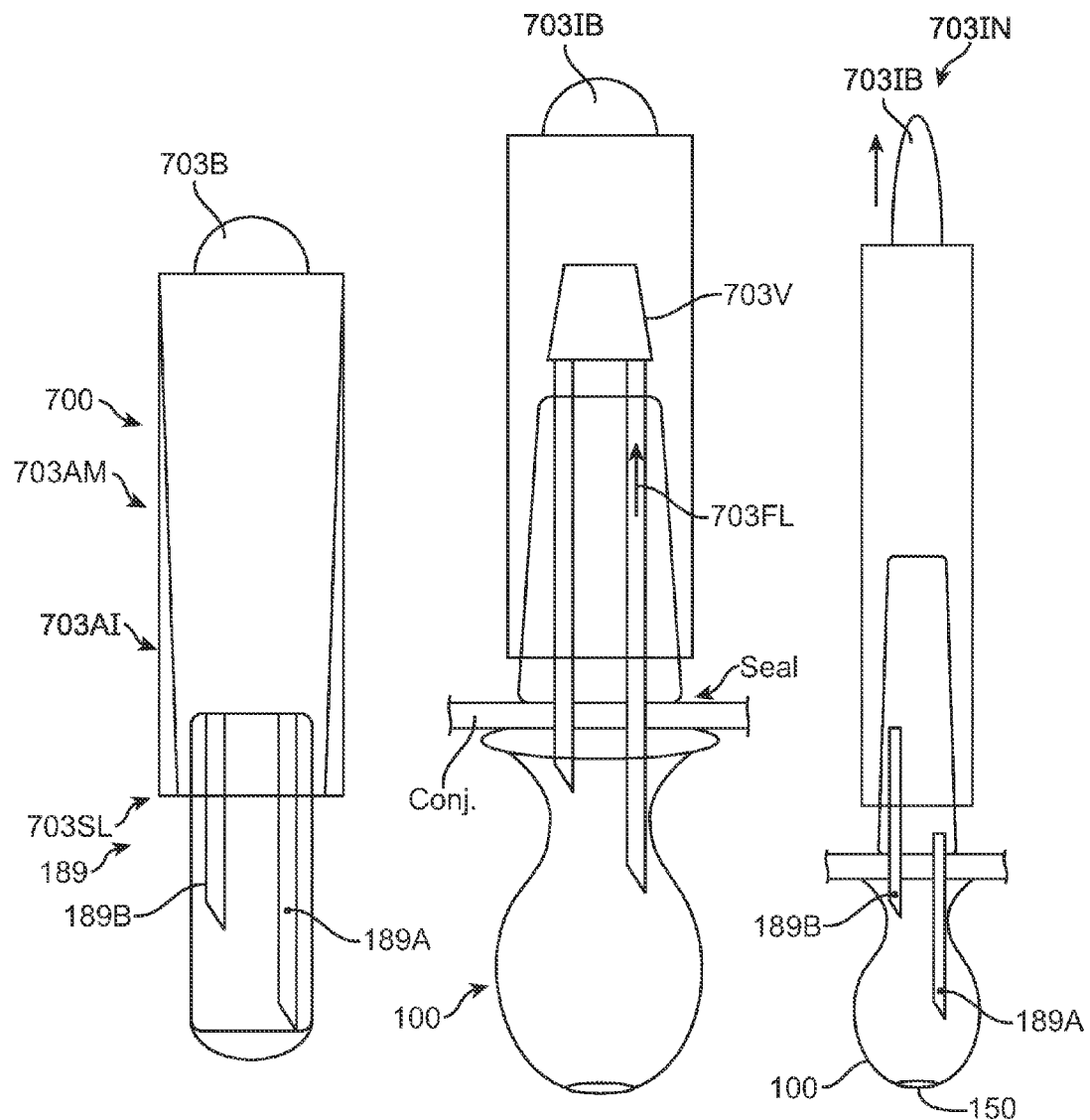

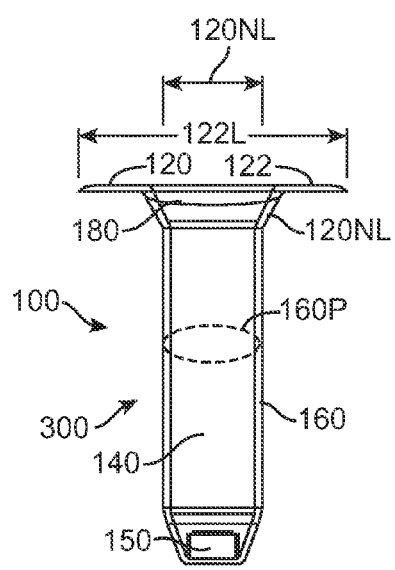
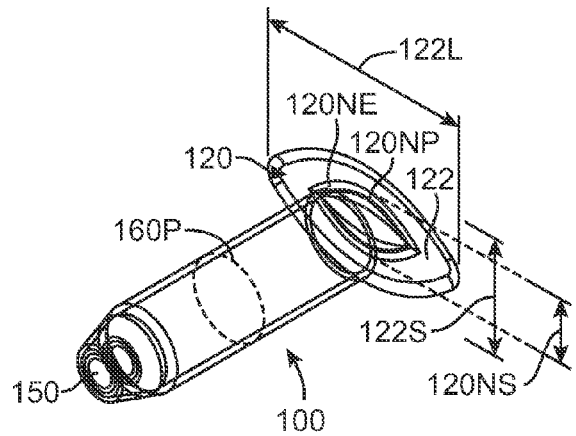
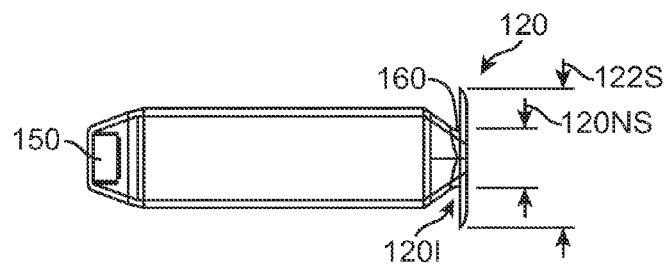
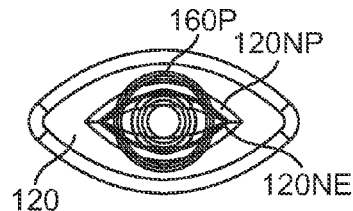
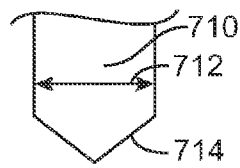
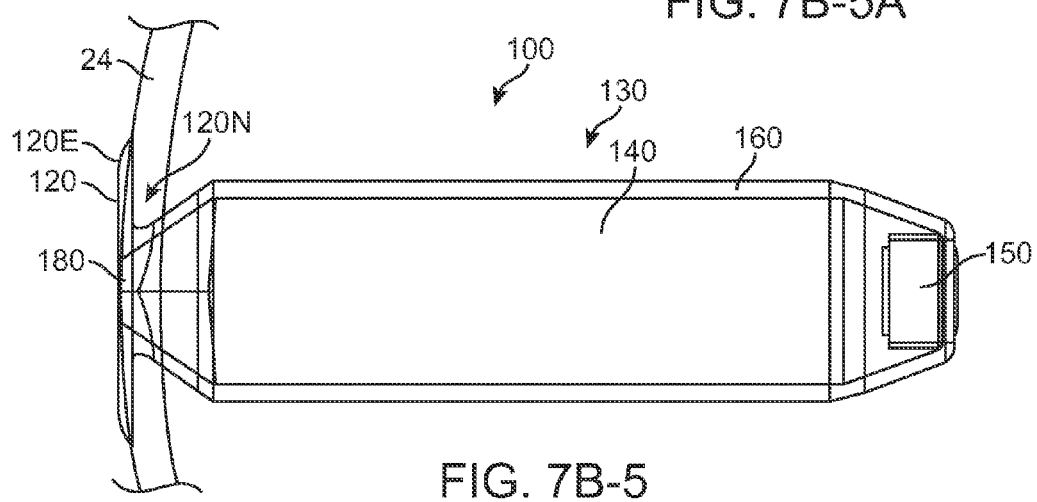
FIG. 7B-1
FIG. 7B-2
FIG. 7B-3
FIG. 7B-4
FIG. 7B-5A
FIG. 7B-5

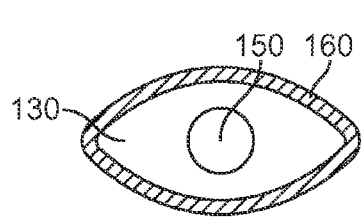
FIG. 7B-6A
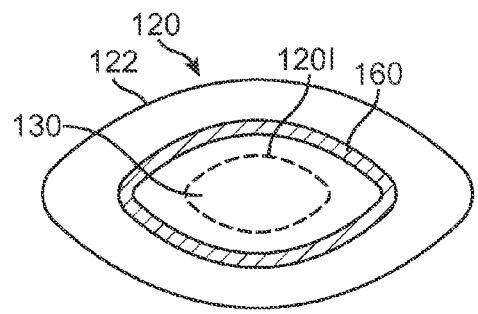
FIG. 7B-6B
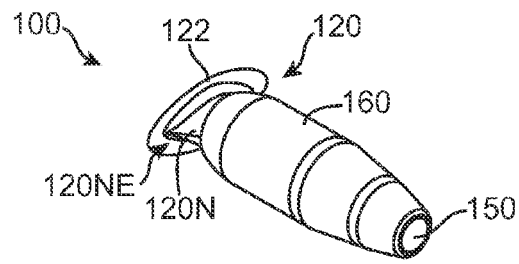
FIG. 7B-6C
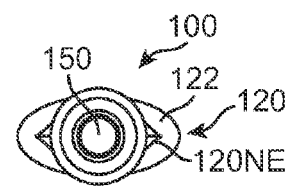
FIG. 7B-6D
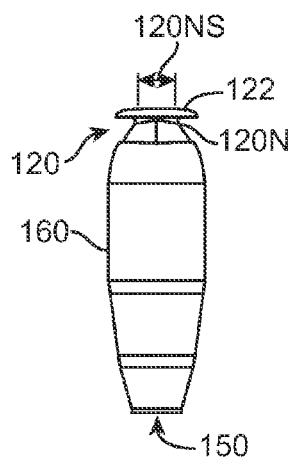
FIG. 7B-6E1
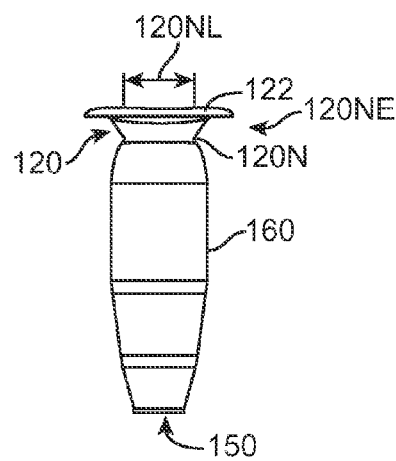
FIG. 7B-6E2
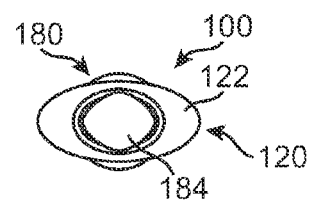
FIG. 7B-6F

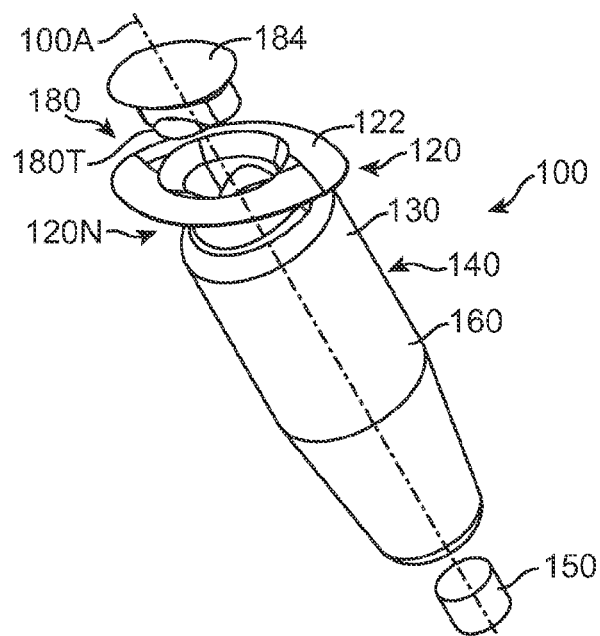
FIG. 7B-6G
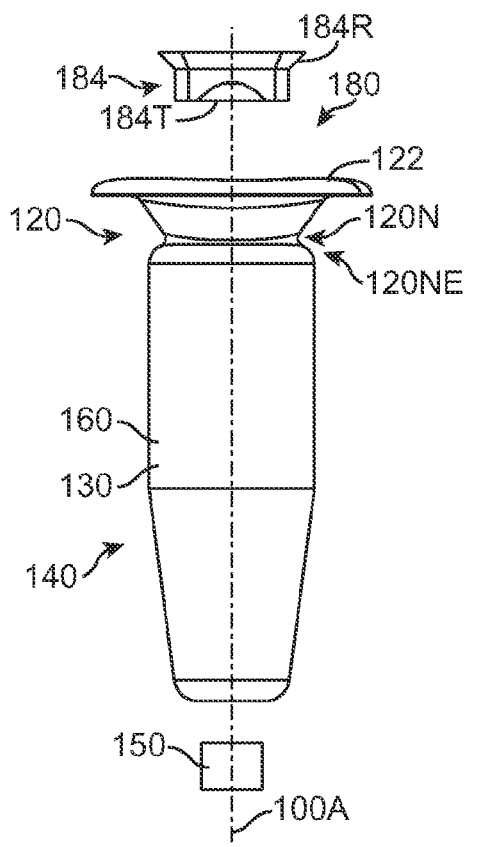 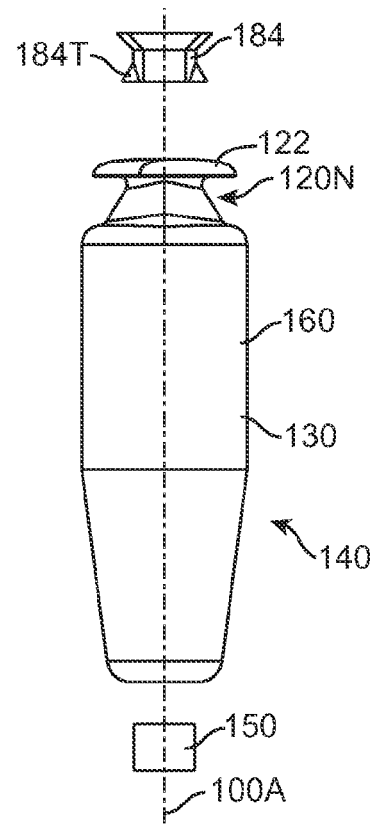
FIG. 7B-6H  FIG. 7B-6I

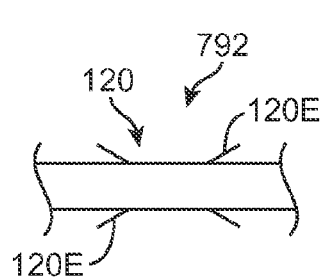
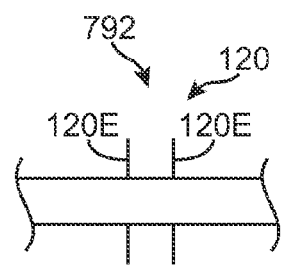
FIG. 7C-4A      FIG. 7C-4B
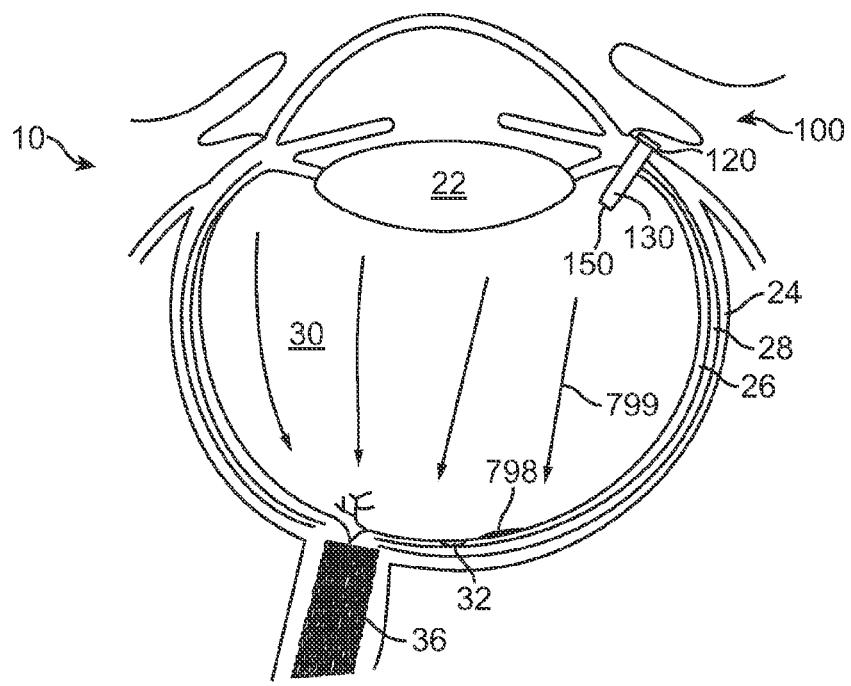
FIG. 7D
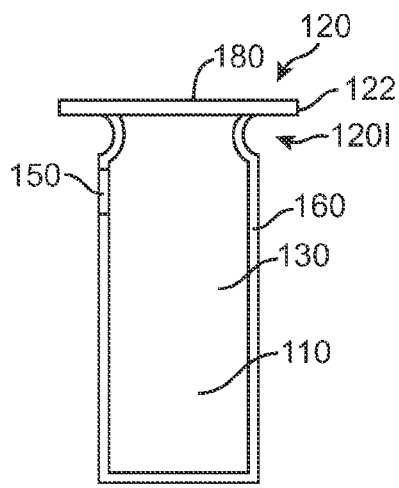
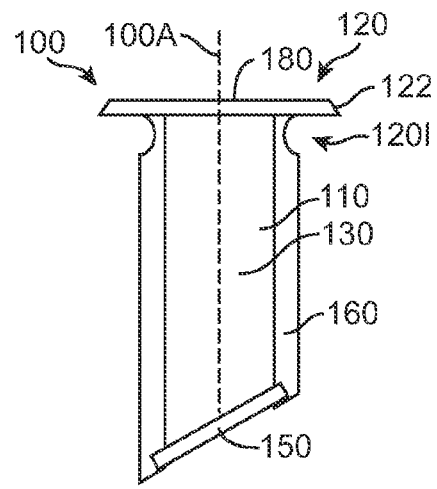
FIG. 7E      FIG. 7F

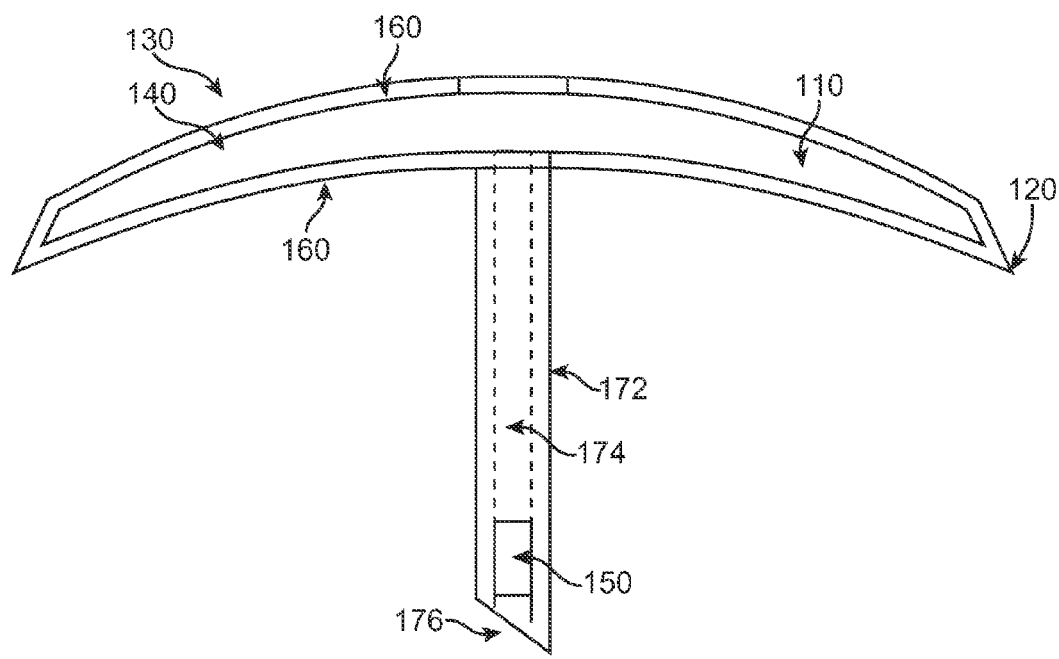
FIG. 8A
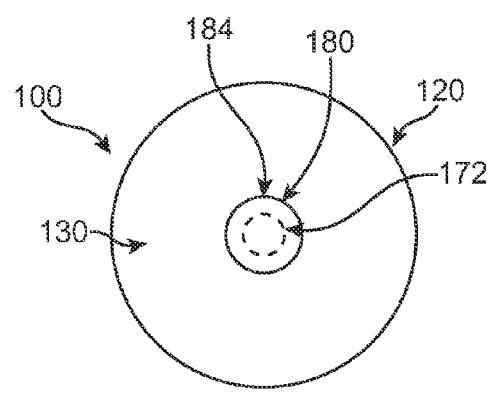
FIG. 8A1

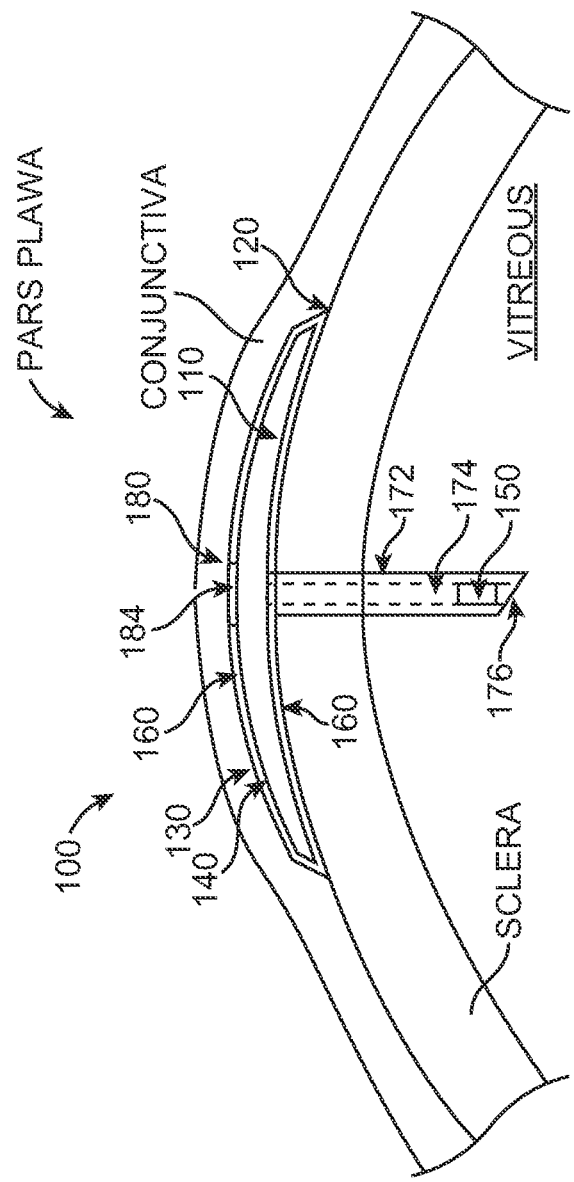
FIG. 8A2

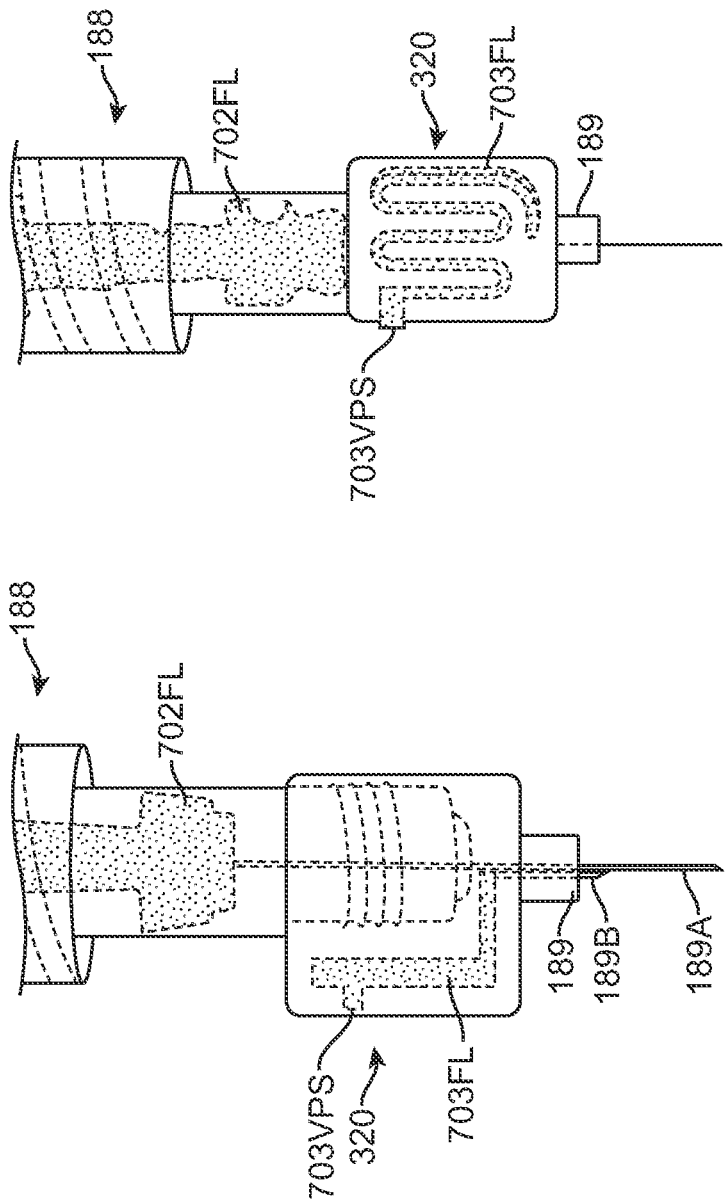

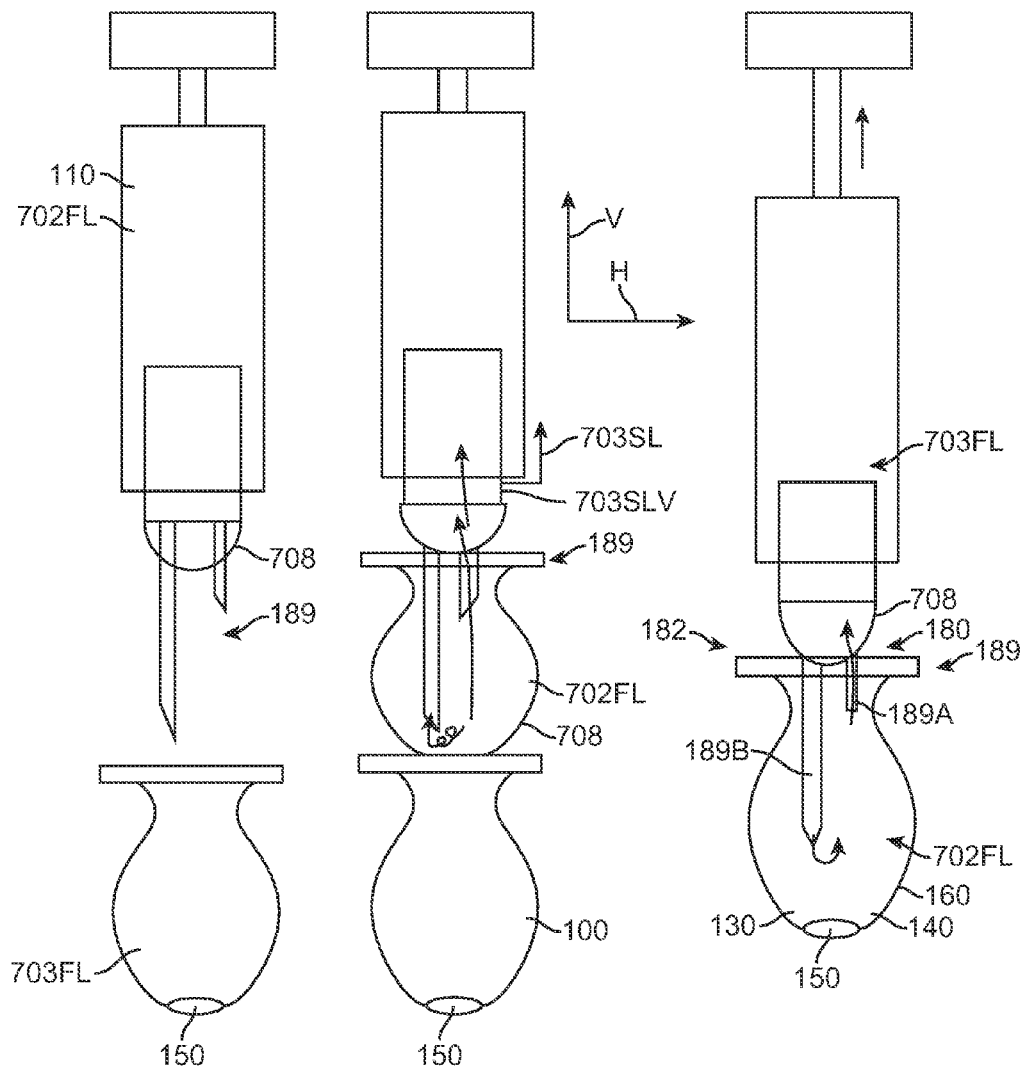

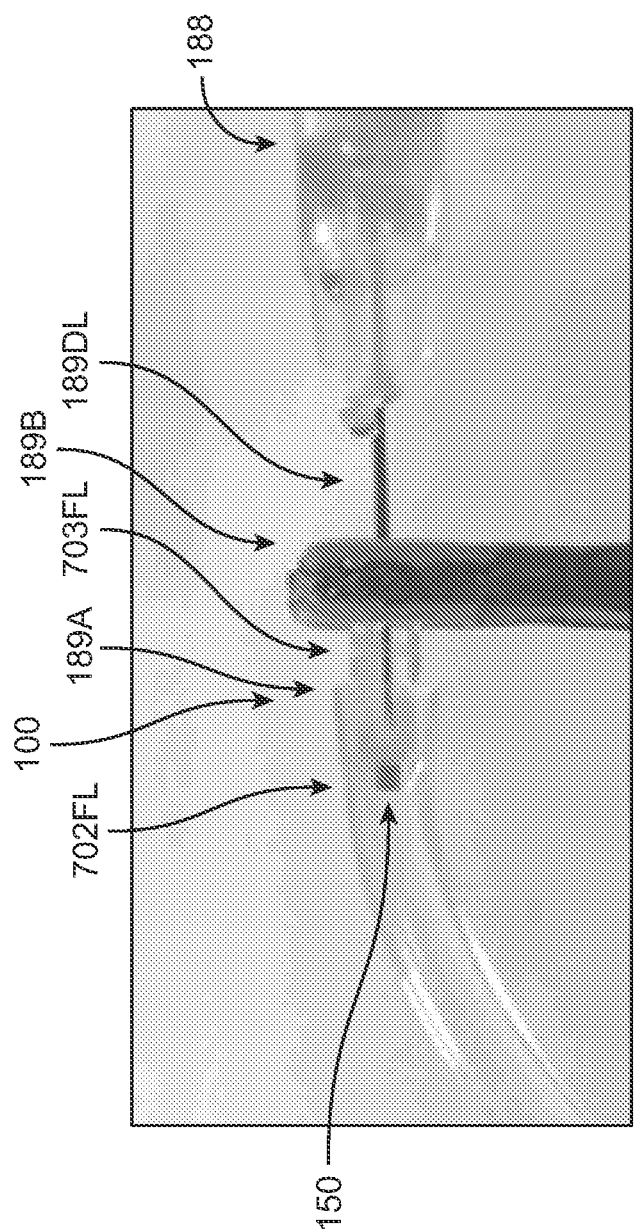

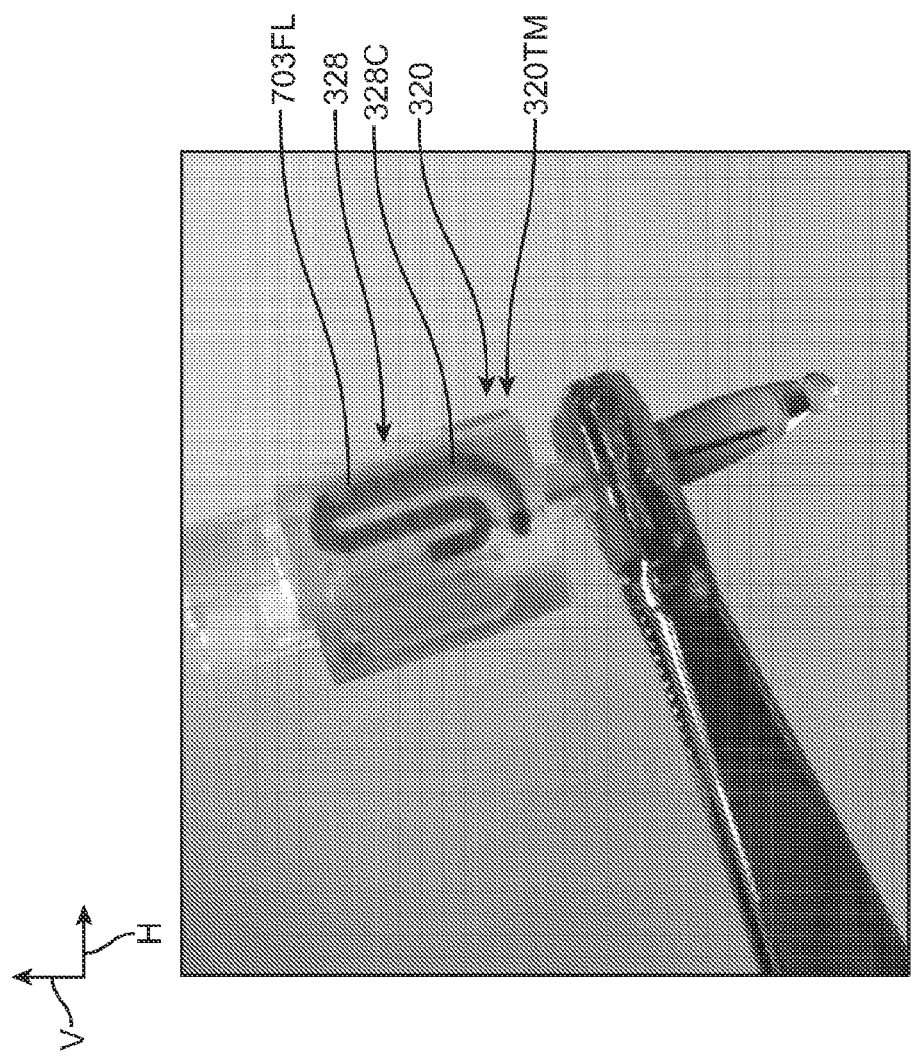

INJECTOR APPARATUS AND METHOD FOR DRUG DELIVERY

CROSS-REFERENCES TO RELATED APPLICATIONS

The present PCT patent application claims priority to the following U.S. Patent Applications 61/371,154, entitled "INJECTOR APPARATUS AND METHOD FOR DRUG DELIVERY", filed 5 Aug. 2010; U.S. Patent App. Ser. No. 61/499,095, entitled "Injector Apparatus and Method for Drug Delivery", filed Jun. 20, 2011; U.S. Patent App. Ser. No. 61/501,021, entitled, "Injector Apparatus and Method for Drug Delivery", filed: Jun. 24, 2011; U.S. Patent App. Ser. No. 61/504,038, entitled "Injector Apparatus and Method for Drug Delivery", filed Jul. 1, 2011; 61/371,169, entitled IMPLANTABLE THERAPEUTIC DEVICE", filed on 5 Aug. 2010; U.S. Patent App. Ser. No. 61/495,251, entitled "Diagnostic Methods and Apparatus", filed, Jun. 9, 2011; and U.S. Patent App. Ser. No. 61/495,718, entitled "Diagnostic Methods and Apparatus" filed, Jun. 10, 2011; the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

The present invention is generally directed to devices implanted in the body and apparatus to replace a fluid of the implanted device with a therapeutic fluid.

The prior methods and apparatus for treating diseases of the eye can be less than ideal in at least some instances. For example, eye drops may have limited penetration of the external tissue of the eye, such that at least some therapeutic agents may not be delivered effectively with eye drops in at least some instances, for example high molecular weight therapeutic agents. Further, drops administered to the eye may not remain in the tear of the eye as long as would be ideal and can be washed away, for example when the patient blinks so as to provide less than ideal therapeutic benefit in at least some instance.

Implantable devices have been proposed to deliver treatment to the eye. However, in at least some instances, the therapeutic agent of the implantable device can be depleted, and the device may be removed or additional therapeutic agent placed in the device.

Prior methods and apparatus to place a therapeutic fluid in a device implanted in the eye can provide less than ideal results in at least some instances. For example, the amount of therapeutic agent placed in the device may be less than ideal in at least some instances. Further at least some of the prior methods to place of a therapeutic fluid in a device implanted in an eye may take longer than would be ideal. In at least some instances, the fluid placed initial in the device may be forced out of the therapeutic device, such that the amount of therapeutic agent placed in the treatment device can be less than ideal for sustained release of the therapeutic agent.

Work in relation to embodiment of the present invention also suggests that at least some prior injection apparatus may result in leakage during injection of the therapeutic agent. In at least some instances the injected fluid may comprise amounts of therapeutic agent that may be not be suitable for direct contact with tissue, such that leakage, or potential leakage, may limit available treatment options.

In light of the above, it would be desirable to provide improved methods and apparatus to place a therapeutic agent in a device implanted in the eye to provide improved treatments of diseases of the eye.

SUMMARY OF THE INVENTION

Embodiments of the present invention provide improved methods and apparatus to provide a therapeutic fluid to devices implanted in the body, for example to containers of devices implanted in the eye of a patient. The methods and apparatus may comprise an injector to increase an amount of therapeutic agent injected into the device implanted in the eye, or a structure to receive the therapeutic fluid within the device implanted in the eye, or combinations thereof. The device implanted in the eye may comprise a reservoir chamber coupled to a porous structure so as to release the therapeutic agent for an extended time. In many embodiments, the volume of the reservoir chamber is sized to fit within the eye without substantially affecting vision. The porous structure may have a high resistance to flow, and in many embodiments the therapeutic fluid injected into the device may be exchanged with a fluid of the device implanted in the eye.

In many embodiments, the container implanted in the eye comprises a fluid having a density different than the fluid therapeutic fluid of the container implanted in the body. The therapeutic fluid may comprise a formulation of a therapeutic agent having a density greater than a fluid of the device implanted in the eye, such that the therapeutic formulation injected into the implanted chamber may separate at least partially. In many embodiments, the at least partial separation of the therapeutic fluid from the fluid of the implanted device can be used to improve an efficiency of exchange of the therapeutic fluid with the fluid of the chamber, so as to increase the amount of therapeutic fluid in the chamber. While the methods and apparatus as described herein can be used with many devices to increase the amount of therapeutic fluid in the implanted device, the increased the efficiency can be especially beneficial with implanted devices having a reservoir chamber comprising a substantially constant volume. Also, with implants located at least partially in the vitreous humor of the eye, the size of the reservoir chamber can somewhat limited to provide a clear optical path for vision, and the embodiments described herein can be used to increase the amount of fluid placed in the chamber so as to increase the therapeutic benefit of the implanted device and provide sustained release for an extended time.

In many embodiments, one or more of the therapeutic device or the injector can be configured to increase the amount of therapeutic fluid placed in the device based on the at least partial separation. The injector may comprise a first channel sized to extend to a first opening at a first location of the implanted device reservoir chamber so as to pass the therapeutic fluid into the chamber, and a second channel can be sized to extend to a second opening at a second location of the implanted device chamber so receive the fluid of the implanted device, such that the efficiency of the exchange can be increased based on the at least partial separation and the separation of the first location and the second location. The first channel may comprise a first lumen of at least one needle, and the second channel can be sized and shaped in many ways and may comprise a second lumen of the at least one needle. The second opening may comprise a vent to receive fluid from the chamber of the therapeutic device and inhibit excessive pressurization of the reservoir chamber so as to maintain substantially the integrity and function of the therapeutic device implanted in the eye.

In many embodiments, the injector comprises a stop coupled to the at least one needle. The first opening can be located a first distance from the stop and the second opening can be located a second distance from the stop, such that the first opening and the second opening are placed at locations of the implanted device so as to increase the at least partial separation when the stop engages a tissue surface such as the conjunctiva. In many embodiments, the therapeutic fluid can be denser than the fluid of the implanted device and, and the first opening to inject the therapeutic fluid may be located below the second opening when placed in the reservoir chamber, such that the denser therapeutic fluid can be placed in the reservoir chamber below the less dense fluid of the reservoir chamber so as to enhance the at least partial separation.

The stop may comprise a soft material, such as an elastomer. The soft material may form a seal when placed against a tissue surface such as the conjunctiva, and can maintain integrity of the conjunctival epithelium when the seal engages the conjunctiva. The sealing can decrease leakage of the therapeutic fluid, which can be helpful to increase an amount of fluid placed in the reservoir chamber of the therapeutic device. The sealing of the soft stop engaging the conjunctiva may also decrease interaction of the therapeutic fluid with the conjunctiva, which can be beneficial when the therapeutic fluid comprises a concentration or amount of therapeutic agent that may have a potentially undesirable interaction with the conjunctiva, for example with an antineoplastic therapeutic agent.

In many embodiments, the injector can be configured to pass a bolus of therapeutic fluid through the porous structure of the therapeutic device. The injector may comprise a valve that closes to push therapeutic fluid through the porous structure of the implanted device. The valve may comprise one or more of a mechanism, a porous structure, or a resistance to flow to pass the therapeutic fluid through the porous structure. The mechanism may comprise one or more movable components such as a slider, a piston, a sleeve or a deflectable component. The porous structure may comprise a porous material having resistance to flow that increase substantially when the displaced fluid of the implanted device contacts the porous structure. The resistance to flow may correspond to a restriction or other structure along the outflow path of the second channel. The resistance to flow can be sufficient so as to encourage the therapeutic fluid to pass through the therapeutic structure. The structure corresponding to the resistance to flow along the outflow path may comprise a lumen coupled to a vent placed in the therapeutic device.

In many embodiments, the injector comprises a flow rate to provide the at least partial separation.

In many embodiments, one or more of the therapeutic device or the injector can be configured to mix the therapeutic fluid with the implanted device fluid when the therapeutic fluid is injected so as to increase the amount of therapeutic fluid in the chamber. In many embodiments, the injector is configured to inject the therapeutic fluid at a rate of no more than about 100 uL per second, for example, and one or more of the injector or the implanted comprises structures to mix the therapeutic fluid with the fluid of the implanted device at the flow rate capable of providing the at least partial separation.

In a first aspect, embodiments of the present invention provide an apparatus to treat a patient. The apparatus comprises an injector to inject a therapeutic fluid into a chamber of a therapeutic device implantable in the patient with at least partial separation of a fluid of the implantable therapeutic device from the therapeutic fluid.

In another aspect, embodiments of the present invention provide an apparatus to treat an eye. The apparatus comprises an injector to inject a therapeutic fluid into a chamber of a therapeutic device implantable in the eye with at least partial separation of a fluid of the implantable therapeutic device from the therapeutic fluid.

In many embodiments, the therapeutic fluid comprises a therapeutic fluid density different from a density of the fluid of the implantable therapeutic device so as to provide the at least partial separation.

In many embodiments, the fluid of the implantable therapeutic device comprises a density different from the therapeutic fluid density. The therapeutic fluid density may differ from the density of the implantable device fluid by at least about 1% so as to provide the at least partial separation, for example by at least about 2% so as to provide the at least partial separation. The therapeutic fluid density may differ from the density of the implantable device fluid by at least about 3% so as to provide the at least partial separation. The therapeutic fluid density may differs from the density of the implantable device fluid by no more than about 30% so as to provide the at least partial separation, for example by no more than about 20% so as to provide the at least partial separation. In many embodiments, the therapeutic fluid density differs from the density of the implantable device fluid by no more than about 10% so as to provide the at least partial separation.

In many embodiments, a difference of the therapeutic fluid density relative to the density of the implantable device fluid is within a range from about 1% to about 30% so as to provide the at least partial separation, for example within a range from about 2% to about 20% so as to provide the at least partial separation. The difference of the therapeutic fluid density relative to the density of the implantable device fluid can be within a range from about 3% to about 10% so as to provide the at least partial separation.

In many embodiments, the injector comprises at least one needle comprising a first lumen to pass the therapeutic fluid into the therapeutic device and a second lumen to receive the therapeutic fluid from the chamber, and the injector is configured to inject the therapeutic fluid at a flow rate so as to inhibit mixing of the therapeutic fluid with the implantable device fluid such that the second lumen receives a portion of the device fluid substantially separated from the therapeutic fluid.

In many embodiments, the injector is configured to inject the therapeutic agent at a flow rate so as to provide the at least partial separation. The at least partial separation can be based on a therapeutic fluid density different from a therapeutic fluid density.

In many embodiments, the chamber has a substantially constant volume. The substantially constant volume can be within a range from about 1 uL to about 100 uL or more. The substantially constant volume can be within a range from a range from about 15 uL to about 75 uL, for example within a range from about 25 uL to about 75 uL.

In many embodiments, the injector is configured to inject the therapeutic fluid into the chamber over a period of time. The time can be within a range from about 1 second to about 30 seconds, for example within a range from about 2 seconds to about 8 seconds.

In many embodiments, the injector comprises one or more of a structure resistant to flow, a restriction, a porous structure, a sintered porous structure, or a mechanism to inject the agent at the rate sufficient to provide the at least partial separation.

The mechanism comprises one or more of a spring, a gas, or a liquid to inject the liquid at the rate.

In many embodiments, the implantable device comprises a porous structure to release the therapeutic agent. The porous structure has a resistance to flow, and the injector structure resistant to flow comprises a resistance to flow proportional to the resistance to flow of the porous structure, such that a portion of the therapeutic fluid passes through the porous structure.

In many embodiments, the implant fluid comprises a remaining portion of a first therapeutic fluid placed in the therapeutic device for at least about one week, and the therapeutic fluid is similar to the first therapeutic fluid.

In many embodiments, the fluid of the implantable device comprises a remaining portion of a first amount of first therapeutic agent of a first therapeutic fluid placed in the therapeutic device and components of the vitreous humor of the eye. The remaining portion of the first therapeutic fluid placed in the implantable device may comprise a remaining amount of the therapeutic agent. The remaining amount of the therapeutic agent corresponds to no more than about half of a first amount of the first therapeutic agent so as to provide the density difference. The remaining portion may comprise a remaining stabilizer, and an amount of the remaining stabilizer may correspond to no more than about half of a first amount of the stabilizer of the first therapeutic fluid so as to provide the density difference.

In many embodiments, one or more components of the vitreous humor correspond to the density of the fluid of the implantable therapeutic device less than the therapeutic fluid therapeutic fluid density so as to provide the at least partial separation.

In many embodiments, the therapeutic fluid density is within a range. The range can be from about 0.5 g/cm3 to about 2 g/cm3 and the implantable device density is within a range from about 0.5 to about 2 g/cm3, for example within a range from about 1.01 to about 1.5 g/cm3. The therapeutic fluid density can be within a range from about 1.03 to about 1.5 g/cm3.

In many embodiments, the injector comprises at least one needle having at least one lumen to couple the chamber to a syringe comprising the therapeutic agent. The at least one lumen may comprise a first lumen to pass the therapeutic fluid into the implantable device and a second lumen to receive liquid from the implantable therapeutic device. The first lumen may extend to a first opening and the second lumen may extend to a second opening, in which the first opening is spaced apart from the second opening so as to encourage the at least partial separation. The first opening can be located distal to the second opening, such that the therapeutic fluid is passed to a distal portion of the chamber and the fluid of the implantable therapeutic device is received with the proximal portion of the chamber to encourage the at least partial separation.

In many embodiments, a container receives the fluid of the therapeutic device received through the second lumen, and the container comprises a vent to pass air displaced from the container. The vent can be fluidicly coupled to the second opening so as to define a flow path extending from the opening to the vent.

In many embodiments, the flow path comprises a resistance to flow so as to encourage the at least partial separation. The flow path may comprises one or more structures to inhibit flow of the fluid of the therapeutic device, the one or more structures comprising one or more of a size of the second opening, a restriction along the flow path or a porous structure along the flow path.

In many embodiments, the injector porous structure comprises a plurality of interconnecting channels located along the flow path on a downstream portion of the container. The injector porous structure comprises a resistance to liquid flow greater than a porous structure of the implantable device such that the therapeutic fluid is passed through the porous structure of the implantable device when the fluid of the implantable device contacts the injector porous structure located along the flow path on the downstream portion of the container.

In many embodiments, the second lumen is coupled to a vent and the vent comprises a resistance to flow to pressurize the chamber and pass a portion of the therapeutic fluid through the porous structure when the fluid of the implantable device passes through the vent.

In many embodiments, the injector comprises a cartridge comprising the at least one needle to couple to the syringe. The cartridge may comprise a vent having a resistance to flow sufficient to encourage the at least partial separation of the therapeutic agent fluid from the fluid of the implantable device.

In many embodiments, the at least one lumen comprises a first lumen to pass the therapeutic fluid into the implantable device and a second lumen to receive liquid from the implantable therapeutic device.

In many embodiments, the at least one needle comprises a first needle and a second needle.

In many embodiments, the at least one needle comprises a first needle having a first lumen extending along a first axis and a second needle having a second lumen extending along a second axis, and the first axis is separated from the second axis so as to increase the at least partial separation of the therapeutic fluid from the implantable device fluid.

In many embodiments, the at least one needle comprises a double lumen needle having a first needle having a first lumen extending along a first axis and a second needle having a second lumen extending along the first needle such that the second needle is substantially concentric with the first axis.

In many embodiments, the at least one needle comprises an axis extending along an elongate dimension of the at least one needle and wherein the at least partial separation corresponds to an angle of the axis away from horizontal when the therapeutic formulation is injected. The at least partial separation may correspond to an increase of at least about one percent of an amount of therapeutic fluid placed in the therapeutic device when the angle away from horizontal comprises at least about 10 degrees. The at least partial separation may correspond to an increase of at least about two percent of an amount of therapeutic fluid placed in the therapeutic device when the angle away from horizontal comprises at least about 35 degrees.

In many embodiments, the injector is configured to inject the therapeutic fluid with the at least partial separation such that a 1 percent increase in density of the therapeutic fluid relative to the density of the chamber fluid corresponds to at least about a 1 percent increase of the amount of therapeutic fluid placed in the chamber.

In many embodiments, the injector is configured to inject the therapeutic fluid with the at least partial separation such that a 1 percent increase in density of the therapeutic fluid relative to the density of the chamber fluid corresponds to at least about a 2 percent increase of the amount of therapeutic fluid placed in the chamber with an injection of the therapeutic fluid into the container.

In many embodiments, the injector is configured to inject the therapeutic fluid with the at least partial separation such that a 3 percent increase in density of the therapeutic fluid relative to the density of the chamber fluid corresponds to at least about a 4 percent increase of the amount of therapeutic fluid placed in the chamber with an injection of the therapeutic fluid into the container.

In many embodiments, the at least about 1 percent increase of the amount of therapeutic fluid placed in the chamber corresponds to an angle of injection away from horizontal. The angle of injection away from horizontal corresponds to at least about 10 degrees away from horizontal, and may correspond to at least about 15 degrees away from horizontal.

In many embodiments, the fluid of the implantable device comprises a liquid composed of water, components of the vitreous humor of the eye, and the therapeutic agent. The fluid of the implantable device may comprise a stabilizer.

In many embodiments, the therapeutic fluid comprises a liquid composed of water and the therapeutic agent. The therapeutic fluid may comprise a stabilizer.

In many embodiments, the fluid of the implantable device is displaced at a rate within a range from about 1 uL per second to about 200 uL per second. The fluid of the implantable device can be displaced at a rate within a range from about 2 uL per second to about 100 uL per second, for example from about 5 uL per second to about 50 uL per second.

In many embodiments, the fluid of the implantable device is displaced with an efficiency of at least about 70%. The fluid of the implantable device can be displaced with an efficiency of at least about 80%, for example at least about 90%.

In many embodiments, the valve comprises one or more of a float valve coupled to an opening or a hard stop coupled to a piston.

In many embodiments, the injector comprises a cartridge comprising the at least one needle to couple to the syringe.

In another aspect, embodiments of the present invention provide apparatus to treat an eye. The apparatus comprises a cartridge to inject a therapeutic fluid into a chamber of a therapeutic device implantable in the eye with at least partial separation of a fluid of the implantable therapeutic device from the therapeutic fluid.

In many embodiments, the cartridge comprises a connector to couple to a syringe, a vent and at least one needle. The at least one needle comprising a first lumen and a second lumen, the first lumen sized to extend from the connector into the chamber to pass the therapeutic fluid from the syringe, the second lumen comprising the vent and sized to place the vent in the chamber and extend to a collection container so as to receive the fluid of the implantable therapeutic device with the collection container, wherein cartridge is adapted to the density of the therapeutic fluid so as to provide a refill efficiency of the chamber of at least about 70%.

In many embodiments, the vent comprises a resistance to flow corresponding to a resistance to flow of a porous structure of the implantable device to pass an amount of the therapeutic fluid through the porous structure when the therapeutic device fluid is displaced.

In many embodiments, the resistance to flow of the vent structure is proportional to the resistance to flow of the porous structure so as to pass the amount of the therapeutic fluid through the porous structure.

In many embodiments, the resistance to flow of the vent structure is substantially greater than to the resistance to flow of the porous structure so as to pass the amount of the therapeutic fluid through the porous structure. The vent structure may comprise a channel sized to provide a substantial portion of the resistance to flow of the vent structure. The vent structure may comprise a porous material to provide a substantial portion of the resistance to flow of the vent structure.

In many embodiments, the at least one needle comprises a first needle and the second needle.

In many embodiments, the at least one needle comprises a double lumen needle.

In another aspect embodiments provide, apparatus to treat a patient. An implantable device comprises a chamber and a penetrable barrier coupled to a porous structure. The device is capable of receiving a pressure of at least about 50 PSI to the chamber and the porous structure without rupturing.

In many embodiments, the device is capable of receiving a pressure of at least about 100 PSI to the chamber, the penetrable barrier and the porous structure without rupturing.

In many embodiments, the device is capable of receiving a pressure of at least about 200 PSI to the chamber, the penetrable barrier and the porous structure without rupturing.

In another aspect, embodiments provide an apparatus to treat a patient. An implantable device comprises a chamber and a penetrable barrier coupled to a porous structure. The chamber comprises a proximal end and a distal end. The porous structure is located away from the distal of the chamber in increase an amount of therapeutic fluid placed in the chamber with one or more of injection or aspiration.

In another aspect, embodiments provide an apparatus to treat a patient. The apparatus comprises a therapeutic device comprising a reservoir chamber and a fluid separator within the reservoir chamber of the device to separate a therapeutic fluid injected into the device from a fluid of the implantable device.

In many embodiments, the fluid separator comprises one or more of movable fluid separator or a container within the reservoir chamber of the therapeutic device.

In another aspect, embodiments provide an apparatus. The apparatus comprises an injector configured to inject air into a chamber of a device implantable in the eye to replace a fluid of the device with a therapeutic fluid.

In another aspect, embodiments provide an apparatus to treat a patient. An injector device comprises a needle and a stop. The needle comprises a tip. An implantable device comprises a chamber and a penetrable barrier coupled to a porous structure. A structure to divert flow of a therapeutic fluid is located within the chamber. The stop is configured to position the tip of the needle within the chamber with a gap extending the between the tip and the structure when the stop contacts a conjunctiva of the eye.

In another aspect, embodiments provide apparatus to treat an eye. A connector to couple to a container having a therapeutic fluid comprises therapeutic agent to treat the eye. At least one needle comprises a first lumen to pass the therapeutic fluid and a second lumen to receive the fluid from the therapeutic device. The first lumen extends to a first opening, and the second lumen extends to a second opening. A container receives a fluid form a therapeutic device implantable in the eye. The second lumen is fluidicly coupled to the container so as to define a flow path extending from the second opening to the container. The flow path comprises a resistance so as to at least partially separate the therapeutic fluid from the fluid of the implantable device when the therapeutic fluid displaces the fluid of the implantable device.

In another aspect, embodiments provide an apparatus to treat an eye with a therapeutic agent. At least one needle comprises a lumen extending to an opening to inject a therapeutic fluid comprising the therapeutic agent into a chamber of a therapeutic device implantable in the eye. A vent structure is configured to receive a fluid of the therapeutic device. The vent structure comprises a resistance to flow of the fluid of the therapeutic device.

In many embodiments, the resistance to flow of the vent structure corresponds to a resistance to flow of a porous structure of the therapeutic device so as to pass an amount of the therapeutic fluid through the porous structure.

In many embodiments, the amount comprises at least about 0.1 percent of an injection amount into the therapeutic device.

In many embodiments, the vent structure comprises a vent and a channel coupled to the vent so as to provide the resistance to flow of the vent structure.

In many embodiments, the apparatus further comprises a stop, in which the stop comprises a lower surface to engage a conjunctiva of the eye. The at least one needle extends a distance along an axis from the lower surface to the opening, and the distance is dimensioned to place the opening and the vent in the reservoir chamber when the lower surface engages the conjunctiva.

In many embodiments, the apparatus further comprises a cartridge, and the cartridge comprises the at least one needle and the vent structure. The cartridge comprises a connector to couple to a syringe, and the at least one needle comprises a first lumen and a second lumen. The first lumen can be sized to extend from the connector into the chamber to pass the therapeutic fluid from the syringe, and the second lumen may extend to the vent and be sized so as to place the vent in the chamber and extend to a collection container so as to receive the fluid of the implantable therapeutic device with the collection container. The cartridge can be adapted to the density of the therapeutic fluid so as to provide a refill efficiency of the chamber of at least about 70%.

In many embodiments, the resistance to flow of the vent structure is substantially greater than the resistance to flow of the porous structure of the implantable device so as to pass the amount of the therapeutic fluid through the porous structure.

In many embodiments, the resistance to flow of the vent structure is substantially less than the resistance to flow of the porous structure of the implantable device so as to pass the amount of the therapeutic fluid through the porous structure.

In many embodiments, the at least one needle comprises a first needle and the second needle.

In many embodiments, the at least one needle comprises a double lumen needle.

In another aspect, embodiments provide method of treating a patient with an implantable device. A therapeutic fluid is injected into a chamber of a therapeutic device implanted in the patient, such that the therapeutic fluid entering the chamber is at least partially separated from a fluid of the chamber.

In another aspect, embodiments provide method of treating an eye. A therapeutic fluid is injected into a chamber of a therapeutic device implanted in the eye, such that the therapeutic fluid entering the chamber is at least partially separated from a fluid of the chamber.

In many embodiments, the therapeutic fluid comprises a density and the fluid of the device comprises a density different from the density of the therapeutic fluid.

In many embodiments, the therapeutic device comprises a penetrable barrier on a proximal end and a porous structure on a distal end with an axis extending between the penetrable barrier and porous structure and wherein the axis is oriented away from horizontal to provide the at least partial separation. The patient can be positioned such that the porous structure is located above the penetrable barrier.

In many embodiments, the patient is reclined in a chair with a tilted head such that the porous structure is located above the penetrable barrier when the implanted device is located in the pars plana region of the eye.

In many embodiments, the patient is positioned such that the porous structure is located below the penetrable barrier.

In many embodiments, the therapeutic fluid is injected upward to at least partially separate the therapeutic fluid from the fluid of the implanted therapeutic device.

In many embodiments, the therapeutic fluid is injected downward to at least partially separate the therapeutic fluid from the fluid of the implanted therapeutic device.

In many embodiments, at least one needle is advanced through a penetrable barrier of the implanted device such that a first opening of the at least one needle is placed at a distal portion of the chamber and a second opening of the at least one needle is placed at a proximal portion of the chamber such that the first opening is located below the second opening and wherein the therapeutic fluid comprises a density greater than the implanted device fluid and is passed through the first opening below the second opening so as to at least partially separate the therapeutic fluid from the therapeutic device fluid within the chamber.

In many embodiments, the therapeutic fluid is injected with the at least partial separation such that a percent change in density of the therapeutic fluid corresponds to a percent change in fill efficiency of the chamber greater than the percent change in density of the therapeutic fluid.

In another aspect, embodiments provide a method of treating an eye. Air is injected into a chamber of a therapeutic device implanted in the eye to at least partially replace a fluid of the implanted device with a therapeutic fluid.

In another aspect, embodiments provide an apparatus to inject a therapeutic agent into a patient. The apparatus comprises at least one needle capable of penetrating an external tissue of the patient and extending to a depth within the patient and one or more chambers to hold a therapeutic agent coupled to the at least one needle. A deformable indicator extends at least partially around the at least one needle to indicate needle penetration of the needle to the depth.

In many embodiments, the deformable visual indicator comprises a first configuration having a first cross sectional width prior to contact with the tissue and a second configuration having a second cross sectional width, in which the second cross sectional width is greater than the first cross sectional width to indicate the needle at the depth with increased visibility of the visual indicator.

In many embodiments, the at least one needle is supported with an annular support structure having a distance across and wherein the deformable visual indicator comprises an annular deformable structure extending around the at least one needle, and the first cross sectional width is less than the distance across and the second cross sectional width is greater than the distance across.

In many embodiments, the deformable visual indicator comprises a modulus to resist deformation to indicate the needle inserted to the depth with a force to maintain the at least one needle at the depth.

In many embodiments, the deformable visual indicator visible comprises a visible color to indicate the needle at the depth to the user.

In many embodiments, the at least one needle comprises a first lumen extending from the visual indicator to a first opening located first distance from the visual indicator and a second lumen extending from the visual indicator to a second opening located a second distance from the visual indicated and wherein visual indicator indicates the first opening at a first depth and the second opening at a second depth.

In many embodiments, the at least one needle comprises a silicon needle having a gauge of at least about 25.

In many embodiments, the deformable visual indicator comprises a Shore A hardness within a range from about 5 to about 30 to indicate the needle inserted to the depth with a force to maintain the at least one needle at the depth.

In many embodiments, the apparatus further comprises an implantable therapeutic device, the implantable therapeutic device having a reservoir chamber to hold a quantity of therapeutic agent, the reservoir chamber extending along an axis of the therapeutic device, and wherein the at least one needle has an lumen extending to opening separated from the deformable visual indicator such that the opening is located in the reservoir chamber when the visual indicator is deformed to indicate the needle positioned at the distance.

In many embodiments, the implantable therapeutic device comprises a porous structure to release therapeutic amounts of the therapeutic agent for an extended time. The porous structure may comprise a release rate index of no more than about 0.5 to release the therapeutic agent for an extended time of at least about one month.

In many embodiments, the opening is positioned in a proximal half of the reservoir chamber when the visual indicator is deformed.

In many embodiments, the opening is positioned in a distal half of the reservoir chamber when the visual indicator is deformed.

In another aspect, embodiments provide a method of treating a patient having a tissue. At least one needle is advanced into the tissue such that a deformable visual indicator couples to the tissue and deforms to indicate the at least one needle at a depth. A therapeutic agent is injected from one or more chambers coupled to the at least one needle such that the therapeutic agent is injected through a lumen of the at least one needle at the depth when the visual indicator is deformed.

In many embodiments, the deformable visual indicator comprises a first configuration having a first cross sectional width prior to contact with the tissue and a second configuration having a second cross sectional width when the indicator is coupled to the external penetrable tissue, in which the second cross sectional width is greater than the first cross sectional width to indicate the needle at the depth with increased visibility of the visual indicator.

In many embodiments, the apparatus further comprises an implantable therapeutic device. The implantable therapeutic device has a reservoir chamber to hold a quantity of therapeutic agent. The reservoir chamber has a thickness and a width sized for placement between the conjunctiva and the sclera, and wherein the at least one needle has an lumen extending to opening separated from the deformable visual indicator such that the opening is located in the reservoir chamber when the visual indicator is deformed to indicate the needle positioned at the distance.

BRIEF DESCRIPTION OF THE DRAWINGS

FIG. 1A-1 shows a therapeutic device implanted at least partially within the sclera of the eye as in FIG. 1;

FIGS. 1A-1-1 and 1A-1-2 show a therapeutic device implanted under the conjunctiva and extending through the sclera to release a therapeutic agent into vitreous humor of the eye so as to treat the retina of the, in accordance with embodiments of the present invention;

FIG. 1A-2 shows structures of a therapeutic device configured for placement in an eye as in FIGS. 1A-1 and 1A-1-1, according to embodiments of the present invention;

FIG. 1A-2-1 shows a therapeutic device loaded into an insertion cannula, in which the device comprises an elongate narrow shape for insertion into the sclera, and in which the device is configured to expand to a second elongate wide shape for retention at least partially in the sclera;

FIG. 1A-2-2 shows a therapeutic device comprising a reservoir suitable for loading in a cannula;

FIG. 1B shows a therapeutic device configured for placement in an eye as in FIGS. 1A-1 and 1A-1-1, in accordance with embodiments of the present invention;

FIG. 1C-A shows at least one exit port, according to embodiments of the present invention;

FIG. 1C-1 shows a method of removing a binding material, according to embodiments of the present invention;

FIG. 1C-2 and inserting the therapeutic agent with a second insert having the TA bound thereon;

FIG. 1C-3 shows syringe being filled with a commercially available formulation of therapeutic agent for injection into the therapeutic device, in accordance with embodiments;

FIG. 1E-1 shows a therapeutic device configured for placement in an eye as in FIGS. 1A-1 and 1A-1-1, in which the device comprises a needle stop located at the bottom of the therapeutic device and the shape of the device encourages the movement of the therapeutic agent within the chamber of the therapeutic device;

FIG. 1E-2 shows a therapeutic device configured for placement in an eye as in FIGS. 1A-1 and 1A-1-1, in which the device comprises a needle stop located in the middle of the therapeutic device;

FIG. 1E-3 shows a therapeutic device configured for placement in an eye as in FIGS. 1A-1 and 1A-1-1, in which the device comprises a needle stop located in the middle of the therapeutic device and the shape of the device encourages the movement of the therapeutic agent within the chamber of the therapeutic device;

FIG. 1E-3-1 shows a top view of the therapeutic device configured for placement in an eye as in FIGS. 1E-3;

FIG. 1F-1 shows a therapeutic device comprising a flow diverter, in accordance with embodiments of the present invention;

FIG. 1F-2 shows a therapeutic device comprising a fluid separator having sufficient volume so as to retain at least a portion of the therapeutic fluid, such that at least a portion of the implanted device fluid is urged through the porous structure with at least partial separation, in accordance with embodiments of the present invention;

FIG. 1F-3 shows a therapeutic device comprising a fluid separator having sufficient volume so as to retain at least a portion of the therapeutic fluid, such that at least a portion of the implanted device fluid 703FL is urged through the porous structure with at least partial separation, in accordance with embodiments of the present invention;

FIG. 2 shows an access port suitable for incorporation with the therapeutic device, in accordance with embodiments of the present invention;

FIG. 5A-1 shows a therapeutic device coupled to an injector to simultaneously inject and remove material from the device;

FIG. 5C-1 shows a therapeutic device comprising a tortuous channel;

FIG. 5C-2 shows a therapeutic device comprising a coiled channel;

FIG. 6A-1 shows a therapeutic device comprising a container having a penetrable barrier disposed on a first end, a porous structure disposed on a second end to release therapeutic agent for an extended period, and a retention structure comprising an extension protruding outward from the container to couple to the sclera and the conjunctiva;

FIG. 6A-2 shows a therapeutic device as in FIG. 6A comprising a rounded distal end;

FIG. 6B-1 shows interconnecting channels extending from a first side to a second side of the porous structure as in FIG. 6B;

FIG. 6B-2 shows a plurality of paths of the therapeutic agent along the interconnecting channels extending from a first side to a second side of the porous structure as in FIGS. 6B and 6B 1;

FIG. 6B-3 shows blockage of the openings with a covering and the plurality of paths of the therapeutic agent along the interconnecting channels extending from a first side to a second side of the porous structure as in FIGS. 6B and 6B-1;

FIG. 6B-4 shows blockage of the openings with particles and the plurality of paths of the therapeutic agent along the interconnecting channels extending from a first side to a second side of the porous structure as in FIGS. 6B and 6B-1;

FIG. 6B-5 shows an effective cross-sectional size and area corresponding to the plurality of paths of the therapeutic agent along the interconnecting channels extending from a first side to a second side of the porous structure as in FIGS. 6B and 6B-1;

FIG. 7-1 shows a concentric exchange needle apparatus comprising a needle to inject therapeutic fluid and a vent structure to receive the fluid of the implantable device, in accordance with embodiments of the present invention;

FIG. 7-2 shows a cross sectional view along an axis of the concentric exchange needle of FIG. 7-1 having an annular channel having a cross sectional size and length to provide a resistance to flow proportional to the porous structure of the therapeutic device, in accordance with embodiments of the present invention;

FIG. 7A-1 shows a therapeutic device comprising a penetrable barrier coupled to an injector needle 189 comprising a stop that positions the distal end of the needle near the proximal end of the reservoir of the device to flush the reservoir with ejection of liquid formulation through the porous frit structure, in accordance with embodiments;

FIG. 7A-2 shows a therapeutic device comprising a penetrable barrier coupled to a needle of an injector to inject and remove material from the device such that the liquid in the reservoir 130 is exchanged with the injected formulation;

FIG. 7A-3 shows a deformable visual indicator;

FIG. 7A-4 shows the visual indicator coupled to soft tissue, such as tissue of an eye, for example the conjunctiva positioned over the penetrable barrier of the therapeutic device;

FIG. 7A-5 shows a therapeutic device 100 coupled to injector 701 with one or more of potentially insufficient force prior to injection or potentially insufficient depth;

FIG. 7A-6 shows a therapeutic device 100 coupled to injector 701 with one or more of potentially insufficient force prior to injection or potentially insufficient depth;

FIG. 7A-7A to FIG. 7A-9B show sliding coupling of a valve to a plunger coupled to a piston to exchange a first intended volume of liquid within the reservoir with a volume of formulation of therapeutic agent and close the valve so as to inject a second volume of liquid through the porous fit structure;

FIG. 7A-10A and FIG. 7A-10B show a first configuration of an injector to maintain the rate of flow into device to within about +/−50%, for example to within about +/−25%, such that the time to inject the therapeutic agent into device 100 remains substantially constant amount devices and injections;

FIG. 7A-11A shows an injection apparatus comprising a valve comprising a shut off button coupled to a sleeve to provide a bolus injection, in accordance with embodiments of the present invention;

FIG. 7A-11B shows the injector apparatus of FIG. 7A-11B with the sleeve covering the valve and the valve closed, in accordance with embodiments of the present invention;

FIG. 7A-12A shows an injection apparatus comprising a valve to provide a bolus injection and comprising lumen extending along a first axis and lumen extending along a second axis spaced apart from the first lumen to provide axial separation and in which the injection lumen is located closer to the porous structure than the vent lumen and in which valve is configured to provide a bolus injection through the porous structure, in accordance with embodiments of the present invention;

FIG. 7A-13A shows an injection apparatus comprising a float valve to provide the bolus injection when the received implant fluid closes valve, in accordance with embodiments of the present invention;

FIG. 7A-13B shows the double lumen needle of the injection apparatus of FIG. 7A-13A, in accordance with embodiments of the present invention;

FIG. 7A-13C shows a cross sectional view along an axis of the double lumen needle 189DL of FIGS. 7A-13A and 7A-13B, in accordance with embodiments of the present invention;

FIG. 7A-14A shows an injection apparatus comprising a valve having a hard stop to engage a piston to provide a bolus injection. The lumen extends along a first axis and lumen extends along a second axis spaced apart from the first lumen to provide separation and in which the injection lumen is located closer to the porous structure than the vent lumen, in accordance with embodiments of the present invention;

FIG. 7A-15A shows an injection apparatus comprising a valve having a porous structure similar to porous structure to provide a bolus injection and in which the lumen is coupled to channel having a volume with a gas therein so as to provide the bolus injection when the fluid of the implanted device has displaced the gas and contacts the porous structure, in accordance with embodiments of the present invention;

FIG. 7A-15B shows an injection apparatus comprising a valve having a porous structure similar to porous structure to provide a bolus injection and in which the porous structure has a resistance to flow proportional to the porous structure so as to provide the bolus based on the proportional resistance to flow of the porous structures, in accordance with embodiments of the present invention;

FIG. 7A-15C1 shows an injection apparatus comprising a valve having a sliding component such as a piston to close the valve to deliver the bolus.

FIG. 7A-15C2 shows the piston in the lumen of valve as in FIG. 7A-15C1, in accordance with embodiments of the present invention;

FIG. 7A-16 shows a schematic illustration of an injector apparatus configured to provide a bolus injection to the eye based on flow resistance of the injector apparatus proportional to flow resistance of porous structure, in accordance with embodiments;

FIG. 7A-17A to 7A-17C show a schematic illustration of an automated injector apparatus configured to provide an automated injection with user input and output to decrease leakage, in accordance with embodiments;

FIG. 7B-1 shows a side cross-sectional view of a therapeutic device comprising a retention structure having a cross-section sized to fit in an elongate incision, in accordance with embodiments;

FIG. 7B-2 shows an isometric view of the therapeutic device as in FIG. 7B-1;

FIG. 7B-3 shows a top view of the therapeutic device as in FIG. 7B-1;

FIG. 7B-4 shows a side cross sectional view along the short side of the retention structure of the therapeutic device as in FIG. 7B-1;

FIG. 7B-5 shows a bottom view of the therapeutic device as in FIG. 7B-1 implanted in the sclera;

FIG. 7B-5A shows a cutting tool comprising a blade having a width corresponding to the perimeter of the barrier and the perimeter of the narrow retention structure portion;

FIGS. 7B-6A and 7B-6B show distal cross-sectional view and a proximal cross-sectional view, respectively, of a therapeutic device comprising an elongate and non-circular cross-sectional size, in accordance with embodiments;

FIG. 7B-6C shows an isometric view of the therapeutic device having a retention structure with an elongate cross-sectional size, in accordance with embodiments;

FIG. 7B-6D shows a distal end view of the therapeutic device as in FIG. 7B-6C;

FIG. 7B-6E1 shows a side view of the short axis of the narrow neck portion of the therapeutic device as in FIG. 7B-6C;

FIG. 7B-6E2 shows a side view of the long axis of the narrow neck portion of the therapeutic device as in FIG. 7B-6C;

FIG. 7B-6F shows a proximal view of the therapeutic device as in FIGS. 7B-6C;

FIG. 7B-6G to FIG. 7B-6I show exploded assembly drawings for the therapeutic device as in FIGS. 7B-6C to 7B-6F;

FIG. 7C-1 shows an expandable therapeutic device comprising an expandable barrier material and support in an expanded configuration for extended release of the therapeutic agent, in accordance with embodiments;

FIG. 7C-1A shows the distal end portion of the support 160S as in FIG. 7C-1;

FIG. 7C-1B shows the support disposed inside the barrier, in accordance with embodiments;

FIG. 7C-1C shows the support disposed along the inner surface of the barrier, in accordance with embodiments;

FIG. 7C-2 shows the expandable therapeutic device as in FIG. 7C1 in a narrow profile configuration;

FIG. 7C-3 shows the expandable therapeutic device as in FIG. 7C1 in an expanded profile configuration;

FIGS. 7C-4A and 7C-4B show an expandable retention structure, in accordance with embodiments;

FIG. 7D shows a therapeutic device comprising a porous structure positioned in an eye to deliver a therapeutic agent to a target location on the retina, in accordance with embodiments FIG. 7E shows a therapeutic device comprising a porous structure located on the device to deliver a therapeutic agent to one or more of the ciliary body or the trabecular meshwork when positioned in the eye, in accordance with embodiments;

FIG. 7F shows therapeutic device 100 comprising porous structure oriented to release the therapeutic agent away from the lens and toward the retina, in accordance with embodiments;

FIGS. 8A and 8A1 show a side cross sectional view and a top view, respectively, of therapeutic device for placement substantially between the conjunctiva and the sclera;

FIG. 8A2 shows the therapeutic device implanted with the reservoir between the conjunctiva and the sclera, such that elongate structure extends through the sclera to couple the reservoir chamber to the vitreous humor;

FIG. 9 shows the elongate structure coupled to the container away from the center of container and near and located near an end of the container;

FIG. 10A shows a cartridge ton inject fluid into the therapeutic device, in which the cartridge container is placed in a packaging container, in accordance with embodiments of the present invention;

FIG. 10B shows a syringe coupled to the cartridge as in FIG. 10A to inject the formulation;

FIGS. 10E and 10F show side a front views of an injector apparatus comprising a transparent material to view the liquid received from the implanted device, in accordance with embodiments of the present invention;

FIG. 11A shows needle comprising a plurality of openings spaced radially and axially along the axis of the needle so as to mix the therapeutic fluid with the fluid of the implantable device to inhibit separation of the fluids and pass the implantable device fluid through porous structure with the injection, in accordance with embodiments of the present invention;

FIG. 11B shows needle comprising a plurality of openings spaced radially and axially along the axis of the needle and an opening on the distal tip so as to mix the therapeutic fluid with the fluid of the implantable device 100 to inhibit separation of the fluids, in accordance with embodiments of the present invention;

FIGS. 12A to 12C show an injector comprising an expandable chamber to inhibit excessive pressure of the therapeutic device, in accordance with embodiments.

FIG. 13A shows a therapeutic device receiving a therapeutic fluid having a density less than the implanted device fluid, in accordance with embodiments of the present invention;

FIG. 14A shows a therapeutic device receiving a therapeutic fluid having a density greater than the implanted device fluid and in which the needle and deformable stop are coupled to the syringe with a flexible tube such that the needle can be decoupled from the syringe, in accordance with embodiments.

FIGS. 15A-1 to 15A-3 show the device in an angle up position (10 degrees up off the horizontal), and the clear solution inside the device has an approximate density of 1 g/ml, while the yellow refill solution has an approximate density of 1.03 g/ml., in accordance with embodiments of the present invention;

FIGS. 15B-1 to 15B-3 show the device in an angle down position (35 down off the horizontal, porous structure below penetrable barrier). Clear solution inside the device has an approximate density of 1 g/ml, while the yellow refill solution has an approximate density of 1.03 g/ml;

FIGS. 16A-1 to 16A-3 show an injector cartridge having a container to receive the implanted device fluid and a porous vent structure down stream of the device fluid collection container such that the porous structure of the cartridge comprises a valve to provide a bolus injection;

FIGS. 16A-4 and 16A-5 shows a side view and front views, respectively, of the exchange needle, in which this is a bi-needle system has the longer needle doing the injection while the short needle allows the fluid to exscape into the containment track; and FIGS. 17A-1 to 17A-3 show injection into the implantable device so as to determine the presence of stream flow of the injected liquid within the implantable device.

DETAILED DESCRIPTION OF THE INVENTION

Figure 1:
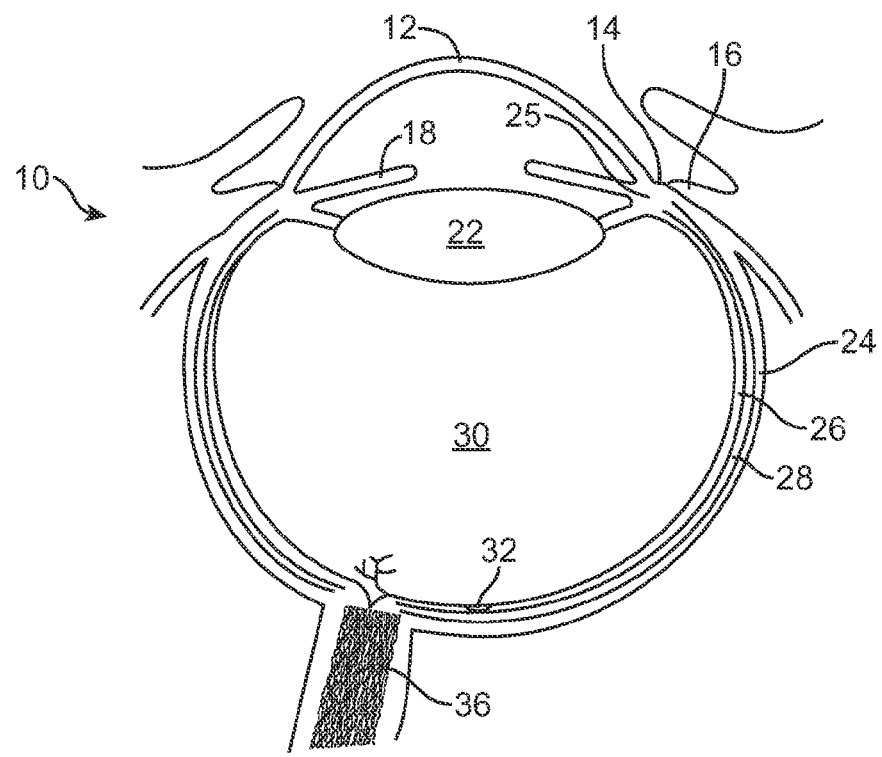
FIG. 1 shows an eye suitable for incorporation of the therapeutic device, in accordance with embodiments of the present invention.

Embodiments of the present invention as described herein can be combined in many ways and combined with many therapies to treat the eye.

Therapeutic devices and injector apparatus are described in U.S. patent application Ser. No. 12/696,678, entitled "POSTERIOR SEGMENT DRUG DELIVERY", filed on 29 Jan. 2010, the full disclosures of which is incorporated by reference, and suitable for combination with at least some embodiments as described herein Embodiments of the present invention as described herein can be combined in many ways to treat one or more of many diseases such as diseases of the eye. The embodiments of the present invention can be beneficially combined with many known diagnostics, medicines and procedures, for example combined with known methods of diagnosing and treating eye with a device implanted in the eye, and combinations thereof.

Although specific reference is made to the delivery of macromolecules comprising antibodies or antibody fragments to the posterior segment of the eye, embodiments of the present invention can be used to deliver many therapeutic agents to many tissues of the body. For example, embodiments of the present invention can be used to deliver therapeutic agent for an extended period to one or more of the following tissues: intravascular, intra articular, intrathecal, pericardial, intraluminal and gut.

In many embodiments, efficiency as described herein encompasses a percentage of therapeutic fluid placed in the implanted device chamber with displacement of the fluid of the implanted device. The refill efficiency may correspond to an amount therapeutic fluid placed in the implanted device with displacement of at least a portion the therapeutic fluid away from the chamber of the device.

The embodiments of the present invention as described herein can be used in many implanted device applications and can be well suited for use with implanted devices having an implanted device fluid which is displaced, for example replaced, at least partially with a therapeutic fluid. The implanted device fluid may comprise a component of the vitreous humor of the eye and can be more dense, or less dense, or approximately the same density as the therapeutic fluid. In many embodiments the fluid is of the device is displaced with a gravity so as to provide at least partial separation of the liquids, or such that gravitational density based separation may occur. The embodiments as described herein can be particularly well suited for use in which the therapeutic fluid displaces the fluid of the implanted device with a flow rate sufficient to provide the at least partial separation. The embodiments described herein may comprise an apparatus that injects the therapeutic fluid. Alternatively or in combination, the apparatus may comprise an apparatus that draws fluid from the implanted therapeutic device such that the therapeutic fluid is drawn into the therapeutic device. For example, aspiration of the fluid from the implanted therapeutic device with at least partial vacuum can result in the therapeutic fluid being drawn into the implanted therapeutic device from a container comprising the therapeutic fluid. Work in relation to embodiments of the present invention suggests that aspiration of a fluid from the device may result in greater amounts of time to displace the fluid of the therapeutic device container, as the aspiration pressure can be limited to atmospheric pressure, such that the embodiments as described herein can be particularly well suited for combination with devices that place the therapeutic fluid in the device chamber with aspiration. Alternatively or in combination, the apparatus to displace the fluid of the implanted device may comprise an injector to inject the therapeutic fluid with an internal pressure of the injector device providing an internal pressure to the therapeutic device greater than atmospheric pressure such that the amount of time to displace the fluid of the implanted device with the therapeutic fluid can be substantially decreased.

In many embodiments, the horizontal axis H with respect to gravity and the vertical axis V with respect to gravity can be determined by one of ordinary skill in the art and are shown and described in the drawings. The therapeutic liquid can be placed slowly in the implanted device chamber slowly, for example over the course of about 1 to 30 seconds, for example injected slowly over the course of about 1 to 30 seconds. And the device may comprise a volume as described herein. The flow rate may correspond to about 1% of the device volume per second or 100% of the device volume per second and the full range extending between.

In many embodiments, the density of the injected fluid 702FL is different than the density of the device fluid 703FL. The difference can be at least about 1%, for example at least about 2%, and in many embodiments at least about 3%. The density difference can be substantially greater, for example the density of the therapeutic fluid can be within a range from about 0.5 g/cm3 to about 2 g/cm3. In many embodiments, the density of the therapeutic fluid can be within a range from about 1.01 to about 1.1 g/cm3, for example. The density of the fluid of the implanted device can be within a range from about 0.5 to about 2.0, and may correspond to the density of the vitreous humor of the eye, for example near 1.03 g/cm3. In many embodiments, the density of the fluid of the implanted device is closer to the density of the vitreous humor of the eye than the therapeutic fluid. For example, the fluid of the implanted device may comprise one or more components of a therapeutic fluid previously injected into the eye, in which the one or more components of the therapeutic fluid has passed through the porous structure to treat the eye, such that the density of the device fluid corresponds at least partially to the density of the vitreous humor of the eye. In many embodiments, the therapeutic fluid comprises an excipient such as a stabilizer and a therapeutic agent, such that the density of the therapeutic fluid can be greater than the density of the implanted device fluid. The therapeutic fluid may comprise one or more known therapeutic fluids, for example. In many embodiments, a density of the therapeutic fluid is within a range from about 1.03 g/cm3 to about 1.13 g/cm3 such that the density of the therapeutic fluid is greater than the density of the fluid of the therapeutic device.

In many embodiments, the fluid of the device can be at least partially replaced in many ways, for example with one or more of aspiration or injection, and in many embodiments the therapeutic device can be pressurized at least about 1 atmosphere (about 29.92 in Hg, 14.696 psi, 1013.25 millibars/hectopascal), for example with a pressurization of the device chamber of at least about two atmospheres, and in many embodiments with a pressurization of at least about 4 atmospheres over the duration of the placement of the therapeutic fluid in the implanted device chamber. With these pressures of the device chamber, it can be helpful to seal the injection site.

The therapeutic device 100 as described herein can be configured to withstand the injection pressure pressures for the duration of the placement of therapeutic fluid within the chamber of the therapeutic device. The access port comprising the penetrable barrier such as a septum, and wall of the device, and the porous structure can be configured to withstand the pressurization. In many embodiments, the injector comprises a deformable needle stop to support the penetrable barrier of the device and to deform when contacting the conjunctiva. The deformable stop as described herein that may form a seal of the injection site with when placed against the conjunctiva for the injection. The deformable stop can support the penetrable barrier through the conjunctiva when placed on the outer surface of the conjunctiva such that the conjunctiva extends between the penetrable barrier and deformable stop.

The devices and injector apparatus as described herein can be configured to provide injection rates corresponding to at least partial separation, and may comprise one or more structures to increase efficiency of the fluid replaced.

Embodiments of the present invention can be used to provide sampling of a component of the eye from a device implanted in the eye and sustained release of a therapeutic agent to the posterior segment of the eye or the anterior segment of the eye, or combinations thereof, and may be combined with embodiments disclosed in U.S. Patent Appln No. 61/495,251, entitled "Diagnostic Methods and Apparatus" ☐Filed, Jun. 9, 2011☐ and U.S. Patent Appln No. 61/495,718, entitled "Diagnostic Methods and Apparatus" ☐Filed, Jun. 10, 2011☐, the full disclosures of which are incorporated herein by reference. Therapeutic amounts of a therapeutic agent can be released into the vitreous humor of the eye, such that the therapeutic agent can be transported by at least one of diffusion or convection to the retina or other ocular tissue, such as the choroid or ciliary body, for therapeutic effect.

As used herein the release rate index encompasses (PA/FL) where P comprises the porosity, A comprises an effective area, F comprises a curve fit parameter corresponding to an effective length and L comprises a length or thickness of the porous structure. The units of the release rate index (RRI) comprise units of mm unless indicated otherwise and can be determine by a person of ordinary skill in the art in accordance with the teachings described hereon.

As used herein, sustained release encompasses release of therapeutic amounts of an active ingredient of a therapeutic agent for an extended period of time. The sustained release may encompass first order release of the active ingredient, zero order release of the active ingredient, or other kinetics of release such as intermediate to zero order and first order, or combinations thereof.

As used herein a therapeutic agent referred to with a trade name encompasses one or more of the formulation of the therapeutic agent commercially available under the tradename, the active ingredient of the commercially available formulation, the generic name of the active ingredient, or the molecule comprising the active ingredient.

As used herein, similar numerals indicate similar structures and/or similar steps.

The therapeutic agent may be contained within a chamber of a container, for example within a reservoir comprising the container and chamber. The therapeutic agent may comprise a formulation such as solution of therapeutic agent, a suspension of a therapeutic agent or a dispersion of a therapeutic agent, for example. Examples of therapeutic agents suitable for use in accordance with embodiments of the therapeutic device are described herein, for example with reference to Table 1A below and elsewhere.

The therapeutic agent may comprise a macromolecule, for example an antibody or antibody fragment. The therapeutic macromolecule may comprise a VEGF inhibitor, for example commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™, Avastin™, Macugen™, and VEGF Trap.

The therapeutic agent may comprise small molecules such as of a corticosteroid and analogues thereof. For example, the therapeutic corticosteroid may comprise one or more of trimacinalone, trimacinalone acetonide, dexamethasone, dexamethasone acetate, fluocinolone, fluocinolone acetate, or analogues thereof. Alternatively or in combination, he small molecules of therapeutic agent may comprise a tyrosine kinase inhibitor comprising one or more of axitinib, bosutinib, cediranib, dasatinib, erlotinib, gefitinib, imatinib, lapatinib, lestaurtinib, nilotinib, semaxanib, sunitinib, toceranib, vandetanib, or vatalanib, for example.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™), sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™, Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; Regeneron™ (VEGF Trap) or complement inhibitor (POT-4).

The therapeutic agent may comprise a kinase inhibitor such as one or more of bevacizumab (monoclonal antibody), BIBW 2992 (small molecule targeting EGFR/Erb2), cetuximab (monoclonal antibody), imatinib (small molecule), trastuzumab (monoclonal antibody), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2NEGFR2, small molecule commercially available from Esai, Co.)

The amount of therapeutic agent within the therapeutic device may comprise from about 0.01 mg to about 50 mg, for example from about 0.01 mg to about 10 mg. The amount of therapeutic agent can be determined based on the therapeutic agent and the target threshold therapeutic concentration to treat the target tissue for an extend time. The amount of therapeutic agent can provide therapeutic amounts of the therapeutic agent for the extended time, for example an amount Lucentis™ as described herein. The extended time may comprise at least 90 days or more, for example at least 180 days or for example at least 1 year, at least 2 years or at least 3 years or more. The target threshold therapeutic concentration of a therapeutic agent such as Lucentis™ in the vitreous may comprise at least a therapeutic concentration of 0.1 ug/mL. For example the target threshold concentration may comprise from about 0.1 ug/mL to about 5 ug/mL for the extended time, where the upper value is based upon calculations shown in Example 9 using published data. The target threshold concentration is drug dependent and thus may vary for other therapeutic agents.

The delivery profile may be configured in many ways to obtain a therapeutic benefit from the sustained release device. For example, an amount of the therapeutic agent may be inserted into the container at monthly intervals so as to ensure that the concentration of therapeutic device is above a safety protocol or an efficacy protocol for the therapeutic agent, for example with monthly or less frequent injections into the container. The sustained release can result in an improved delivery profile and may result in improved results. For example, the concentration of therapeutic agent may remain consistently above a threshold amount, for example 0.1 ug/mL, for the extended time.

The insertion method may comprise inserting a dose into the container of the therapeutic device. For example, a single injection of Lucentis™ may be injected into the therapeutic device.

The duration of sustained delivery of the therapeutic agent may extend for twelve weeks or more, for example four to six months from a single insertion of therapeutic agent into the device when the device is inserted into the eye of the patient.

The therapeutic agent may be delivered in many ways so as to provide a sustained release for the extended time. For example, the therapeutic device may comprise a therapeutic agent and a binding agent. The binding agent may comprise small particles configured to couple releasably or reversibly to the therapeutic agent, such that the therapeutic agent is released for the extended time after injection into the vitreous humor. The particles can be sized such that the particles remain in the vitreous humor of the eye for the extended time.

The therapeutic agent may be delivered with a device implanted in the eye. For example, the drug delivery device can be implanted at least partially within the sclera of the eye, so as to couple the drug delivery device to the sclera of the eye for the extended period of time. The therapeutic device may comprise a drug and a binding agent. The drug and binding agent can be configured to provide the sustained release for the extended time. A membrane or other diffusion barrier or mechanism may be a component of the therapeutic device to release the drug for the extended time.

The lifetime of the therapeutic device and number of injections can be optimized for patient treatment. For example, the device may remain in place for a lifetime of 30 years, for example with AMD patients from about 10 to 15 years. For example, the device may be configured for an implantation duration of at least two years, with 8 injections (once every three months) for sustained release of the therapeutic agent over the two year duration. The device may be configured for implantation of at least 10 years with 40 injections (once every three months) for sustained release of the therapeutic agent.

The therapeutic device can be refilled in many ways. For example, the therapeutic agent can be refilled into the device in the physician's office.

The therapeutic device may comprise many configurations and physical attributes, for example the physical characteristics of the therapeutic device may comprise at least one of a drug delivery device with a suture, positioning and sizing such that vision is not impaired, and biocompatible material. The device may comprise a reservoir capacity from about 0.005 cc to about 0.2 cc, for example from about 0.01 cc to about 0.1 cc, and a device volume of no more than about 2 cc. A vitrectomy may be performed for device volumes larger than 0.1 cc. The length of the device may not interfere with the patient's vision and can be dependent on the shape of the device, as well as the location of the implanted device with respect to the eye. The length of the device may also depend on the angle in which the device is inserted. For example, a length of the device may comprise from about 4 to 6 mm. Since the diameter of the eye is about 24 mm, a device extending no more than about 6 mm from the sclera into the vitreous may have a minimal effect on patient vision.

Embodiments may comprise many combinations of implanted drug delivery devices. The therapeutic device may comprise a drug and binding agent. The device may also comprise at least one of a membrane, an opening, a diffusion barrier, a diffusion mechanism so as to release therapeutic amounts of therapeutic agent for the extended time.

FIG. 1 shows an eye 10 suitable for incorporation of the therapeutic device. The eye has a cornea 12 and a lens 22 configured to form an image on the retina 26. The cornea can extend to a limbus 14 of the eye, and the limbus can connect to a sclera 24 of the eye. A conjunctiva 16 of the eye can be disposed over the sclera. The lens can accommodate to focus on an object seen by the patient. The eye has an iris 18 that may expand and contract in response to light. The eye also comprises a choroid 28 disposed the between the sclera 24 and the retina 26. The retina comprises the macula 32. The eye comprises a pars plana 25, which comprises an example of a region of the eye suitable for placement and retention, for example anchoring, of the therapeutic device 100 as described herein. The pars plana region may comprise sclera and conjunctiva disposed between the retina and cornea. The therapeutic device can be positioned so as to extend from the pars plana region into the vitreous humor 30 to release the therapeutic agent. The therapeutic agent can be released into the vitreous humor 30, such that the therapeutic agent arrives at the retina and choroids for therapeutic effect on the macula. The vitreous humor of the eye comprises a liquid disposed between the lens and the retina. The vitreous humor may comprise convection currents to deliver the therapeutic agent to the macula.

Figures 1, 1A:
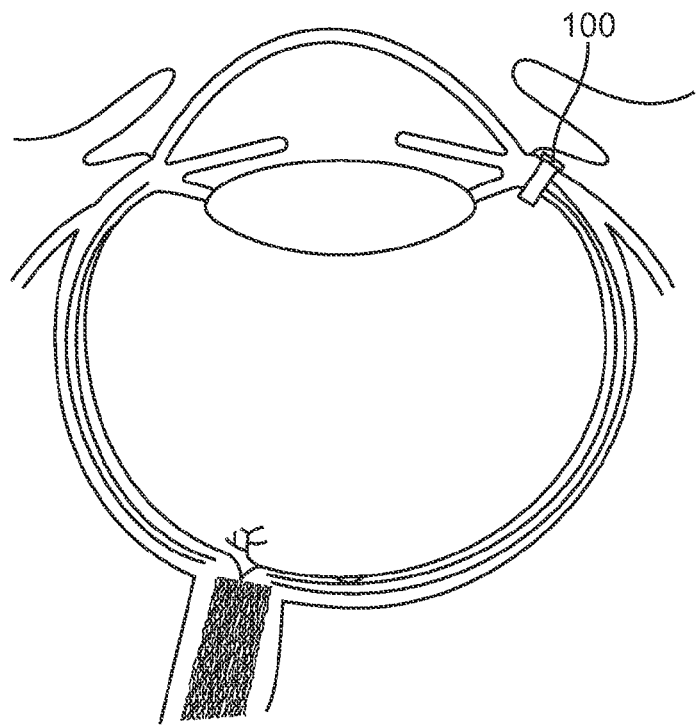
Figures 1, 1A:
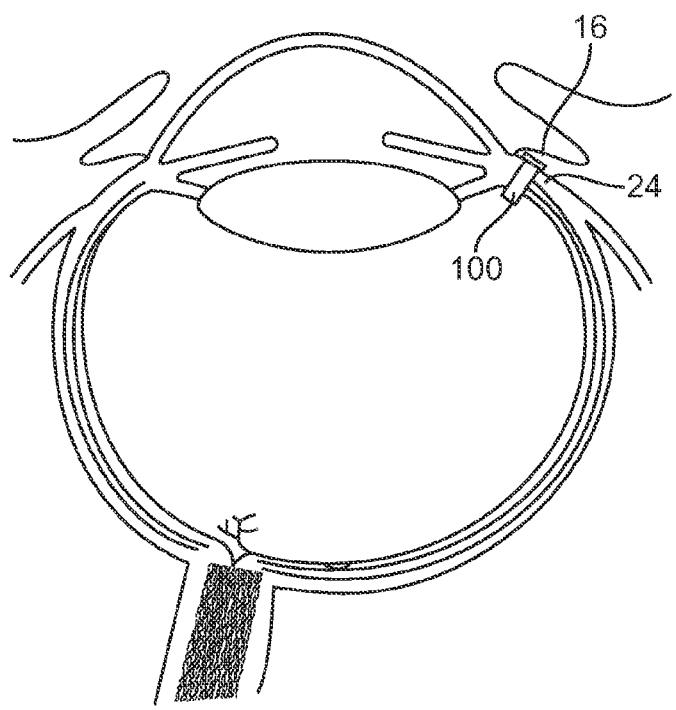

FIG. 1A-1 shows a therapeutic device 100 implanted at least partially within the sclera 24 of the eye 10 as in FIG. 1. The therapeutic device may comprise a retention structure, for example a protrusion, to couple the device to the sclera. The therapeutic device may extend through the sclera into vitreous humor 30, such that the therapeutic device can release the therapeutic agent into the vitreous humor.

Figures 1, 1A, 2:
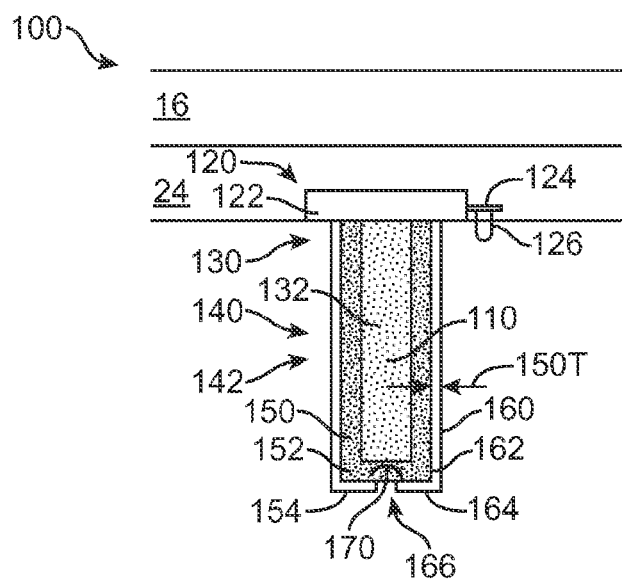
Figures 1, 1A, 2:
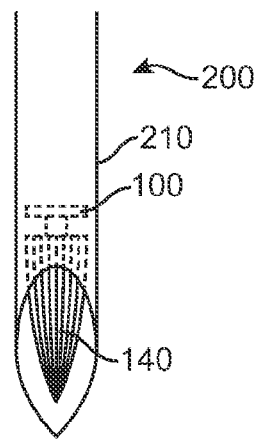
Figures 1, 1A, 2:
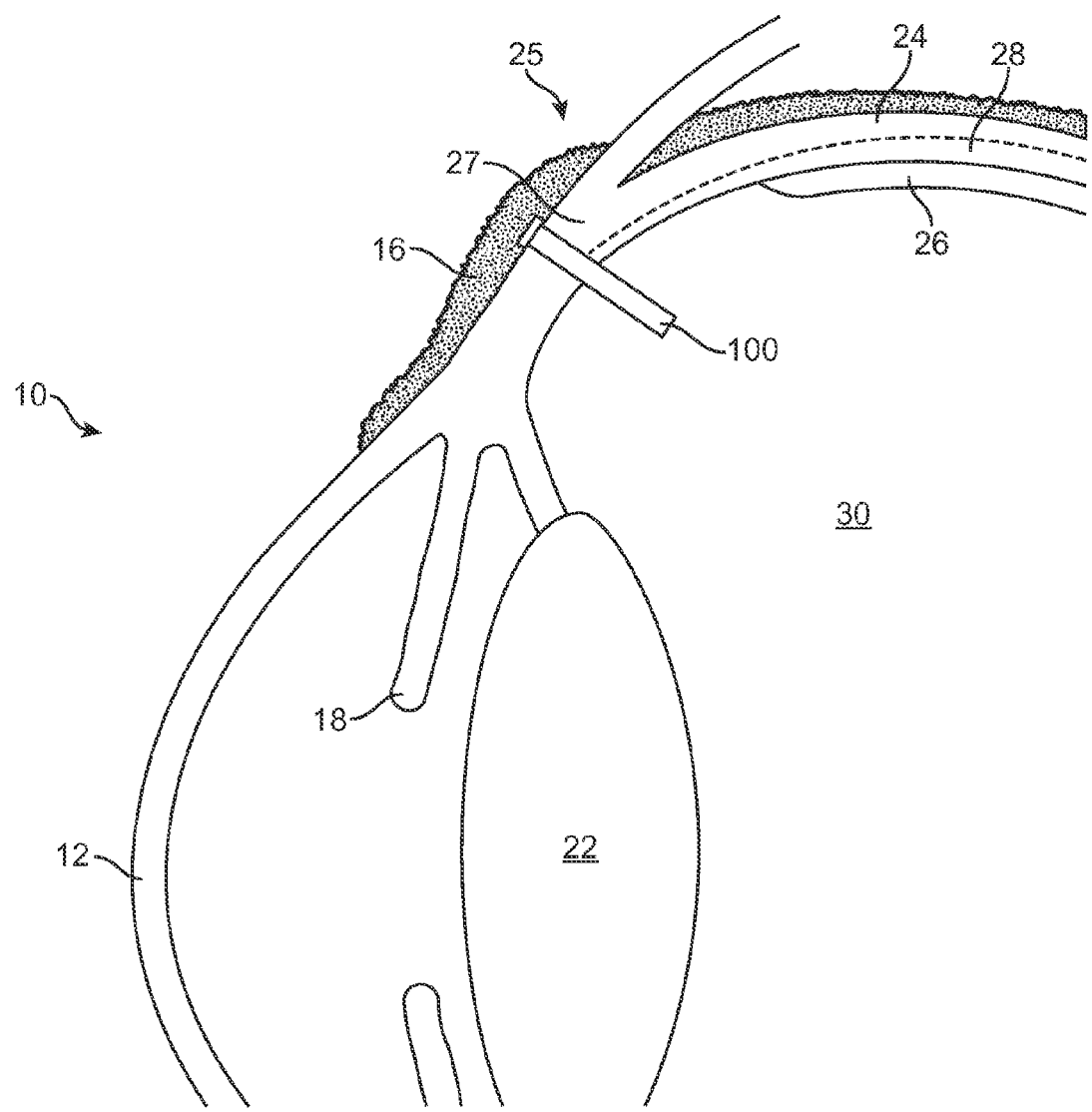

FIGS. 1A-1-1 and 1A-1-2 shows a therapeutic device 100 implanted under the conjunctiva 16 and extending through the sclera 24 to release a therapeutic agent 110 into vitreous humor 30 of the eye 10 so as to treat the retina of the eye. The therapeutic device 100 may comprise a retention structure 120 such as a smooth protrusion configured for placement along the sclera and under the conjunctiva, such that the conjunctiva can cover the therapeutic device and protect the therapeutic device 100. When the therapeutic agent 110 is inserted into the device 100, the conjunctiva may be lifted away, incised, or punctured with a needle to access the therapeutic device. The eye may comprise an insertion of the tendon 27 of the superior rectus muscle to couple the sclera of the eye to the superior rectus muscle. The device 100 may be positioned in many locations of the pars plana region, for example away from tendon 27 and one or more of posterior to the tendon, posterior to the tendon, under the tendon, or with nasal or temporal placement of the therapeutic device.

While the implant can be positioned in the eye in many ways, work in relation to embodiments suggests that placement in the pars plana region can release therapeutic agent into the vitreous to treat the retina, for example therapeutic agent comprising an active ingredient composed of large molecules.

Therapeutic agents 110 suitable for use with device 100 includes many therapeutic agents, for example as listed in Table 1A, herein below. The therapeutic agent 110 of device 100 may comprise one or more of an active ingredient of the therapeutic agent, a formulation of the therapeutic agent, a commercially available formulation of the therapeutic agent, a physician prepared formulation of therapeutic agent, a pharmacist prepared formulation of the therapeutic agent, or a commercially available formulation of therapeutic agent having an excipient. The therapeutic agent may be referred to with generic name or a trade name, for example as shown in Table 1A.

The therapeutic device 100 can be implanted in the eye to treat the eye for as long as is helpful and beneficial to the patient. For example the device can be implanted for at least about 5 years, such as permanently for the life of the patient. Alternatively or in combination, the device can be removed when no longer helpful or beneficial for treatment of the patient.

FIG. 1A-2 shows structures of therapeutic device 100 configured for placement in an eye as in FIGS. 1A-1, 1A-1-1 and 1A-1-2. The device may comprise retention structure 120 to couple the device 100 to the sclera, for example a protrusion disposed on a proximal end of the device. The device 100 may comprise a container 130 affixed to the retention structure 120. An active ingredient, for example therapeutic agent 110, can be contained within a reservoir 140, for example a chamber 132 defined by a container 130 of the device. The container 130 may comprise a porous structure 150 comprising a porous material 152, for example a porous glass frit 154, and a barrier 160 to inhibit release of the therapeutic agent, for example non-permeable membrane 162. The non-permeable membrane 162 may comprise a substantially non-permeable material 164. The non-permeable membrane 162 may comprise an opening 166 sized to release therapeutic amounts of the therapeutic agent 110 for the extended time. The porous structure 150 may comprise a thickness 150T and pore sizes configured in conjunction with the opening 166 so as to release therapeutic amounts of the therapeutic agent for the extended time. The container 130 may comprise reservoir 140 having a chamber with a volume 142 sized to contain a therapeutic quantity of the therapeutic agent 110 for release over the extended time. The device may comprise a needle stop 170. Proteins in the vitreous humor may enter the device and compete for adsorption sites on the porous structure and thereby may contribute to the release of therapeutic agent. The therapeutic agent 110 contained in the reservoir 140 can equilibrate with proteins in the vitreous humor, such that the system is driven towards equilibrium and the therapeutic agent 110 is released in therapeutic amounts.

The non-permeable membrane 162, the porous material 152, the reservoir 140, and the retention structure 120, may comprise many configurations to deliver the therapeutic agent 110. The non-permeable membrane 162 may comprise an annular tube joined by a disc having at least one opening formed thereon to release the therapeutic agent. The porous material 152 may comprise an annular porous glass fit 154 and a circular end disposed thereon. The reservoir 140 may be shape-changing for ease of insertion, i.e. it may assume a thin elongated shape during insertion through the sclera and then assume an extended, ballooned shape, once it is filled with therapeutic agent.

The porous structure 150 can be configured in many ways to release the therapeutic agent in accordance with an intended release profile. For example, the porous structure may comprise a porous structure having a plurality of openings on a first side facing the reservoir and a plurality of openings on a second side facing the vitreous humor, with a plurality of interconnecting channels disposed therebetween so as to couple the openings of the first side with the openings of the second side, for example a sintered rigid material. The porous structure 150 may comprise one or more of a permeable membrane, a semi-permeable membrane, a material having at least one hole disposed therein, nano-channels, nano-channels etched in a rigid material, laser etched nano-channels, a capillary channel, a plurality of capillary channels, one or more tortuous channels, tortuous microchannels, sintered nano-particles, an open cell foam or a hydrogel such as an open cell hydrogel.

FIG. 1A-2-1 shows therapeutic device 100 loaded into an insertion cannula 210 of an insertion apparatus 200, in which the device 100 comprises an elongate narrow shape for insertion into the sclera, and in which the device is configured to expand to a second elongate wide shape for retention at least partially in the sclera;

FIG. 1A-2-2 shows a therapeutic device 100 comprising reservoir 140 suitable for loading in a cannula, in which the reservoir 140 comprises an expanded configuration.

Figure 7:
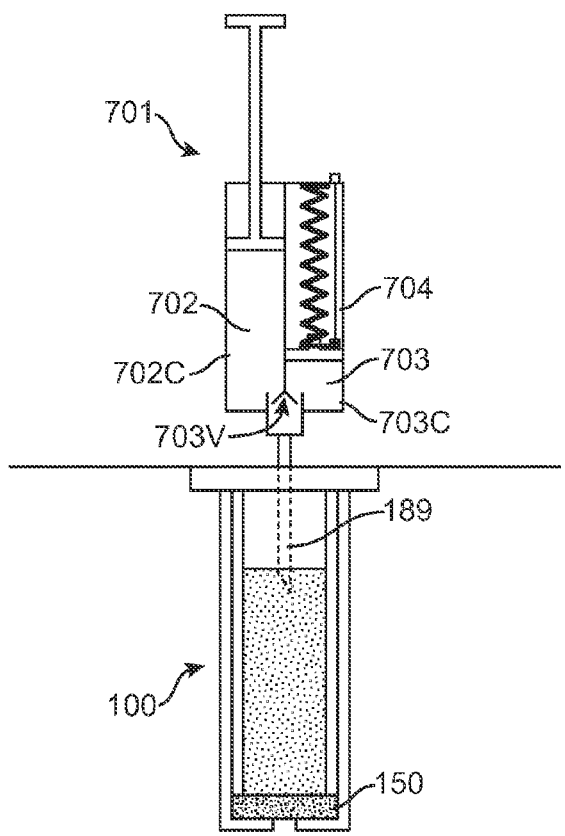
FIG. 7 shows a therapeutic device coupled to an injector that removes material from the device and injects therapeutic agent into the device, according to embodiments.
Figure 7A:
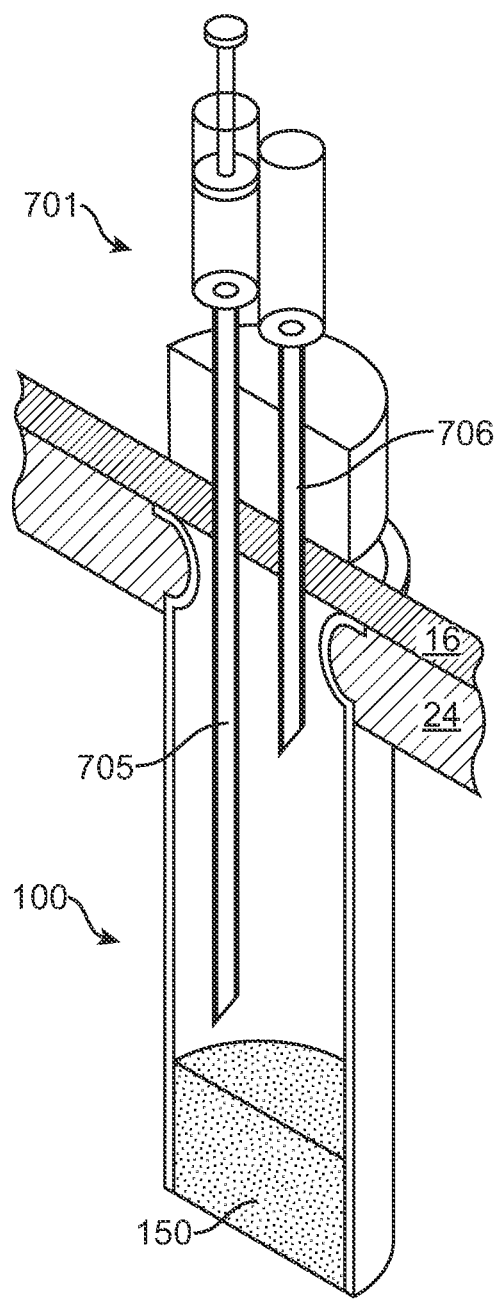
FIG. 7A shows a therapeutic device comprising a porous structure and a penetrable barrier as in FIG. 6E, with the penetrable barrier coupled to an injector to inject and remove material from the device, in accordance with embodiments.
Figures 1, 2, 7:
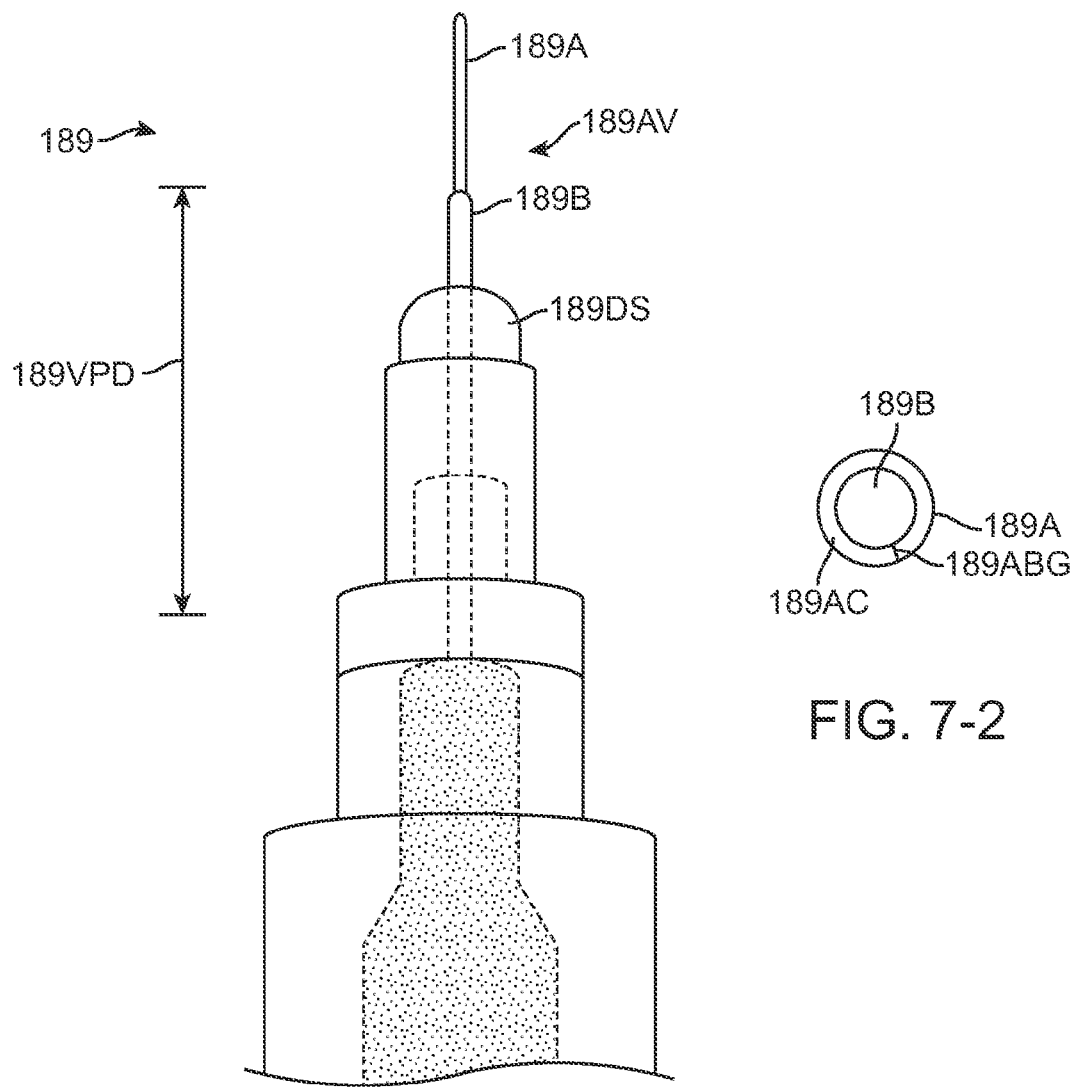
Figure 7A:
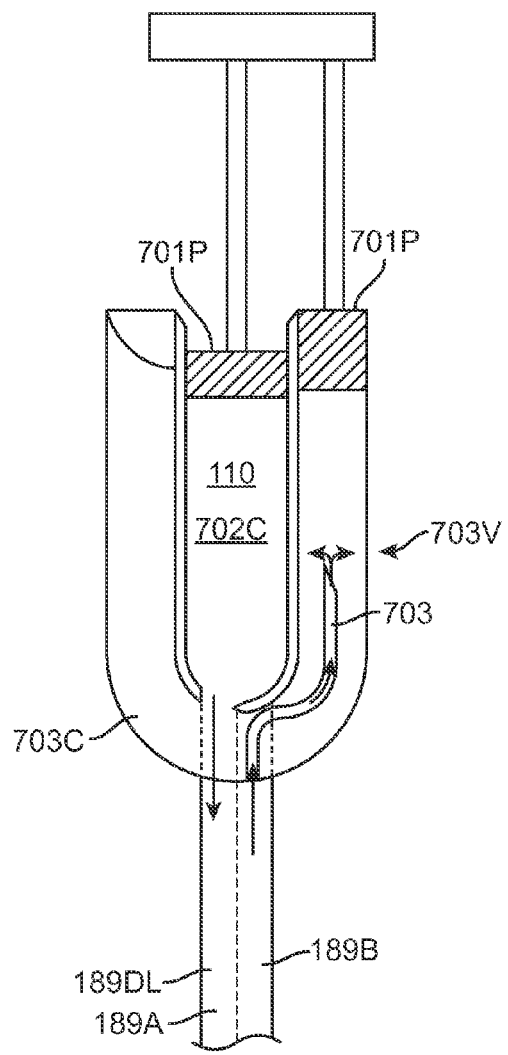
Figure 7B:
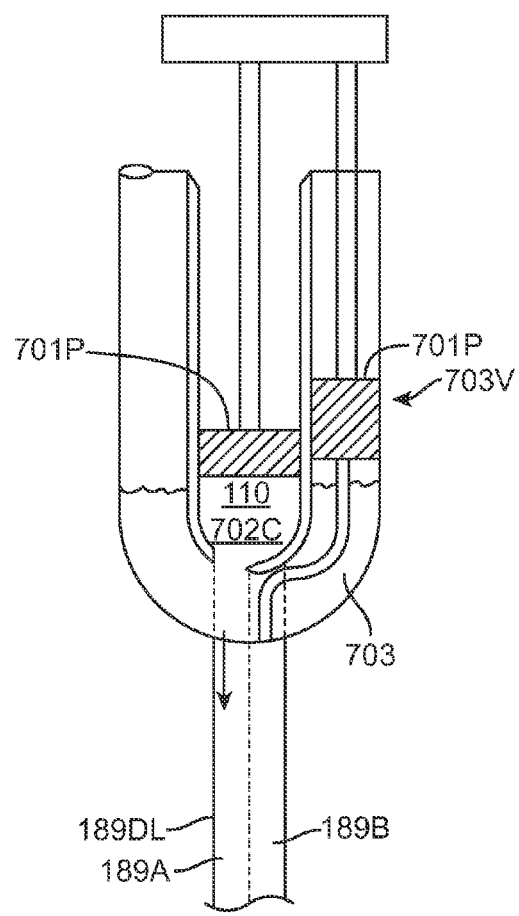
Figures 7, 7A, 8, 9, 9A:
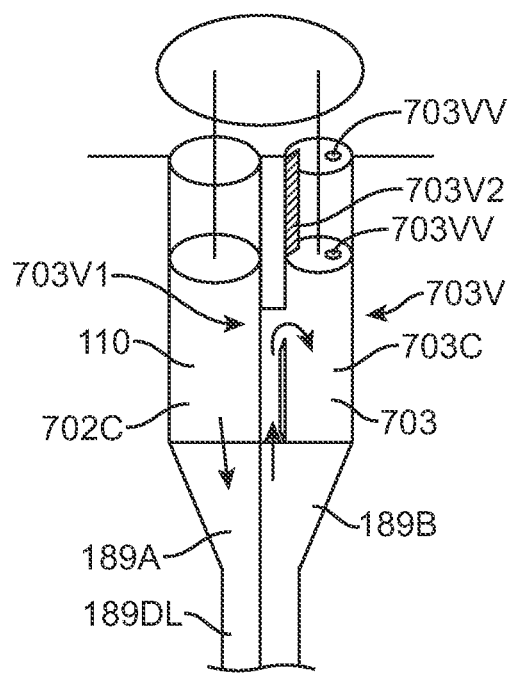
Figures 7, 7A, 8, 9, 9B:
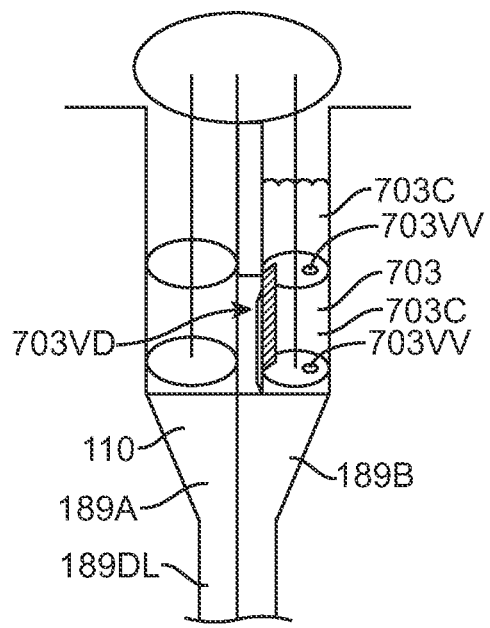
Figures 7, 7A, 8, 9, 10, 10A:
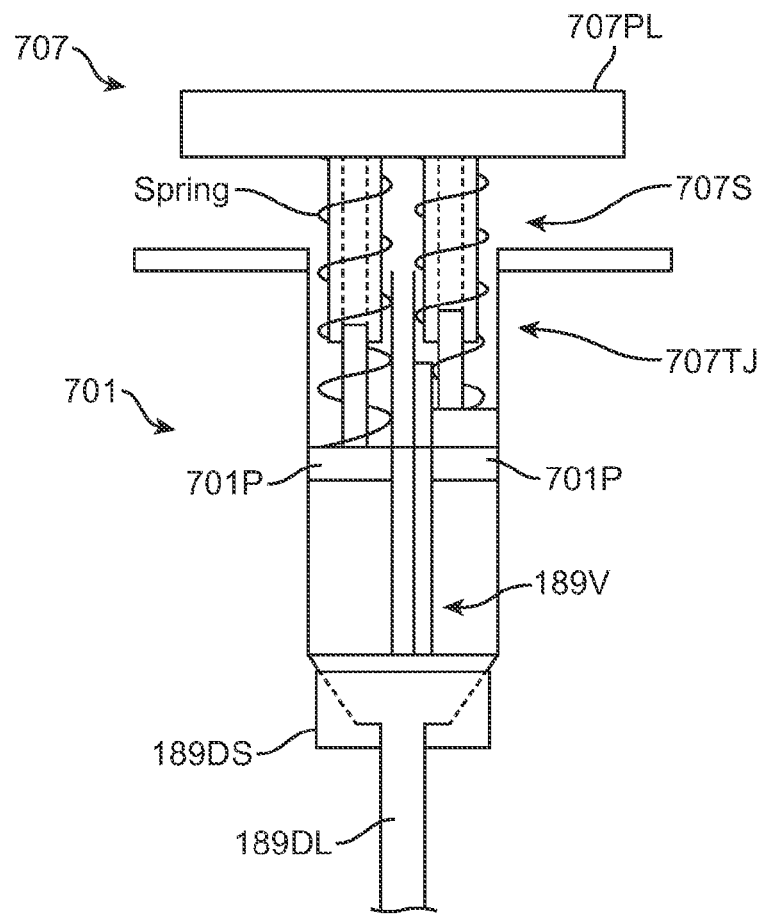
Figures 7, 7A, 8, 9, 10, 10B:
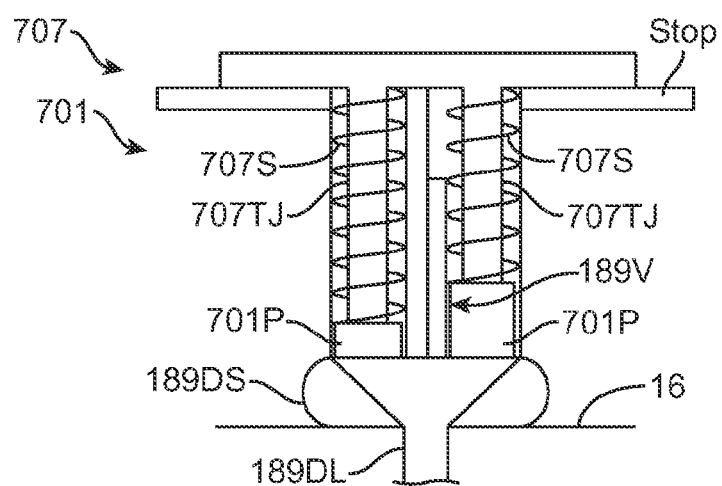
Figures 7, 7A, 8, 9, 10, 11, 12, 12A:
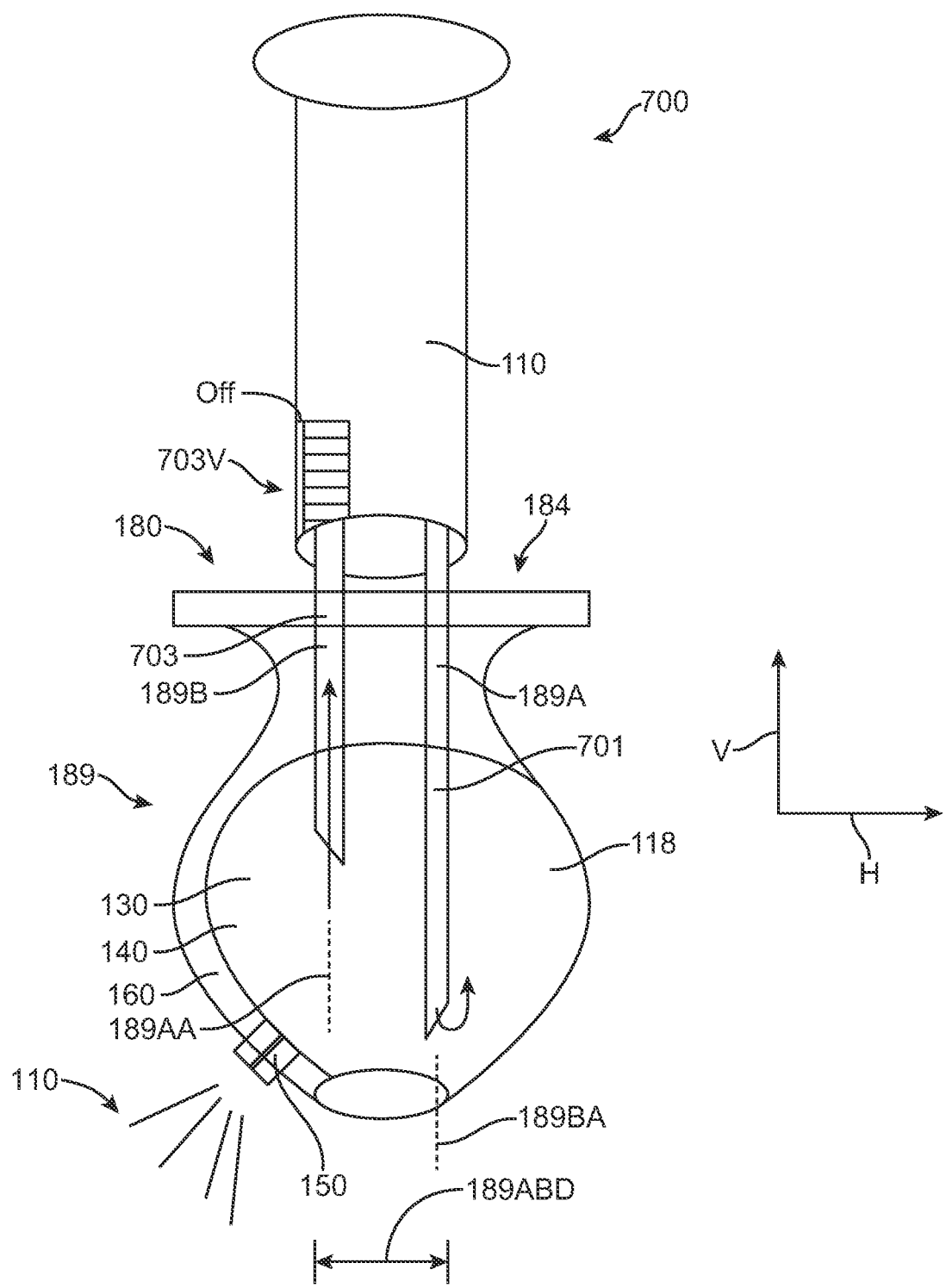
Figures 7, 7A, 8, 9, 10, 11, 12, 13, 14, 14A:
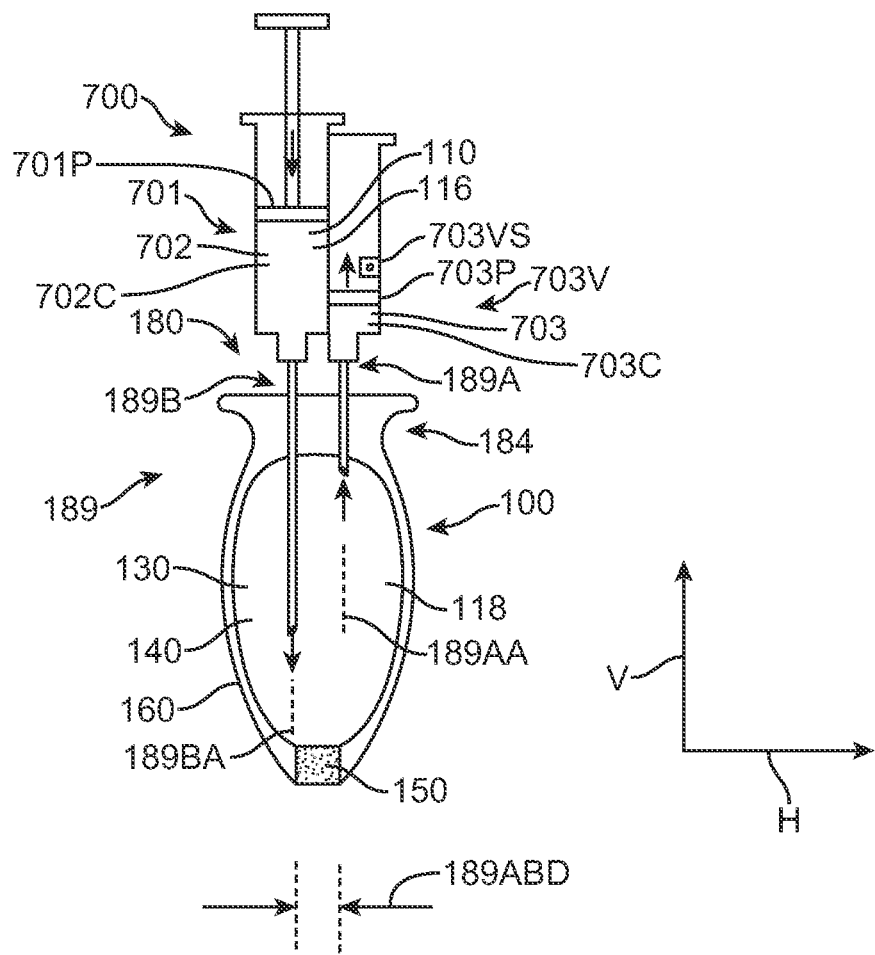
Figures 1, 7C:
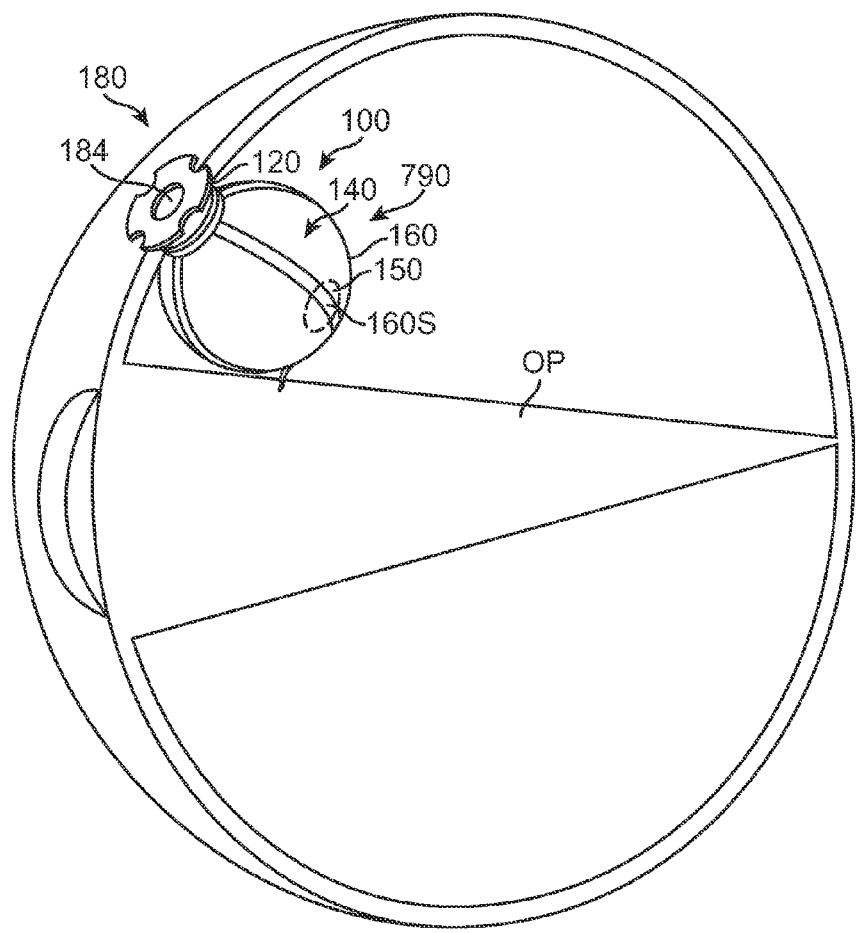
Figures 1A, 7C:
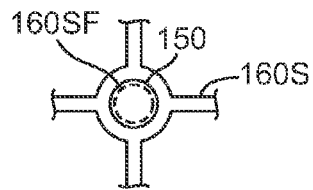
Figures 1B, 7C:
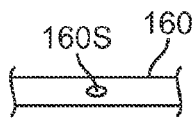
Figures 1C, 7C:
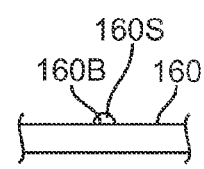
Figures 2, 7C:
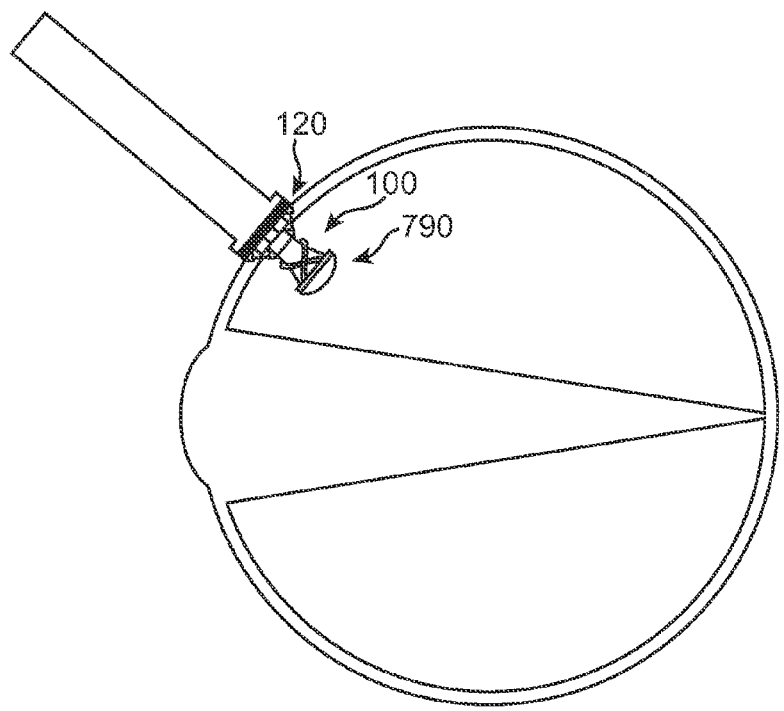
Figures 3, 7C:
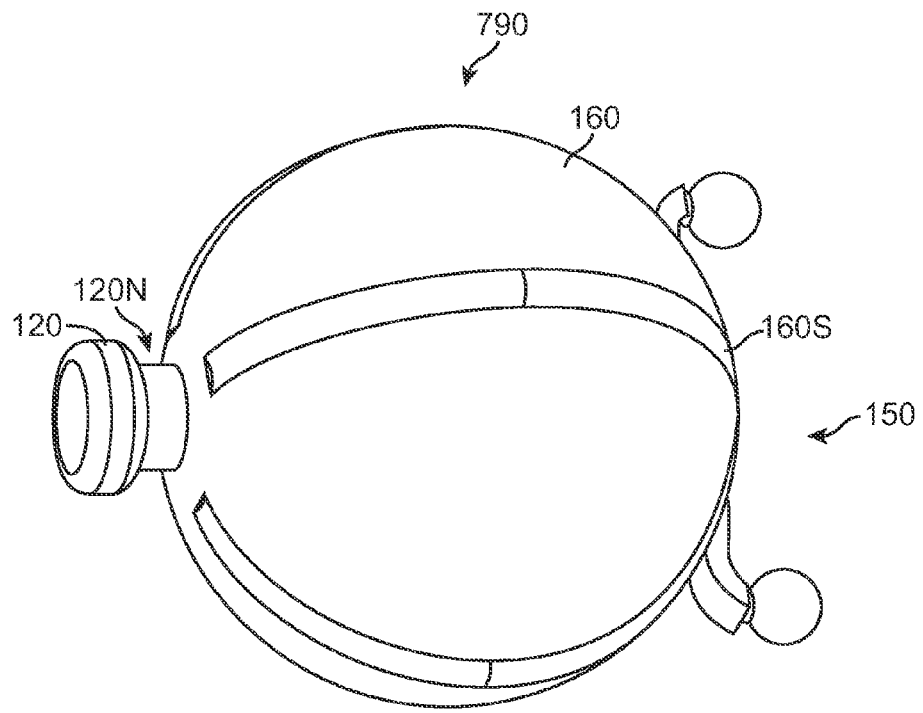

FIG. 1B shows therapeutic device 100 configured for placement in an eye as in FIGS. 1A-1 and 1A-1-1. The device comprises retention structure 120 to couple to the sclera, for example flush with the sclera, and the barrier 160 comprises a tube 168. An active ingredient 112 comprising the therapeutic agent 110 is contained within tube 168 comprising non-permeable material 164. A porous material 152 is disposed at the distal end of the tube 168 to provide a sustained release of the therapeutic agent at therapeutic concentrations for the extended period. The non-permeable material 164 may extend distally around the porous material 152 so as to define an opening to couple the porous material 152 to the vitreous humor when the device is inserted into the eye.

The tube 168 and retention structure 120 may be configured to receive a glass rod, which is surface treated, and the glass rod can be injected with therapeutic agent. When the therapeutic agent has finished elution for the extended time, the rod can be replaced with a new rod.

The device 100 may comprise therapeutic agent and a carrier, for example a binding medium comprising a binding agent to deliver the therapeutic agent. The therapeutic agent can be surrounded with a column comprising a solid support that is eroded away.

Figures 1, 1C:
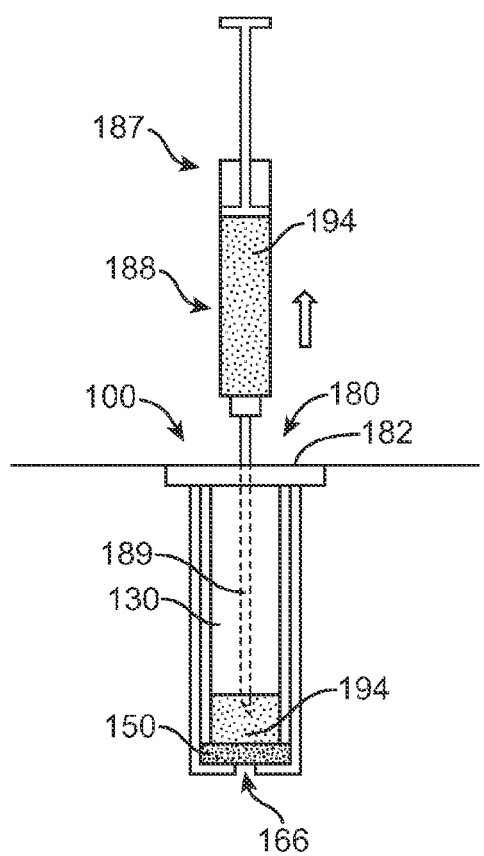
FIG. 1C shows a therapeutic device configured for placement in an eye as in FIGS. 1A-1 and 1A-1-1, in accordance with embodiments of the present invention.
Figures 1, 1C, 2:
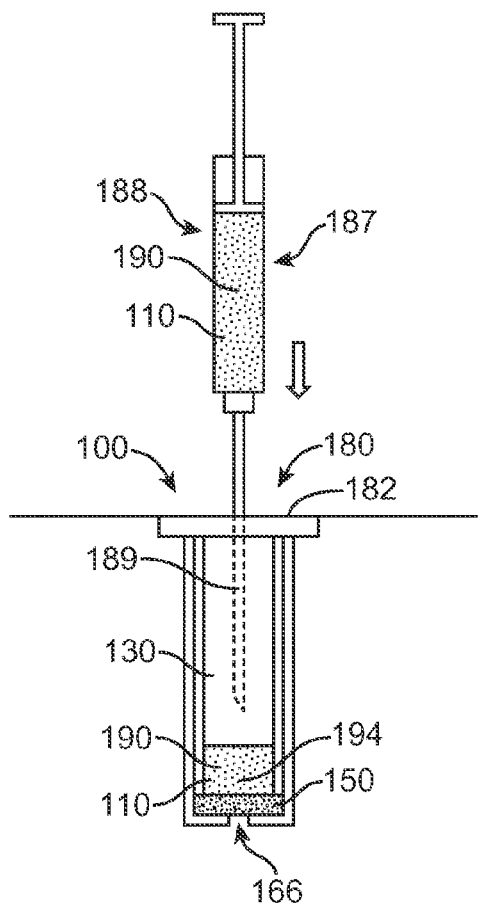

FIG. 1C shows a therapeutic device configured for placement in an eye as in FIGS. 1A-1 and 1A-1-1. A binding medium 192 comprising a binding agent 190 such as glass wool may be loaded with therapeutic agent 110 prior to injection into the device through an access port 180. The device 100 may comprise binding, leak, and barrier functions to deliver the therapeutic agent for the extended time. The binding medium 192 and therapeutic agent 110 can be aspirated to replace the binding medium and therapeutic agent. The binding medium can be at least one of flushed or replaced when at least majority of the therapeutic agent has been released, such that additional therapeutic agent can be delivered from a second, injected binding medium comprising therapeutic agent. A membrane 195 can be disposed over the periphery of the therapeutic device 100. The membrane 195 may comprise methylcellulose, regenerated cellulose, cellulose acetate, nylon, polycarbonate, poly(tetrafluoroethylene) (PTFE), polyethersulfone, and polyvinylidene difluoride (PVDF). The therapeutic device may comprise barrier 160 shaped such that opening 166 comprises an exit port. The therapeutic agent may be released through at least one of a diffusion mechanism or convection mechanism. The number, size, and configuration of exit ports may determine the release rate of the therapeutic agent. The exit port may comprise a convection port, for example at least one of an osmotically driven convection port or a spring driven convection port. The exit port may also comprise a tubular path to which the therapeutic agent may temporarily attach, and then be released under certain physical or chemical conditions.

FIG. 1C-A shows at least one exit port 167, the exit port can be disposed on the device 100 to allow liquid to flow from inside the device outward, for example when fluid is injected into an injection port 182 of the device or when an insert such as a glass fit is inserted into the device. The therapeutic device may comprise an access port 180 for injection and/or removal, for example a septum. Additionally or in the alternative, when the therapeutic device is refilled, the contents of the device may be flushed into the vitreous of the eye.

FIG. 1C-1 shows a method of removing a binding agent 194. A needle 189 coupled to a syringe 188 of an injector 187 can be inserted into an access port 180 of the therapeutic device 100. The binding agent 194 can be aspirated with a needle.

FIG. 1C-2 shows a method of inserting the therapeutic agent 110 with a second binding agent 190 having the therapeutic agent 110 bound thereon. The therapeutic agent can be injected into a container 130 of the device for sustained release over the extended time.

FIG. 1C-3 shows syringe being filled with a formulation of therapeutic agent for injection into the therapeutic device. The needle 189 coupled to syringe 188 of injector 187 can be used to draw therapeutic agent 110 from a container 110C. The container 110C may comprise a commercially available container, such as a bottle with a septum, a single dose container, or a container suitable for mixing formulations. A quantity 110V of therapeutic agent 110 can be drawn into injector 187 for injection into the therapeutic device 100 positioned within the eye. The quantity 110V may comprise a predetermined quantity, for example based on the volume of the container of the therapeutic device 110 and an intended injection into the vitreous humor. The example the quantity 110V may exceed the volume of the container so as to inject a first portion of quantity 110V into the vitreous humor through the therapeutic device and to contain a second portion of quantity 110V within the container of the therapeutic device 110. Container 110C may comprise a formulation 110F of the therapeutic agent 110. The formulation 110F may comprise a commercially available formulations of therapeutic agent, for example therapeutic agents as described herein and with reference to Table 1A. Non-limiting examples of commercially available formulations that may be suitable for use in accordance with the embodiments described herein include Lucentis™ and Triamcinolone, for example. The formulation 110F may be a concentrated or diluted formulation of a commercially available therapeutic agent, for example Avastin™. The osmolarity and tonicity of the vitreous humor can be within a range from about 290 to about 320. For example, a commercially available formulation of Avastin™ may be diluted so as to comprise a formulation having an osmolarity and tonicity substantially similar to the osmolarity and tonicity of the vitreous humor, for example within a range from about 280 to about 340, for example about 300 mOsm. While the therapeutic agent 110 may comprise an osmolarity and tonicity substantially similar to the vitreous humor, the therapeutic agent 110 may comprise a hyper osmotic solution relative to the vitreous humor or a hypo osmotic solution relative to the vitreous humor. A person or ordinary skill in the art can conduct experiments based on the teachings described herein so as to determine empirically the formulation and osmolarity of the therapeutic agent to provide release of therapeutic agent for an extended time.

For example, in the United States of America, Lucentis™ (active ingredient ranibizumab) is supplied as a preservative-free, sterile solution in a single-use glass vial designed to deliver 0.05 mL of 10 mg/mL Lucentis™ aqueous solution with 10 mM histidine HCl, 10% a, α-trehalose dihydrate, 0.01% polysorbate 20, at pH 5.5. In Europe, the Lucentis™ formulation can be substantially similar to the formulation of the United States.

For example, the sustained release formulation of Lucentis™ in development by Genentech and/or Novartis, may comprise the therapeutic agent injected in to the device 100. The sustained release formulation may comprise particles comprising active ingredient.

For example, in the United States, Avastin™ (bevacizumab) is approved as an anticancer drug and in clinical trials are ongoing for AMD. For cancer, the commercial solution is a pH 6.2 solution for intravenous infusion. Avastin™ is supplied in 100 mg and 400 mg preservative-free, single-use vials to deliver 4 mL or 16 mL of Avastin™ (25 mg/mL). The 100 mg product is formulated in 240 mg α,α-trehalose dihydrate, 23.2 mg sodium phosphate (monobasic, monohydrate), 4.8 mg sodium phosphate (dibasic, anhydrous), 1.6 mg polysorbate 20, and Water for Injection, USP. The 400 mg product is formulated in 960 mg α,α-trehalose dihydrate, 92.8 mg sodium phosphate (monobasic, monohydrate), 19.2 mg sodium phosphate (dibasic, anhydrous), 6.4 mg polysorbate 20, and Water for Injection, USP. The commercial formulations are diluted in 100 mL of 0.9% sodium chloride before administration and the amount of the commercial formulation used varies by patient and indication. Based on the teachings described herein, a person of ordinary skill in the art can determine formulations of Avastin™ to inject into therapeutic device 100. In Europe, the Avastin™ formulation can be substantially similar to the formulation of the United States.

For example, in the United States, there are 2 forms of Triamcinolone used in injectable solutions, the acetonide and the hexacetonide. The acetamide is approved for intravitreal injections in the U.S. The acetamide is the active ingredient in TRIVARIS (Allergan), 8 mg triamcinolone acetonide in 0.1 mL (8% suspension) in a vehicle containing w/w percent of 2.3% sodium hyaluronate; 0.63% sodium chloride; 0.3% sodium phosphate, dibasic; 0.04% sodium phosphate, monobasic; and water, pH 7.0 to 7.4 for injection. The acetamide is also the active ingredient in Triesence™ (Alcon), a 40 mg/ml suspension.

A person of ordinary skill in the art can determine the osmolarity for these formulations. The degree of dissociation of the active ingredient in solution can be determined and used to determined differences of osmolarity from the molarity in these formulations. For example, considering at least some of the formulations may be concentrated (or suspensions), the molarity can differ from the osmolarity.

The formulation of therapeutic agent may injected into therapeutic device 100 may comprise many known formulations of therapeutic agents, and the formulation therapeutic agent comprises an osmolarity suitable for release for an extended time from device 100. Table 1B shows examples of osmolarity (Osm) of saline and some of the commercially formulations of Table 1A.

TABLE 1B

Summary of Calculations

| Description | Osm (M) |
| --- | --- |
| Saline (0.9%) | 0.308 |
| Phosphate Buffered Saline (PBS) | 0.313 |
| Lucentis ™ | 0.289 |
| Avastin ™ | 0.182 |
| Triamcinolone Acetonide (Trivaris-Allergan) | 0.342 |
| Triamcinolone Acetonide (Triessence-Alcon) | Isotonic* |
| Triamcinolone Acetonide (Kenalog-Apothecon) | Isotonic* |

*As described in package insert

The vitreous humor of the eye comprises an osmolarity of about 290 mOsm to about 320 mOsm. Formulations of therapeutic agent having an osmolarity from about 280 mOsm to about 340 mOsm are substantially isotonic and substantially iso-osmotic with respect to the vitreous humor of the eye. Although the formulations listed in Table 1B are substantially iso-osmotic and isotonic with respect to the vitreous of the eye and suitable for injection into the therapeutic device, the formulation of the therapeutic agent injected into the therapeutic device can be hypertonic (hyper-osmotic) or hypotonic (hypo-osmotic) with respect to the tonicity and osmolarity of the vitreous. Work in relation to embodiments suggests that a hyper-osmotic formulation may release the active ingredient of the therapeutic agent into the vitreous somewhat faster initially when the solutes of the injected formulation equilibrate with the osmolarity of the vitreous, and that a hypo-osmotic formulation such as Avastin™ may release the active ingredient of the therapeutic agent into the vitreous somewhat slower initially when the solutes of the injected formulation equilibrate with the eye. A person of ordinary skill in the art can conduct experiments based on the teaching described herein to determine empirically the appropriate reservoir chamber volume and porous structure for a formulation of therapeutic agent disposed in the reservoir chamber, so as to release therapeutic amounts of the therapeutic agent for an extended time and to provide therapeutic concentrations of therapeutic agent in the vitreous within a range of therapeutic concentrations that is above the minimum inhibitory concentration for the extended time.

Figures 1, 1C, 2, 3:
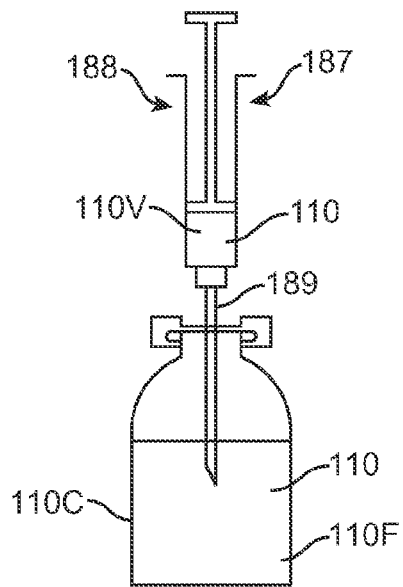
Figure 1D:
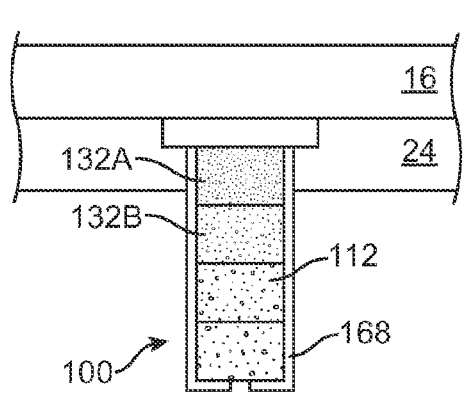
FIG. 1D shows a therapeutic device configured for placement in an eye as in FIGS. 1A-1 and 1A-1-1, in which the device comprises a plurality of chambers and channels connecting the chambers so as to linearize the release of the therapeutic agent.

FIG. 1D shows a therapeutic device 100 configured for placement in an eye as in FIGS. 1A-1 and 1A-1-1, in which the device comprises a plurality of chambers and channels connecting the chambers so as to linearize the release of the therapeutic agent. A first chamber 132A may comprise a reservoir having a first volume to contain the therapeutic quantity of the therapeutic agent. For example, the therapeutic agent comprises the active ingredient contained within the reservoir. A second chamber 132B can be disposed distally to the first chamber, with a first opening connecting the first chamber and the second chamber. The therapeutic agent can diffuse through the first opening into the second chamber. The second chamber comprises a second volume, such that therapeutic agent is temporarily stored in the second chamber so as to linearize, for example toward zero order, the delivery of the therapeutic agent. A second opening can extend from the second chamber toward the vitreous humor. The first opening, the second opening and the second volume can be sized so as to linearize the delivery of the therapeutic agent for the sustained release at therapeutic levels for the extended time. More than one therapeutic agent can be inserted into the therapeutic device. In such a case the two or more therapeutic agents may be mixed together or injected into separate chambers.

Additional chambers and openings can be disposed on the device to linearize the delivery of the drug. For example, a third chamber can be disposed distally to the second chamber. The second opening can couple the second chamber to the third chamber. For example, a fourth chamber can be disposed distally to the third chamber, a third opening can connect the third chamber and the fourth chamber.

Additionally or in the alternative, the therapeutic device may comprise at least one gate to provide for sustained drug delivery. The gate can be moved from "closed" to "open" position using magnetism or by applying electrical current. For example the gates can slide or twist. The gates can be spring-loaded, and may comprise a pump that can be re-loaded. The gates may comprise an osmotic pump.

Figure 1E:
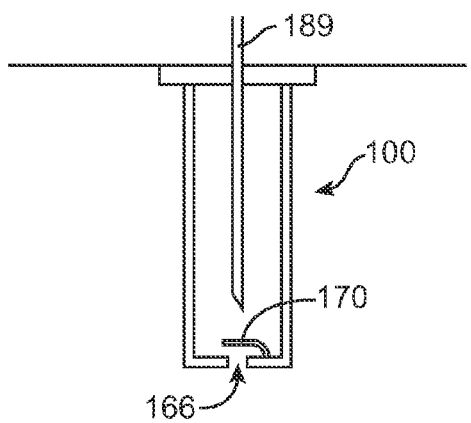
FIG. 1E shows a therapeutic device configured for placement in an eye as in FIGS. 1A-1 and 1A-1-1, in which the device comprises a needle stop located at the bottom of the therapeutic device.
Figures 1, 1E:
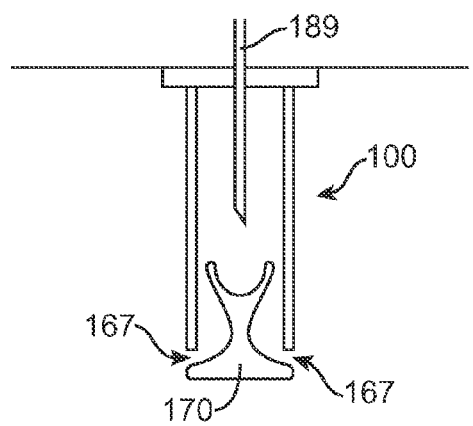
Figures 1, 1E, 2:
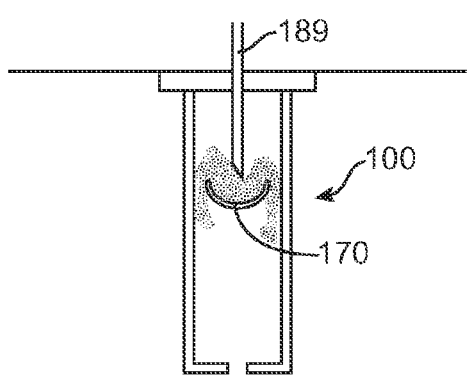
Figures 1, 1E, 2, 3:
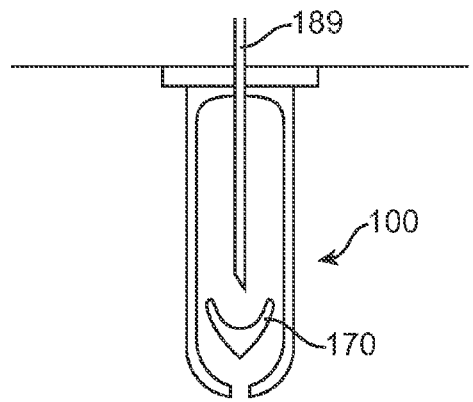
Figures 1, 1E, 2, 3:
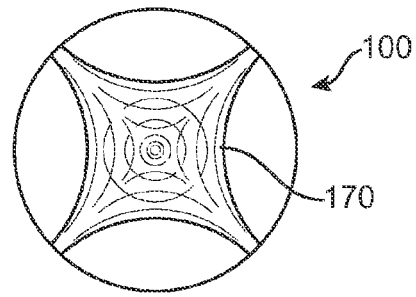

FIG. 1E shows a therapeutic device configured for placement in an eye as in FIGS. 1A-1 and 1A-1-1, in which the device comprises 100 needle stop 170 located at the bottom of the therapeutic device. The needle stop that may be included in the therapeutic device to keep the injection needle 189 from penetrating through and possibly damaging the exit port(s) 166 of the therapeutic device 100. The needle stop will desirably be made of a material of sufficient rigidity to prevent the advancement of the injection needle past a certain level in the therapeutic device. Additionally or in the alternative, the length of the injector's needle may be designed so that it may not penetrate through and possibly damage the exit port(s) of the therapeutic device.

As shown in FIGS. 1E and 1E-1, the needle stop 170 may be positioned at the posterior end of the therapeutic device. FIGS. 1E-2, 1E-3 and 1E-3-1 show other embodiments that may include needle stops placed in the middle of the device. The needle stop may be designed in such a manner as to function as a flow diverter for the therapeutic agent. The shape of the needle stop may encourage the mixing of the therapeutic agent with the rest of the fluids present in the inner chamber(s) of the therapeutic device.

FIG. 1E-1 shows a therapeutic device configured for placement in an eye as in FIGS. 1A-1 and 1A-1-1, in which the device comprises needle stop 170 located at the bottom of the therapeutic device and the shape of the device encourages the movement of the therapeutic agent within the chamber of the therapeutic device 100.

FIG. 1E-2 shows a therapeutic device configured for placement in an eye as in FIGS. 1A-1 and 1A-1-1, in which the device comprises needle stop 170 located in the middle of the therapeutic device.

FIG. 1E-3 shows a therapeutic device configured for placement in an eye as in FIGS. 1A-1 and 1A-1-1, in which the device comprises needle stop 170 located in the middle of the therapeutic device and the shape of the device encourages the movement of the therapeutic agent within the chamber of the therapeutic device.

FIG. 1E-3-1 shows a top view of the therapeutic device configured for placement in an eye as in FIGS. 1E-3.

Figures 1, 1F:
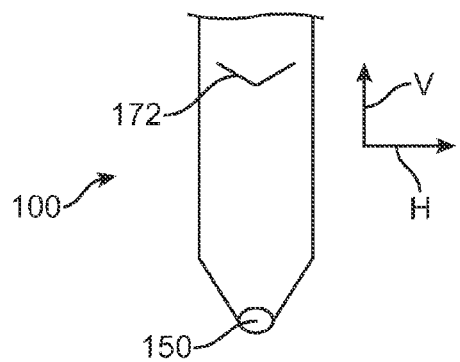
Figures 1, 1F, 2:
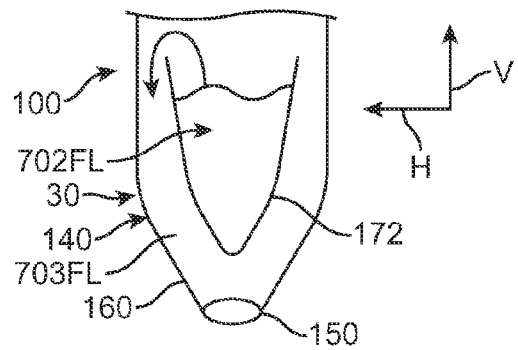
Figures 1, 1F, 2, 3:
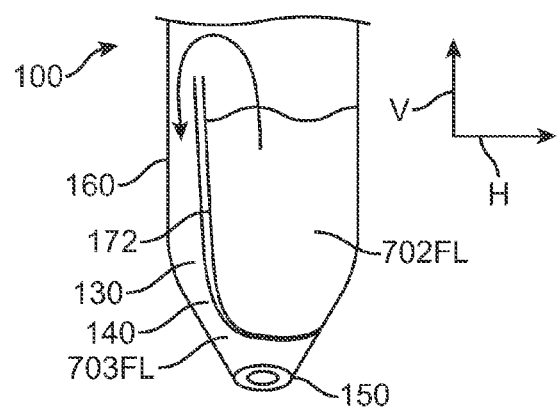

FIG. 1F-1 shows a therapeutic device 100 comprising a flow diverter 172. The flow diverter 172 can be combined with the deformable needle stop 189DS coupling to the conjunctiva outside the device, such that needle 189 extends into the container 130 between the access port 180 and flow diverter.

FIG. 1F-2 shows a therapeutic device 100 comprising a fluid separator 174 having sufficient volume so as to retain at least a portion of the therapeutic fluid 702FL, such that at least a portion of the implanted device fluid 703FL is urged through the porous structure 150 with at least partial separation. The fluid separator may comprise a container located within the reservoir chamber. The container to separate fluid may comprise a substantial volume within the reservoir chamber, for example at least about 50% of the volume of the reservoir chamber. The flow fluid separator may comprise a cupped shape configuration and can be effective when the density of the therapeutic fluid 702FL is greater than the density of the implanted device fluid 703FL, for example. When the cup shaped structure is substantially filled with therapeutic fluid, the therapeutic fluid is passed through porous structure 150 and after a substantial portion of device fluid 703FL is passed through porous structure 150.

FIG. 1F-3 shows a therapeutic device 100 comprising a fluid separator 174 having sufficient volume so as to retain at least a portion of the therapeutic fluid 702FL, such that at least a portion of the implanted device fluid 703FL is urged through the porous structure 150 with at least partial separation, in accordance with embodiments of the present invention. The fluid separator may comprise a container located within the reservoir chamber. The container to separate fluid may comprise a substantial volume within the reservoir chamber, for example at least about 50% of the volume of the reservoir chamber. The flow fluid separator may comprise a cupped shape configuration and can be effective when the density of the therapeutic fluid 702FL is greater than the density of the implanted device fluid 703FL, for example. The cup shaped structure can be off center to axis 100A of device 100.

Figure 1G:
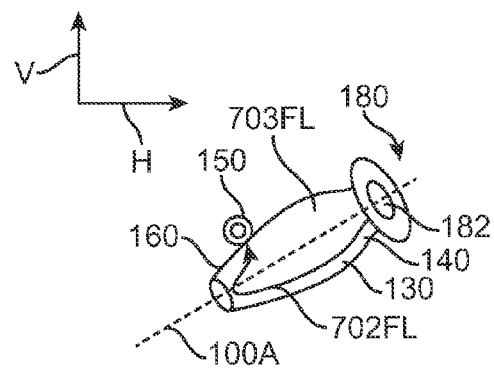
FIG. 1G shows a therapeutic device comprising porous structure located away from a distal end and axis, such that therapeutic fluid settles toward the distal end and the implanted fluid is passed through the porous structure with at least partial separation, in accordance with embodiments of the present invention.
Figure 1H:
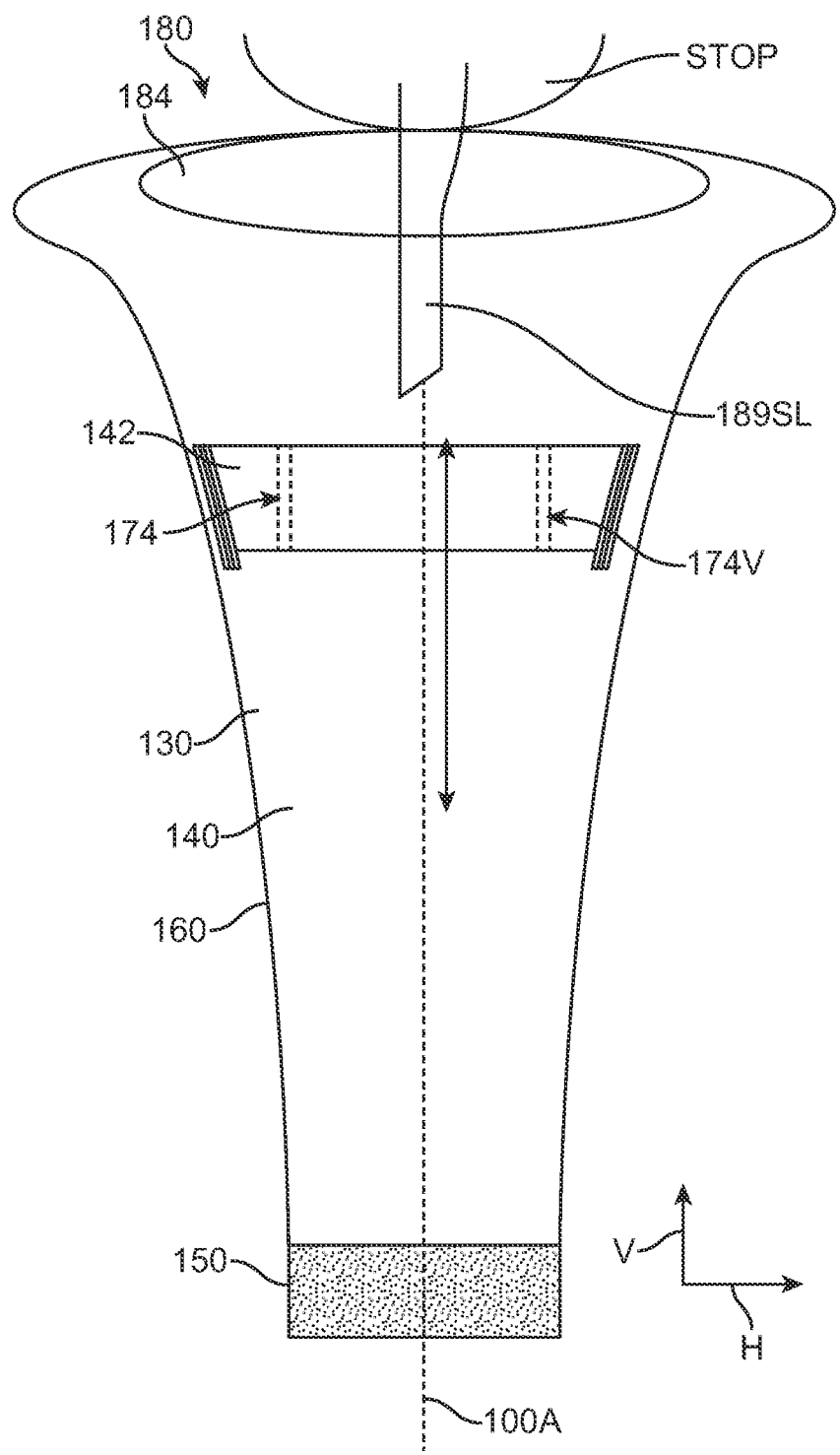
FIG. 1H shows a therapeutic device comprising a fluid separator, in which the fluid separator is configured to move distally with injection of therapeutic fluid so as to separate the fluids during injection, in accordance with embodiments of the present invention.

FIG. 1G shows a therapeutic device 100 comprising porous structure 150 located away from a distal end and axis 100A, such that therapeutic fluid settles toward the distal end and the implanted fluid is passed through the porous structure 150 with at least partial separation, in accordance with embodiments of the present invention;

FIG. 1H shows a therapeutic device 100 comprising a movable fluid separator 174, in which the fluid separator is configured to move distally along axis 100A with injection of therapeutic fluid 702FL so as to separate the fluids during injection. The fluid separator may comprise a compressible closed cell sponge or hydrogel to slide along axis 100A of device 100 when the therapeutic fluid is injected and pass the fluid 703FL through porous structure 150. The separator may comprise a plurality of small vents to pass fluid such that the separator can move proximally toward port 180 when fluid passes through the small ports prior to the next injection. The at least one needle 189 may comprise a single lumen needle 189SL, for example. The single lumen needle 189SL and provide sufficient pressure to push the movable separator 174 distally toward the porous structure 150

Figure 1I:
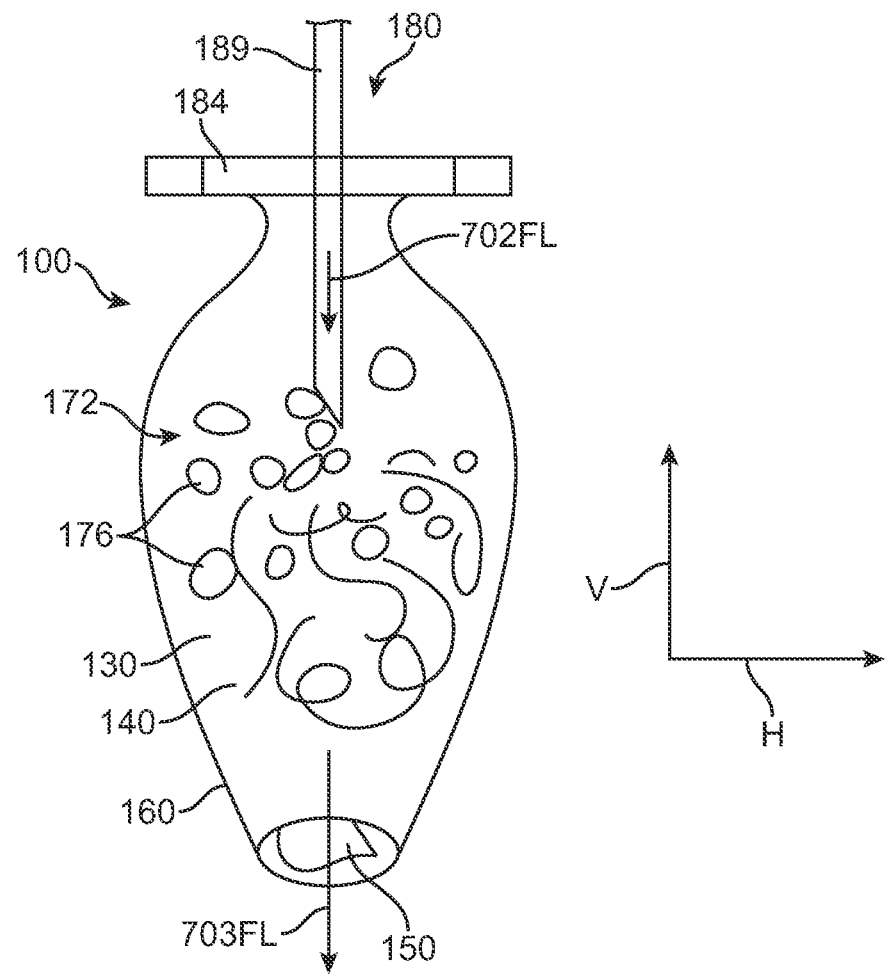
FIG. 1I shows a therapeutic device comprising a plurality of beads so as to mix the fluids during injection and inhibit separation such that device fluid is passed through porous structure, in accordance with embodiments of the present invention.
Figure 2:
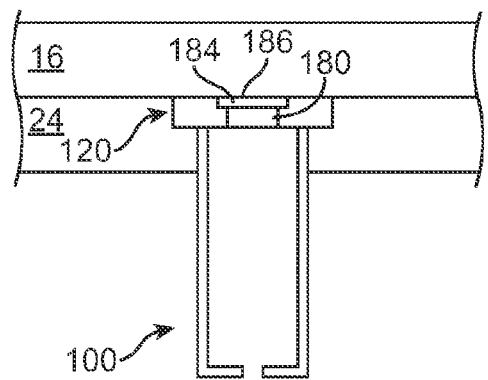

FIG. 1I shows a therapeutic device 100 comprising a plurality of beads 176 so as to mix the fluids during injection and inhibit separation such that device fluid 703FL is passed through porous structure 150. The plurality of beads 176 can mix the therapeutic fluid passed through needle 189 so as to inhibit separation and increase the amount of device fluid 703FL passed through porous structure 150, for example when fluid 702FL comprises a greater density than fluid 703FL.

FIG. 2 shows an access port 180 suitable for incorporation with the therapeutic device 100. The access port 180 may be combined with the therapeutic devices described herein, for example with reference to FIGS. 1A-1 to 1D. The access port may be disposed on a proximal end of the device. The access port 180 may comprise an opening formed in the retention structure 120 with a penetrable barrier 184 comprising a septum 186 disposed thereon. The access port may 180 be configured for placement under the conjunctiva 16 of the patient and above the sclera 24.

Figure 3A:
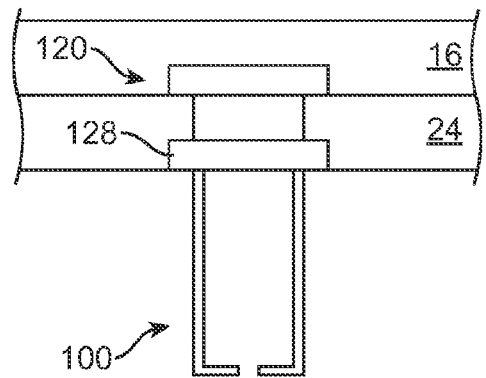
FIG. 3A shows a collar suitable for incorporation with the therapeutic device, in accordance with embodiments of the present invention.

FIG. 3A shows a collar 128 suitable for incorporation with the therapeutic device 100. The retention structure 120 configured to couple to the sclera 24 may comprise the collar 128. The collar may comprise an expandable collar.

Figure 3B:
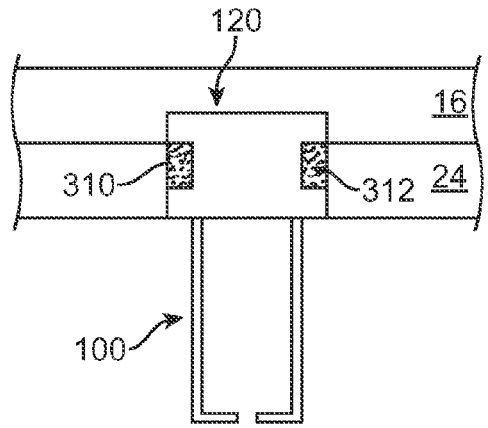
FIG. 3B shows biocompatible material impregnated with an anti-bacterial agent on the therapeutic device to inhibit bacterial growth along the device from the sclera to the vitreous humor.

FIG. 3B shows biocompatible material impregnated with an anti-bacterial agent 310 on the therapeutic device 100 to inhibit bacterial growth along the device from the sclera to the vitreous humor. The biocompatible material may comprise collagen, for example a collagen sponge 312, and the anti-bacterial agent may comprise silver impregnated in the collagen. The biocompatible material impregnated with the bactericide agent may extend around at least a portion of the outer surface of the device. The anti-bacterial agent may comprise a portion of the retention structure 120, such that the anti-bacterial agent is disposed at least partially within the sclera when the device is inserted into the eye.

Figure 4A:
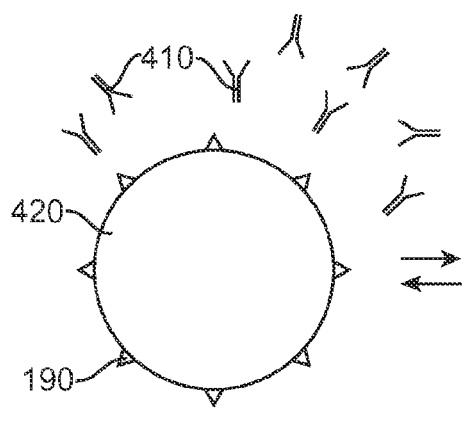
FIG. 4A shows released fragments of antibodies.
Figure 4B:
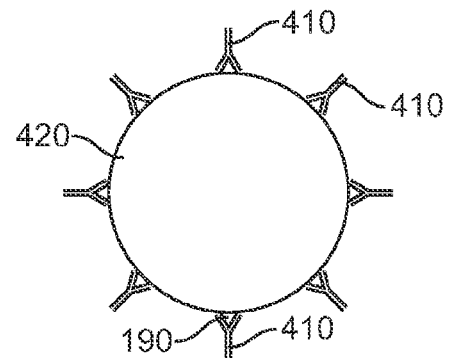
FIG. 4B shows antibody fragments reversibly bound to a substrate, in accordance with embodiments of the present invention.

FIG. 4A shows released antibodies comprising antibody fragments 410 and a substrate 420 comprising binding agent 190, and FIG. 4B shows an antibody fragments 410 reversibly bound to a substrate 420 with binding agent 190, in accordance with embodiments of the present invention. The antibody fragments can be reversibly bound to the substrate comprising the binding agent, such that the bound antibody fragments are in equilibrium with the unbound antibody fragments. One of ordinary skill in the art will recognize many substrates comprising binding agent to reversibly bind at least a portion of an antibody based on the teachings described herein. Examples of binding media may include particulates used in chromatography, such as: Macro-Prep t-Butyl HIC Support, Macro-Prep DEAE Support, CHT Ceramic, Hydroxyapatite Type I, Macro-Prep CM Support, Macro-Prep Methyl HIC Support, Macro-Prep Ceramic Hydroxapatite Type II, UNOsphere S Cation Exchange Support, UNOsphere Q Strong Anion Exchange Support, Macro-Prep High-S Support, and Macro-Prep High-Q Support. Additional media to test for binding include ion exchange and bioaffinity chromatography media based on a hydrophilic polymeric support (GE Healthcare) that bind proteins with high capacity, and a hydrophilic packing material from Harvard Apparatus made from poly(vinyl alcohol) that binds more protein than silica. Other candidates would be known to those knowledgeable in the art.

Figure 5A:
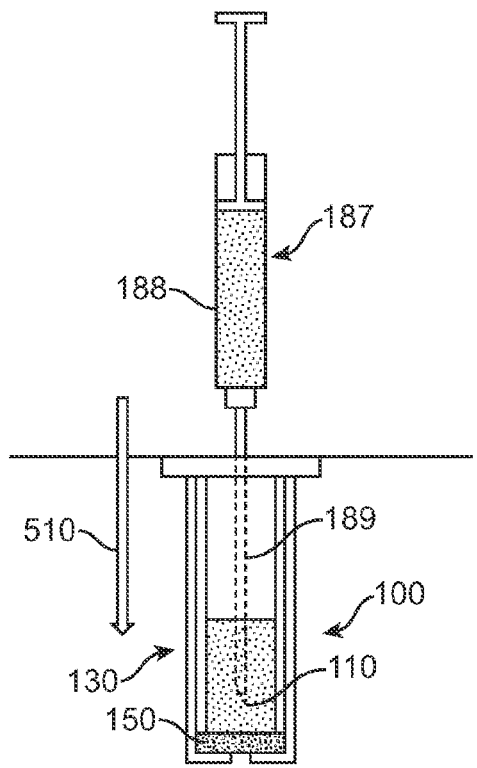
FIG. 5A shows a therapeutic device coupled to an injector to insert therapeutic agent into the device.
Figures 1, 5A:
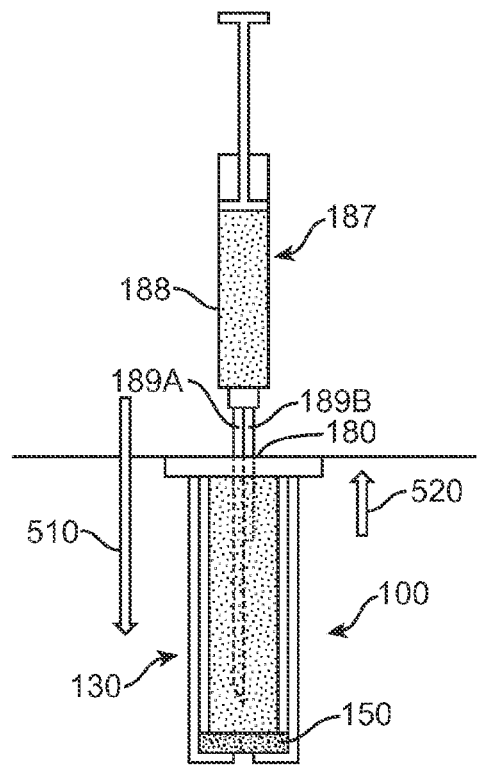

FIG. 5A shows therapeutic device 100 coupled to injector 187 to insert therapeutic agent 110 into container 130 of the device. The injector 187 may comprise needle 189 coupled to a syringe 188.

FIG. 5A-1 shows a therapeutic device 100 coupled to an injector 187 to inject and remove material from the device. The injector may comprise needle 189 having a first lumen 189A and a second lumen 189B configured to insert into a container of the device. The injector may simultaneously inject 510 therapeutic agent into and withdraw 520 liquid from the device. The injector may comprise a first one way valve and a second one way valve coupled to the first lumen and the second lumen, respectively.

Figure 5B:
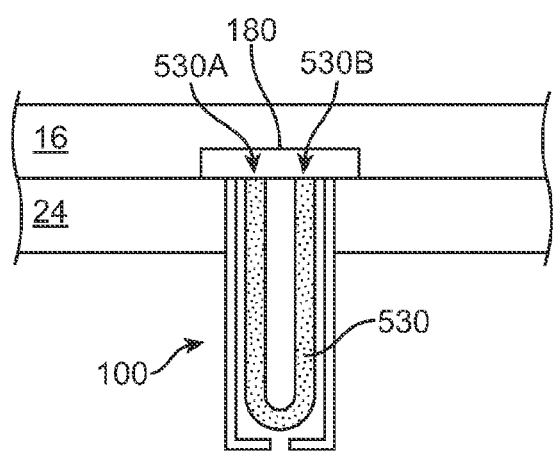
FIG. 5B shows a therapeutic device comprising a micro loop channel.

FIG. 5B shows a therapeutic device comprising a microloop channel 530. The microloop channel may extend to a first port 530A and a second port 530B, such the therapeutic agent can be injected into the first port, for example with a binding agent, and flowable material, for example liquid comprising binding agent, can be drawn from the microloop channel 530.

Figures 1, 5C:
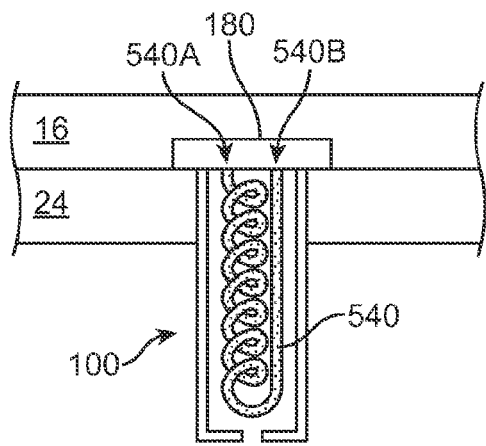
Figures 2, 5C:
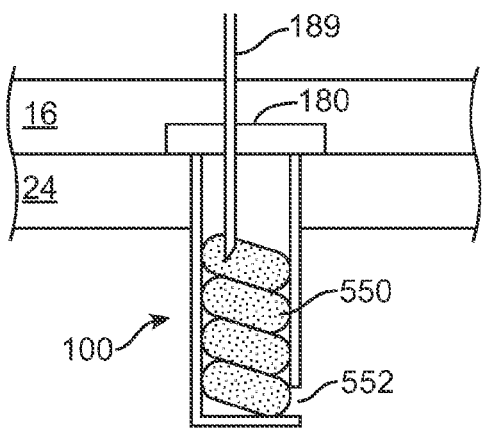

FIG. 5C-1 shows therapeutic device 100 comprising a tortuous channel 540. The tortuous channel may comprise extend from a first port 540A to a second port 540B, such that the therapeutic agent can be injected into the first port and flowable material, for example liquid comprising the binding agent, can be drawn from the second channel.

FIG. 5C-2 shows a therapeutic device comprising a tortuous coiled channel 550. The coiled channel 550 can extend to an exit port 552. A needle 189 can be inserted into the port 180 to inject therapeutic agent into device 100.

Figure 5D:
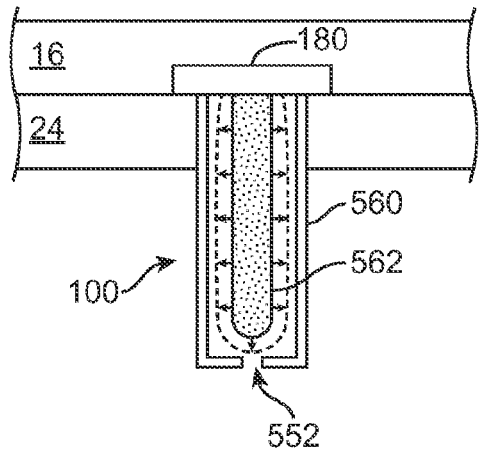
FIG. 5D shows an expandable and contractible structure to retain the therapeutic agent and an outer rigid casing to couple to the sclera.

FIG. 5D shows an expandable and contractible structure 562 to retain the therapeutic agent and an outer rigid casing 560 to couple to the sclera. The expandable structure 562 may comprise a membrane, such as at least one of a bag, a balloon, a flexible reservoir, a diaphragm, or a bag. The outer rigid casing may extend substantially around the structure 562 and may comprise an opening to release liquid into the vitreous humor when the structure is expanded and to draw vitreous humor inside a chamber of the casing when material is drawn from the structure and the structure contacts.

Figure 5E:
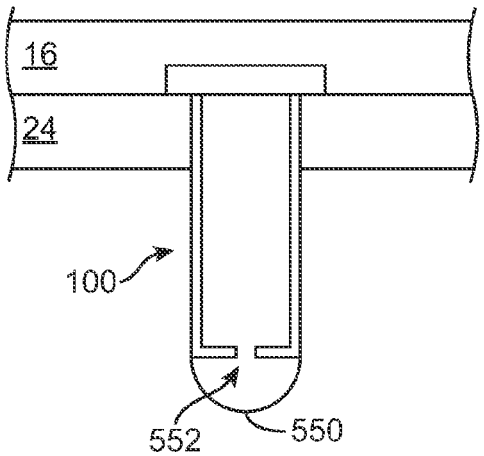
FIG. 5E shows a membrane disposed over an exit port of a therapeutic device.

FIG. 5E shows a membrane 550 disposed over an exit port 552 of therapeutic device 100.

Figure 5F:
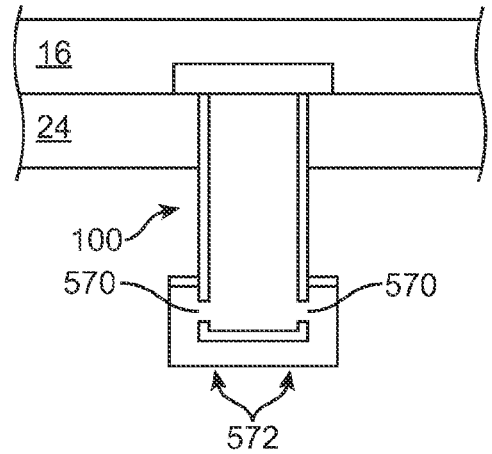
FIG. 5F shows a therapeutic device comprising a tubular membrane clamped onto the therapeutic device.

FIG. 5F shows therapeutic device 100 comprising a tubular membrane 572 clamped onto the therapeutic device over side ports 570 of device 100.

When the protective membranes have pores of 0.2 μm diameter, they are 20 or more times larger than the proteins of interest, which may comprise a model for delivery of the therapeutic agent. For example, molecular weights and diameters of models of proteins of therapeutic interest are

| (a) | IgG | 150 kDa | 10.5 nm |
| (b) | BSA | 69 kDa | 7.2 nm |
| (c) | Fab fragment of IgG | 49 kDa | hydrodynamic diameter not reported |

Therefore, solutions of therapeutic compounds in the size range of IgG and BSA should flow relatively easily through 0.2 um pore size protective membranes used to stop passage of bacterial and other cells.

Binding Materials/Agents may comprise at least one of a chemical binding agent/material, a structural binding agent or material, or an electrostatic binding agent or material. The types of binding agent may comprise a classification composed of non-biodegradable material, for example at glass beads, glass wool or a glass rod. A surface can be derivatized with at least one functional group so as to impart the binding agent or material with the potential for at least one of ionic, hydrophobic, or bioaffinity binding to at least one therapeutic compound.

The binding agent may comprise a biodegradable material. For example, the biodegradation, binding, or a combination of the previous processes may control the diffusion rate.

The binding agent may comprise ion exchange, and the ion exchange may comprise at least one of a functional group, a pH sensitive binding or a positive or negative charge. For example, ion exchange with at least one of diethylaminoethyl or carboxymethyl functional groups.

The binding agent may comprise a pH sensitive binding agent. For example the binding agent can be configured to elute therapeutic agent at a pH of 7, and to bind the therapeutic agent at a pH from about 4 to about 6.5. A cation exchange binding agent can be configured, for example, such that at a pH of 7, the net negative charge of the binding agent decreases causing a decrease in binding of the positively charged drug and release of the therapeutic agent. A target buffer can be provided with the binding agent to reversibly couple the binding agent to the therapeutic agent. The rate of release can be controlled, for example slowed down, by using insolubility of the buffer in the vitreous. Alternatively or in combination the elution can be limited by using a porous membrane or a physical property such as a size of an opening.

The ion exchange may comprise positive or negative ion exchange.

The binding agent may comprise hydrophobic interaction. For example, the binding agent may comprise at least one binding to hydrophobic pockets, for example at least one of methyl, ethyl, propyl, butyl, t-butyl or phenyl functional groups.

The binding agent may comprise affinity, for example at least one of a macromolecular affinity or a metal chelation affinity. Examples can include a hydroxyapatite, or chelated metal, for example zinc. Iminodiacetic acid can be chelated with zinc.

The binding agent may comprise at least one of the following functions: charging, recharging or elution. The charging may comprise a porous material injected therein so as to release the active ingredient. The porous matter may have an extremely large inert surface area, which surface area is available for binding. The recharging may comprise removing carrier+therapeutic agent; and adding freshly "charged" carrier+therapeutic agent.

The elution may comprise a byproduct, for example unbound binding agent that can be removed. For example, diffusion (plug flow) of vitreous to change conditions, e.g. pH to reduce interaction of therapeutic agent+carriers.

Additionally or in the alternative, a sustained drug delivery system of the therapeutic agent may comprise drug delivery packets, e.g. microspheres, that are activated. The packets can be activated with at least one of photochemical activation, thermal activation or biodegradation.

The therapeutic device may comprise at least one structure configured to provide safety precautions. The device may comprise at least one structure to prevent at least one of macrophage or other immune cell within the reservoir body; bacterial penetration; or retinal detachment.

The therapeutic device may be configured for other applications in the body. Other routes of administration of drugs may include at least one of intraocular, oral, subcutaneous, intramuscular, intraperitoneal, intranasal, dermal, intrathecal, intravascular, intra articular, pericardial, intraluminal in organs and gut or the like.

Conditions that may be treated and/or prevented using the drug delivery device and method described herein may include at least one of the following: hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves disease, systemic lupus erythematosus and rheumatoid arthritis, shock and wasting disorders, cystic fibrosis, lactose intolerance, Crohn's disease, inflammatory bowel disease, gastrointestinal or other cancers, degenerative diseases, trauma, multiple systemic conditions such as anemia, and ocular diseases such as, for example, retinal detachment, proliferative retinopathy, proliferative diabetic retinopathy, degenerative disease, vascular diseases, occlusions, infection caused by penetrating traumatic injury, endophthalmitis such as endogenous/systemic infection, post-operative infections, inflammations such as posterior uveitis, retinitis or choroiditis and tumors such as neoplasms and retinoblastoma.

Examples of therapeutic agents 110 that may be delivered by the therapeutic device 100 are described in Table 1A and may include Triamcinolone acetonide, Bimatoprost (Lumigan), Ranibizumab (Lucentis™), Travoprost (Travatan, Alcon), Timolol (Timoptic, Merck), Levobunalol (Betagan, Allergan), Brimonidine (Alphagan, Allergan), Dorzolamide (Trusopt, Merck), Brinzolamide (Azopt, Alcon). Additional examples of therapeutic agents that may be delivered by the therapeutic device include antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluoromethalone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol Hcl and betaxolol Hcl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors. Other therapeutic agents known to those skilled in the art which are capable of controlled, sustained release into the eye in the manner described herein are also suitable for use in accordance with embodiments of the present invention.

The therapeutic agent 110 may comprise one or more of the following: Abarelix, Abatacept, Abciximab, Adalimumab, Aldesleukin, Alefacept, Alemtuzumab, Alpha-1-proteinase inhibitor, Alteplase, Anakinra, Anistreplase, Antihemophilic Factor, Antithymocyte globulin, Aprotinin, Arcitumomab, Asparaginase, Basiliximab, Becaplermin, Bevacizumab, Bivalirudin, Botulinum Toxin Type A, Botulinum Toxin Type B, Capromab, Cetrorelix, Cetuximab, Choriogonadotropin alfa, Coagulation Factor IX, Coagulation factor VIIa, Collagenase, Corticotropin, Cosyntropin, Cyclosporine, Daclizumab, Darbepoetin alfa, Defibrotide, Denileukin diftitox, Desmopressin, Dornase Alfa, Drotrecogin alfa, Eculizumab, Efalizumab, Enfuvirtide, Epoetin alfa, Eptifibatide, Etanercept, Exenatide, Felypressin, Filgrastim, Follitropin beta, Galsulfase, Gemtuzumab ozogamicin, Glatiramer Acetate, Glucagon recombinant, Goserelin, Human Serum Albumin, Hyaluronidase, Ibritumomab, Idursulfase, Immune globulin, Infliximab, Insulin Glargine recombinant, Insulin Lyspro recombinant, Insulin recombinant, Insulin, porcine, Interferon Alfa-2a, Recombinant, Interferon Alfa-2b, Recombinant, Interferon alfacon-1, Interferonalfa-n1, Interferon alfa-n3, Interferon beta-1b, Interferon gamma-1b, Lepirudin, Leuprolide, Lutropin alfa, Mecasermin, Menotropins, Muromonab, Natalizumab, Nesiritide, Octreotide, Omalizumab, Oprelvekin, OspA lipoprotein, Oxytocin, Palifermin, Palivizumab, Panitumumab, Pegademase bovine, Pegaptanib, Pegaspargase, Pegfilgrastim, Peginterferon alfa-2a, Peginterferon alfa-2b, Pegvisomant, Pramlintide, Ranibizumab, Rasburicase, Reteplase, Rituximab, Salmon Calcitonin, Sargramostim, Secretin, Sermorelin, Serum albumin iodonated, Somatropin recombinant, Streptokinase, Tenecteplase, Teriparatide, Thyrotropin Alfa, Tositumomab, Trastuzumab, Urofollitropin, Urokinase, or Vasopressin. The molecular weights of the molecules and indications of these therapeutic agents are set for below in Table 1A, below.

The therapeutic agent 110 may comprise one or more of compounds that act by binding members of the immunophilin family of cellular proteins. Such compounds are known as "immunophilin binding compounds." Immunophilin binding compounds include but are not limited to the "limus" family of compounds. Examples of limus compounds that may be used include but are not limited to cyclophilins and FK506-binding proteins (FKBPs), including sirolimus (rapamycin) and its water soluble analog SDZ-RAD, tacrolimus, everolimus, pimecrolimus, CCI-779 (Wyeth), AP23841 (Ariad), and ABT-578 (Abbott Laboratories).

The limus family of compounds may be used in the compositions, devices and methods for the treatment, prevention, inhibition, delaying the onset of, or causing the regression of angiogenesis-mediated diseases and conditions of the eye, including choroidal neovascularization. The limus family of compounds may be used to prevent, treat, inhibit, delay the onset of, or cause regression of AMD, including wet AMD. Rapamycin may be used to prevent, treat, inhibit, delay the onset of, or cause regression of angiogenesis-mediated diseases and conditions of the eye, including choroidal neovascularization. Rapamycin may be used to prevent, treat, inhibit, delay the onset of, or cause regression of AMD, including wet AMD.

The therapeutic agent 110 may comprise one or more of: pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; .alpha.v/.beta.-3 integrin antagonists; .alpha.-v/.beta.-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1 phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; Visudyne™, snET2 and other photo sensitizers, which may be used with photodynamic therapy (PDT); inhibitors of hepatocyte growth factor (antibodies to the growth factor or its receptors, small molecular inhibitors of the c-met tyrosine kinase, truncated versions of HGF e.g. NK4).

The therapeutic agent 110 may comprise a combination with other therapeutic agents and therapies, including but not limited to agents and therapies useful for the treatment of angiogenesis or neovascularization, particularly CNV. Non-limiting examples of such additional agents and therapies include pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; .alpha.-v/.beta.-3 integrin antagonists; .alpha.v/.beta.-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; Visudyne™, snET2 and other photo sensitizers with photodynamic therapy (PDT); and laser photocoagulation.

The therapeutic agents may be used in conjunction with a pharmaceutically acceptable carrier such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols; aqueous media in the presence of a suspending agent, for example, sodium carboxymethylcellulose, sodium hyaluronate, sodium alginate, poly(vinyl pyrrolidone) and similar compounds, either alone, or with suitable dispensing agents such as lecithin, polyoxyethylene stearate and the like. The carrier may also contain adjuvants such as preserving, stabilizing, wetting, emulsifying agents or other related materials.

The therapeutic device may comprise a container configured to hold at least one therapeutic agent, the container comprising a chamber to hold the at least one therapeutic agent with at least one opening to release the at least one therapeutic agent to the vitreous humor and porous structure 150 placed within the at least one opening. The porous structure 150 may comprise a fixed tortuous, porous material such as a sintered metal, a sintered glass or a sintered polymer with a defined porosity and tortuosity that controls the rate of delivery of the at least one therapeutic agent to the vitreous humor. The rigid porous structures provide certain advantages over capillary tubes, erodible polymers and membranes as a mechanism for controlling the release of a therapeutic agent or agents from the therapeutic device. These advantages include the ability of the rigid porous structure to comprise a needle stop, simpler and more cost effective manufacture, flushability for cleaning or declogging either prior to or after implantation, high efficiency depth filtration of microorganisms provided by the labyrinths of irregular paths within the structure and greater robustness due to greater hardness and thickness of the structure compared to a membrane or erodible polymer matrix. Additionally, when the rigid porous structure is manufactured from a sintered metal, ceramic, glass or certain plastics, it can be subjected to sterilization and cleaning procedures, such as heat or radiation based sterilization and depyrogenation, that might damage polymer and other membranes. In certain embodiments, as illustrated in example 9, the rigid porous structure may be configured to provide a therapeutically effective, concentration of the therapeutic agent in the vitreous for at least 6 months. This release profile provided by certain configurations of the rigid porous structures enables a smaller device which is preferred in a small organ such as the eye where larger devices may alter or impair vision.

Figures 1, 6A:
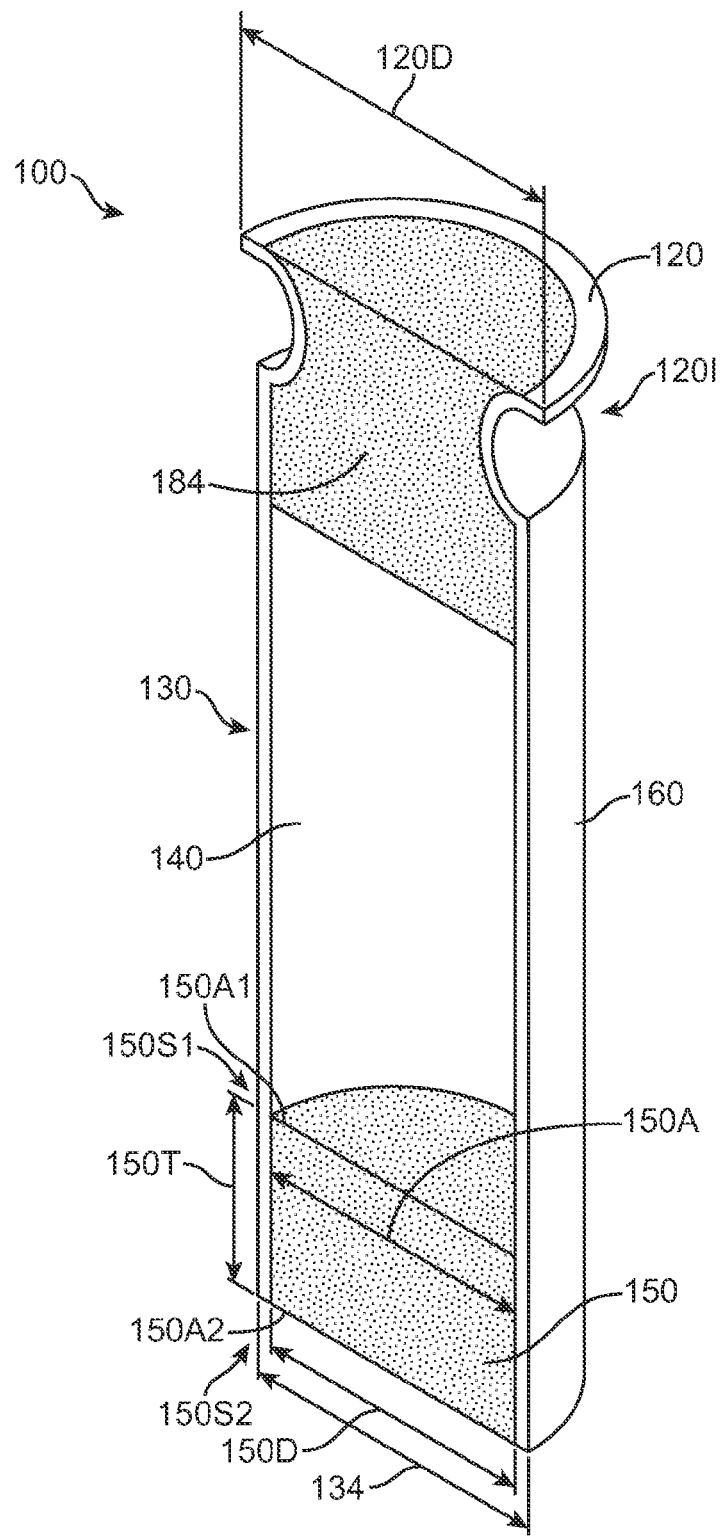
Figures 2, 6A:
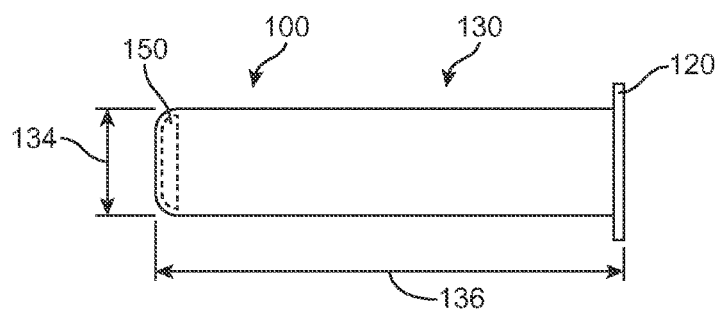

FIG. 6A1 shows a therapeutic device 100 comprising a container 130 having a penetrable barrier 184 disposed on a first end, a porous structure 150 disposed on a second end to release therapeutic agent for an extended period, and a retention structure 120 comprising an extension protruding outward from the container to couple to the sclera and the conjunctiva. The extending protrusion of the retention structure may comprise a diameter 120D. The retention structure may comprise an indentation 1201 sized to receive the sclera. The container may comprise a tubular barrier 160 that defines at least a portion of the reservoir, and the container may comprise a width, for example a diameter 134. The diameter 134 can be sized within a range, for example within a range from about 0.5 to about 4 mm, for example within a range from about 1 to 3 mm and can be about 2 mm, for example. The container may comprise a length 136, sized so as to extend from the conjunctive to the vitreous to release the therapeutic agent into the vitreous. The length 136 can be sized within a range, for example within a range from about 2 to about 14 mm, for example within a range from about 4 to 10 mm and can be about 7 mm, for example. The volume of the reservoir may be substantially determined by an inner cross sectional area of the tubular structure and distance from the porous structure to the penetrable barrier. The retention structure may comprise an annular extension having a retention structure diameter greater than a diameter of the container. The retention structure may comprise an indentation configured to receive the sclera when the extension extends between the sclera and the conjunctive. The penetrable barrier may comprise a septum disposed on a proximal end of the container, in which the septum comprises a barrier that can be penetrated with a sharp object such as a needle for injection of the therapeutic agent. The porous structure may comprise a cross sectional area 150A sized to release the therapeutic agent for the extended period.

The porous structure 150 may comprise a first side coupled to the reservoir 150 S1 and a second side to couple to the vitreous 150S2. The first side may comprise a first area 150A1 and the second side may comprise a second area 150A2. The porous structure may comprise a thickness 105T. The porous structure many comprise a diameter 150D.

The volume of the reservoir 140 may comprise from about 5 uL to about 2000 uL of therapeutic agent, or for example from about 10 uL to about 200 uL of therapeutic agent.

The therapeutic agent stored in the reservoir of the container comprises at least one of a solid comprising the therapeutic agent, a solution comprising the therapeutic agent, a suspension comprising the therapeutic agent, particles comprising the therapeutic agent adsorbed thereon, or particles reversibly bound to the therapeutic agent. For example, reservoir may comprise a suspension of a cortico-steroid such as triamcinolone acetonide to treat inflammation of the retina. The reservoir may comprise a buffer and a suspension of a therapeutic agent comprising solubility within a range from about 1 ug/mL to about 100 ug/mL, such as from about 1 ug/mL to about 40 ug/mL. For example, the therapeutic agent may comprise a suspension of triamcinolone acetonide having a solubility of approximately 19 ug/mL in the buffer at 37 C when implanted.

The release rate index may comprise many values, and the release rate index with the suspension may be somewhat higher than for a solution in many embodiments, for example. The release rate index may be no more than about 5, and can be no more than about 2.0, for example no more than about 1.5, and in many embodiments may be no more than about 1.2, so as to release the therapeutic agent with therapeutic amounts for the extended time.

The therapeutic device, including for example, the retention structure and the porous structure, may be sized to pass through a lumen of a catheter.

The porous structure may comprise a needle stop that limits penetration of the needle. The porous structure may comprise a plurality of channels configured for the extended release of the therapeutic agent. The porous structure may comprise a rigid sintered material having characteristics suitable for the sustained release of the material.

FIG. 6A2 shows a therapeutic device as in FIG. 6A comprising a rounded distal end.

Figure 6B:
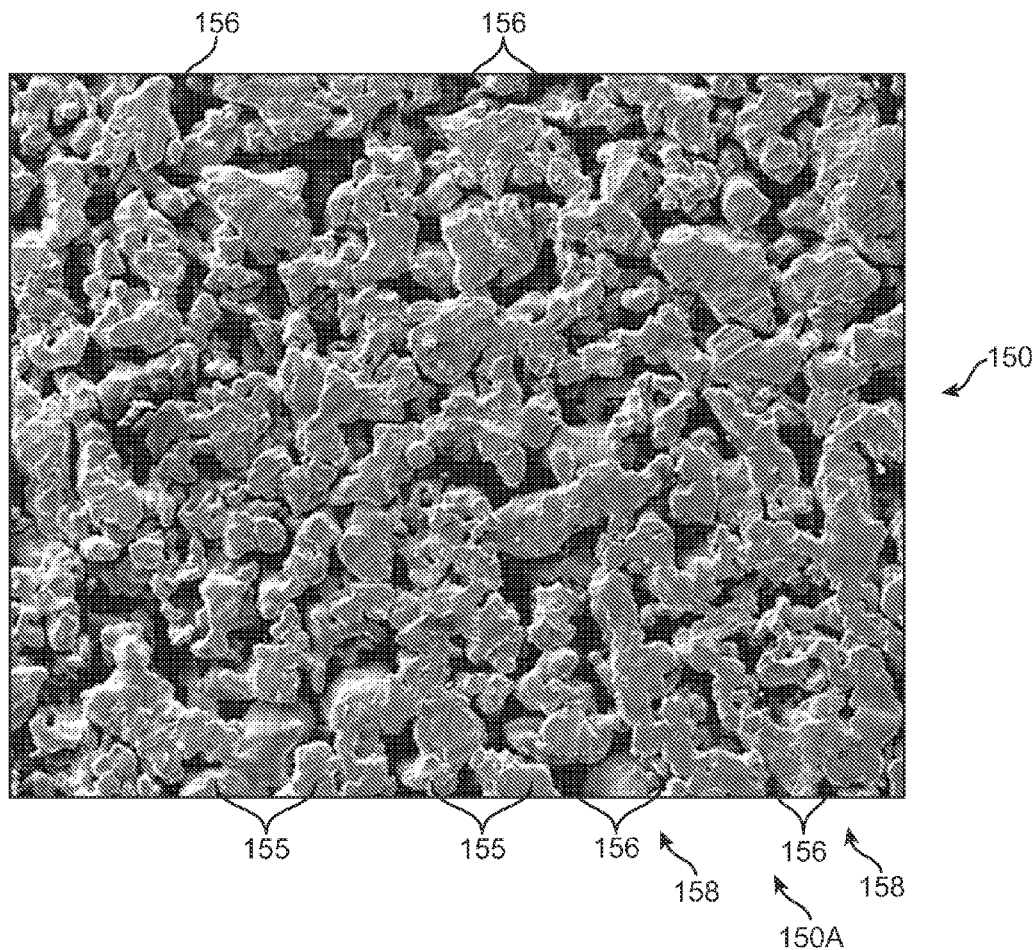
FIG. 6B shows a rigid porous structure configured for sustained release with a device as in FIG. 6A.
Figures 1, 6B:
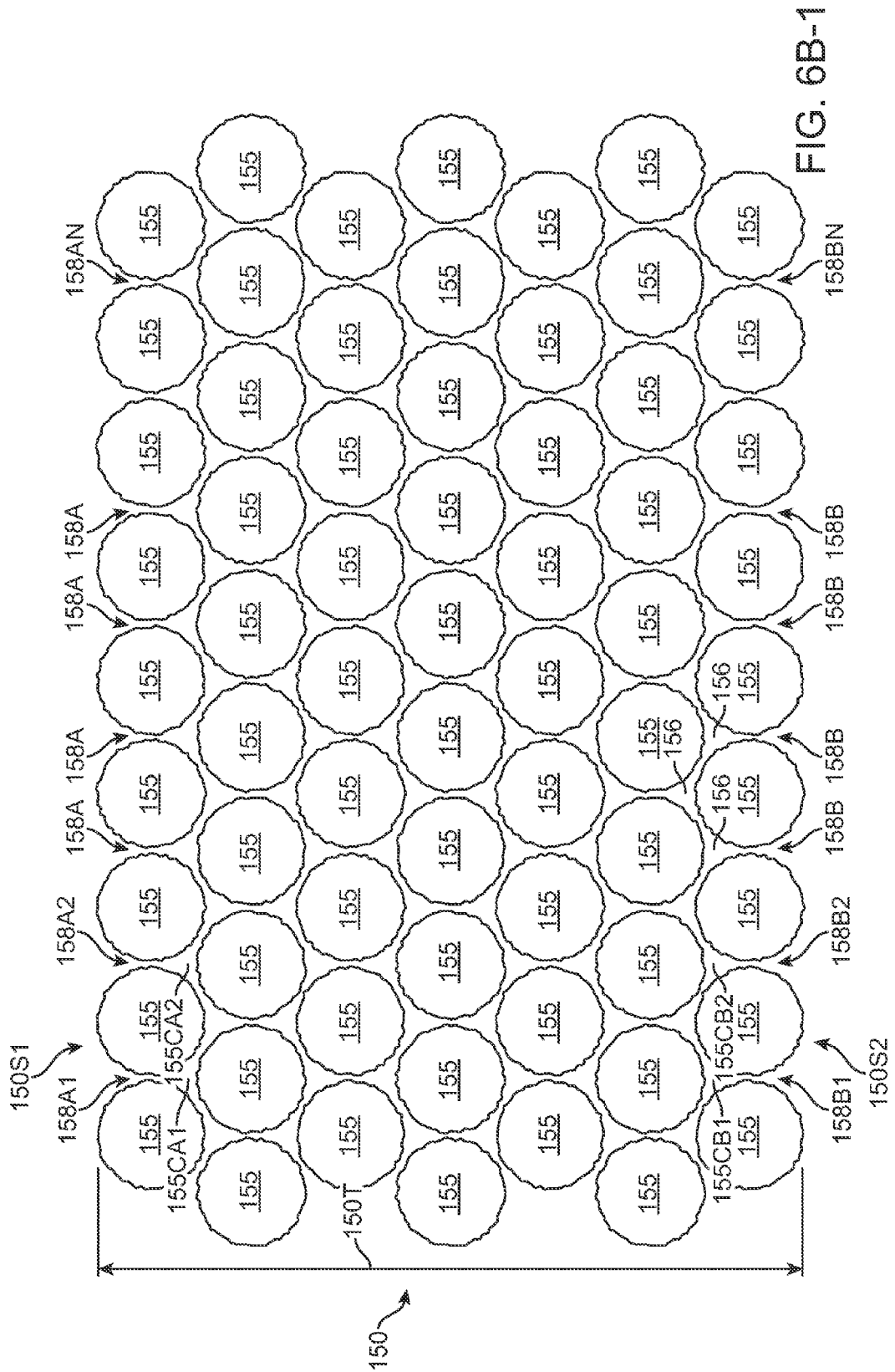
Figures 2, 6B:
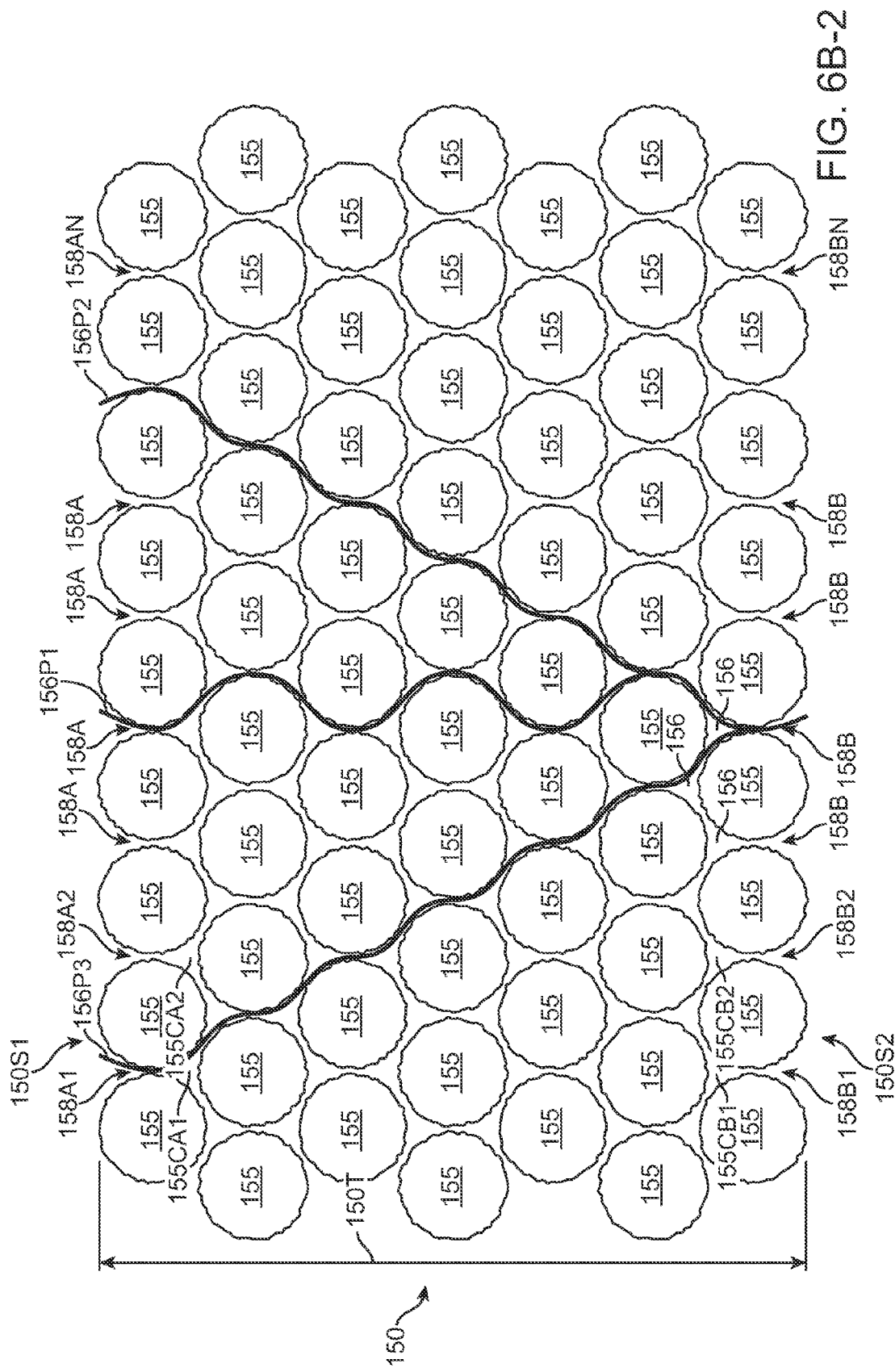
Figures 3, 6B:
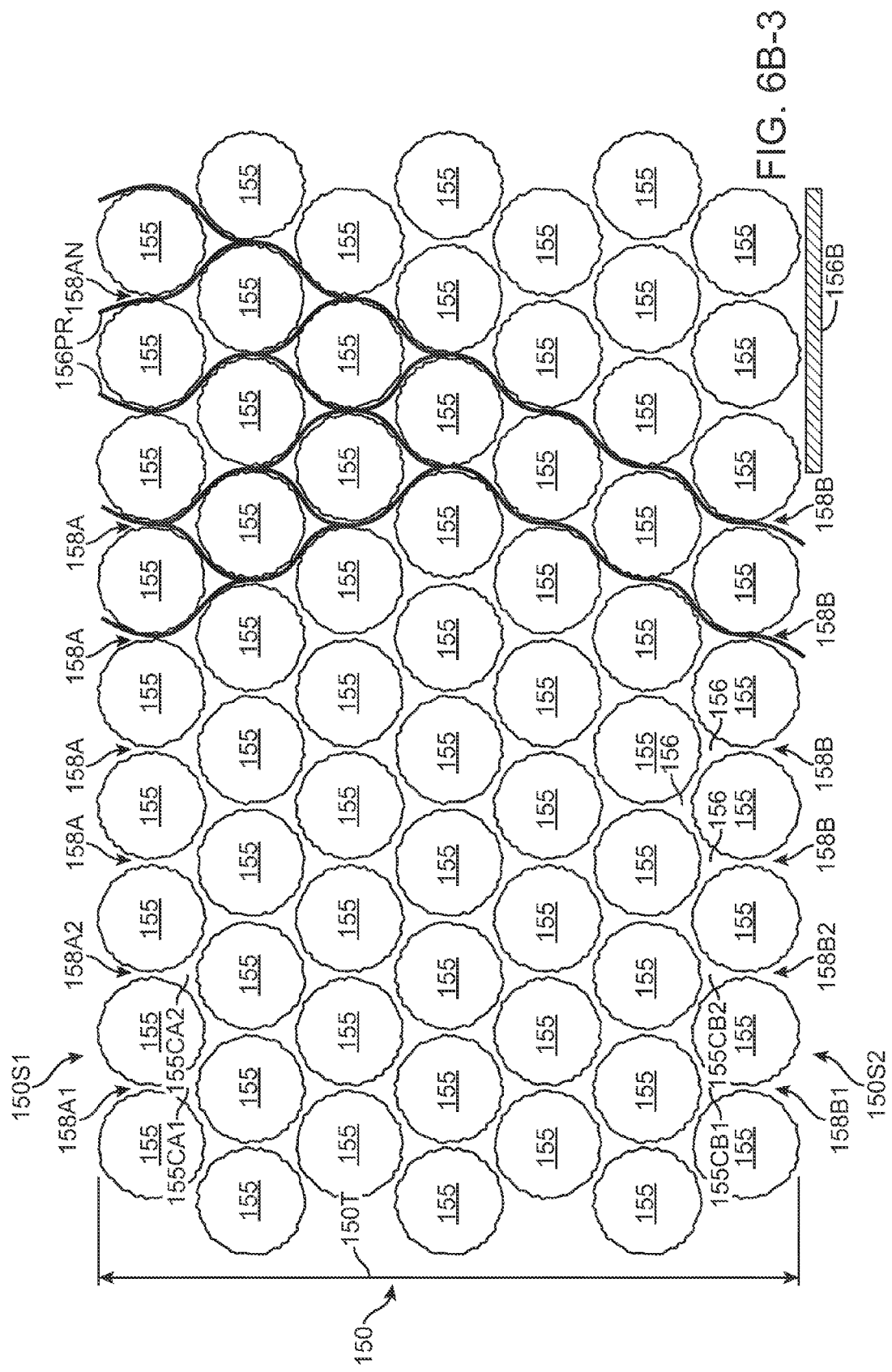

FIG. 6B shows a rigid porous structure as in FIG. 6A. The rigid porous structure 158 comprises a plurality of interconnecting channels 156. The porous structure comprises a sintered material composed of interconnected grains 155 of material. The interconnected grains of material define channels that extend through the porous material to release the therapeutic agent. The channels may extend around the sintered grains of material, such that the channels comprise interconnecting channels extending through the porous material.

The rigid porous structure can be configured for injection of the therapeutic agent into the container in many ways. The channels of the rigid porous structure may comprise substantially fixed channels when the therapeutic agent is injected into the reservoir with pressure. The rigid porous structure comprises a hardness parameter within a range from about 160 Vickers to about 500 Vickers. In some embodiments the rigid porous structure is formed from sintered stainless steel and comprises a hardness parameter within a range from about 200 Vickers to about 240 Vickers. In some embodiments it is preferred to inhibit ejection of the therapeutic agent through the porous structure during filling or refilling the reservoir of the therapeutic device with a fluid. In these embodiments the channels of the rigid porous structure comprise a resistance to flow of an injected solution or suspension through a thirty gauge needle such that ejection of said solution or suspension through the rigid porous structure is substantially inhibited when said solution or suspension is injected into the reservoir of the therapeutic device. Additionally, these embodiments may optionally comprise an evacuation vent or an evacuation reservoir under vacuum or both to facilitate filling or refilling of the reservoir.

The reservoir and the porous structure can be configured to release therapeutic amounts of the therapeutic agent in many ways. The reservoir and the porous structure can be configured to release therapeutic amounts of the therapeutic agent corresponding to a concentration of at least about 0.1 ug per ml of vitreous humor for an extended period of at least about three months. The reservoir and the porous structure can be configured to release therapeutic amounts of the therapeutic agent corresponding to a concentration of at least about 0.1 ug per ml of vitreous humor and no more than about 10 ug per ml for an extended period of at least about three months. The therapeutic agent may comprise at least a fragment of an antibody and a molecular weight of at least about 10 k Daltons. For example, the therapeutic agent may comprise one or more of ranibizumab or bevacizumab. Alternatively or in combination, the therapeutic agent may comprise a small molecule drug suitable for sustained release. The reservoir and the porous structure may be configured to release therapeutic amounts of the therapeutic agent corresponding to a concentration of at least about 0.1 ug per ml of vitreous humor and no more than about 10 ug per ml for an extended period of at least about 3 months or at least about 6 months. The reservoir and the porous structure can be configured to release therapeutic amounts of the therapeutic agent corresponding to a concentration of at least about 0.1 ug per ml of vitreous humor and no more than about 10 ug per ml for an extended period of at least about twelve months or at least about two years or at least about three years. The reservoir and the porous structure may also be configured to release therapeutic amounts of the therapeutic agent corresponding to a concentration of at least about 0.01 ug per ml of vitreous humor and no more than about 300 ug per ml for an extended period of at least about 3 months or 6 months or 12 months or 24 months.

The channels of the rigid porous structure comprise a hydrogel configured to limit a size of molecules passed through the channels of the rigid porous structure. For example, the hydrogel can be formed within the channels and may comprise an acrylamide gel. The hydrogel comprises a water content of at least about 70%. For example, the hydrogel may comprise a water content of no more than about 90% to limit molecular weight of the therapeutic agent to about 30 k Daltons. The hydrogel comprises a water content of no more than about 95% to limit molecular weight of the therapeutic agent to about 100 k Daltons. The hydrogel may comprise a water content within a range from about 90% to about 95% such that the channels of the porous material are configured to pass Lucentis™ and substantially not pass Avastin™.

The rigid porous structure may comprise a composite porous material that can readily be formed in or into a wide range of different shapes and configurations. For example, the porous material can be a composite of a metal, aerogel or ceramic foam (i.e., a reticulated inter-cellular structure in which the interior cells are interconnected to provide a multiplicity of pores passing through the volume of the structure, the walls of the cells themselves being substantially continuous and non-porous, and the volume of the cells relative to that of the material forming the cell walls being such that the overall density of the intercellular structure is less than about 30 percent theoretical density) the through pores of which are impregnated with a sintered powder or aerogel. The thickness, density, porosity and porous characteristics of the final composite porous material can be varied to conform with the desired release of the therapeutic agent.

Embodiments comprise a method of making an integral (i.e., single-component) porous structure. The method may comprise introducing particles into a mold having a desired shape for the porous structure. The shape includes a proximal end defining a plurality of proximal porous channel openings to couple to the reservoir, a distal end defining a plurality of outlet channel openings to couple to the vitreous humor of the eye, a plurality of blind inlet cavities extending into the filter from the proximal openings, and a plurality of blind outlet cavities extending into the porous structure from the outlet channel openings. The method further includes applying pressure to the mold, thereby causing the particles to cohere and form a single component, and sintering the component to form the porous structure. The particles can be pressed and cohere to form the component without the use of a polymeric binder, and the porous structure can be formed substantially without machining.

The mold can be oriented vertically with the open other end disposed upwardly, and metal powder having a particle size of less than 20 micrometers can be introduced into the cavity through the open end of the mold while vibrating the mold to achieve substantially uniform packing of the metal powder in the cavity. A cap can be placed on the open other end of the mold, and pressure is applied to the mold and thereby to the metal powder in the cavity to cause the metal powder to cohere and form a cup-shaped powdered metal structure having a shape corresponding to the mold. The shaped powdered metal structure can be removed from the mold, and sintered to obtain a porous sintered metal porous structure.

The metal porous structure can be incorporated into the device by a press fit into an impermeable structure with an opening configured to provide a tight fit with the porous structure. Other means, such as welding, known to those skilled in the art can be used to incorporate the porous structure into the device. Alternatively, or in combination, the powdered metal structure can be formed in a mold where a portion of the mold remains with the shaped powdered metal structure and becomes part of the device. This may be advantageous in achieving a good seal between the porous structure and the device.

The release rate of therapeutic agent through a porous body, such as a sintered porous metal structure or a porous glass structure, may be described by diffusion of the of the therapeutic agent within the porous structure with the channel parameter, and with an effective diffusion coefficient equal to the diffusion coefficient of the therapeutic agent in the liquid that fills the reservoir multiplied by the Porosity and a Channel Parameter of the porous body:

Release Rate=$(D\,P/F)A(c_R - c_v)/L$, where:

$c_R$=Concentration in reservoir
$c_v$=Concentration outside of the reservoir or in the vitreous D=Diffusion coefficient of the therapeutic agent in the reservoir solution P=Porosity of porous structure F=Channel parameter that may correspond to a tortuosity parameter of channels of porous structure A=Area of porous structure L=Thickness (length) of porous structure $$\text{Cumulative Release} = 1 - cR/cR0 = 1 - \exp((-D\,PA/FL\,V_R)t), \text{ where}$$

t=time, Vr=reservoir volume

The release rate index can (hereinafter RRI) be used to determine release of the therapeutic agent. The RRI may be defined as (PA/FL), and the RRI values herein will have units of mm unless otherwise indicated. Many of the porous structures used in the therapeutic delivery devices described here have an RRI of no more than about 5.0, often no more than about 2.0, and can be no more than about 1.2 mm.

The channel parameter can correspond to an elongation of the path of the therapeutic agent released through the porous structure. The porous structure may comprise many interconnecting channels, and the channel parameter can correspond to an effective length that the therapeutic agent travels along the interconnecting channels of the porous structure from the reservoir side to the vitreous side when released. The channel parameter multiplied by the thickness (length) of the porous structure can determine the effective length that the therapeutic agent travels along the interconnecting channels from the reservoir side to the vitreous side. For example, the channel parameter (F) of about 1.5 corresponds to interconnecting channels that provide an effective increase in length traveled by the therapeutic agent of about 50%, and for a 1 mm thick porous structure the effective length that the therapeutic agent travels along the interconnecting channels from the reservoir side to the vitreous side corresponds to about 1.5 mm. The channel parameter (F) of at least about 2 corresponds to interconnecting channels that provide an effective increase in length traveled by the therapeutic agent of about 100%, and for a 1 mm thick porous structure the effective length that the therapeutic agent travels along the interconnecting channels from the reservoir side to the vitreous side corresponds to at least about 2.0 mm. As the porous structure comprises many interconnecting channels that provide many alternative paths for release of the therapeutic agent, blockage of some of the channels provides no substantial change in the effective path length through the porous structure as the alternative interconnecting channels are available, such that the rate of diffusion through the porous structure and the release of the therapeutic agent are substantially maintained when some of the channels are blocked.

If the reservoir solution is aqueous or has a viscosity similar to water, the value for the diffusion coefficient of the therapeutic agent (TA) in water at the temperature of interest may be used. The following equation can be used to estimate the diffusion coefficient at 37° C. from the measured value of $D_{BSA,20C}$=6.1 e−7 cm2/s for bovine serum albumin in water at 20° C. (Molokhia et al, *Exp Eye Res* 2008):

$$D_{TA,37C} = D_{BSA,20C}(\eta_{20C}/\eta_{37C})(MW_{BSA}/MW_{TA})^{1/3}$$

where

MW refers to the molecular weight of either BSA or the test compound and η is the viscosity of water. The following lists diffusion coefficients of proteins of interest.

| Compound | MW | Temp C. | Diff Coeff (cm 2/s) |
|---|---|---|---|
| BSA | 69,000 | 20 | 6.1E−07 |
| BSA | 69,000 | 37 | 9.1E−07 |
| Ranibizumab | 48,000 | 20 | 6.9E−07 |
| Ranibizumab | 48,000 | 37 | 1.0E−06 |
| Bevacizumab | 149,000 | 20 | 4.7E−07 |
| Bevacizumab | 149,000 | 37 | 7.1E−07 |

Small molecules have a diffusion coefficient similar to fluorescein (MW=330, D=4.8 to 6 e-6 cm²/s from Stay, M S et al. *Pharm Res* 2003, 20(1), pp. 96-102). For example, the small molecule may comprise a glucocorticoid such as triamcinolone acetonide having a molecular weight of about 435.

The porous structure comprises a porosity, a thickness, a channel parameter and a surface area configured to release therapeutic amounts for the extended period. The porous material may comprise a porosity corresponding to the fraction of void space of the channels extending within the material. The porosity comprises a value within a range from about 3% to about 70%. In other embodiments, the porosity comprises a value with a range from about 5% to about 10% or from about 10% to about 25%, or for example from about 15% to about 20%. Porosity can be determined from the weight and macroscopic volume or can be measured via nitrogen gas adsorption The porous structure may comprise a plurality of porous structures, and the area used in the above equation may comprise the combined area of the plurality of porous structures.

The channel parameter may comprise a fit parameter corresponding to the tortuosity of the channels. For a known porosity, surface area and thickness of the surface parameter, the curve fit parameter F, which may correspond to tortuosity of the channels can be determined based on experimental measurements. The parameter PA/FL can be used to determine the desired sustained release profile, and the values of P, A, F and L determined. The rate of release of the therapeutic agent corresponds to a ratio of the porosity to the channel parameter, and the ratio of the porosity to the channel parameter can be less than about 0.5 such that the porous structure releases the therapeutic agent for the extended period. For example, the ratio of the porosity to the channel parameter is less than about 0.1 or for example less than about 0.2 such that the porous structure releases the therapeutic agent for the extended period. The channel parameter may comprise a value of at least about 1, such as at least about 1.2. For example, the value of the channel parameter may comprise at least about 1.5, for example at least about 2, and may comprise at least about 5. The channel parameter can be within a range from about 1.1 to about 10, for example within a range from about 1.2 to about 5. A person of ordinary skill in the art can conduct experiments based on the teachings described herein to determine empirically the channel parameter to release the therapeutic agent for an intended release rate profile.

The area in the model originates from the description of mass transported in units of flux; i.e., rate of mass transfer per unit area. For simple geometries, such as a porous disc mounted in an impermeable sleeve of equal thickness, the area corresponds to one face of the disc and the thickness, L, is the thickness of the disc. For more complex geometries, such as a porous body in the shape of a truncated cone, the effective area is a value in between the area where therapeutic agent enters the porous body and the area where therapeutic agent exits the porous body.

A model can be derived to describe the release rate as a function of time by relating the change of concentration in the reservoir to the release rate described above. This model assumes a solution of therapeutic agent where the concentration in the reservoir is uniform. In addition, the concentration in the receiving fluid or vitreous is considered negligible ($c_V=0$). Solving the differential equation and rearrangement yields the following equations describing the concentration in the reservoir as a function of time, t, and volume of the reservoir, $V_R$, for release of a therapeutic agent from a solution in a reservoir though a porous structure.

$$c_R = c_{R0} \exp((-D\ PA/FL\ V_R)t)$$

and Cumulative Release=$1-c_R/c_{R0}$

When the reservoir contains a suspension, the concentration in reservoir, $c_R$, is the dissolved concentration in equilibrium with the solid (i.e., the solubility of the therapeutic agent). In this case, the concentration in the reservoir is constant with time, the release rate is zero order, and the cumulative release increases linearly with time until the time when the solid is exhausted.

Therapeutic concentrations for many ophthalmic therapeutic agents may be determined experimentally by measuring concentrations in the vitreous humor that elicit a therapeutic effect. Therefore, there is value in extending predictions of release rates to predictions of concentrations in the vitreous. A one-compartment model may be used to describe elimination of therapeutic agent from eye tissue.

Current intravitreal administration of therapeutic agents such as Lucentis™ involves a bolus injection. A bolus injection into the vitreous may be modeled as a single exponential with rate constant, k=0.693/half-life and a cmax=dose/$V_v$, where $V_v$ is the vitreous volume. As an example, the half-life for ranibizumab is approximately 3 days in the rabbit and the monkey (Gaudreault et al) and 9 days in humans (Lucentis™ package insert). The vitreous volume is approximately 1.5 mL for the rabbit and monkey and 4.5 mL for the human eye. The model predicts an initial concentration of 333 ug/mL for a bolus injection of 0.5 mg Lucentis™ into the eye of a monkey. This concentration decays to a vitreous concentration of 0.1 ug/mL after about a month.

For devices with extended release, the concentration in the vitreous changes slowly with time. In this situation, a model can be derived from a mass balance equating the release rate from the device (described by equations above) with the elimination rate from the eye, $k\ c_v\ V_v$. Rearrangement yields the following equation for the concentration in the vitreous:

$$c_v = \text{Release rate from device}/k\ V_v.$$

Since the release rate from a device with a solution of therapeutic agent decreases exponentially with time, the concentration in the vitreous decreases exponentially with the same rate constant. In other words, vitreous concentration decreases with a rate constant equal to D PA/FL $V_R$ and, hence, is dependent on the properties of the porous structure and the volume of the reservoir.

Since the release rate is zero order from a device with a suspension of therapeutic agent, the vitreous concentration will also be time-independent. The release rate will depend on the properties of the porous structure via the ratio, PA/FL, but will be independent of the volume of the reservoir until the time at which the drug is exhausted.

The channels of the rigid porous structure can be sized in many ways to release the intended therapeutic agent. For example, the channels of the rigid porous structure can be sized to pass therapeutic agent comprising molecules having a molecular weight of at least about 100 Daltons or for example, at least about 50 k Daltons. The channels of the rigid porous structure can be sized to pass therapeutic agent comprising molecules comprising a cross-sectional size of no more than about 10 nm. The channels of the rigid porous structure comprise interconnecting channels configured to pass the therapeutic agent among the interconnecting channels. The rigid porous structure comprises grains of rigid material and wherein the interconnecting channels extend at least partially around the grains of rigid material to pass the therapeutic agent through the porous material. The grains of rigid material can be coupled together at a loci of attachment and wherein the interconnecting channels extend at least partially around the loci of attachment.

The porous structure and reservoir may be configured to release the glucocorticoid for an extended time of at least about six months with a therapeutic amount of glucocorticoid of corresponding to an in situ concentration within a range from about 0.05 ug/mL to about 4 ug/mL, for example from 0.1 ug/mL to about 4 ug/mL, so as to suppress inflammation in the retina-choroid.

The porous structure comprises a sintered material. The sintered material may comprise grains of material in which the grains comprise an average size of no more than about 20 um. For example, the sintered material may comprise grains of material in which the grains comprise an average size of no more than about 10 um, an average size of no more than about 5 um, or an average size of no more than about 1 um. The channels are sized to pass therapeutic quantities of the therapeutic agent through the sintered material for the extended time based on the grain size of the sintered material and processing parameters such as compaction force and time and temperature in the furnace. The channels can be sized to inhibit penetration of microbes including bacteria and fungal spores through the sintered material.

The sintered material comprises a wettable material to inhibit bubbles within the channels of the material.

The sintered material comprises at least one of a metal, a ceramic, a glass or a plastic. The sintered material may comprises a sintered composite material, and the composite material comprises two or more of the metal, the ceramic, the glass or the plastic. The metal comprises at least one of Ni, Ti, nitinol, stainless steel including alloys such as 304, 304L, 316 or 316L, cobalt chrome, elgiloy, hastealloy, c-276 alloy or Nickel 200 alloy. The sintered material may comprise a ceramic. The sintered material may comprise a glass. The plastic may comprise a wettable coating to inhibit bubble formation in the channels, and the plastic may comprise at least one of polyether ether ketone (PEEK), polyethylene, polypropylene, polyimide, polystyrene, polycarbonate, polyacrylate, polymethacrylate, or polyamide.

The rigid porous structure may comprise a plurality of rigid porous structures coupled to the reservoir and configured to release the therapeutic agent for the extended period. For example, additional rigid porous structure can be disposed along the container, for example the end of the container may comprise the porous structure, and an additional porous structure can be disposed along a distal portion of the container, for example along a tubular sidewall of the container.

The therapeutic device can be tuned to release therapeutic amounts of the therapeutic agent above the minimum inhibitory concentration for an extended time based on bolus injections of the therapeutic agent. For example, the volume of the chamber of the reservoir can be sized with the release rate of the porous structure based on the volume of the bolus injection. A formulation of a therapeutic agent can be provided, for example a known intravitreal injection formulation. The therapeutic agent can be capable of treating the eye with bolus injections, such that the formulation has a corresponding period between each of the bolus injections to treat the eye. For example the bolus injections may comprise monthly injections. Each of the bolus injections comprises a volume of the formulation, for example 50 uL. Each of the bolus injections of the therapeutic agent may correspond to a range of therapeutic concentrations of the therapeutic agent within the vitreous humor over the time course between injections, and the device can be tuned so as to release therapeutic amounts of the therapeutic agent such that the vitreous concentrations of the released therapeutic agent from the device are within the range of therapeutic concentrations of the corresponding bolus injections. For example, the therapeutic agent may comprise a minimum inhibitory concentration to treat the eye, for example at least about 3 ug/mL, and the values of the range of therapeutic concentrations can be at least about 3 ug/mL. The therapeutic device can be configured to treat the eye with an injection of the monthly volume of the formulation into the device, for example through the penetrable barrier. The reservoir of the container has a chamber to contain a volume of the therapeutic agent, for example 35 uL, and a mechanism to release the therapeutic agent from the chamber to the vitreous humor.

The volume of the container and the release mechanism can be tuned to treat the eye with the therapeutic agent with vitreous concentrations within the therapeutic range for an extended time with each injection of the quantity corresponding to the bolus injection, such that the concentration of the therapeutic agent within the vitreous humor remains within the range of therapeutic concentrations and comprises at least the minimum inhibitory concentration. The extended time may comprise at least about twice the corresponding period of the bolus injections. The release mechanism comprises one or more of a porous frit, a sintered porous frit, a permeable membrane, a semi-permeable membrane, a capillary tube or a tortuous channel, nano-structures, nano-channels or sintered nano-particles. For example, the porous fit may comprises a porosity, cross sectional area, and a thickness to release the therapeutic agent for the extended time. The volume of the container reservoir can be sized in many ways in relation to the volume of the injected formulation and can be larger than the volume of injected formulation, smaller than the volume of injected formulation, or substantially the same as the volume of injected formulation. For example, the volume of the container may comprise no more than the volume of the formulation, such that at least a portion of the formulation injected into the reservoir passes through the reservoir and comprises a bolus injection to treat the patient immediately. As the volume of the reservoir is increased, the amount of formulation released to the eye through the porous structure upon injection can decrease along with the concentration of active ingredient of the therapeutic agent within the reservoir, and the release rate index can be increased appropriately so as to provide therapeutic amounts of therapeutic agent for the extended time. For example, the volume of the reservoir of the container can be greater than the volume corresponding to the bolus injection, so as to provide therapeutic amounts for at least about five months, for example 6 months, with an injection volume corresponding to a monthly injection of Lucentis™. For example, the formulation may comprise commercially available Lucentis™, 50 uL, and the reservoir may comprise a volume of about 100 uL and provide therapeutic vitreous concentrations of at least about 3 ug/mL for six months with 50 uL of Lucentis™ injected into the reservoir.

The chamber may comprise a substantially fixed volume and the release rate mechanism comprises a substantially rigid structure to maintain release of the therapeutic agent above the minimum inhibitory concentration for the extended time with each injection of a plurality of injections.

A first portion of the injection may pass through the release mechanism and treat the patient when the formulation is injected, and a second portion of the formulation can be contained in the chamber when the formulation is injected.

FIG. 6B-1 shows interconnecting channels 156 extending from first side 150S1 to second side 150S2 of the porous structure as in FIG. 6B. The interconnecting channels 156 extend to a first opening 158A1, a second opening 158A2 and an Nth opening 158AN on the first side 150S1. The interconnecting channels 156 extend to a first opening 158B1, a second opening 158B2 and an Nth opening 158BN on the second side 150S2. Each of the openings of the plurality of channels on the first side is connected to each of the openings of plurality of channels on the second side, such that effective length traveled along the channels is greater than thickness 150T. The channel parameter can be within a range from about 1.1 to about 10, such that the effective length is within a range from about 1.1 to 10 times the thickness 150T. For example, the channel parameter can be about 1 and the porosity about 0.2, such that the effective length corresponds to at least about 5 times the thickness 150T.

FIG. 6B-2 shows a plurality of paths of the therapeutic agent along the interconnecting channels extending from a first side 150S1 to a second side 150S2 of the porous structure as in FIGS. 6B and 6B-1. The plurality of paths comprises a first path 156P1 extending from the first side to the second side, a second path 156P2 extending from the first side to the second side and a third path 156P3 extending from the first side to the second side, and many additional paths. The effect length of each of first path P1, second path P2 and third path P3 is substantially similar, such that each opening on the first side can release the therapeutic agent to each interconnected opening on the second side. The substantially similar path length can be related to the sintered grains of material and the channels that extend around the sintered material. The porous structure may comprise randomly oriented and connected grains of material, packed beads of material, or combinations thereof. The channel parameter can be related to the structure of the sintered grains of material and corresponding interconnecting channels, porosity of the material, and percolation threshold. Work in relation to embodiments shows that the percolation threshold of the sintered grains may be below the porosity of the porous fit structure, such that the channels are highly inter-connected. The sintered grains of material can provide interconnected channels, and the grains can be selected to provide desired porosity and channel parameters and RRI as described herein.

The channel parameter and effective length from the first side to the second side can be configured in many ways. The channel parameter can be greater than 1 and within a range from about 1.2 to about 5.0, such that the effective length is within a range about 1.2 to 5.0 times the thickness 150T, although the channel parameter may be greater than 5, for example within a range from about 1.2 to 10. For example, the channel parameter can be from about 1.3 to about 2.0, such that the effective length is about 1.3 to 2.0 times the thickness 150T. For example, experimental testing has shown the channel parameter can be from about 1.4 to about 1.8, such that the effective length is about 1.4 to 1.8 times the thickness 150T, for example about 1.6 times the thickness. These values correspond to the paths of the channels around the sintered grains of material, and may correspond, for example, to the paths of channels around packed beads of material.

FIG. 6B-3 shows blockage of the openings with a covering 156B and the plurality of paths of the therapeutic agent along the interconnecting channels extending from a first side to a second side of the porous structure as in FIGS. 6B and 6B-1. A plurality of paths 156PR extend from the first side to the second side couple the first side to the second side where one of the sides is covered, such that the flow rate is maintained when one of the sides is partially covered.

Figures 5, 6B:
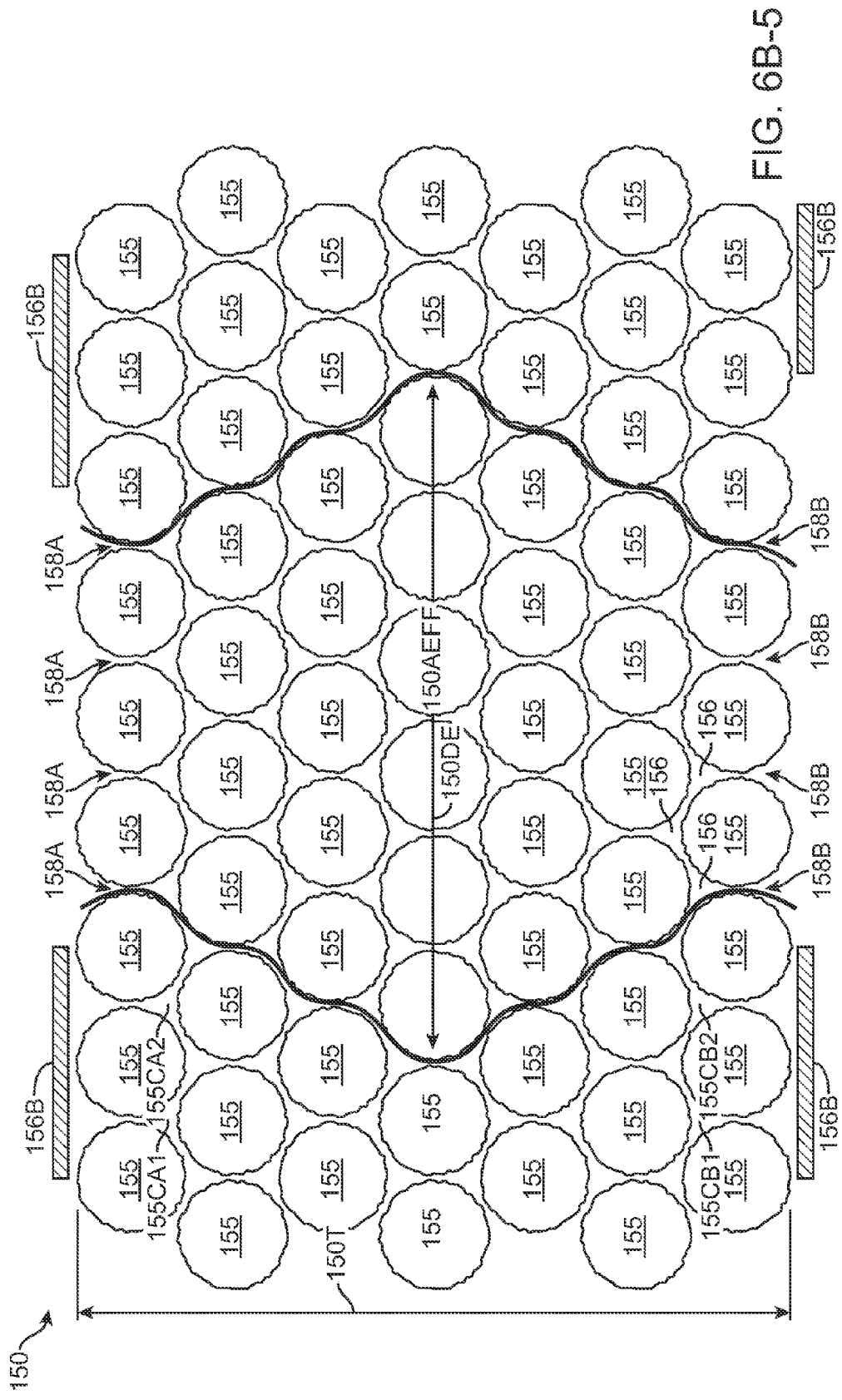
Figures 1, 16A:
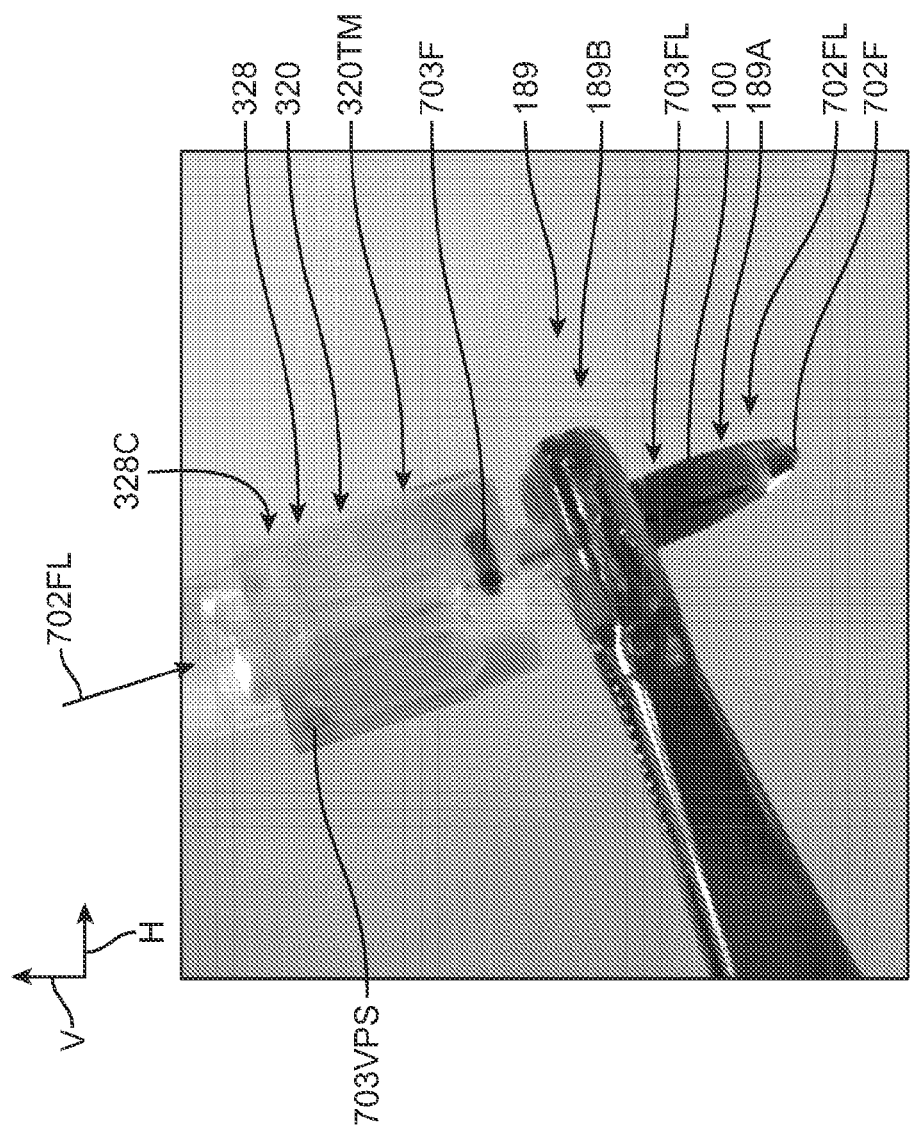
Figures 3, 16A:
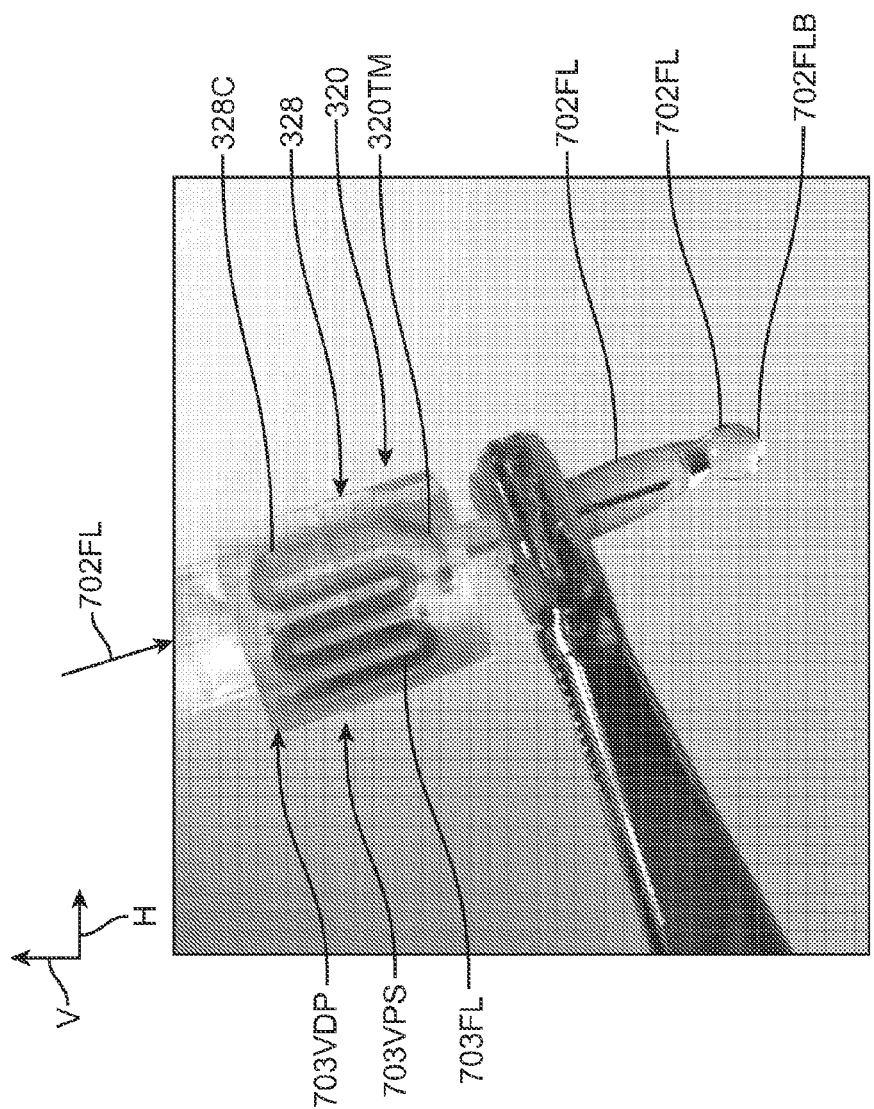
Figures 4, 16A:
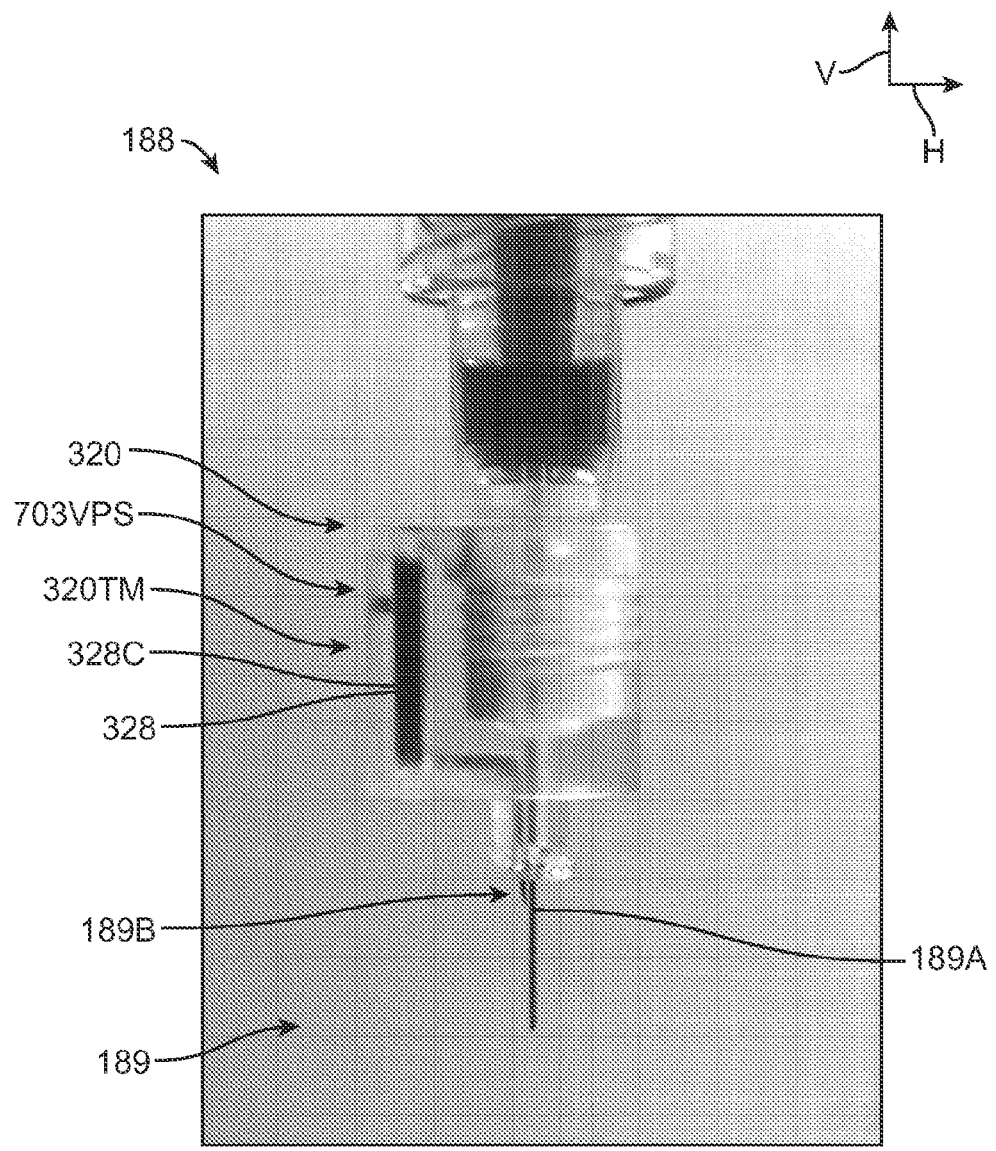
Figures 5, 16A:
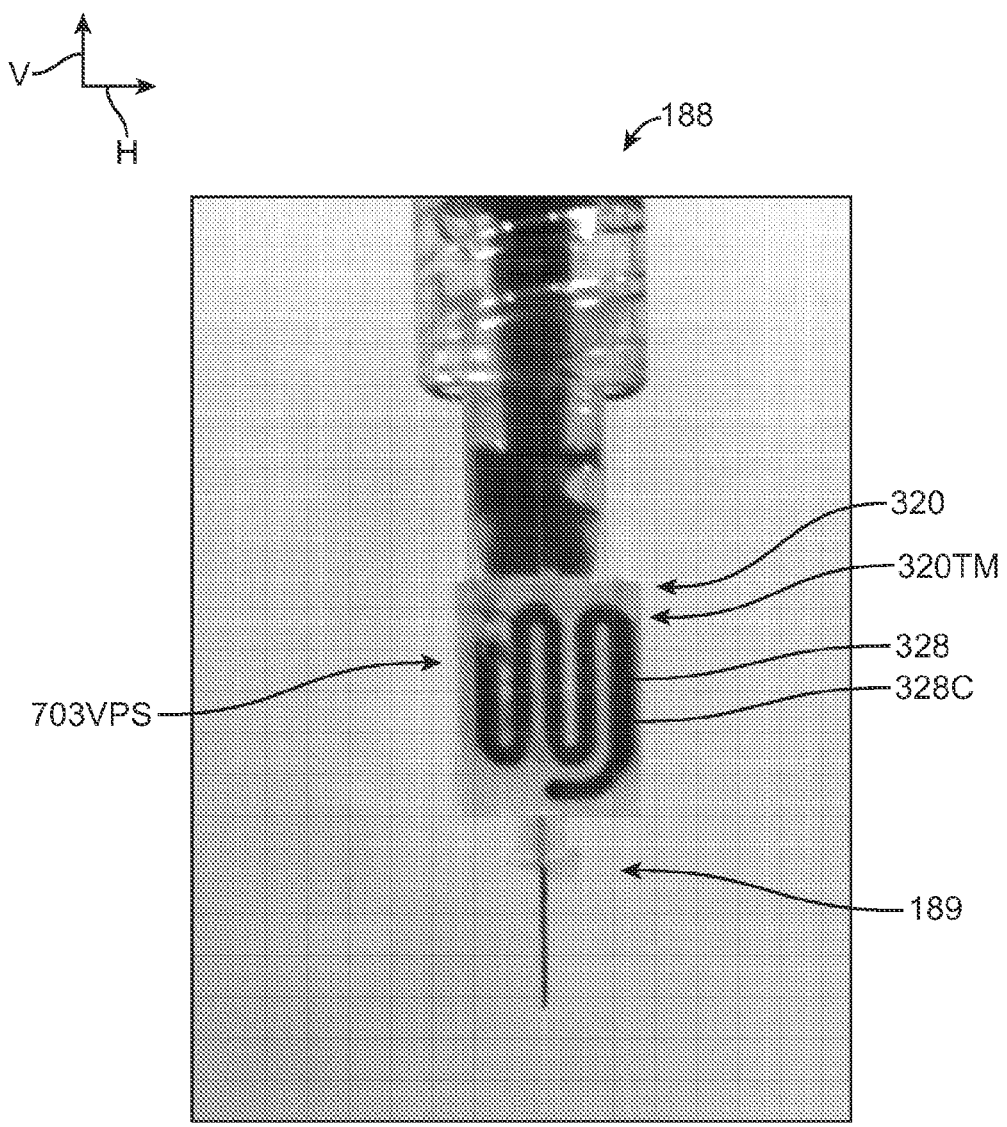

FIG. 6B-4 shows blockage of the openings with particles 156PB and the plurality of paths of the therapeutic agent along the interconnecting channels extending from a first side to a second side of the porous structure as in FIGS. 6B and 6B-1. The plurality of paths 156PR extend from the first side to the second side couple the first side to the second side where one of the sides is covered, such that the flow rate is maintained when one of the sides is partially covered FIG. 6B-5 shows an effective cross-sectional size 150DE and area 150EFF corresponding to the plurality of paths of the therapeutic agent along the interconnecting channels extending from a first side to a second side of the porous structure as in FIGS. 6B and 6B-1. The effective cross sectional area of the interconnecting channels corresponds to the internal cross-sectional area of the porous structure disposed between the openings of the first side and the openings of the second side, such that the rate of release can be substantially maintained when the channels are blocked on the first side and the second side.

The rigid porous structure can be shaped and molded in many ways for example with tubular shapes, conical shapes, discs and hemispherical shapes. The rigid porous structure may comprise a molded rigid porous structure. The molded rigid porous structure may comprises at least one of a disk, a helix or a tube coupled to the reservoir and configured to release the therapeutic agent for the extended period.

Figure 6C:
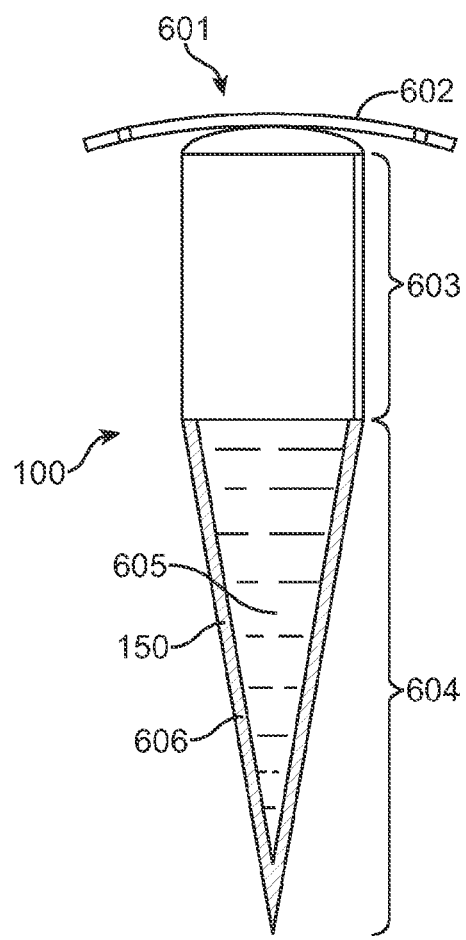
FIG. 6C shows a rigid porous structure as in FIG. 6B incorporated into a scleral tack.

FIG. 6C shows a rigid porous structure as in FIG. 6B incorporated into a scleral tack 601 as described in U.S. Pat. No. 5,466,233. The scleral tack comprises a head 602, a central portion 603 and a post 604. The post may comprise the reservoir 605 and the rigid porous structure 606 as described above. The porous structure may comprise a molded conical structure having a sharp tip configured for insertion into the patient. Alternatively or in combination, the tip may be rounded.

Figure 6D:
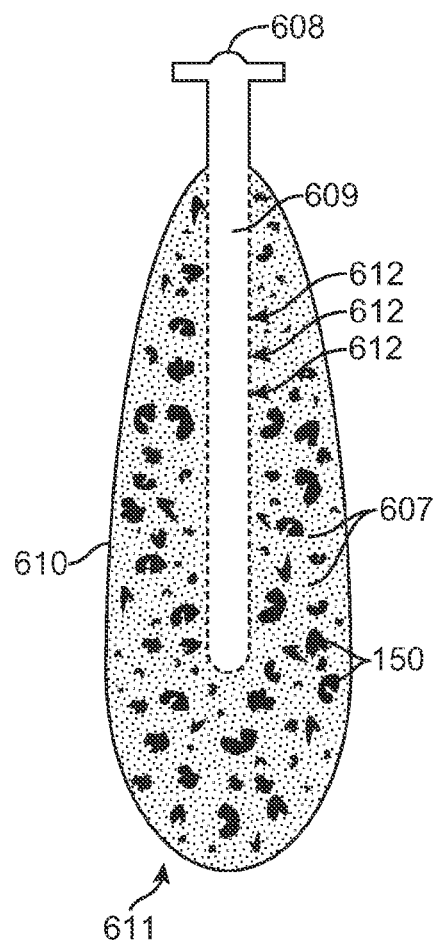
FIG. 6D, shows a rigid porous structure as in FIG. 6B coupled with a reservoir for sustained release.
Figure 6E:
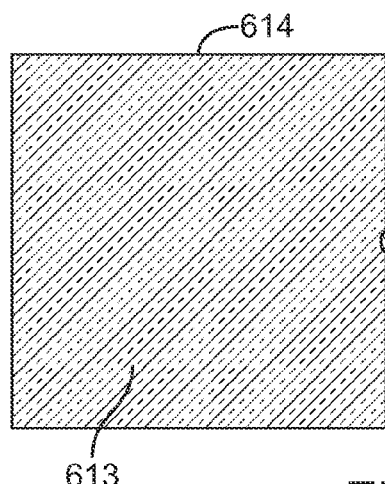
FIG. 6E shows a rigid porous structure as in FIG. 6B comprising a hollow body or tube for sustained release.

FIG. 6E, shows a plurality of rigid porous structures as in FIG. 6B incorporated with a drug delivery device for sustained release as described in U.S. Pat. No. 5,972,369. The therapeutic device comprises a reservoir 613 to contain the therapeutic agent and an impermeable and non-porous outer surface 614. The reservoir is coupled to a rigid porous structure 615 that extends to a distal end 617. The rigid porous structure comprises an exposed area 616 on the distal end to release the therapeutic agent, and the impermeable and non-porous outer surface may extend to the distal end.

FIG. 6D shows a rigid porous structure as in FIG. 6B incorporated with a delivery device for sustained release as described in U.S. Pat. Pub. 2003/0014036 A1. The drug delivery device comprises an inlet port 608 on the proximal end and a hollow body 609 coupled to the inlet port. The hollow body comprises many openings 612 that allow a solution injected into the inlet port to pass from the hollow body into a balloon 610. The balloon comprises a distal end 611 disposed opposite the injection port. The balloon comprises a plurality of the rigid porous structures 607, as described above. Each of the plurality of porous rigid structures comprises a first surface exposed to the interior of the balloon and a second surface configured to contact the vitreous. The calculated area can be the combined area of the plurality of porous rigid structures as noted above.

Figure 6F:
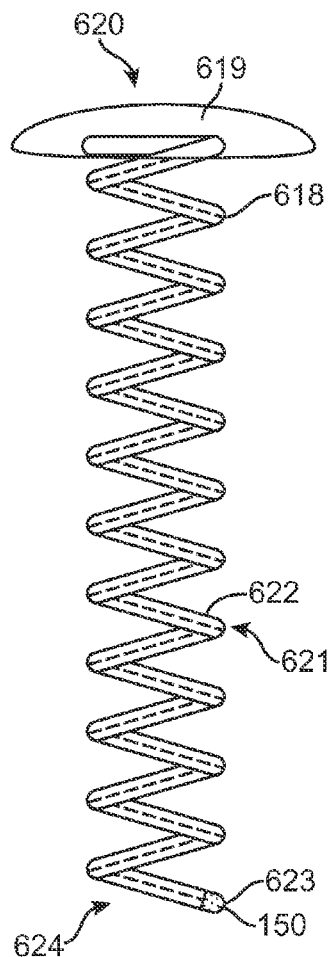
FIG. 6F shows a rigid porous structure as in FIG. 6B comprising a non-linear helical structure for sustained release.

FIG. 6F shows a rigid porous structure as in FIG. 6B incorporated with a non-linear body member 618 for sustained release as described in U.S. Pat. No. 6,719,750. The non-linear member may comprise a helical shape. The non-linear member can be coupled to a cap 619 on the proximal end 620. The non-linear member may comprise a lumen 621 filled with therapeutic agent so as to comprise a reservoir 622. The porous structure 623 can be disposed on a distal end 624 of the non-linear member to release the therapeutic agent. The porous structure may be located at additional or alternative locations of the non-linear member. For example a plurality of porous structures may be disposed along the non-linear member at locations disposed between the cap and distal end so as to release therapeutic agent into the vitreous humor when the cap is positioned against the sclera.

Figure 6G:
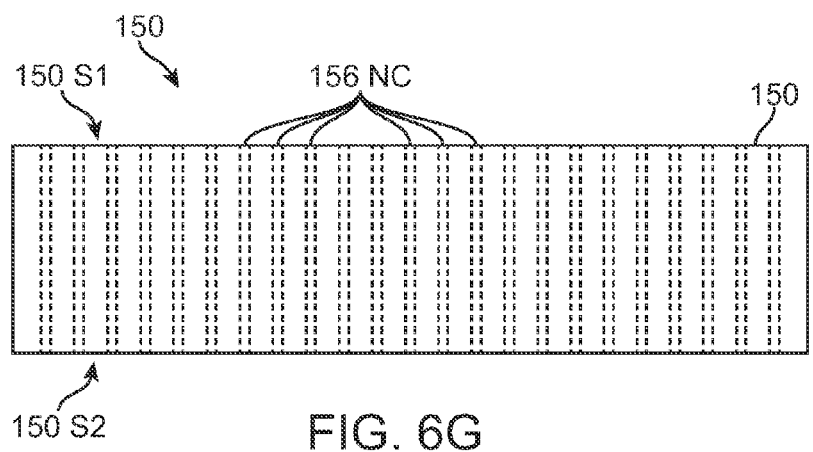
FIG. 6G shows porous nanostructures, in accordance with embodiments.

FIG. 6G shows porous nanostructures, in accordance with embodiments. The porous structure 150 may comprise a plurality of elongate nano-channels 156NC extending from a first side 150S1 of the porous structure to a second side 150S2 of the porous structure. The porous structure 150 may comprise a rigid material having the holes formed thereon, and the holes may comprise a maximum dimension across such as a diameter. The diameter of the nano-channels may comprise a dimension across, for example from about 10 nm across, to about 1000 nm across, or larger. The channels may be formed with etching of the material, for example lithographic etching of the material. The channels may comprise substantially straight channels such that the channel parameter F comprises about 1, and the parameters area A, and thickness or length L correspond to the combined cross-sectional area of the channels and the thickness or length of the porous structure.

The porous structure 150 may comprise interconnecting nano-channels, for example formed with a sintered nano-material.

The injection of therapeutic agent into the device 100 as described herein can be performed before implantation into the eye or alternatively when the therapeutic device is implanted into the eye.

FIG. 7 shows a therapeutic device 100 coupled to an injector 701 that removes material from the device and injects therapeutic agent 702 into the device. The injector picks up spent media 703 and refills the injector with fresh therapeutic agent. The therapeutic agent is injected into the therapeutic device. The spent media is pulled up into the injector. The injector may comprise a stopper mechanism 704.

The injector 701 may comprise a first container 702C to contain a formulation of therapeutic agent 702 and a second container 703C to receive the spent media 703. Work in relation to embodiments suggests that the removal of spent media 703 comprising material from the container reservoir of the therapeutic device can remove particulate from the therapeutic device, for example particles comprised of aggregated therapeutic agent such as protein. The needle 189 may comprise a double lumen needle with a first lumen coupled to the first container and a second lumen coupled to the second container, such that spent media 703 passes from the container reservoir of device 100 to the injector. A valve 703V, for example a vent, can be disposed between the second lumen and the second container. When the valve is open and therapeutic agent is injected, spent media 703 from the container reservoir of the therapeutic device 100 passes to the second container of the injector, such that at least a portion of the spent media within the therapeutic device is exchanged with the formulation. When the valve is closed and the therapeutic agent is injected, a portion of the therapeutic agent passes from the reservoir of the therapeutic device into the eye. For example, a first portion of formulation of therapeutic agent can be injected into therapeutic device 100 when the valve is open such that the first portion of the formulation is exchanged with material disposed within the reservoir; the valve is then closed and a second portion of the formulation is injected into therapeutic device 100 such that at least a portion of the first portion passes through the porous structure into the eye. Alternatively or in combination, a portion of the second portion of injected formulation may pass through the porous structure when the second portion is injected into the eye. The second portion of formulation injected when the valve is closed may correspond to a volume of formulation that passes through the porous structure into the vitreous humor to treat the patient immediately.

The needle 189 may comprise a dual lumen needle, for example as described with reference to FIG. 7A2 shown below.

FIG. 7-1 shows a concentric exchange needle and FIG. 7-2 shows a cross sectional view along an axis of the concentric exchange needle. The exchange needle may comprise a vent structure comprising a channel and an opening to receive fluid of the implantable device, The vent structure may comprise an annular channel 189AC having a cross sectional size and length to provide a resistance to flow proportional to the porous structure of the therapeutic device.

The vent opening and lumen 189A to receive the fluid of the implant comprises a resistance to flow proportional to the resistance to flow of the porous structure so as to provide a bolus injection with the needle when the fluid of the implanted device chamber passes through the vent. Based on the teachings and embodiments described herein, a person of ordinary skill in the art can determine empirically the dimensions of lumen 189A to receive the fluid of the implanted device, such that the lumen 189A has a resistance to flow proportional to the resistance to flow of the porous structure 150 to provide the bolus injection as described herein. For example, lumen 189A may comprise an outer diameter defined by an outer needle and an inner diameter defined by an inner needle and a distance extending along the inside of outer needle from a vent opening placed in the chamber to a second opening to a container to store the fluid 703FL. The lumen 189A having a gap distance 189ABG can extend a vent path distance 189VPD with the annular channel so as to provide a majority of the resistance to flow R2 of the second flow path as described herein. Alternatively, the vent path may comprise no substantial resistance to flow, such that the injection lumen provides a majority of the resistance to flow of the injector apparatus and the therapeutic fluid can at least partially separate from the implantable device fluid with no substantial bolus of therapeutic fluid released from the therapeutic device through porous structure 150.

FIG. 7A shows a therapeutic device 100 coupled to an injector 701 to inject and remove material from the device. The injector may comprise a two needle system configured to insert into a container of the device. The injector may simultaneously inject therapeutic agent through the first needle 705 (the injection needle) while withdrawing liquid from the device through the second needle 706 (the vent needle). The injection needle may be longer and/or have a smaller diameter than the vent needle to facilitate removal of prior material from the device. The vent needle may also be attached to a vacuum to facilitate removal of prior material from the device.

FIG. 7A-1 shows a therapeutic device 100 comprising a penetrable barrier coupled to an injector needle 189 comprising a stop 1895 that positions the distal end of the needle near the proximal end of the reservoir 130 of the device to flush the reservoir with ejection of liquid formulation through the porous fit structure, in accordance with embodiments. For example, the injector needle may comprise a single lumen needle having a bevel that extends approximately 0.5 mm along the shaft of the needle from the tip of the needle to the annular portion of the needle. The stop can be sized and positioned along an axis of the needle such that the needle tip extends a stop distance 189SD into the reservoir as defined by the length of the needle from the stop to the tip and the thickness of the penetrable barrier, in which the stop distance is within a range from about 0.5 to about 2 mm. The reservoir may extend along an axis of the therapeutic device distance within a range from about 4 to 8 mm. A volume comprising a quantity of liquid formulation within a range from about 20 to about 200 uL, for example about 50 uL can be injected into the therapeutic device with the needle tip disposed on the distal end. The volume of the reservoir can be less than the injection volume of the formulation of therapeutic agent, such that liquid is flushed through the porous structure 150. For example, the reservoir may comprise a volume within a range from about 20 to 40 uL, and the injection volume of the liquid formulation of therapeutic agent may comprise about 40 to 100 uL, for example about 50 uL.

FIG. 7A-2 shows a therapeutic device comprising a penetrable barrier coupled to a needle 189 of an injector 701 to inject and remove material from the device such that the liquid in the reservoir 130 is exchanged with the injected formulation. The needle comprises at least one lumen and may comprise a concentric double lumen needle 189DL with a distal end coupled to the inner lumen to inject formulation of the therapeutic agent into the therapeutic device and a proximal vent 189V to receive liquid into the needle when the formulation is injected. Alternatively, the vent may correspond to an opening on the distal end of the inner lumen of the needle and the outer lumen may comprise a proximal opening to inject therapeutic agent formulation into a proximal portion of the container reservoir.

Work in relation to the injector embodiments indicates that a filling efficiency of at least about 80%, for example 90% or more can be achieved with injector apparatus and needles as described above.

FIG. 7A-3 shows a deformable visual indicator 189DS. The deformable visual indicator can be coupled to a support, for example stop 1895, such that the visual indicator can deform to indicate when the needle is positioned to an appropriate depth 189SD. The visual indicator can be used with an injector such as a syringe and can be used for injections into one or more of many tissues such as dental, internal tissues during surgery and ocular tissues such as the conjunctiva of the eye. The needle 189 may comprise a silicon needle, for example a 25 GA or more needle, for example a 30 GA needle.

The visual indicator 189DS may comprise a bright color and may comprise a soft deformable material such as silicone, and may have a Shore A hardness from about 5 to about 30, for example. The stop 1895 may comprise a dark color, such that the deformable indicator becomes visible when coupled to tissue. Prior to contact with the tissue, the deformable indicator 189DS has a first width 189DSW1.

FIG. 7A-4 shows the visual indicator 189DS coupled to soft tissue, such as tissue of an eye, for example the conjunctiva positioned over the penetrable barrier of the therapeutic device 100. The visual indicator has been deformed and comprises a second width 189DSW2 that is greater than the first width such that the deformable indicator is visible when viewed when coupled to the tissue surface. Such visual indication of coupling can be helpful to ensure that the correct amount of pressure is applied by the health care provider and also so that the needle tips is located at an intended distance below the surface of the tissue.

FIG. 7A-5 shows a therapeutic device 100 coupled to injector 701 with one or more of potentially insufficient force prior to injection or potentially insufficient depth. As noted above, the therapeutic device may provide at least some resistance to flow, and the visual indicator 189DS can indicate when operator has applied sufficient force to counter reactive force of the injection. Also, the percent mixing can be related to the accuracy of the injection, for example with a bolus injection through the therapeutic device, and placement of the needle tip at depth 189SD with an accuracy of better than about 1 mm or less can ensure that the mixing and/or exchange amount injections is consistent such that the dosage of therapeutic agent can be delivered accurately.

FIG. 7A-6 shows a therapeutic device 100 coupled to injector 701 with one or more of potentially insufficient force prior to injection or potentially insufficient depth. Although the exchange apparatus as described herein can substantially reduce pressure of the liquid exchanged in the device, the exchange apparatus can be combined with the deformable stop so as to provide improved sealing to inhibit leakage of the therapeutic agent. For example, an insufficient force to form a seal with the conjunctiva may occur with a sufficient depth of penetration of aperture 189A1 of first injection lumen 189A into the reservoir chamber to inject therapeutic fluid 702FL and sufficient depth of penetration of vent aperture 189B1 of second lumen 189B to receive fluid 703FL. Alternatively, for example, a seal with the conjunctiva may be formed with elastomeric deformation of deformable stop 189DS when the aperture 189A1 and the aperture 189B1 are positioned at distal and proximal locations, respectively, within the reservoir chamber of therapeutic device 100.

FIGS. 7A-7A to FIG. 7A-9B show sliding coupling of a valve to a plunger coupled to a piston to exchange a first intended volume of liquid within the reservoir with a volume of formulation of therapeutic agent and close the valve so as to inject a second volume of liquid through the porous frit structure. FIG. 7A-7A, FIG. 7A-8A, and FIG. 7A-9A show a first configuration with the injector 701 coupled to a double lumen needle 189L such that a first lumen 189A injects therapeutic agent 110 from a chamber 702C into device 100. A second container 703C is coupled to a second lumen 189B that extends to the chamber of the reservoir container and receives liquid from device 100, such that liquid of device 100 is exchanged. A switching valve 703V comprises a first moving component, for example a sliding component, and a second component comprising an opening that can be blocked, for example covered, with the moving component. A piston 701P is moved toward the device 100 with a plunger, and the sliding component of switching valve 703V is coupled to the plunger and piston. When the piston has advanced to exchange an intended amount of liquid and an intended amount of the formulation the therapeutic agent 110 remains in chamber 702C, the sliding component of valve 703 covers and blocks the opening component of valve 703V. With valve 703 closed, an intended amount of therapeutic agent is injected into device 100, for example such that a bolus amount of therapeutic agent can be injected from device 100. A portion of the formulation of therapeutic agent injected into device 100 can be retained in device 100 for release for an extended time.

The moving component of the valve may comprise one or more of many components such as a ball valve, a sleeve, a gasket, a piston having holes, or a one way pressure valve, a solenoid, or a servo, for example. The valve 703V may comprise an opening 703V1 and a sliding component 703V2 such as a piston to slide over the opening 703V1 and block the opening. The sliding component 703V2 may comprise vents 703VV to inhibit pressure build up as the sliding component moves to cover the opening.

FIGS. 7A-10A and FIG. 7A-10B show a first configuration of an injector to maintain the rate of flow into device to within about +/−50%, for example to within about +/−25%, such that the time to inject the therapeutic agent into device 100 remains substantially constant amount devices and injections. For example, as the release rate index can be less than about 0.5, for example less than about 0.1, for example less than about 0.05, and the amount of time to inject fully substantially fixed volume of the therapeutic device can be inversely related to the release rate index.

The injector 701 comprises a mechanism to maintain the rate of flow into the device an limit a maximum amount of flow, for example with a spring. The mechanism may comprise one or more of a mechanical mechanism, an electrical mechanism, a pneumatic mechanism, or an hydraulic mechanism, or combinations thereof. Although a mechanical mechanism is shown, the above described mechanisms can provide similar results.

The visible indicator 189DS can be used to indicate to the operator that injector is coupled to the therapeutic device implanted in the eye at a depth for injection. The operator can then depress the plunger.

The plunger comprises a telescopic joint 707TJ and a spring 707S, such that the joint can be slid together such that the plunger 707PL is urged downward to contact the stop. When the plunger is urged downward, the spring is compressed when the ends of the telescopic joint come together. The compressed spring urges the piston 701P toward the therapeutic device such that the formulation of therapeutic agent is injected into the therapeutic device with the force of the spring. The valve 703V can close as described above. The second portion of the injection corresponding to the bolus injection is injected into the therapeutic device 100 and through porous structure 150.

FIG. 7B-1 shows a side cross-sectional view of therapeutic device 100 comprising a retention structure having a cross-section sized to fit in an elongate incision. The cross-section sized to fit in the elongate incision may comprise a narrow portion 120N of retention structure 120 that is sized smaller than the flange 122. The narrow portion 120N sized to fit in the elongate incision may comprise an elongate cross section 120NE sized to fit in the incision. The narrow portion 120N may comprise a cross-section having a first cross-sectional distance across, or first dimensional width, and a second cross-sectional distance across, or second dimensional width, in which the first cross-sectional distance across is greater than the second cross-sectional distance across such that the narrow portion 120N comprises an elongate cross-sectional profile.

The elongate cross section 120NE of the narrow portion 120N can be sized in many ways to fit the incision. The elongate cross section 120NE comprises a first dimension longer than a second dimension and may comprise one or more of many shapes such as dilated slot, dilated slit, lentoid, oval, ovoid, or elliptical. The dilated slit shape and dilated slot shape may correspond to the shape sclera tissue assumes when cut and dilated. The lentoid shape may correspond to a biconvex lens shape. The elongate cross-section of the narrow portion may comprise a first curve along an first axis and a second curve along a second axis different than the first curve.

Similar to the narrow portion 120N of the retention structure, the container reservoir may comprise a cross-sectional profile FIG. 7B-2 shows an isometric view of the therapeutic device as in FIG. 7B-1.

FIG. 7B-3 shows a top view of the therapeutic device as in FIG. 7B-1.

FIG. 7B-4 shows a side cross sectional view along the short side of the retention structure of the therapeutic device as in FIG. 7B-1.

FIG. 7B-5 shows a bottom view of the therapeutic device as in FIG. 7B-1 implanted in the sclera.

FIG. 7B-5A shows a cutting tool 710 comprising a blade 714 having a width 712 corresponding to perimeter 160P of the barrier 160 and the perimeter 160NP of the narrow portion. The cutting tool can be sized to the narrow portion 120N so as to seal the incision with the narrow portion when the narrow portion is positioned against the sclera. For example, the width 712 may comprise about one half of the perimeter 160P of the barrier 160 and about one half of the perimeter 160NP of the narrow portion 160N. For example, the outside diameter of the tube of barrier 160 may comprise about 3 mm such that the perimeter of 160P comprises about 6 mm, and the narrow portion perimeter 160NP may comprise about 6 mm. The width 712 of the blade 710 may comprise about 3 mm such that the incision comprises an opening having a perimeter of about 6 mm so as to seal the incision with the narrow portion 160P. Alternatively, perimeter 160P of barrier 160 may comprise a size slightly larger than the incision and the perimeter of the narrow portion.

The retention structure comprises a narrow section 120N having a short distance 120NS and a long distance 120NL so as to fit in an elongate incision along the pars plana of the eye. The retention structure comprises an extension 122. The extension of the retention structure 120E comprises a short distance across 122S and a long distance across 122S, aligned with the short distance 122NS and long distance 122NL of the narrow portion 120N of the retention structure 120. The narrow portion 120 may comprise an indentation 1201 sized to receive the sclera.

FIGS. 7B-6A and 7B-6B show distal cross-sectional view and a proximal cross-sectional view, respectively, of therapeutic device 100 comprising a non-circular cross-sectional size. The porous structure 150 can be located on a distal end portion of the therapeutic device, and the retention structure 120 can be located on a proximal portion of therapeutic device 100. The barrier 160 defines a size of reservoir 130. The barrier 160 and reservoir 130 may each comprise an elliptical or oval cross-sectional size, for example. The barrier 160 comprises a first cross-sectional distance across reservoir 130, and a second cross-sectional distance across reservoir 130, and the first distance across may extend across a long (major) axis of an ellipse and the second distance across may extend across a short (minor) axis of the ellipse. This elongation of the device along one direction can allow for increased drug in the reservoir with a decrease interference in vision, for example, as the major axis of the ellipse can be aligned substantially with the circumference of the pars plana region of the eye extending substantially around the cornea of the eye, and the minor axis of the ellipse can be aligned radially with the eye so as to decrease interference with vision as the short axis of the ellipse extends toward the optical axis of the eye corresponding to the patient's line of sight through the pupil. Although reference is made to an elliptical or oval cross-section, many cross-sectional sizes and shapes can be used such as rectangular with a short dimension extending toward the pupil of the eye and the long dimension extending along the pars plana of the eye.

The retention structure 120 may comprise structures corresponding to structure of the cross-sectional area. For example, the extension 122 may comprise a first distance across and a second distance across, with the first distance across greater than the second distance across. The extension may comprise many shapes, such as rectangular, oval, or elliptical, and the long distance across can correspond to the long distance of the reservoir and barrier. The retention structure 120 may comprise the narrow portion 120N having an indentation 1201 extending around an access port to the therapeutic device, as described above. The indentation 1201 and extension 122 may each comprise an elliptical or oval profile with a first long (major) axis of the ellipse extending in the first direction and a second short (minor) axis of the ellipse extending in the second direction. The long axis can be aligned so as to extend circumferentially along the pars plana of the eye, and the short axis can be aligned so as to extend toward the pupil of the eye, such that the orientation of device 100 can be determined with visual examination by the treating physician.

FIG. 7B-6C shows an isometric view of the therapeutic device having a retention structure comprising a narrow portion 120N with an elongate cross-sectional size 120NE.

FIG. 7B-6D shows a distal end view of the therapeutic device as in FIG. 7B-6C.

FIG. 7B-6E1 shows a side view of the short distance 120NS of the narrow portion 120N of the therapeutic device as in FIG. 7B-6C.

FIG. 7B-6E2 shows a side view of the long distance 120NL of the narrow portion 120N of the therapeutic device 100 as in FIG. 7B-6C.

FIG. 7B-6F shows a proximal view of the therapeutic device as in FIG. 7B-6C.

FIG. 7B-6G to FIG. 7B-6I show exploded assembly drawings for the therapeutic device 100 as in FIGS. 7B-6C to 7B-6F. The assembly drawings of FIGS. 7B-6G, FIG. 7B-6H and FIG. 7B-6I show isometric and thin side profiles views, respectively, of the elongate portion 120NE of the narrow portion of the retention structure 120N. The therapeutic device 100 has an elongate axis 100A.

The penetrable barrier 184, for example the septum, can be inserted into the access port 180. The penetrable barrier may comprise an elastic material sized such that the penetrable barrier can be inserted into the access port 180. The penetrable barrier may comprise one or more elastic materials such as siloxane or rubber. The penetrable barrier may comprise tabs 184T to retain the penetrable barrier in the access port. The penetrable barrier 184 may comprise a beveled upper rim 184R sized to seal the access port 180. The access port 180 of the reservoir container 130 may comprise a beveled upper surface to engage the beveled rim and seal the penetrable barrier against the access port 180 when the tabs 184T engage an inner annular or elongate channel of the access port. The penetrable barrier 184 may comprise an opaque material, for example a grey material, for example silicone, such that the penetrable barrier can be visualized by the patient and treating physician.

The reservoir container 130 of the device may comprise a rigid biocompatible material that extends at least from the retention structure to the rigid porous structure, such that the reservoir comprises a substantially constant volume when the therapeutic agent is released with the rigid porous structure so as to maintain a stable release rate profile, for example when the patient moves. Alternatively or in combination, the reservoir container 130 may comprise an optically transmissive material such that the reservoir container 130 can be translucent, for example transparent, such that the chamber of reservoir 140 can be visualized when the device is loaded with therapeutic agent outside the patient prior to implantation, for example when injected with a formulation of therapeutic agent prior to implantation in the physician's office. This visualization of the reservoir 140 can be helpful to ensure that the reservoir 140 is properly filled with therapeutic agent by the treating physician or assistant prior to implantation. The reservoir container may comprise one or more of many biocompatible materials such as acrylates, polymethylmethacrylate, siloxanes, metals, titanium stainless steel, polycarbonate, polyetheretherketone (PEEK), polyethylene, polyethylene terephthalate (PET), polyimide, polyamide-imide, polypropylene, polysulfone, polyurethane, polyvinylidene fluoride or PTFE. The biocompatible material of the reservoir container may comprise an optically transmissive material such as one or more of acrylate, polyacrylate, methlymethacraylate, polymethlymethacrylate (PMMA), polyacarbonate or siloxane. The reservoir container 130 can be machined from a piece of material, or injection molded, so as to form the retention structure 120 comprising flange 122 and the elongate narrow portion 120NE. The flange 122 may comprise a translucent material such that the physician can visualize tissue under the flange to assess the patient and to decrease appearance of the device 100 when implanted. The reservoir container 130 may comprise a channel extending along axis 100A from the access port 180 to porous structure 150, such that formulation injected into device 100 can be release in accordance with the volume of the reservoir and release rate of the porous structure 150 as described herein. The porous structure 150 can be affixed to the distal end of therapeutic device 100, for example with glue. Alternatively or in combination, the distal end of the reservoir container 130 may comprise an inner diameter sized to receive the porous structure 150, and the reservoir container 130 may comprise a stop to position the porous structure 150 at a predetermined location on the distal end so as to define a predetermined size of reservoir 140.

FIG. 7C-1 shows an expandable therapeutic device 790 comprising expandable barrier material 160 and support 160S in an expanded configuration for extended release of the therapeutic agent. The expanded configuration can store an increased amount of therapeutic agent, for example from about 30 uL to about 100 uL. The expandable device comprises a retention structure 120, an expandable reservoir 140. The support 160S may comprise a resilient material configured for compression, for example resilient metal or thermoplastic. Alternatively, the expandable support may be bent when expanded. The expandable device comprises the porous structure 150 disposed on a distal end, and affixed to the expandable support. The expandable device may comprise an access port 180, for example with a penetrable barrier 184. In the expanded configuration, the device is substantially clear from a majority of the optical path OP of the patient The support 160S of the barrier 160 can provide a substantially constant volume of the reservoir in the expanded configuration. The substantially constant volume, for example +/−25%, can be combined with the release rate index of the porous structure 150 so as to tune the expanded reservoir and porous structure to the volume of therapeutic agent to be injected into the therapeutic device as described herein. The barrier 160 may comprise a thin compliant material, for example a membrane, and the support 160S can urge the barrier 160 to an expanded configuration so as to define the reservoir chamber having the substantially constant volume.

FIG. 7C-1A shows the distal end portion of the support 160S. The support 160S may comprise struts that extend to an annular flange 160SF that supports the porous structure 150 on the distal end of device 100.

FIG. 7C-1B shows the support 160S disposed inside the barrier 160 so as to provide the substantially constant expanded volume of the reservoir chamber.

FIG. 7C-1C shows the support 160S disposed along the inner surface of the barrier 160 so as to provide the substantially constant expanded volume of the reservoir chamber. The support 160 can be bonded to the barrier 160 in many ways, for example with a bonding agent such as glue or resin, or with thermal bonding. The support 160S can be disposed on the outside of barrier 160.

FIG. 7C-2 shows the expandable therapeutic device 790 as in FIG. 7C-1 in a narrow profile configuration suitable for use in an injection lumen.

FIG. 7C-3 shows the expandable therapeutic device as in FIG. 7C-1 in an expanded profile configuration, suitable for retention, for example with the sclera.

FIGS. 7C-4A and 7C-4B show an expandable retention structure 792. The expandable retention structure 792 can be used with the expandable therapeutic device 790, or with a substantially fixed reservoir and container device as described above. The expandable retention structure 792 comprises many compressible or expandable or resilient materials or combinations thereof. The expandable retention structure 792 comprise an extension 120E that can expand from the narrow profile configuration to the expanded configuration, for example with tabs and flanges comprising resilient material. The upper portion can be inclined proximally and the distal portion can be inclined distally, such that the retention structure expands to engage opposite sides of the sclera. The resilient material may comprise a thermoplastic material, a resilient metal, a shape memory material, and combinations thereof.

FIG. 7D shows therapeutic device 100 comprising porous structure 150 positioned in an eye 10 to deliver a therapeutic agent to a target location on or near the retina 26, for example choroidal neovasculaturization of a lesion on or near the retina. For example, the lesion may comprise one or more buckling, folding, bending or separation of the retina from the choroid related to neovascularization of corresponding vascular tissue associated with blood supply to the retina, and the neovascular tissue corresponding to the lesion of the retina may be targeted. Work in relation to embodiments indicates that the vitreous humor 30 of the eye may comprise convective current flows that extend along flow paths 799. The convective flow paths may comprise flow channels. Although small molecules can be delivered to a target location of the retina 26 in accordance with the flow paths, therapeutic agent comprising large molecules, for example with antibody fragments or antibodies, can be delivered substantially with the convective flow paths as the molecular diffusion of large molecules in the vitreous humor can be somewhat lower than small molecules.

The therapeutic device can be sized such that porous structure 150 is positioned along a flow path extending toward a target location of the retina. The therapeutic agent can be released along the flow path, such that the flow of vitreous humor transports the therapeutic agent to the retina. The porous structure can be disposed on a distal portion of the therapeutic device, for example on a distal end, and the reservoir 130 can be sized for delivery for the extended time. The retention structure 120 can be located on the proximal. The therapeutic device 100 can be sized such that the porous structure is positioned in the flow patch corresponding to the target region. The surgeon may identify a target region 798 of the retina, for example corresponding to a lesion, and the therapeutic device 100 can be positioned along the pars plana or other location such that the therapeutic agent is released to the target region.

FIG. 7E shows therapeutic device 100 comprising porous structure 150 located on a proximal portion of the device to deliver a therapeutic agent to one or more of the ciliary body or the trabecular meshwork when implanted in the eye. The porous structure 150 can be located near retention structure 120 such that the porous structure is positioned in the vitreous substantially away from the flow paths extending to retina, as noted above. The porous structure can be located on a side of the therapeutic device so as to release the therapeutic agent toward a target tissue. While many therapeutic agents can be used, the therapeutic agent may comprise a prostaglandin or analog, such as bimatoprost or latanoprost, such that the therapeutic agent can be released toward one or more of the ciliary body or trabecular meshwork when implanted in the vitreous humor with the retention structure coupled to the sclera.

FIG. 7F shows therapeutic device 100 comprising porous structure 150 oriented to release the therapeutic agent 110 away from the lens and toward the retina. For example, the therapeutic agent 110 may comprise a steroid, and the steroid can be released from porous structure 150 away from the lens and toward the retina. For example, the porous structure can be oriented relative to an axis 100A of the therapeutic device. The outer side of porous structure 150 can be oriented at least partially toward the retina and away from the lens, for example along a flow path as described above so as to treat a target region of the retina. The barrier 160 can extend between the porous structure 160 and the lens of the eye when implanted such that release of therapeutic agent toward the lens can be inhibited with barrier 160. The retention structure 120 may comprise a long distance across and a short distance across as described above. The porous structure can be oriented in relation to the short and long distances of the extensions 122, such that the outer side of porous structure 150 is oriented at least partially toward the retina and along the flow path when the long distance of the retention structure extends along the pars plana and the short distance extends toward the pupil.

Figure 7G:
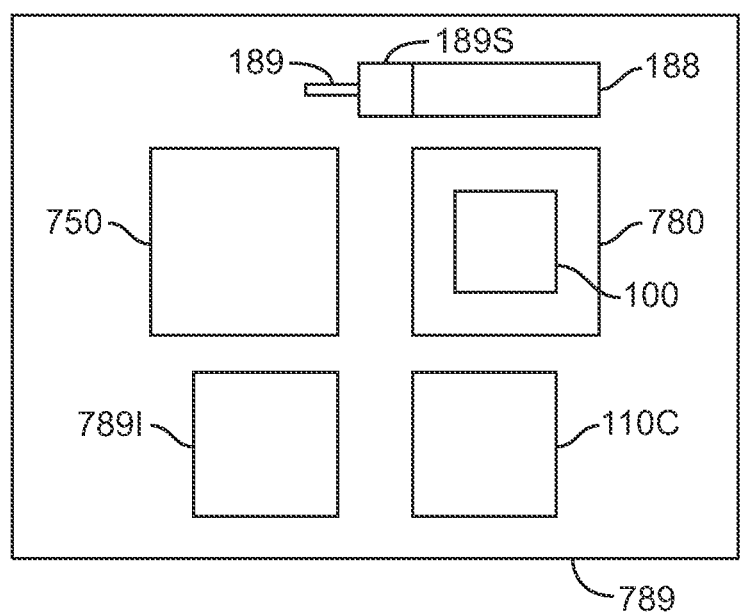
FIG. 7G shows a kit comprising a placement instrument, a container, and a therapeutic device within the container, in accordance with embodiments.

FIG. 7G shows a kit 789 comprising a placement instrument 750, a container 780, and a therapeutic device 100 disposed within the container. The reservoir of the therapeutic device 100 disposed in the container may comprise a non-therapeutic solution, for example saline, such that the channels of the porous structure comprise liquid water to inhibit bubble formation when the formulation of therapeutic agent is injected into the device 100. The kit may also comprise the syringe 188, needle 189 and stop 189S to insert the needle tip to a maximum stop distance within the reservoir as described above. The kit may contain instructions for use 7891, and may contain a container 110C comprising a formulation of therapeutic agent. The instructions for use may correspond to the injector apparatus and indicate an orientation of the injector device when coupled to the implanted device. The instructions may comprise instructions to orient the device with the penetrable barrier in relation to the porous structure during injection of the therapeutic agent, for example with the penetrable barrier located above the porous structure when the therapeutic fluid is injected. The instructions may correspond to the configuration of the fluid displacement apparatus such as the injector as described herein.

Tuning of Therapeutic Device for Sustained Release Based on an Injection of a Formulation The therapeutic device 100 can be tuned to deliver a target therapeutic concentration profile based on the volume of formulation injected into the device. The injected volume may comprise a substantially fixed volume, for example within about +/−30% of an intended predetermined target volume. The volume of the reservoir can be sized with the release rate index so as to release the therapeutic agent for an extended time substantially greater than the treatment time of a corresponding bolus injection. The device can also be tuned to release the therapeutic agent based on the half life of the therapeutic agent in the eye. The device volume and release rate index comprise parameters that can be tuned together based on the volume of formulation injected and the half life of the therapeutic agent in the eye. The following equations can be used to determine therapeutic device parameters suitable for tuning the device.

$$\text{Rate} = Vr(dCr/dt) = -D(PA/TL)Cr$$

where
Rate=Rate of release of therapeutic agent from device
Cr=concentration of therapeutic agent in reservoir
Vr=volume of reservoir
D=Diffusion constant
PA/TL=RRI
P=porosity
A=area
T=tortuosity=F=channel parameter.
For a substantially fixed volume injection, $$Cr0 = (\text{Injection Volume})(\text{Concentration of Formulation})/Vr$$

Where Cr0=initial concentration in reservoir following injection of formulation
For Injection Volume=50 uL $$Cr0 = (0.05\ \text{mL})(10\ \text{mg/mL})/Vr(1000\ ug/1\ \text{mg}) = 500\ ug/Vr$$

$$\text{Rate} = x(500\ ug)\exp(-xt)$$

where t=time $$x = (D/Vr)(PA/TL)$$

With a mass balance on the vitreous
$Vv(dCv/dt)=\text{Rate from device}=kVvCv$
where Vv=volume of vitreous (about 4.5 ml)
Cv=concentration of therapeutic agent in vitreous
k=rate of drug from vitreous (proportional to 1/half life of drug in vitreous)
For the situation appropriate for the embodiments as described herein where Cv remains substantially constant and changes slowly with time (i.e. dCv/dt is approximately 0), $$Cv = (\text{Rate from device})/(kVv)$$

Since kVv is substantially constant, the max value of Cv will correspond to conditions that maximize the Rate from the device. At a given time since injection into the device (e.g., 180 days), the maximum Cv is found at the value of x that provides the maximum rate. The optimal value of x satisfies $$d(\text{Rate})/dx = 0 \text{ at a given time.}$$

$$\text{Rate} = 500(x)\exp(-xt) = f(x)g(x) \text{ where } f(x) = 500x \text{ and } g(x) = \exp(-xt)$$

$$d(\text{Rate})/dx = f(x)g(x) + f(x)g'(x) = 500(1-xt)\exp(-xt)$$

For a given time, t, d(Rate)/dx=0 when 1−xt=0 and xt=1
The rate is maximum when (D/Vr)(PA/TL)t=1.

For a given volume, optimal PA/TL=optimal RRI=Vr/(Dt)
Therefore the highest Cv at a given time, t, occurs for the optimal RRI=(PA/FL) for a given Vr.
Also, the ratio (Vr)/(RRI)=(Vr)/(PA/TL)=Dt will determine the optimal rate at the time.

The above equations provide approximate optimized values that, when combined with numerical simulations, can provide optimal values of Vr and PA/TL. The final optimum value can depend on additional parameters, such as the filling efficiency.

The above parameters can be used to determine the optimal RRI, and the therapeutic device can be tuned to the volume of formulation injected into the device with a device reservoir volume and release rate index within about +/−50% of the optimal values, for example +/−30% of the optimal values. For example, for an optimal release rate index of the porous structure and an optimal reservoir volume sized to receive a predetermined quantity of therapeutic agent, e.g. 50 uL, so as to achieve therapeutic concentrations above a minimum inhibitory concentration for a predetermined extended time such as 90 days, the maximum volume of the reservoir can be limited to no more than about twice the optimal volume. This tuning of the reservoir volume and the porous structure to the injected volume of the commercially available formulation can increase the time of release of therapeutic amounts from the device as compared to a much larger reservoir volume that receives the same volume of commercially available injectable formulation. Although many examples as described herein show a porous fit structure and reservoir volume tuned together to receive a quantity of formulation and provide release for an extended time, the porous structure tuned with the reservoir may comprise one or more of a porous frit, a permeable membrane, a semi-permeable membrane, a capillary tube or a tortuous channel, nano-structures, nano-channels or sintered nano-particles, and a person of ordinary skill in the art can determine the release rate characteristics, for example a release rate index, so as to tune the one or more porous structures and the volume to receive the quantity of the formulation and release therapeutic amounts for an extended time.

As an example, the optimal RRI at 180 days can be determined for a reservoir volume of about 125 uL. Based on the above equations (Vr/Dt)=optimal RRI, such that the optimal RRI at 180 days is about 0.085 for the 50 uL formulation volume injected into the device. The corresponding Cv is about 3.19 ug/mL at 180 days based on the Rate of drug released from the device at 180 days and the rate of the drug from the vitreous (k corresponding to a half life of about 9 days). A device with a container reservoir volume of 63 uL and RRI of 0.044 will also provide the optimal Cv at 180 days since the ratio of Vr to PA/TL is also optimal. Although an optimal value can be determined, the therapeutic device can be tuned to provide therapeutic amounts of drug at a targeted time, for example 180 days, with many values of the reservoir volume and many values of the release rate index near the optimal values, for example within about +/−50% of the optimal values. Although the volume of the reservoir can be substantially fixed, the volume of the reservoir can vary, for example within about +/−50% as with an expandable reservoir such as a balloon reservoir.

The half life of the drug in the vitreous humor of the eye can be determined based on the therapeutic agent and the type of eye, for example human, rabbit or monkey, such that the half life may be determined based on the species of the eye, for example. With at least some animal models the half life of the therapeutic agent in the vitreous humor can be shorter than for human eyes, for example by a factor of about two in at least some instances. For example, the half-life of the therapeutic agent Lucentis™ (ranibizumab) can be about nine days in the human eye and about two to four days in the rabbit and monkey animal models. For small molecules, the half life in the vitreous humor of the human eye can be about two to three hours and can be about one hour in the monkey and rabbit animal models. The therapeutic device can be tuned to receive the volume of formulation based on the half life of the therapeutic agent in the human vitreous humor, or an animal vitreous humor, or combinations thereof. Based on the teachings described herein, a person of ordinary skill in the art can determine empirically the half life of the therapeutic agent in the eye based on the type of eye and the therapeutic agent, such that the reservoir and porous structure can be tuned together so as to receive the volume of formulation and provide therapeutic amounts for the extended time.

FIG. 7A-11A shows an injection apparatus 700 comprising a valve 703 comprising a shut off button 703SOB coupled to a sleeve 703SL to provide a bolus injection. The sleeve can be sized such that the shut off button closes when a first quantity of liquid has passed so as to inject a bolus through the porous structure 150 into the eye. The length of the sleeve and piston size can be related to the quantity of liquid injected before and after the valve closes.

FIG. 7A-11B shows the injector apparatus of FIG. 7A-11B with the sleeve covering the valve and the valve closed.

FIG. 7A-12A shows an injection apparatus 700 comprising a valve 703 to provide a bolus injection and comprising lumen 189A extending along a first axis 189AB and lumen 189B extending along a second axis 189BA spaced apart from the first lumen to provide axial separation 189ABD and in which the injection lumen 189A is located closer to the porous structure 150 than the vent lumen and in which valve 703V is configured to provide a bolus injection through the porous structure 150. Work in relation to embodiments suggests that separation of the axis of the first lumen and the second lumen can increase the efficiency of the injection. For example the lumen to inject the therapeutic fluid can be located closer to the porous structure than the lumen to receive fluid from the device, for example when the therapeutic fluid is more dense than the implanted device fluid. The valve 703 can close when a first amount has been injected into device 100 and close to pass a bolus dosage through porous structure 150. The opening to lumen 189B can be located substantially along the axis to couple the therapeutic fluid 702FL to porous structure 150.

FIG. 7A-13A shows an injection apparatus 700 comprising a float valve 703FV to provide the bolus injection when the received implant fluid closes valve 703FV. The float valve may comprise a ball to float upward and fill an opening such that the therapeutic fluid can be passed through porous structure 150 with the bolus injection.

FIG. 7A-13B shows the double lumen needle 189DL of the injection apparatus 700 of FIG. 7A-13A. The double lumen needle may comprise a first injection lumen 189A and a second lumen 189B to receive fluid from device 100.

FIG. 7A-13C shows a cross sectional view along an axis of the double lumen needle 189DL of FIGS. 7A-13A and 7A-13B.

FIG. 7A-14A shows an injection apparatus 700 comprising a valve 703 having a hard stop to engage a piston to provide a bolus injection and comprising lumen 189A extending along a first axis 189AB and lumen 189B extending along a second axis 189BA spaced apart from the first lumen to provide separation. The injection lumen 189B can be located closer to the porous structure 150 than the vent lumen 189A.

FIG. 7A-15A shows an injection apparatus 700 comprising a valve 703 having a porous structure 703VPS similar to porous structure 150 to provide a bolus injection and in which the lumen 189B is coupled to channel having a volume with a gas therein so as to provide the bolus injection when the fluid 703FL of the implanted device has displaced the gas and contacts the porous structure 703VPS. The lumen 189A can inject the therapeutic fluid. The porous structure 703PS may comprise structures similar to porous structure 150, for example a sintered porous material as described herein. The sintered porous material may provide a first resistance to flow for air and a second resistance to flow for fluids comprising liquid, such that the porous structure substantially closes the valve 703 when one or more of fluid 702FL or 703FL contacts porous structure 703VPS. A channel extending between the vent of the lumen 189B may comprise a gas such as air, and an amount of the gas can correspond to the quantity of liquid injected before the valve 703V closes to provide the bolus injection.

FIG. 7A-15B shows an injection apparatus 700 comprising a valve 703 having a porous structure 703VPS similar to porous structure 150 to provide a bolus injection and in which the porous structure 703VPS has a resistance to flow proportional to the porous structure 150 so as to provide the bolus based on the proportional resistance to flow of the porous structures. The porous structure 703VPS may comprise a smaller resistance to flow than the porous structure 150, such that a majority of the fluids may pass through the valve 703 and a portion through structure 150.

The injection lumen 189A can provide pressure to exchange the fluids. The pressure can provide a pressure drop 703VDP across the porous structure 703VPS and a pressure drop 150DP, and the pressure drop across each porous structure can be substantially similar. Amount of fluid passing through each porous structure is inversely proportional to the resistance to flow of the porous structure.

FIG. 7A-15C1 shows an injection apparatus 700 comprising a valve 703 having a sliding component such as a piston 701P coupled to a second sliding component 703P to close the valve to deliver the bolus.

FIG. 7A-15C2 shows the piston 703P in the lumen 189A of valve 703 as in FIG. 7A-15C1.

FIG. 7A-16 shows a schematic illustration of an injector apparatus configured to provide a bolus injection to the eye based on flow resistance of the injector apparatus proportional to the flow resistance of porous structure 150. The therapeutic fluid placement apparatus 700 may comprise at least one needle extending into the reservoir chamber of the therapeutic device 100. The at least one needle provides substantial pressure to the reservoir chamber, for example at least about 1 atmosphere, so as to provide a difference in pressure delta P between the chamber and the reservoir. A first fluid flow path can extend from the reservoir chamber, through the porous structure to the vitreous humor of the eye. The first fluid path provides pressure drop 150DP across porous structure 150. A second fluid flow path can extend from the reservoir chamber, through the valve 703 comprising the porous structure 703VPS, and to an outlet coupled to air. The second fluid path provides pressure drop 703VDP across the porous structure 703VPS. The pressurization of the reservoir chamber of the therapeutic device can be substantially greater than the IOP of the eye, such that the pressure differential across porous structure 150 and the valve porous structure 150PS can be approximately the same.

The rate of flow of liquid along each of the first flow path and the second flow path can be related to the pressure differential and the resistance to flow along each path. In many embodiments, the proportion of fluid that flows along each path is inversely proportional to the resistance to flow of each path, and the proportion is substantially insensitive to fluctuations in pressure of the chamber. The first flow F1 along the first path can be proportional to the pressure differential delta P divided by the first flow resistance R1. The second flow F2 along the second path can be proportional to the pressure differential delta P divided by the second flow resistance R2.

The resistance to flow of the porous structure 703VPS can be determined based on one or more of the total volume to be injected with the injector, the amount of the injection to be released to the vitreous as a bolus injection, the resistance to flow of the porous structure 150 and the volume of the reservoir chamber of device 100. For example, with a 100 uL injection into the eye, an equal resistance to flow of the porous structure 150 and an equal resistance to flow of the valve porous structure 150VPS, approximately 50% of the 100 uL therapeutic fluid injection will be released as a bolus to the vitreous and approximately 50% of the injected therapeutic fluid will be placed in the therapeutic device for extended release through the porous structure 150. With a resistance to flow of the vent porous structure 703VPS that is approximately half of the resistance to flow of the porous structure 150, about two thirds of the implanted device fluid 703FL may pass through the valve porous structure 703 VPS and approximately one third of the therapeutic fluid may pass through the porous structure 150 into the vitreous humor of the eye.

In many embodiments, the vent structure along the outflow path of the injector apparatus can have a much lower resistance to flow than the porous structure 150. The amount of fluid through the porous structure 150 may correspond proportionally to the ratio of the resistance R2 to flow of the vent structure to the resistance R1 to flow of the porous structure 150, and the ratio R2/R1 can be used to determine flow through the porous structure 150. Work in relation to embodiments indicates that a resistance to flow R2 of the vent structure can be sufficiently low such that no more than about 0.2 uL of liquid passes through the porous structure 150. For example, with a 50 uL injection In many embodiments the lumen 189B to inject therapeutic fluid can be sized to extend to a distal portion of device 100 and the lumen 189A to receive implanted device fluid.

The injector apparatus as described herein can be configured to provide at least partially automated injection with an indication to the user that the injection has been completed.

FIG. 7A-17A to 7A-17C show a schematic illustration of an automated injector apparatus 703AI configured to provide an automated injection with user input and output to decrease leakage. The user can push down on the injector apparatus so as to penetrate the conjunctiva and penetrable barrier with the at least one needle. The at least one needle 189 can extend into the device a predetermined distance such that the deformable stop 189DS engages the conjunctiva with at least some pressure so as to form a seal comprising of one or more of the deformable stop, the penetrable barrier or the conjunctiva. The at least one needle 189 may comprise a first lumen 189A and a second lumen 189B. The first lumen 189A can inject therapeutic fluid and the second lumen 189B can receive device fluid. Alternatively, the second lumen 189B can inject therapeutic fluid and the first lumen can receive device fluid 189A. A slider 703SL such as sliding telescopic joint can urge the at least one needle into the therapeutic device 100. The user can initiate injection with the seal formed by pressing an input 703IB such as a button 703B, and the injection may comprise an automatic deployment mechanism 703AM of the injector apparatus such that the therapeutic fluid is injected into the chamber with a pressure within a range so as maintain integrity of the therapeutic device and seal. An output of the injector apparatus may comprise an indicator 7031N such as a click sound or button that pops out so as to indicate that injection has been completed as shown in FIG. 7A-17C. The user may remove the apparatus when the injection has been substantially completed and the chamber pressure has substantially decreased so as to inhibit leakage of the therapeutic fluid.

The injector apparatus may comprise a mechanism to inject 703AM the therapeutic fluid at an appropriate pressure and flow rate corresponding to the at least one needle and the therapeutic device. The injector apparatus may comprise, for example, one or more of a smooth viscous damped spring, a spring, pneumatic injection, so as to provide the corresponding flow rate and pressure of the therapeutic device chamber.

The injector apparatus may be adapted to inject a formulation having a density as described herein, for example within a range from about 1.01 g/cm3 to about 1.10 g/cm3, such that the density difference of the therapeutic fluid and the implantable device fluid is within a range from about 1% to about 10%. Work in relation to embodiments suggests that density modifiers such as sorbitol and mannitol can be combined with the therapeutic agent so to provide therapeutic fluid having the density suitable to provide the at least partial separation as described herein. The formulation may comprise a known formulation, or may be formulated in accordance with known drug formulation principles so as to provide the density. For example an amount of a known density modifier such as sorbitol or mannitol can be provided with a known suspension to decrease settling of the suspension. Examples of formulations having densities suitable for use in accordance with embodiments as described herein are described in MTH Nutanand IK Reddy, General Principles of Suspensions, in Pharmaceutical Suspensions From Formulation Development to Manufacturing, editors A K Kulshreshtha, O N Singh, G M Wall, Spinger, 2010, for example. The therapeutic fluid may comprise a known carbohydrate to increase density of the therapeutic fluid. The carbohydrate may comprise a known disaccharide such as trehalose to increase the density of the formulation. Examples of known trehalose solutions are described in DP Miller, J J de Pablow, J Corti, Thermophysical Properties of Trehalose and Its Concentrated Aqueous Solutions. Pharmaceutical Research, Vol. 14, No 5, 1997, pp 578-590.

The injector apparatus can be configured to place the therapeutic fluid in the chamber with the at least partial separation based on the known density of the known formulation, for example.

FIGS. 8A and 8A1 show a side cross sectional view and a top view, respectively, of therapeutic device 100 for placement substantially between the conjunctiva and the sclera. The therapeutic agent 110 as described herein can be injected with at least partial separation when device 100 is implanted. The therapeutic device 100 can be exchanged with an injector apparatus having a first needle and a second needle as described herein. The therapeutic device 100 comprises container 130 as described herein having penetrable barrier 184 as described herein disposed on an upper surface for placement against the conjunctiva. An elongate structure 172 is coupled to container 130. Elongate structure 172 comprises a channel 174 extending from a first opening coupled to the chamber of the container to a second opening 176 on a distal end of the elongate structure. The porous structure 150 as described herein is located on the elongate structure 172 and coupled to the container 130 so as to release therapeutic agent for an extended period, and a retention structure 120 comprising an extension protruding outward from the container 130 to couple to the sclera and the conjunctiva. The container may comprise barrier 160 as described herein that defines at least a portion of the reservoir, and the container may comprise a width, for example a diameter. The barrier 160 may comprise a rigid material, for example rigid silicone or rigid rubber, or other material as described herein, such that the volume of the chamber of container 130 comprises a substantially constant volume as described herein. Alternatively or in combination, barrier 160 may comprise a soft material, for example when the chamber size is decreased such that the volume can be substantially constant with the decreased chamber size. A soft barrier material can be combined with a rigid material, for example a support material. The diameter can be sized within a range, for example within a range from about 1 to about 8 mm, for example within a range from about 2 to 6 mm and can be about 3 mm, for example.

The container may be coupled to elongate structure 172 sized, and the elongate structure having a length sized so as to extend from the conjunctive to the vitreous to release the therapeutic agent into the vitreous. The length can be sized within a range, for example within a range from about 2 to about 14 mm, for example within a range from about 4 to 10 mm and can be about 7 mm, for example. The penetrable barrier may comprise a septum disposed on a proximal end of the container, in which the septum comprises a barrier that can be penetrated with a sharp object such as a needle for injection of the therapeutic agent. The porous structure may comprise a cross sectional area sized to release the therapeutic agent for the extended period. The elongate structure 172 can be located near a center of the container 130, or may be eccentric to the center.

The elongate structure 172 can be inserted into the sclera at the pars plana region as described herein.

The barrier 160 can have a shape profile for placement between the conjunctiva and sclera. The lower surface can be shaped to contact the sclera and may comprise a concave shape such as a concave spherical or toric surface. The upper surface can be shaped to contact the conjunctivae and may comprise a convex shape such as a convex spherical or toric surface. The barrier 160 may comprise an oval, an elliptical, or a circular shape when implanted and viewed from above, and the elongate structure 172 can be centered or eccentric to the ellipse. When implanted the long dimension of the oval can be aligned so as to extend along a circumference of the pars plana.

The cross sectional diameter of the elongate structure 172 can be sized to decrease the invasiveness of device 100, and may comprise a diameter of no more than about 1 mm, for example no more than about 0.5 mm, for example no more than about 0.25 mm such that the penetrate sclera seals substantially when elongate structure 172 is removed and the eye can seal itself upon removal of elongate structure 172. The elongate structure 172 may comprise a needle, and channel 174 may comprise a lumen of the needle, for example a 30 Gauge needle.

The porous structure 150 may comprise a first side a described herein coupled to the reservoir and a second side to couple to the vitreous. The first side may comprise a first area 150 as described herein and the second side may comprise a second area. The porous structure may comprise a thickness as described herein. The porous structure many comprise a diameter. The porous structure may comprise a release rate index, and the chamber of container 130 that defines the volume of reservoir 140 can be sized such that the porous structure and the volume are tuned to receive and amount of therapeutic agent injected with a volume of formulation of therapeutic agent and tuned to release therapeutic amounts for an extended time. Many release rate mechanisms as described herein can be used to tune the release rate and volume to the quantity of therapeutic agent injected as described herein.

The volume of the reservoir 140 defined by the chamber of the container may comprise from about 5 uL to about 2000 uL of therapeutic agent, or for example from about 10 uL to about 200 uL of therapeutic agent.

The porous structure may comprise a needle stop that limits penetration of the needle. The porous structure may comprise a plurality of channels configured for the extended release of the therapeutic agent. The porous structure may comprise a rigid sintered material having characteristics suitable for the sustained release of the material.

FIG. 8A2 shows the therapeutic device 100 implanted with the reservoir between the conjunctiva and the scleara, such that elongate structure 172 extends through the sclera to couple the reservoir chamber to the vitreous humor. When implanted, the porous structure 150 can be located in the vitreous humor, or located between the conjunctiva and sclera, or may extend through the sclera, or combinations thereof.

Figure 8B:
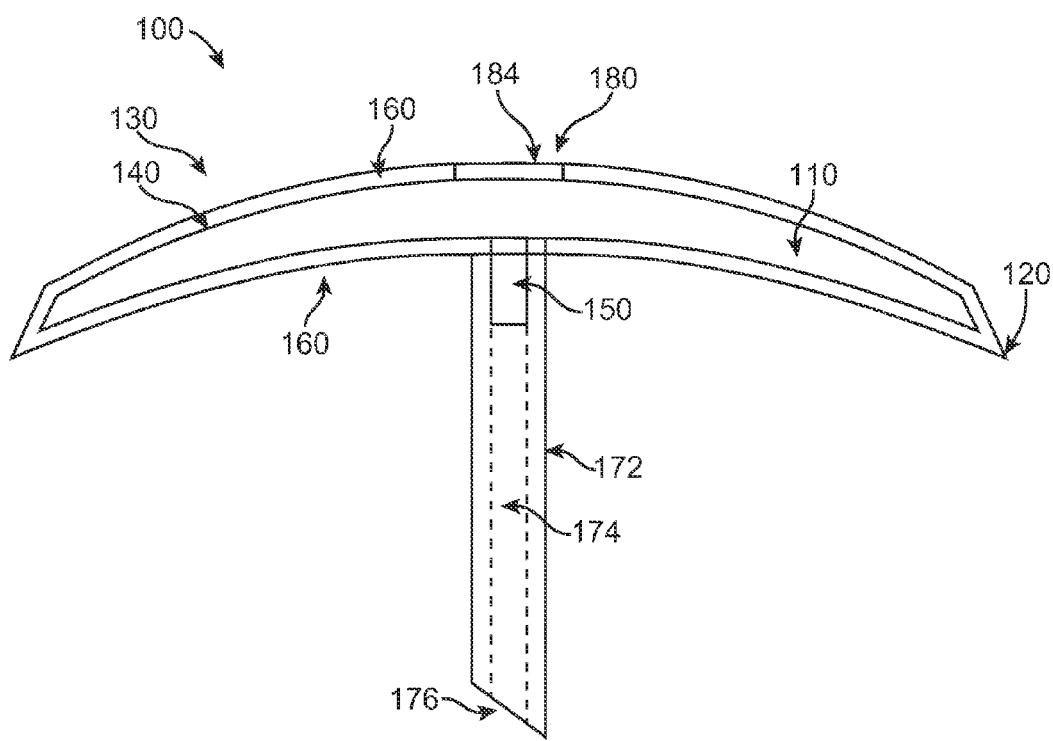
FIG. 8B shows the porous structure of therapeutic device located in channel near the opening to the chamber of the container.

FIG. 8B shows the porous structure 150 of therapeutic device 100 located in channel 174 near the opening to the chamber of the container 130. The porous structure can extend substantially along the length of elongate structure 172.

Figure 8C:
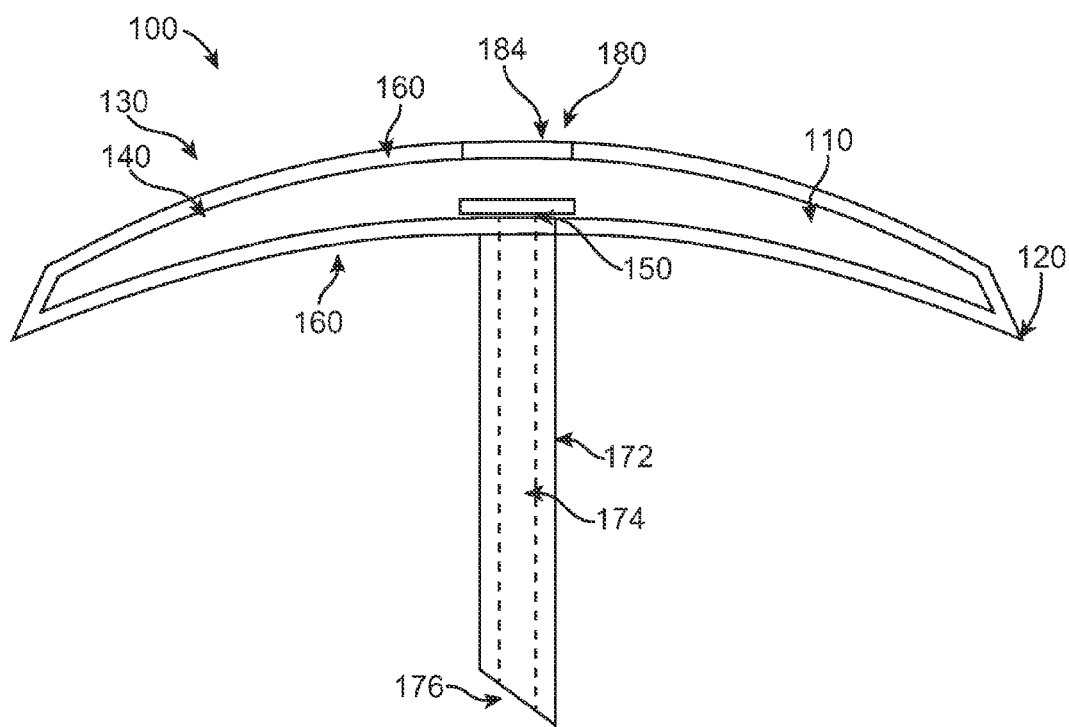
FIG. 8C shows the porous structure located within the chamber of container and coupled to the first opening of the elongate structure so as to provide the release rate profile.

FIG. 8C shows the porous structure 150 located within the chamber of container 150 and coupled to the first opening of the elongate structure 172 so as to provide the release rate profile. The porous structure can cover the opening of elongate structure 172 such that therapeutic amounts are released for the extended time as described herein.

Figure 8D:
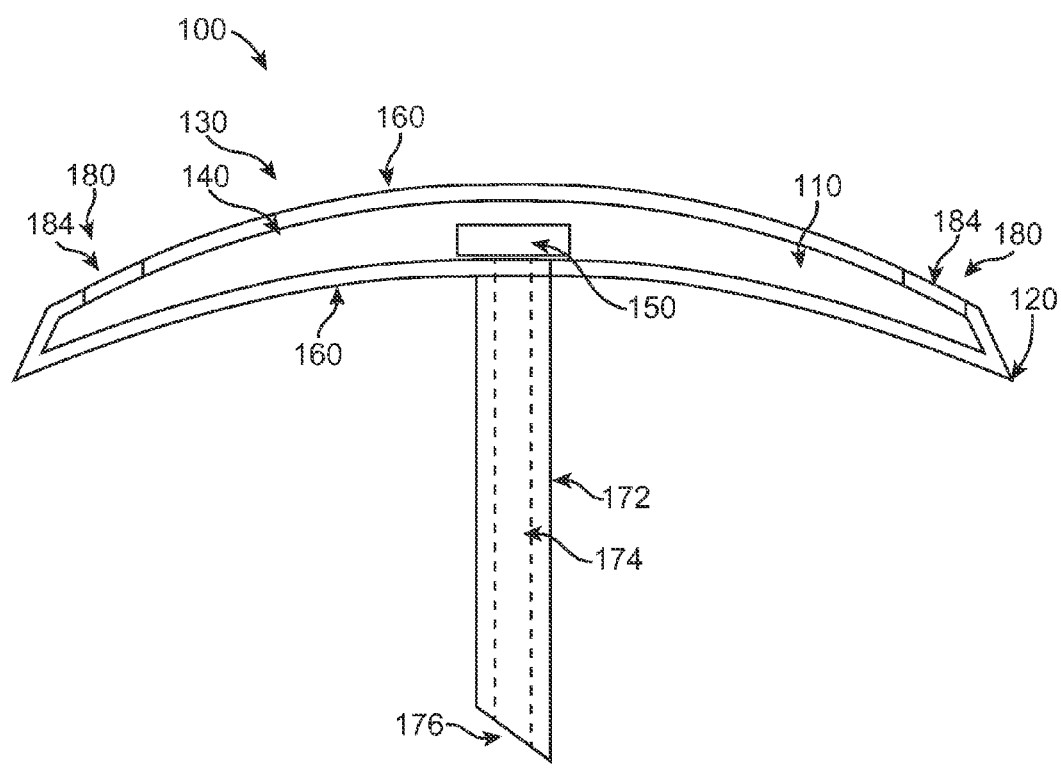
FIG. 8D shows a plurality of injection ports spaced apart so as to inject and exchange the liquid of chamber of the container and inject the therapeutic agent into the reservoir chamber of the container.
Figure 9:
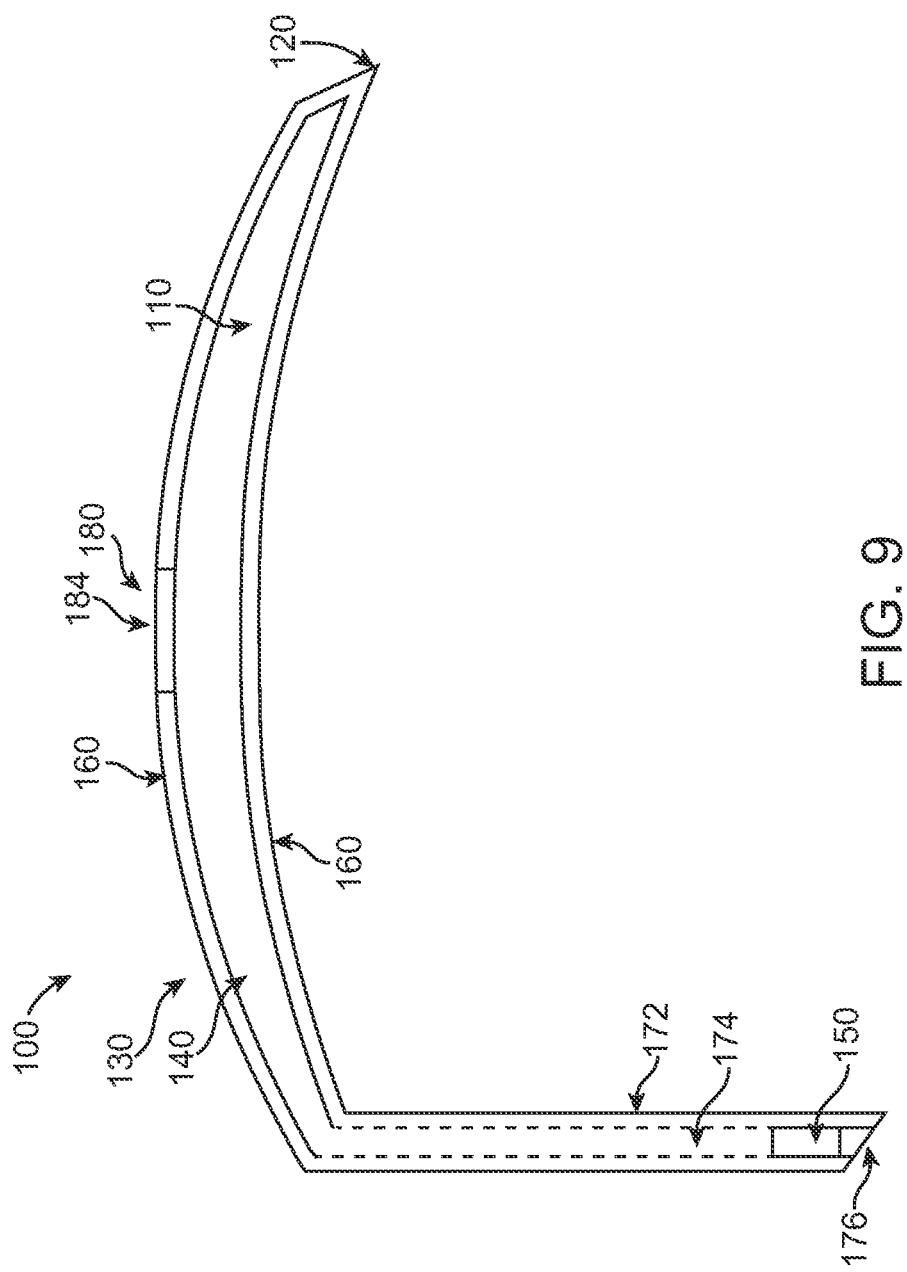

FIG. 8D shows a plurality of injection ports spaced apart so as to inject and exchange the liquid of chamber of the container 130 and inject the therapeutic agent into the reservoir chamber of the container 130. The penetrable barrier 184 may comprise a first penetrable barrier located in a first access port formed in the barrier 160 and a second penetrable barrier located in a second access port formed in the barrier 160, and the first barrier can be separated from the second barrier by at least about 1 mm.

The injector apparatus as can be configured to couple to the reservoir placed between the conjunctiva and the sclera in many ways as describe herein. The injector can be configured to separate at least partially the therapeutic fluid from the device fluid, for example. Alternatively or in combination, the injector can be configured to exchange the device fluid with the therapeutic fluid, for example. The injector apparatus 701 can The injector 701 can be coupled to a double lumen needle 189L such that a second lumen 189B injects therapeutic agent 110 from a chamber 702C into device 100, and the first lumen can be spaced apart from the second lumen with the distance extending therebetween sized to position the first lumen in the first septum as described above and the second lumen in the second septum as described above. The second container 703C can be coupled to a first lumen 189A that extends to the chamber of the reservoir container and receives liquid from device 100, such that liquid of device 100 is exchanged when the chamber of the reservoir container is positioned between the conjunctiva and the sclera. The switching valve 703V to exchange an intended amount of liquid and an intended amount of the formulation the therapeutic agent 110, and inject an intended amount of therapeutic agent injected into device 100, for example such that a bolus amount of therapeutic agent can be injected from device 100 as described above. A portion of the formulation of therapeutic agent injected into device 100 can be retained in device 100 for release for an extended time.

FIG. 9 shows the elongate structure coupled to the container away from the center of container and near and located near an end of the container.

FIG. 10A shows an apparatus 300 to inject fluid into the implanted device. The apparatus 300 comprises a cartridge 320 comprising a container 328 to receive the fluid of the therapeutic device. The cartridge container 328 is placed in a packaging container 310 to protect the cartridge.

The cartridge 320 comprises a connector 322 to couple to a syringe. The connector 322 may comprise one or more standard connectors to couple to a syringe such as a Luer connector or a Hamilton connector. The cartridge 320 may comprise at least one needle 189 having a first lumen 189A and a second lumen 189B as described herein. The cartridge 320 may comprise at least one needle 189 comprising a first needle 324 having a first lumen 324L and a second needle 326 having a second lumen 326L. The first needle and lumen are fluidicly coupled to the connector 322. The second needle 326 and second lumen 326L are fluidicly coupled to the container 328. The at least one needle may comprise a double lumen needle 189DL as described herein. A valve 703V is coupled to the container 328, such that the valve 703V substantially closes when the volume of the container 328 is filled with the implantable device fluid.

The valve 703V may comprise one or more of the valves as described herein. In many embodiments, the valve 703V may comprise a porous structure having a resistance to flow of liquid greater than a resistance to a flow of air, such that the flow of liquid is substantially inhibited when liquid contacts the porous structure. The valve 703V may have a resistance to flow greater than porous structure 150, so as to drive liquid through porous structure 150 when liquid contacts the porous structure of valve 703V. Alternatively, valve 703V have a resistance to flow less than porous structure 150 so as to pass an amount of therapeutic fluid 702FL through the porous structure based 150 on the resistance to flow of valve 703V less than porous structure 150.

The packaging container 310 comprises a removable cover 314 and a housing 312. The housing 312 comprises a channel 316 to receive the at least one needle 324. The height of the housing 312 and channel 316 are sized to receive the cartridge 320 with the at least one needle extending along the channel 316 and the cover 314 placed on the housing 312.

FIG. 10B shows a syringe coupled to the cartridge to inject the formulation and receive liquid. The cartridge 320 is coupled to the syringe 188, and the cartridge 320 is subsequently removed from the housing. The syringe 188 may comprise a standard commercially available syringe having a capacity suitable for injection of the amount of therapeutic agent. The syringe 188 comprises an amount of the therapeutic agent 110 for injection into the device 100.

Figure 10A:
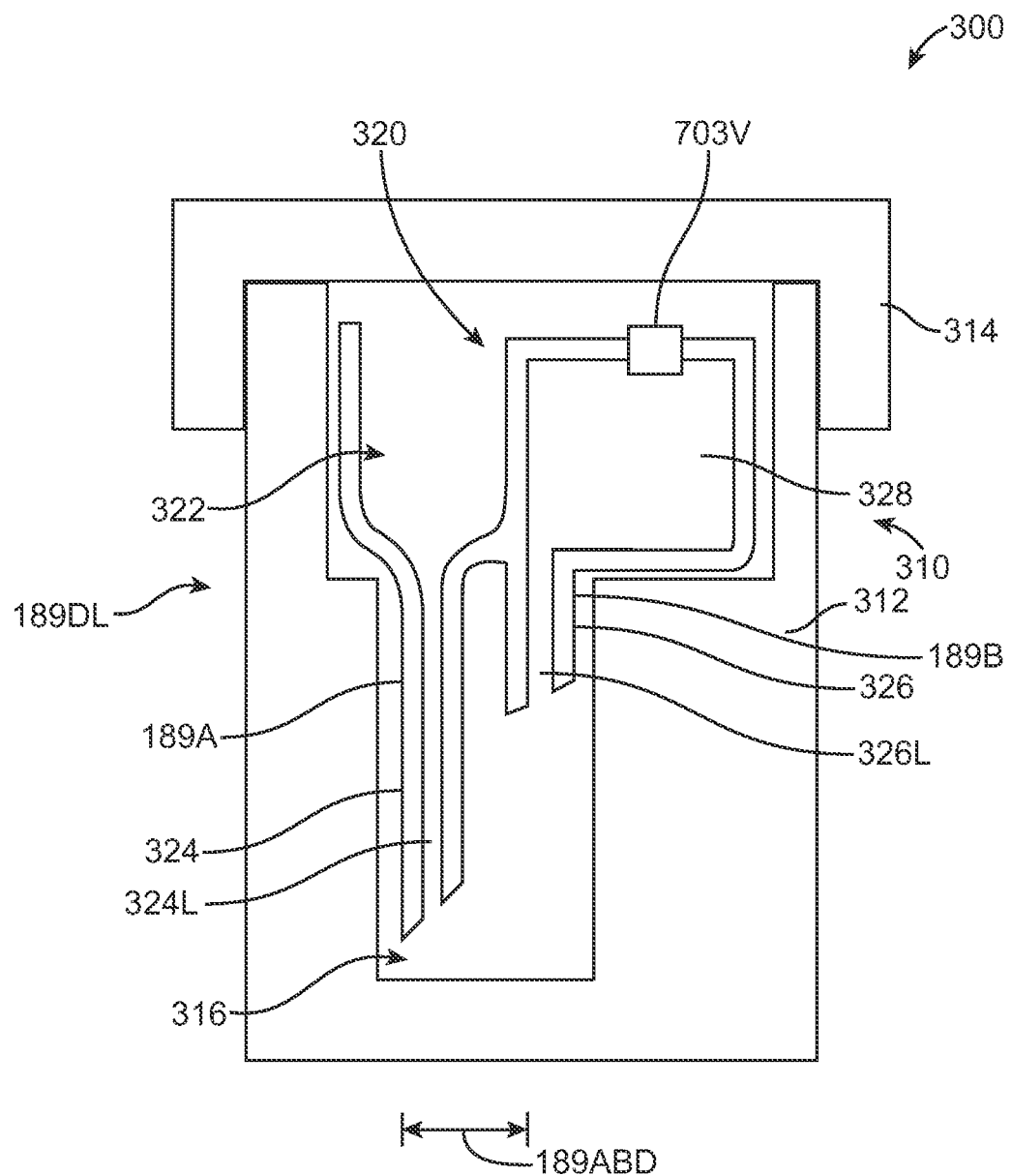
Figure 10B:
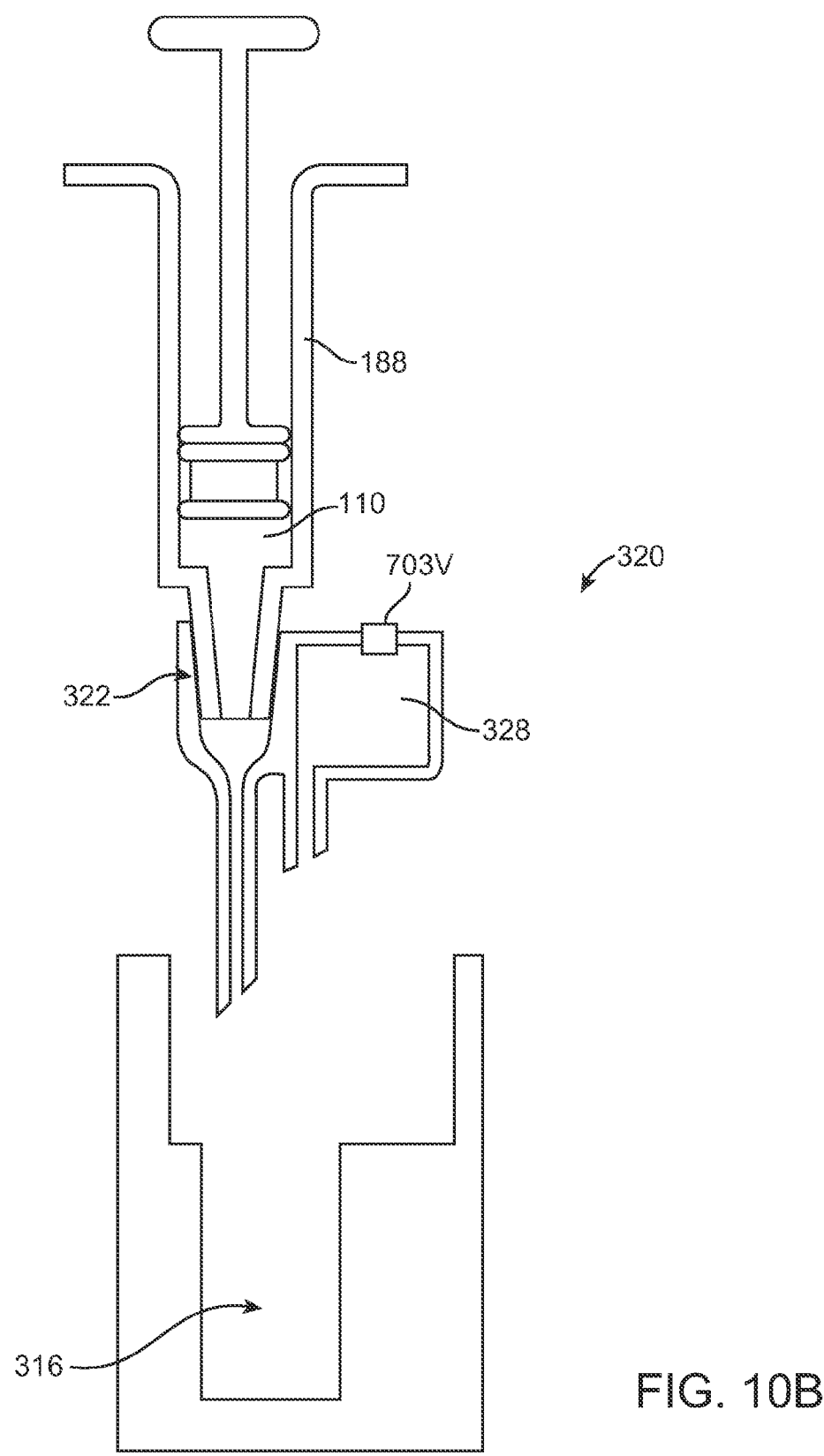
Figure 10C:
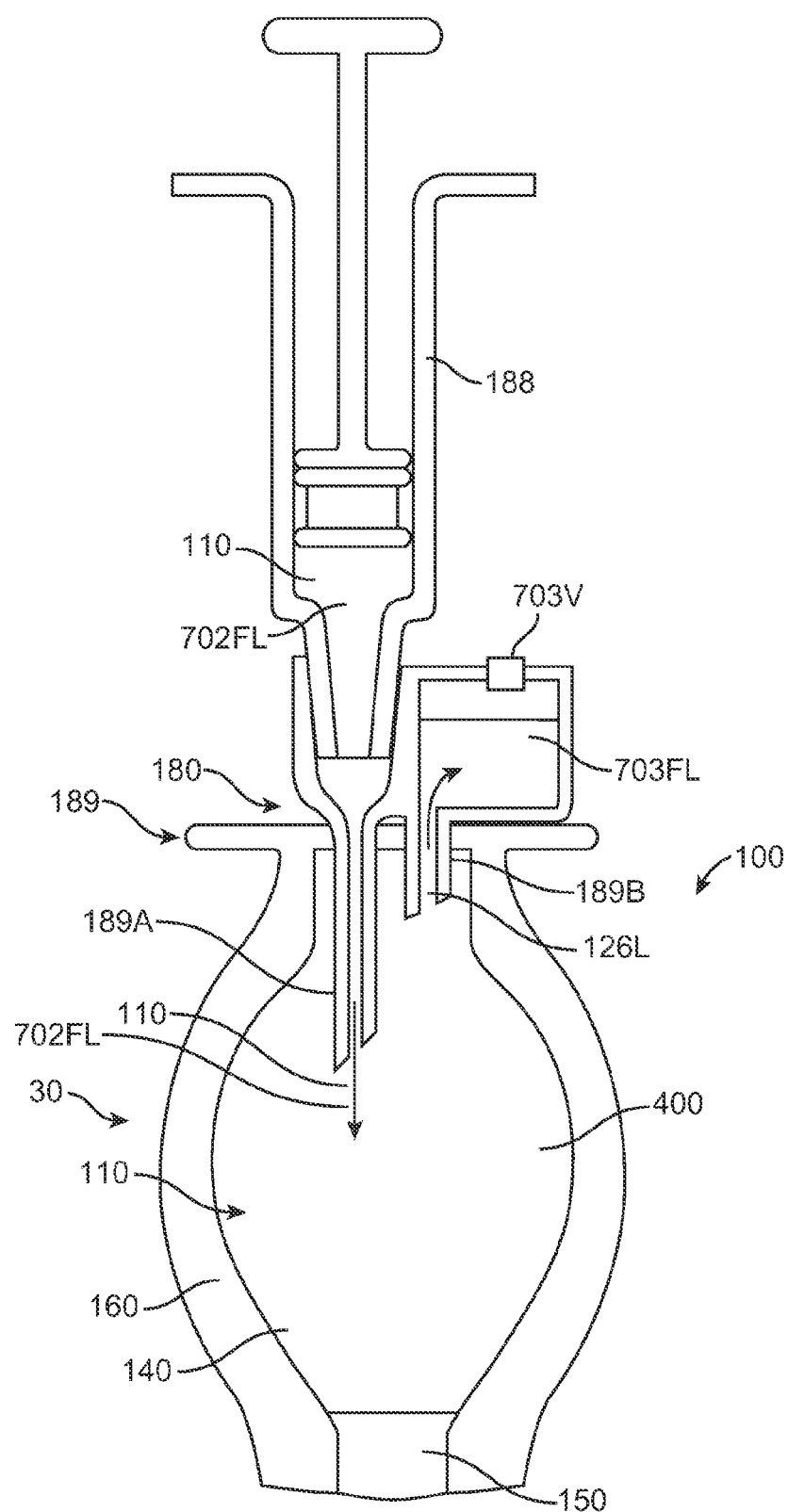
FIG. 10C shows the syringe and cartridge as in FIG. 10B coupled to the device implanted in the eye to inject the therapeutic agent and receive the fluid of the implanted device.

FIG. 10C shows the syringe and cartridge coupled to the device 100 implanted in the eye to inject the therapeutic agent and receive the fluid of the implanted device as described herein.

Work in relation to embodiments of the present invention suggests that the formulation of therapeutic 110 can be more dense than the implantable device fluid 703FL of the device 100, and that it can be helpful to inject the formulation with the porous structure 150 below the penetrable barrier of device 100, such that the formulation of therapeutic agent 110 directed to a location of the reservoir chamber 140 that is below the lumen 124L to receive implantable device fluid 703FL. The plunger of the syringe is depressed to urge the liquid into the device 100. When the level of implantable device fluid 703FL rises to the valve 703, the flow of liquid is substantially inhibited. The valve 703 comprising the porous structure can provide at a user perceptible resistance to air flow such that the formulation of agent 110 is directed to the porous structure with decreased flow that may increase gravity based separation of implantable device fluid 703FL with the formulation.

Figure 10D:
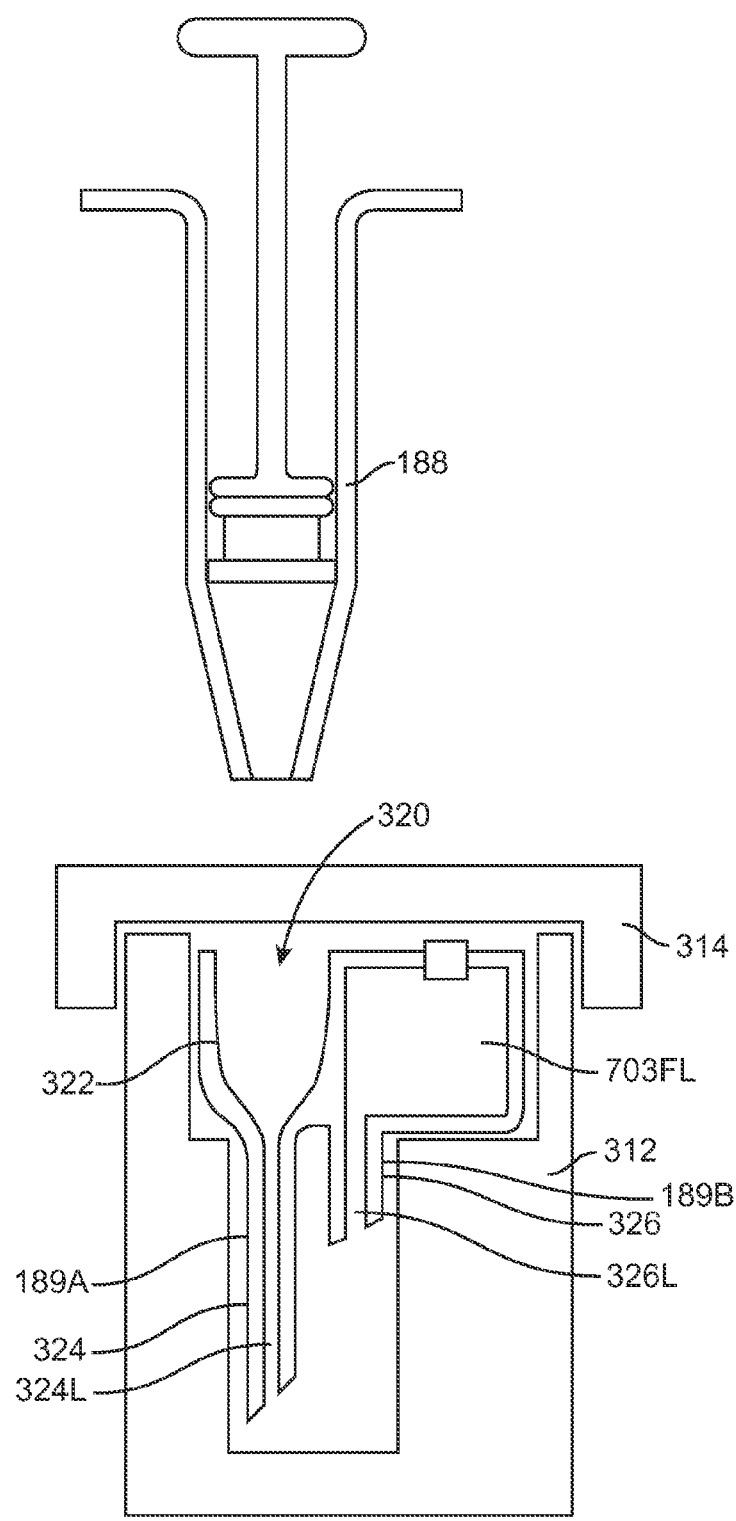
FIG. 10D shows the cartridge of FIG. 10C placed in the packaging container.
Figure 11A:
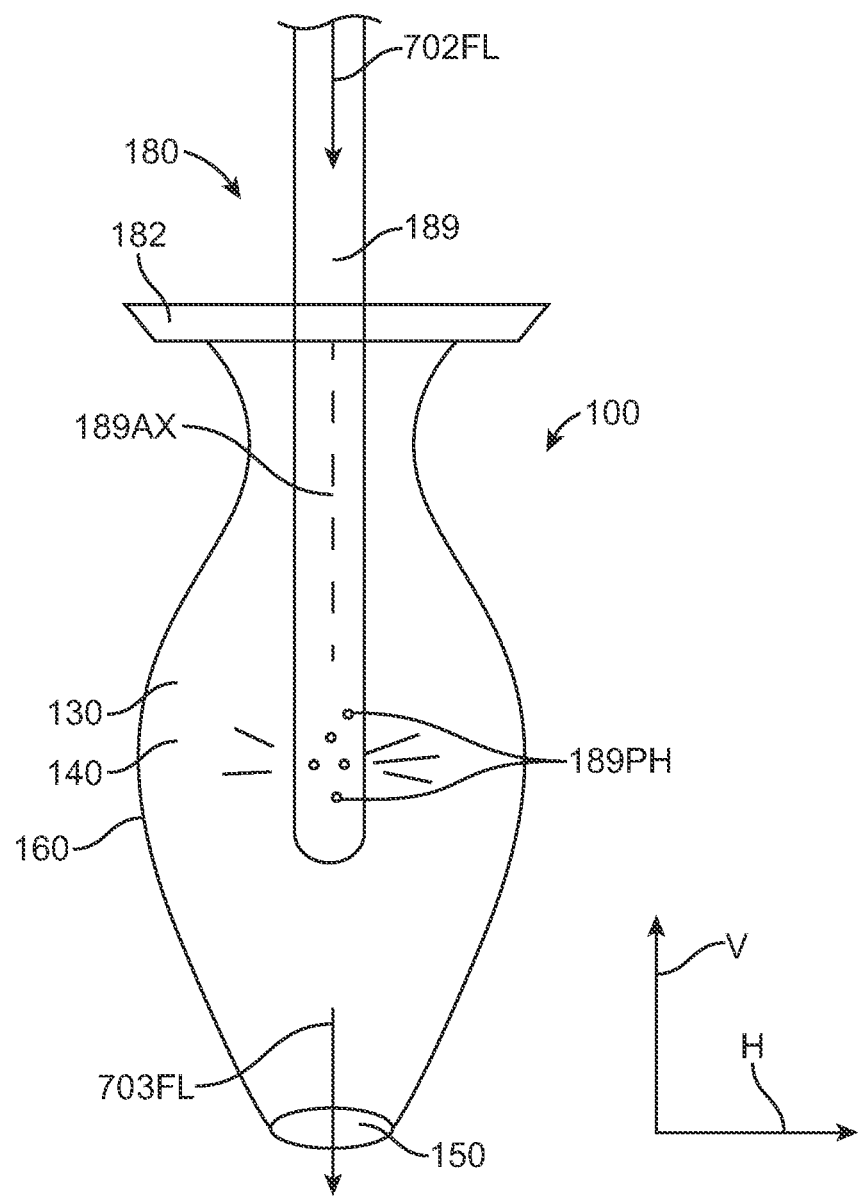

FIG. 10D shows the cartridge 320 placed in the packaging container with the covering placed over the packaging container;

FIGS. 10E and 10F show side a front views of an injector apparatus comprising a transparent material to view the liquid received from the implanted device. The cartridge 320 comprises comprising container 328. Container 328 comprises a channel 328C coupled to porous structure 703VPS. An optically transparent material 320M is disposed over channel 328C to provide a view of channel 328C FIG. 11A shows needle 189 comprising a plurality of openings spaced radially and axially along the axis 189AX of the needle 189 so as to mix the therapeutic fluid 702FL with the fluid of the implantable device 100 to inhibit separation of the fluids and pass the implantable device fluid 702FL through porous structure 150 with the injection.

Figure 11B:
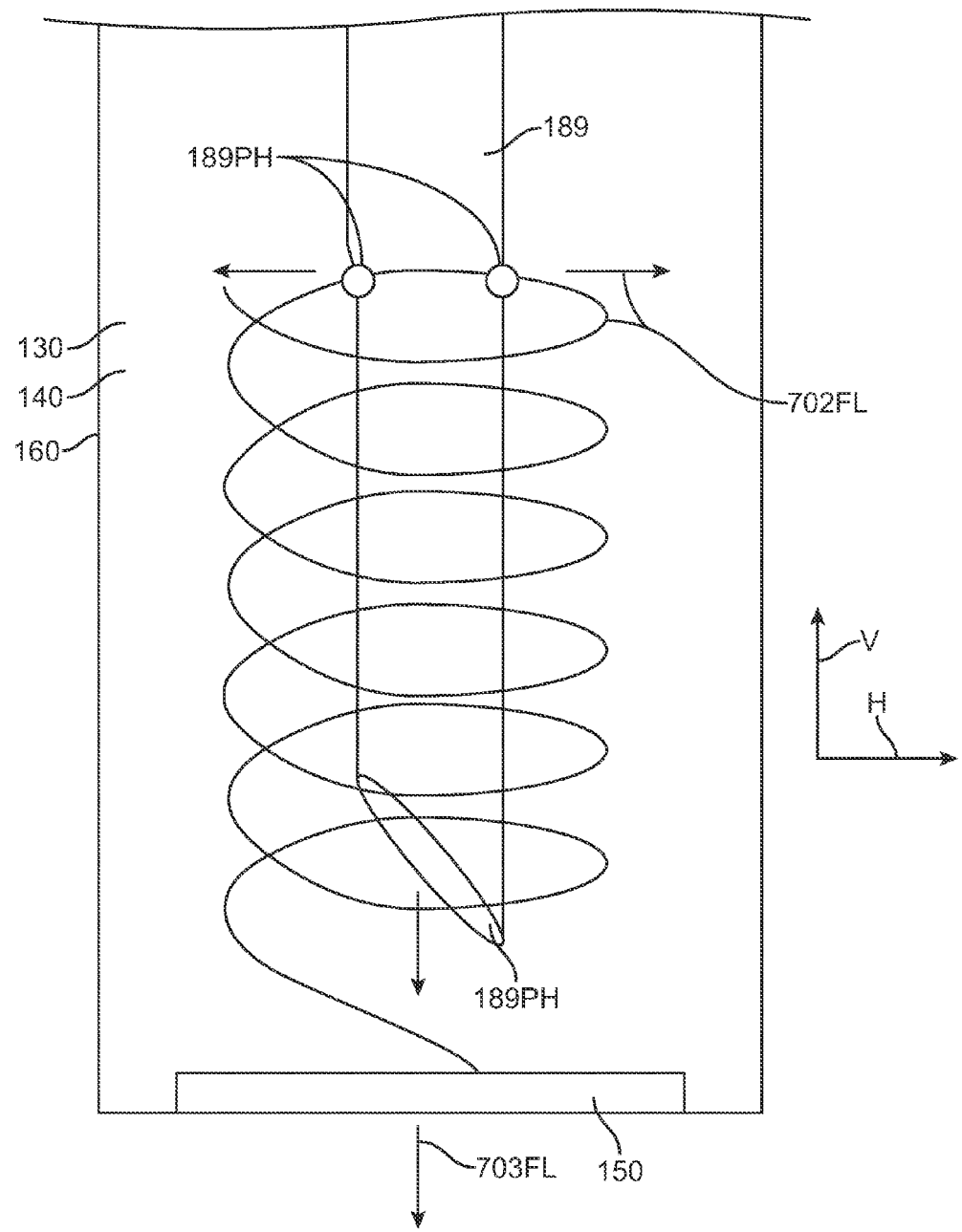

FIG. 11B shows needle 189 comprising a plurality of openings spaced radially and axially along the axis 189AX of the needle 189 and an opening on the distal tip so as to mix the therapeutic fluid 702FL with the fluid of the implantable device 100 to inhibit separation of the fluids. In many embodiments, at least one needle 189 comprises a single lumen needle oriented downward toward a porous structure located below the single lumen needle, and mixing of the fluids can increase the amount of therapeutic agent placed in the reservoir chamber of device 100 and corresponding efficiency. For example, the therapeutic fluid 702FL may comprise a density greater than the fluid of the reservoir chamber.

Figure 11C:
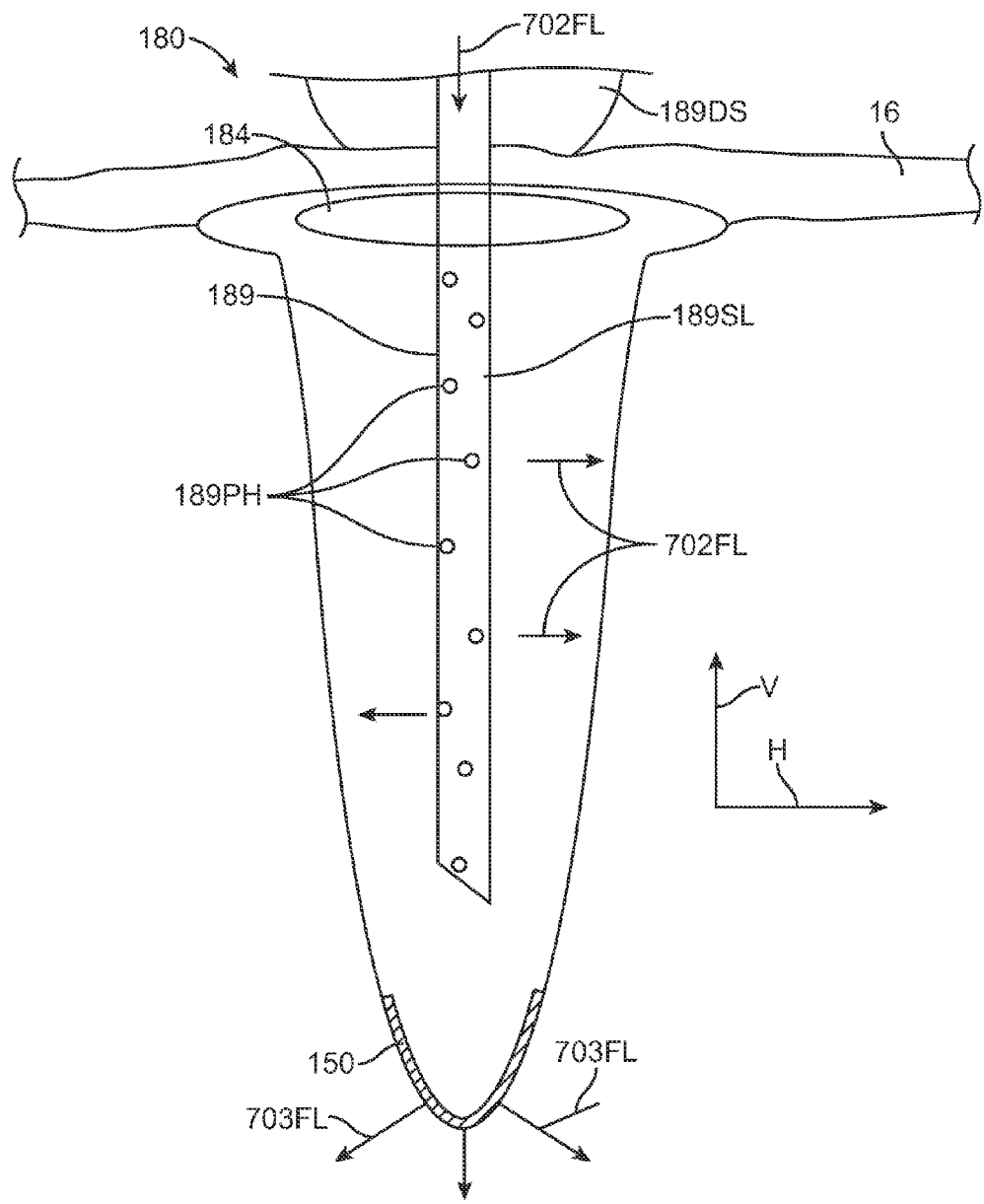
FIG. 11C shows needle comprising a plurality of openings spaced radially and axially along the axis of the needle so as to mix the therapeutic fluid with the fluid of the implantable device to inhibit separation of the fluids and in which the deformable stop is coupled to the conjunctiva, in accordance with embodiments of the present invention.

FIG. 11C shows needle 189 comprising a plurality of openings spaced radially and axially along the axis 189AX of the needle 189 so as to mix the therapeutic fluid 702FL with the fluid of the implantable device 100 to inhibit separation of the fluids and in which the deformable stop 189DS is coupled to the conjunctiva.

FIGS. 12A to 12C show an injector comprising an expandable chamber to inhibit excessive pressure of the therapeutic device 100. The expandable chamber may comprise a protective covering that can stretch and receive the therapeutic fluid 702FL with expansion as shown in FIG. 12B. The injector can be lowered onto the device and the fluid 702FL injected with compressive force of the expandable chamber such that a chamber of the injected receives fluid 703FL and a plunger moves upward as shown in FIG. 12C.

Figure 13A:
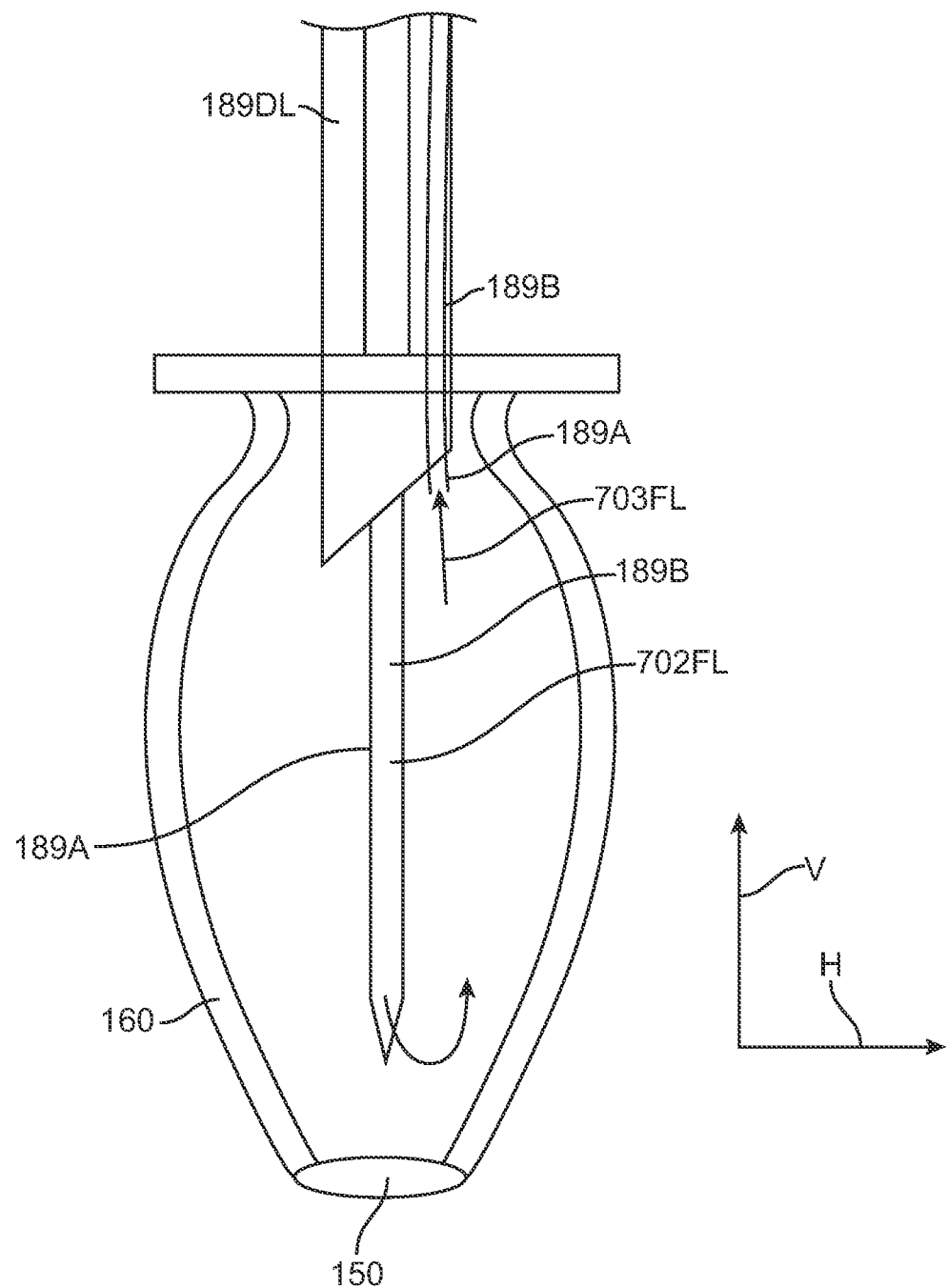
Figure 14A:
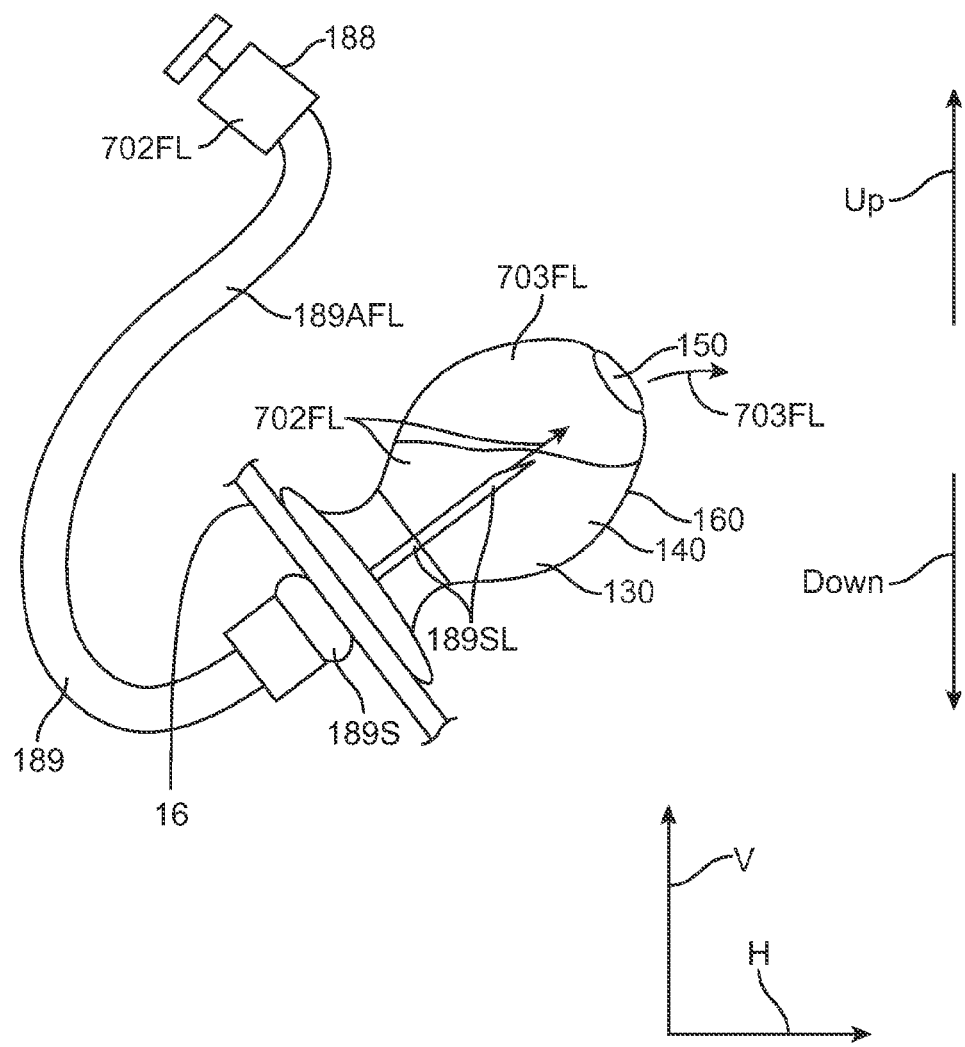

FIG. 13A shows a therapeutic device 100 receiving a therapeutic fluid 702FL having a density less than the implanted device fluid 703FL.

FIG. 14A shows a therapeutic device 100 receiving a therapeutic fluid 702FL having a density greater than the implanted device fluid 703FL and in which the needle 189 and deformable stop are coupled to the syringe with a flexible tube such that the needle can be decoupled from the syringe. The flexible tube permits injection into a patient in an upward direction, such that the therapeutic fluid 702FL can at least partially separate and settle toward a lower and proximal portion of device 150 with at least partial separation as show. The therapeutic device fluid 703FL can be preferentially passed through porous structure 150.

FIG. 13A shows a therapeutic device 100 receiving a therapeutic fluid 702FL having a density less than the implanted device fluid 703FL, in accordance with embodiments of the present invention;

FIG. 14A shows a therapeutic device 100 receiving a therapeutic fluid 702FL having a density greater than the implanted device fluid 703FL and in which the needle 189 and deformable stop are coupled to the syringe with a flexible tube such that the needle can be decoupled from the syringe, in accordance with embodiments of the present invention. The patient can be oriented such that the implant can inject the therapeutic fluid in an upward direction. In many embodiments, the patient can be reclined by the treating physician and/or staff and the patients head tilted to the side to access the implant located at the pars plana region of the eye.

Table X shows examples of device configurations in accordance with embodiments. The location of the porous structure 150 in relation to the penetrable barrier 184 can be related to the efficiency of the injection of therapeutic agent 110 into device 100. The apparatus to place the therapeutic fluid in the chamber of the implanted can be configured to provide placement of the therapeutic fluid corresponding to one or more of the configurations shown in Table X.

EXPERIMENTAL

Based on the teachings in accordance with embodiments described herein a person of ordinary skill in the art can conduct experimental studies to determine empirically the configurations of the injectors and implanted devices to provide amounts of therapeutic fluid to treat the eye for an extended time based on the at least partial separation of the implanted device fluid from the injected therapeutic fluid.

Experiment 1

Refill Efficiency Studies with Fluids Having Different Densities

Trehalose buffer was prepared containing 10 wt % trehalose (Fisher), 0.01 wt %% polysorbate 20 (Fisher) and 10 mM histidine HCl (Spectrum). The pH was adjusted to 7.6 using sodium hydroxide. Fluorescein sodium (AngioFluor) was added to a final concentration of 2.5 wt %. Phosphate buffered saline (hereinafter "PBS", Sigma) was prepared in HPLC grade water and an aliquot of this had fluorescein added to reach a final concentration of 2.5 wt %. Density measurements were made at 23° C. gravimetrically using a 10 mL Class A volumetric flask and an analytical balance measuring to 0.01 mg.

This study used devices with 25 uL reservoir volume and titanium porous structures that produce drug release profiles corresponding to a Release Rate Index of 0.02 mm. Devices were initially filled with 25 uL of PBS using a 1 cc tuberculin syringe (BD) and a 33 G needle (TSK). The distal end of the filled devices was inserted into tubing containing PBS which was pressurized using a pressure gauge and syringe. The syringe pressurized the system to 20 mmHg and then syringe was isolated from the system during the test. The devices were mounted in a mounting in fixture, tube added to distal end, then pressurized. The devices were held in an orientation of 45° from horizontal with the porous structure below the penetrable barrier. Devices (n=4 each) (n=2-3) were refilled with 45 uL of fluorescein containing either PBS or trehalose buffer using a 1 cc tuberculin syringe and a 33 G needle in a needle limiter assembly. Devices refilled with a needle limiter have therapeutic agent entering the device at a location proximal to the penetrable barrier. The time to refill was recorded. The pressure in the tubing increased due to the refill. After refill, the device was removed and the outside of the device was dried with a lab tissue. The contents of each device were removed by needle and syringe and collected into pre-weighed vials. The amount collected was determined gravimetrically. PBS was added to each vial to dilute the sample to the working range of the assay. Concentrations were measured in 96 well plates vs. a standard curve diluted in PBS and absorbance values read at a wavelength of 492 nm on a Molecular Devices VersaMaxPlus Plate Reader. In addition, controls were diluted from the original fluorescein containing solutions to provide a measurement corresponding to 100% refill efficiency. Refill efficiencies for each device were calculated by dividing the measured concentration of the device contents after refill by the corresponding control concentration.

The refill efficiency corresponds to the amount of therapeutic fluid placed in the reservoir chamber of the therapeutic device with the injection of therapeutic fluid and removal of implantable device fluid. In many embodiments, the amount of therapeutic fluid passed through the needle into the reservoir chamber of the implantable device corresponds to a volume greater than the volume of the reservoir chamber.

Table Y shows refill studies using two therapeutic agent fluid densities. The devices had the porous structure located below the penetrable barrier, the therapeutic agent introduced to the proximal portion of the device through the penetrable barrier, and excess fluid exiting from the device passed through the distally located porous structure.

The data in Table Y display results for this refill study with the porous structure below the penetrable barrier, the therapeutic agent introduced proximally near the penetrable barrier, and excess fluid exiting from the device through the distally located porous structure. Refill efficiency of 70% was obtained for devices having therapeutic fluid density matching the device fluid density. Refilling devices with a therapeutic fluid having density only 3% greater than the device fluid lowered the refill efficiency to 28%.

The data showed that PBS had a density of 1.00 which corresponds to the published value of normal saline 1.0046 (See Wikipedia, article entitled "Saline (medicine)"). The measured value of the density of the 10% trehalose solution was 1.03 and was consistent with estimated values.

This study showed that refill efficiency can be sensitive to small changes in density.

Experiment 2

Video Imaging and Efficiency Studies

Video imaging studies with a marker dye were conducted to identify the at least partial separation as described herein.

The exchange needle comprised a coaxial needle system in accordance with the embodiments of FIGS. 7-1 and 7-2, and having an internal needle of 33½ gauge and an outer tube of 0.018" inner diameter. The length of the inner needle was within a range from about 0.15 to about 0.25" long. The length of the outer tube used in the study was within a range from about 0.04" to about 0.09" long so as to provide a majority of the resistance to flow along the vent fluid path.

Figures 2, 15A:
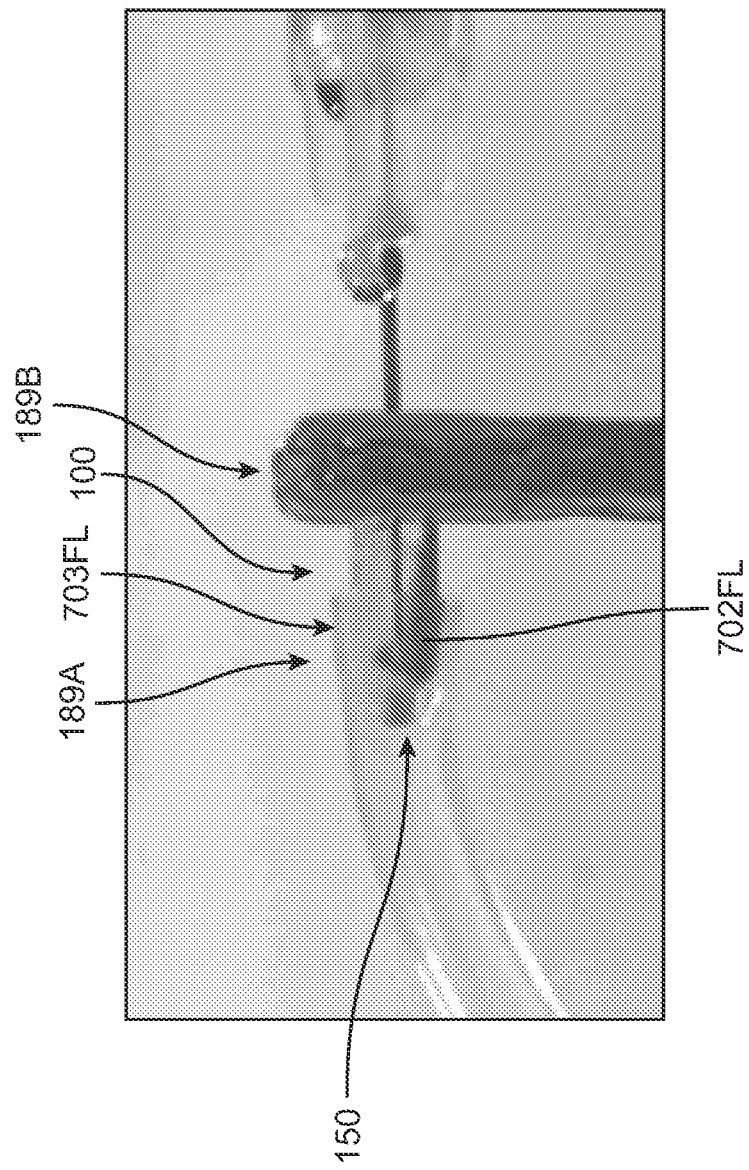
Figures 3, 15A:
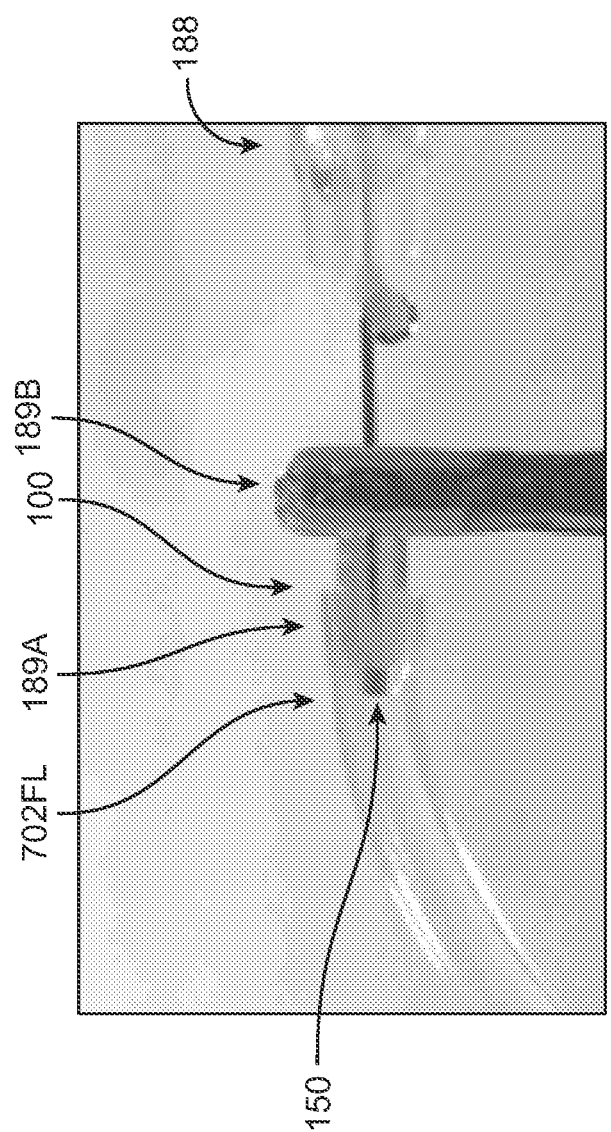

FIGS. 15A-1 to 15A-3 show the therapeutic device in an angle up position (10 degrees up off the horizontal, porous structure above penetrable barrier). The concentric needle and vent of the injector apparatus was constructed in accordance with the apparatus shown in FIGS. 7-1 and 7-2 as described herein. The injector apparatus injected denser liquid through a distal needle tip placed in the distal portion of the device near the porous structure, and a vent was located in the proximal portion of the device near the injector port. Clear PBS solution inside the device had an approximate density of 1.00 g/ml, while the yellow refill solution has an approximate density of 1.03 g/ml. The approximate refill rate was 1.3 ul/sec. A total of 45 ul was injected into a device. The device capacity was 25 ul. This device configuration and refill condition yielded an approximate refill efficiency of 60-90%. The porous structure 150 used had an RRI of 0.02 in accordance with teachings as described herein. The volume of the substantially rigid device reservoir was 25 ul. The time to inject was about 30 to 40 seconds for 45 ul of fluid.

FIG. 15A-1 was taken after approximately 10 ul has been injected into the device. This image shows at least partial separation of the injected fluid within the reservoir chamber of the implantable device, and the visible injected fluid is shown extending along the lower edge of the reservoir chamber.

FIG. 15A-2 was taken after approximately 25 ul has been injected into the device.

FIG. 15A-3 was taken after approximately 45 ul has been injected into the device.

Figures 1, 15B:
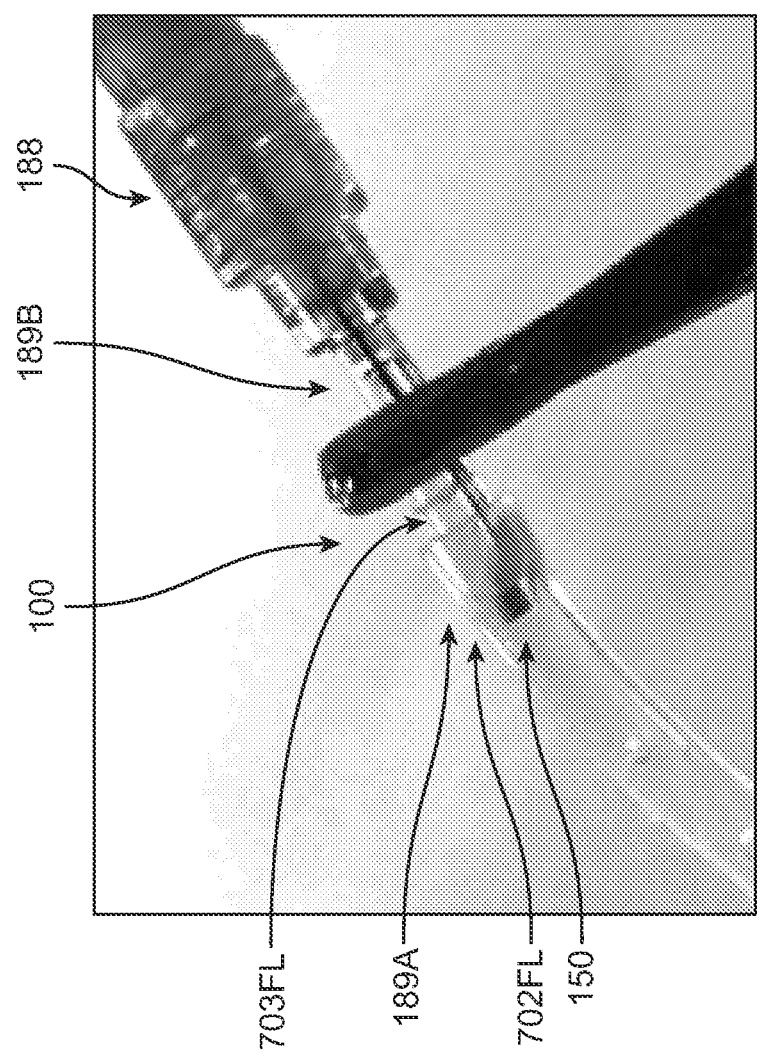
Figures 2, 15B:
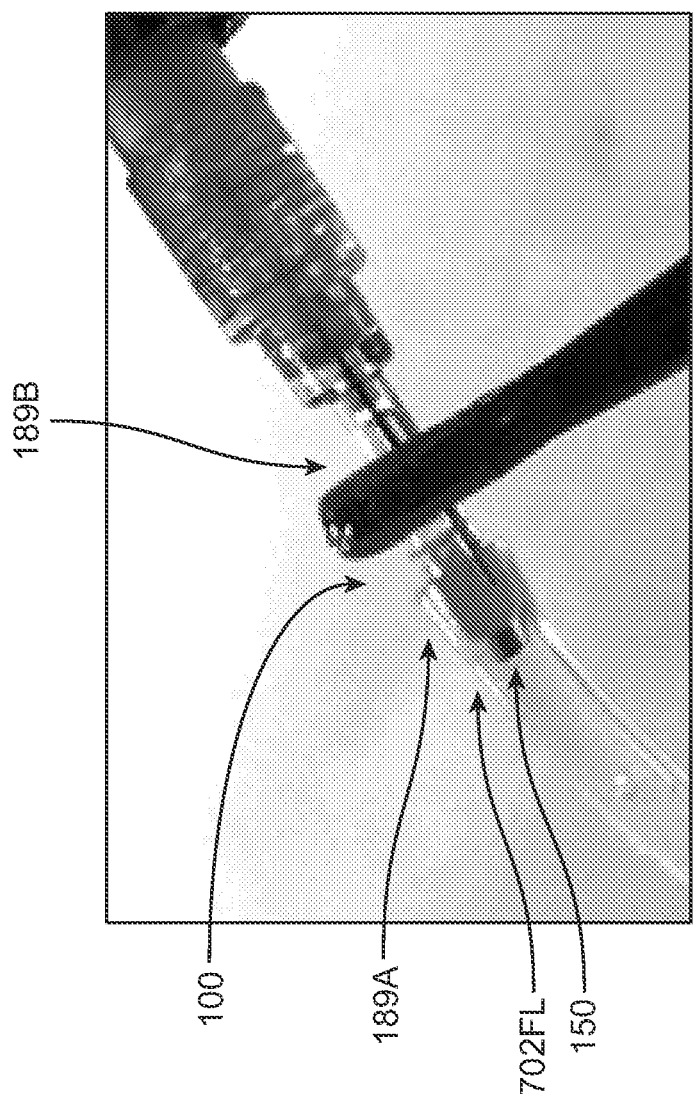
Figures 3, 15B:
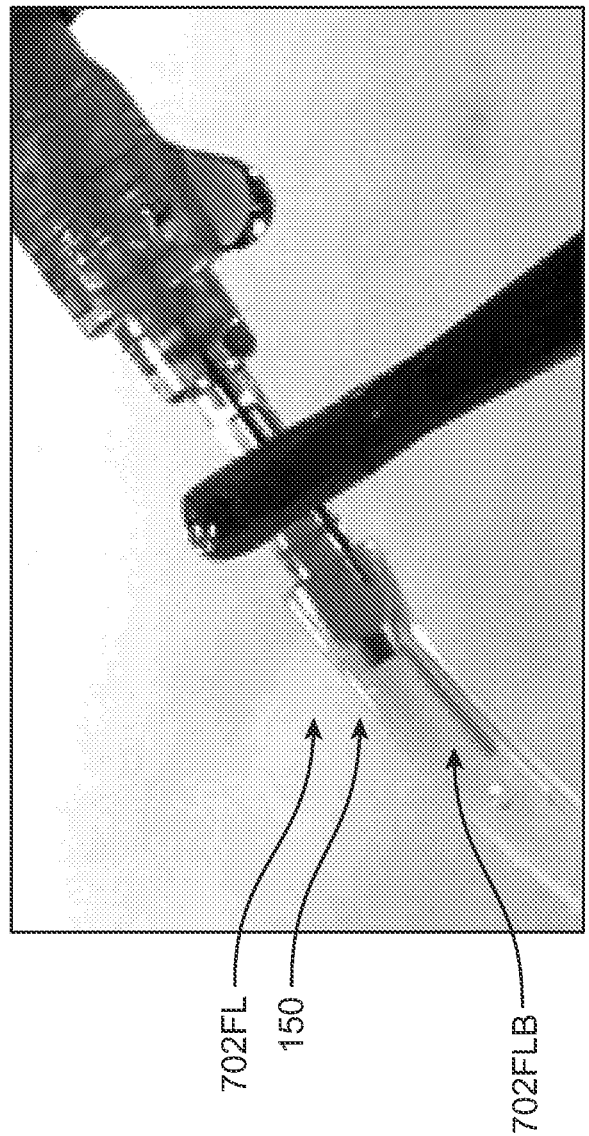

FIGS. 15B-1 to 15B-3 show the device 100 in an angle down position (35 degrees down off the horizontal, porous structure below the penetrable barrier). The concentric needle and vent of the injector apparatus is shown in FIG. 7-1. The injector apparatus injected denser liquid through a distal needle tip placed in the distal portion of the device near the porous structure, and a vent was located in the proximal portion of the device near the injector port having the penetrable barrier. Clear PBS solution inside the device had an approximate density of 1.00 g/ml, while the yellow refill solution had an approximate density of 1.03 g/ml. The color images were converted to grey scale images with yellow darkened. The approximate refill rate was 1.3 ul/sec. A total of 45 ul was injected into a device. The device capacity was 25 ul. This device configuration and refill condition yielded an approximate refill efficiency of 90-95%. The porous structure 150 used had an RRI of 0.02 in accordance with teachings as described herein and similar to FIGS. 15A-1 to 15A-3. The volume of the substantially rigid device reservoir was 25 ul. The time to inject was about 30 to 40 second for 45 ul of fluid.

FIG. 15B-1 was taken after approximately 10 ul has been injected into the implantable device. This image shows at least partial separation of the injected fluid within the reservoir chamber of the implantable device, and the visible fluid injected into the chamber is located near the bottom of the reservoir chamber that contacts the porous frit structure.

FIG. 15B-2 was taken after approximately 25 ul has been injected into the device.

FIG. 15B-3 was taken after approximately 45 ul has been injected into the device.

Experiment 4

Refill Efficiency and Density

Experiments 4-1 to 4-3

Additional studies were conducted to determine refill efficiency with the porous structure above or below the injection port. The substantially rigid implantable devices comprised a reservoir volume of 25 uL and were filled initially with PBS having a density of approximately 1.00, as described in Experiment 1. These devices were injected with 45 uL of fluid to determine the efficiency of the injection based on the amount of injected liquid in the reservoir chamber implantable device upon completion of the injection. As used in these studies, device up refers to the porous structure located above the penetrable barrier of the injection port. Experiments 4-1 to 4-2 used a single approximately 33 Gauge needle extending into the device and Experiment 4-3 used an exchange apparatus comprising a needle and a vent placed within the chamber of the device as shown in FIGS. 7-1 and 7-2. The injected solution was at least about 3% denser than the solution displaced from the implantable therapeutic device. These data show that at a flow rate within a range from about 1-2 uL per second and a density difference of at least about 3%, the at least partial separation can be achieved.

Experiment 4-1

Commercially available Avastin formulation was injected at a flow rate of 1.3 uL per second. The porous structure was located above the penetrable barrier at a 45 degree angle relative to horizontal. The measured efficiency based on the amount of Avastin in the therapeutic device chamber at completion of the injection was within a range from about 90 to about 97%. This amount of Avastin in the reservoir chamber upon completion of the injection corresponds to the at least partial separation within the reservoir chamber as described herein. Experiments 4-1 used a single approximately 33 Gauge needle extending into the device Experiment 4-2

Experiment 4-2 was conducted to detect an affect of density on refill efficiency. Testing was conducted using porous structures having an RRI of 0.02 that comprised Ti. The implantable devices were oriented in a 45 down direction. (Refill 45 ul at a rate of 1.3 ul/sec). The trehalose solution of Experiment 1 was injected into the implantable therapeutic device. Experiment 4-2 used a single approximately 33 Gauge needle extending into the device.
Results:
No change in refill solution density: amount in device 62-71%
0.03 change in density in refill solution: amount in device 27-31%
These data show that density differences and the at least partial separation as described herein can contribute to the measured refill efficiency.

Experiment 4-3

Experiment 4-3 was conducted with commercially available Avastin and a coaxial needle/vent exchange system as shown in FIGS. 7-1 and 7-2. The commercially available Avastin formulation (10 mg/mL) was in injected into devices comprising PBS as described in Experiment 1. These studies show that injection angle and density can be used to provide improved efficiency of the exchange. The refill rate was 1.3 uL per second for a total volume of 45 ul injected into the 25 uL device. Experiment 4-3 used an exchange apparatus comprising a needle and a vent placed within the chamber of the device as shown in FIGS. 7-1 and 7-2.
Results:
10 degrees up, amount placed in device 64-87%
10 degrees down, amount placed in device 82-97%
35 degrees down, amount placed in device 90-94%
60 degrees down, amount placed in device 94-97%
90 degrees down, amount placed in device 96-94%

These studies show that with the therapeutic device pointing down 35 degrees or greater, at least about 90% refill can be provided with an exchange system and a density difference corresponding to at least Avastin and phosphate buffered saline (hereinafter "PBS"). These studies placed the opening of the needle injecting the formulation below the opening to receive displaced liquid from the implantable device. These data show at least partial separation of the injected therapeutic fluid from the implantable device fluid as described herein. Similar studies can be conducted with many formulations injected into the implantable device based on the teachings described herein.

Experiment 5

Efficiency of Fluid Displacement and Angle of Implanted Device to Horizontal

Experiments were conducted to determine the refill efficiency for orientation of the device axis relative to horizontal. The device may be configured for a physician to inject the therapeutic to fluid at an angle and flow rate so as to provide the at least partial fluid separation as described herein. The implanted device was modeled with test devices orientated in relation to horizontal and injection. The injection was made with either a single needle or the exchange apparatus as shown in FIGS. 7-1 and 7-2. The single needle having the injection lumen was approximately 33½ gauge that extended about 0.060" to about 0.090" beyond the deformable needle stop so as to position the opening of the needle in a distal portion of the therapeutic device. The angles of the device were determined that correspond to patient orientation in a treatment chair for angles of the eye and orientations of the head. Trehalose solution was injected into devices filled PBS as described in Experiment 1, so as to model the injection of therapeutic agent formulation into the reservoir chamber of the device implanted in the patient.

The data of the Tables Z1 and Z2 show several device orientations relative to horizontal that correspond to several positions and orientations of the patient. The patient position angle generally corresponds to the back of the patient relative to horizontal such that 90 degrees corresponds to the patient sitting up and the flat on back corresponds to an angle of 0 degrees. The side head angle corresponds to the tilt of the patient head from side to side and the head turn angle corresponds to rotation of the head about an axis extending along the body of the patient. The corresponding device orientations are shown in the column device position in degrees to the horizontal. The efficiency was tested for both a single lumen extending into the device so as to displace the liquid of the chamber by passing the fluid of the device through the porous structure of the implanted device, and for an exchange configuration comprising a first lumen to inject fluid and a second lumen to receive displaced fluid from the implantable device chamber. These data show that for the injection times and angles measured, the at least partial separation can affect the refill efficiency.

These data show that the injection device can be adapted for an orientation of the implanted device and the eye of the patient. For example, with a single needle injected into the device and a therapeutic fluid having a density greater than the density of the device fluid it can be helpful to located the penetrable barrier below the porous structure such that the denser therapeutic fluid separates toward the penetrable barrier and the less then fluid of the implanted device separates toward the porous structure for passage through the porous structure so as to increase the efficiency of the placement of the therapeutic fluid.

Table Z1 shows injector orientation and efficiency for several angles of the device relative to horizontal. Many of these angles correspond to angles of the device that can be provided with the patient instructed to look forward at all times when the device is injected.

For the no exchange refill, the efficiency range from 23-29% with the axis of the device positioned 40 degrees off horizontal and the penetrable barrier above the porous structure. When the angle was inverted to −45 degrees with the penetrable barrier below the porous structure, the efficiency for the increased to at least about 90%.

Table Z2 shows device orientation and refill efficiency data corresponding to the patient instructed to look at the tip of the nose for the injection. These data are consistent with Table Z1, and show increased efficiency for the exchange apparatus with the penetrable barrier above the porous structure and increased efficiency for the single needle injection with the penetrable barrier below the porous structure.

Experiment 6

Injector Cartridge

Experiments have been conducted to show displacement of fluid from an implantable device into an injector cartridge having a container to store fluid from the therapeutic device suitable for analysis as described herein.

FIGS. 16A-1 to 16A-3 show images of an injector cartridge 320 having a container to receive the implanted device fluid and a porous vent structure down stream of the container such that the porous structure of the cartridge comprises a valve to provide a bolus injection. The color images have been converted to grey scale images and enhanced to show red as black. The color images were obtained with red dye corresponding to fluid 703FL. The clear injected fluid corresponds to therapeutic fluid 702FL. The cartridge is coupled to an injection syringe and the at least one needle comprises a first needle and a second needle. The injection lumen extends to a distal end portion of the therapeutic device 100 and vent of the outflow channel is located on a proximal portion of the therapeutic device 100. The injector cartridge comprises the deformable stop 189DS to reversibly deform when coupled to the conjunctiva of the eye. The injector cartridge comprises a transparent material 320TM a window 320W to view the fluid of the implantable device received with the container.

As shown in FIGS. 16A-1 to 16A-3, the implantable device axis extends at an angle about 60 to 70° down off the horizontal. Red solution inside the device has an approximate density of 1 g/ml, while the clear refill solution has an approximate density of 1 g/ml as well. The approximate refill rate is 1.3 ul/sec. A total of 45 ul was injected into a device. The device capacity is 25 ul. This device configuration and refill condition yields an approximate refill efficiency of 60-90%.

FIG. 16A-1 shows the fluid flow after approximately 10 uL of injection. FIG. 16A1 was taken after approximately 10 μl has been injected into the device.

FIG. 16A-2 shows the outflow of the device fluid after approximately 25 uL has been injected into the device 100. FIG. 16A-2 was taken after approximately 25 ul has been injected into the device. A substantial portion of the bolus injection has been passed through the porous structure 150 of device 100.

FIG. 16A-3 shows the outflow and bolus after approximately 45 uL has been injected. FIG. 16A-3 was taken after approximately 45 ul has been injected into the device.

FIGS. 16A-4 and 16A-5 show a side view of the exchange needle apparatus and a front view, respectively of the exchange needle apparatus. The porous structure 703VPS of the outflow path can provide a substantial resistance to flow of the fluid comprising liquid so as to provide the bolus injection. The cartridge comprises the deformable stop 189DS as described herein to couple to the conjunctiva of the eye.

FIG. 16A-4 is a side view of the exchange needle. This is a bi-needle system with the longer needle doing the injection while the short needle allows the fluid to escape into the containment track. FIG. 16A-5 is the front view that shows the containment track with the porous vent at the top left end of the track. This porous vent allows for air to escape with a low amount of resistance while causing a great resistance to the fluid pass through. The resistance to air passing though creates a level of pressure in the system to cause a bolus of new exchange fluid to pass through the implantable device porous structure 150.

Figures 1, 17A:
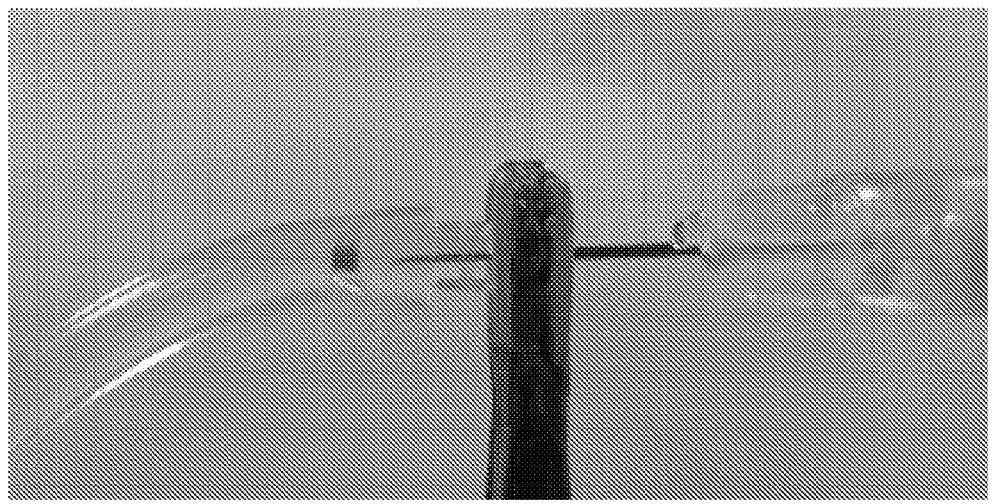
Figures 2, 17A:
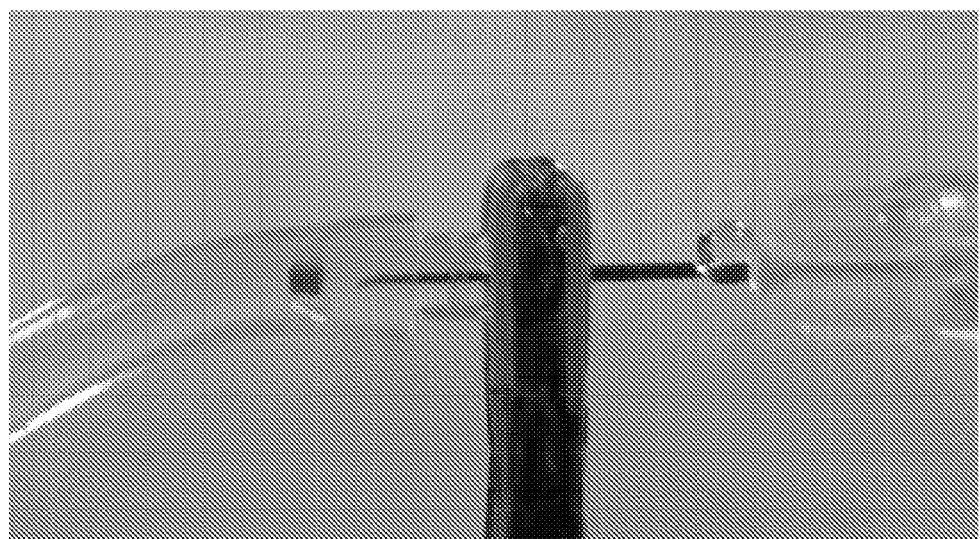
Figures 3, 17A:

FIGS. 17A-1 to 17A-3 show injection into the implantable device so as to determine the presence of stream flow of the injected liquid within the implantable device.

FIG. 17A-1 to 17A-3 show the device in a horizontal position. The clear solution inside the device had an approximate density of 1 g/ml, while the yellow refill solution had an approximate density of 1.03 g/ml. The approximate refill rate was 1.3 ul/sec. A total of 45 ul was injected into a device. The device capacity was 25 ul.

FIG. 17A-1 was taken after approximately 10 ul has been injected into the device. A jet of incoming solution can be seen coming out the end of the needle in a 45 degree stream. The solution hit the end of the device and flowed down past the porous structure and settled at the bottom of the device.

FIG. 17A-2 was taken after approximately 25 ul had been injected into the device. A jet of incoming solution can be seen coming out the end of the needle in a 45 degree stream.

FIG. 17A-3 was taken after approximately 45 ul had been injected into the device.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

TABLE X

| Case | Density of TA fluid | Porous Structure Location (due to patient position) | Location of Lumen delivering TA | Second Lumen |
|---|---|---|---|---|
| 1 | Higher than Implanted fluid by at least 1% | Below the penetrable barrier | Distal | Second lumen is vent with location proximal |
| 2 | Higher than Implanted fluid by at least 1% | Above the penetrable barrier | Proximal | No vent needed - vents into the eye or second lumen is vent with location distal |

TABLE X-continued

| Case | Density of TA fluid | Porous Structure Location (due to patient position) | Location of Lumen delivering TA | Second Lumen |
|---|---|---|---|---|
| 3 | Lower than Implanted fluid by at least 1% | Below the penetrable barrier | Proximal | No vent needed - vents into the eye or second lumen is vent with location distal |
| 4 | Lower than Implanted fluid by at least 1% | Above the penetrable barrier | Distal | Second lumen is vent with location proximal |

TABLE Y

Refill study using two therapeutic agent densities. The devices had porous structure below the penetrable barrier, the therapeutic agent introduced proximal to the penetrable barrier, and excess fluid exiting from the device through the distally located porous structure.

| Solution | Density (g/mL) | Refill Efficiency (%) | RSD (%) | Starting Pressure (mmHg) | Ending Pressure (mmHg) | Refill Time (s) |
|---|---|---|---|---|---|---|
| PBS | 1.00 | NA | NA | NA | NA | NA |
| 2.5 mg/mL Fluorescein in PBS | 1.00 | 70 | 5 | 21 | 51 | 43 |
| 2.5 mg/mL Fluorescein in 10% Trehalose/0.01% Tween | 1.03 | 28 | 3 | 21 | 62 | 43 |

TABLE Z2

Eye position: Make the patient look at the tip of their nose at all times (exposing the refill site)

| Patient position | Side head angle in (°) off horiz | Head turn angle in (°) off horiz | Device position in (°) to the horiz | No exchange Refill | Exchange Refill |
|---|---|---|---|---|---|
| Sitting up | 90 | n/a | 17 | | 82-97% |
| Recline or tilt head back | 70 | n/a | 24 | | |
| Recline or tilt head back | 60 | n/a | 44 | 23-29% | 92-95% |
| Recline or tilt head back | 40 | n/a | 65 | | 94-97% |
| Recline or tilt head back | 10 | n/a | 69 | | 94-97% |
| flat on back | 0 | 90 | 72 | | 94-97% |
| flat on back | 0 | 80 | 65 | | 94-97% |
| flat on back | 0 | 60 | 43 | 23-29% | 94-97% |
| flat on back | 0 | 40 | 28 | | |
| flat on back | 0 | 20 | 5 | | |
| flat on back | 0 | 15 | 0 | | |
| flat on back | 0 | 0 | −12 | | 64-87% |

TABLE Z1

The horizontal is 0°. And angle above is + and angle below is −. The vertical is 90°.
Eye position: making the patient look forward at all times

| Patient position | Side head angle in (°) off horiz | Head turn angle in (°) off horiz | Device position in (°) to the horiz | No exchange Refill | Exchange Refill |
|---|---|---|---|---|---|
| Sitting up | 90 | n/a | 40 | 23-29% | 92-95% |
| Recline or tilt head back | 70 | n/a | 52 | 23-29% | 94-97% |
| Recline or tilt head back | 60 | n/a | 55 | | 94-97% |
| Recline or tilt head back | 40 | n/a | 60 | | 94-97% |
| Recline or tilt head back | 10 | n/a | 52 | 23-29% | 94-97% |
| flat on back | 0 | 90 | 50 | 23-29% | 94-97% |
| flat on back | 0 | 80 | 30 | | 85-95% |
| flat on back | 0 | 60 | 16 | | 82-97% |
| flat on back | 0 | 43 | 0 | | |
| flat on back | 0 | 40 | −6 | | 64-87% |
| flat on back | 0 | 20 | −28 | | |
| flat on back | 0 | 0 | −45 | 90-94% | |

TABLE 1A

Therapeutic Agent List

| Generic Name | Brands (Companies) | Category | Indication | Molecular Weight |
|---|---|---|---|---|
| 2-Methoxyestradiol analogs | (Paloma Pharmaceuticals) | Angiogenesis inhibitors | AMD | |
| 3-aminothalidomide | | | | |
| 13-cis retinoic acid | Accutane TM (Roche Pharmaceuticals) | | | |

TABLE 1A-continued

Therapeutic Agent List

| Generic Name | Brands (Companies) | Category | Indication | Molecular Weight |
|---|---|---|---|---|
| A0003 | (Aqumen BioPharmaceuticals) | A0003 | AMD | |
| A5b1 integrin inhibitor | (Jerini Ophthalmic); (Ophthotech) | Inhibitors of a5b1 integrin | AMD | |
| Abarelix | Plenaxis ™ (Praecis Pharmaceuticals) | Anti-Testosterone Agents; Antineoplastic Agents | For palliative treatment of advanced prostate cancer. | 37731 |
| Abatacept | Orencia ™ (Bristol-Myers Squibb) | Antirheumatic Agents | For the second line reduction of the signs and symptoms of moderate-to-severe active rheumatoid arthritis, inducing inducing major clinical response, slowing the progression of structural damage, and improving physical function in adult patients who have | 37697 |
| Abciximab | ReoPro ™; ReoPro ™ (Centocor) | Anticoagulants; Antiplatelet Agents | For treatment of myocardial infarction, adjunct to percutaneous 138oronary intervention, unstable angina | 42632 |
| ABT-578 | (Abbott Laboratories) | Limus Immunophilin Binding Compounds | | |
| Acetonide | | | | |
| Adalimumab | Humira ™ (Abbott Laboratories) | Antirheumatic Agents; Immunomodulatory Agents | Uveitis, AMD | 25645 |
| Aldesleukin | Proleukin ™; Proleukin ™ (Chiron Corp) | Antineoplastic Agents | For treatment of adults with metastatic renal cell carcinoma | 61118 |
| Alefacept | Amevive ™ | Immunomodulatory Agents; Immunosuppressive Agents | For treatment of moderate to severe chronic plaque psoriasis | 42632 |
| Alemtuzumab | Campath ™; Campath ™ (ILEX Pharmaceuticals LP); MabCampath ™ | Antineoplastic Agents | For treatment of B-cell chronic lymphocytic leukemia | 6614 |
| Alpha-1-proteinase inhibitor | Aralast ™ (Baxter); Prolastin ™ (Talecris Biotherapeutics C formerly Bayer) | Enzyme Replacement Agents | For treatment of panacinar emphysema | 28518 |
| Alteplase | Activase ™ (Genentech Inc) | Thrombolytic Agents | For management of acute myocardial infarction, acute ischemic strok and for lysis of acute pulmonary emboli | 54732 |
| AMG-1470 | | | | |
| Anakinra | Kineret ™ (Amgen Inc) | Anti-Inflammatory Agents, Non-Steroidal; Antirheumatic Agents; Immunomodulatory Agents | For the treatment of adult rheumatoid arthritis. | 65403 |
| Anecortave acetate | | | | |
| Angiostatin | | | | |
| Anistreplase | Eminase ™ (Wulfing Pharma GmbH) | Thrombolytic Agents | For lysis of acute pulmonary emboli, intracoronary emboli and management of myocardial infarction | 54732 |
| Anti-angiogenesis peptides | (Eyecopharm) | Anti-angiogenesis peptides | AMD | |
| Anti-angiogenesis antibodies, TRC093, TRC105 | (TRACON Pharma) | Anti-angiogenesis antibodies | AMD | |
| Anti-angiogeric bifunctional protein | Icon-1 ™ (Iconic Therapeutics) | Anti-angiogeric bifunctional protein, Icon-1 | AMD | |
| Anti-endothelial growth factor | | | | |
| Antihemophilic Factor | Advate ™; Alphanate ™; Bioclate ™; Helixate ™; Helixate FS ™; Hemofil M ™; Humate-P ™; Hyate:C ™; Koate-HP ™; Kogenate ™; Kogenate FS ™; Monarc-M ™; Monoclate-P ™; ReFacto ™; Xyntha ™ | Coagulants; Thrombotic Agents | For the treatment of hemophilia A, von Willebrand diseae and Factor XIII deficiency | 70037 |
| Antithymocyte globulin | Genzyme); Thymoglobulin ™ (SangStat Medical | Immunomodulatory Agents | For prevention of renal transplant rejection | 37173 |
| Anti-hypertensive MC1101 | (MacuCLEAR) | Anti-hypertensive MC1101 | AMD | |
| Anti-platelet devired growth factor | | | | |
| Anti-VEGF | (Neurotech); Avastin ™ (NeoVista) | Anti-VEGF | AMD | |
| AP23841 | (Ariad) | Limus Immunophilin Binding Compounds | | |
| ARC1905 | Ophthotech | Complement Cascade Inhibitor (Factor C5) | | |
| Aprotinin | Trasylol ™ | Antifibrinolytic Agents | For prophylactic use to reduce perioperative blood loss and the need for blood transfusion in patients undergoing cardiopulmonary bypass in the course of coronary artery bypass graft surgery who | 90569 |

TABLE 1A-continued

Therapeutic Agent List

| Generic Name | Brands (Companies) | Category | Indication | Molecular Weight |
|---|---|---|---|---|
| | | | are at an increased risk for blood loss and blood transfusio | |
| Arcitumomab | CEA-Scan ™ | Diagnostic Agents; Imaging Agents | For imaging colorectal tumors | 57561 |
| Asparaginase | Elspar ™ (Merck & Co. Inc) | Antineoplastic Agents | For treatment of acute lympocytic leukemia and non-Hodgkins lymphoma | 132.118 |
| Axitinib | | Tyrosine Kinase Inhibitors | | 386 |
| Basiliximab | Simulect ™ (Novartis Pharmaceuticals) | Immunomodulatory Agents; Immunosuppressive Agents | For prophylactic treatment of kidney transplant rejection | 61118 |
| Becaplermin | Regranex ™; Regranex ™ (OMJ Pharmaceuticals) | Anti-Ulcer Agents; Topical | For topical treatment of skin ulcers (from diabetes) | 123969 |
| Bevacizumab | Avastin ™; Avastin ™ (Genentech Inc) | Antiangiogenesis Agents; Antineoplastic Agents | For treatment of metastatic colorectal cancer | 27043 |
| Bivalirudin | Angiomax ™; Angiomax ™ (Medicines Co or MDCO); Angiox ™ | Anticoagulants; Antithrombotic Agents | For treatment of heparin-induced thrombocytopenia | 70037 |
| Bortezomib | | Proteosome Inhibitors | | |
| Bosutinib | | Tyrosine Kinase Inhibitors | | 530 |
| Botulinum Toxin Type A | BOTOX ™ (Allegran Inc); BOTOX Cosmetic ™ (Allegran Inc); Botox ™; Dysport ™ | Anti-Wrinkle Agents; Antidystonic Agents; Neuromuscular Blocking Agents | For the treatment of cervical dystonia in adults to decrease the severity of abnormal head position and neck pain associated with cervical dystonia. Also for the treatment of severe primary axillary hyperhidrosis that is inadequately managed with topical | 23315 |
| Botulinum Toxin Type B | Myobloc ™ (Solstice Neurosciences); Neurobloc ™ (Solstice Neurosciences) | Antidystonic Agents | For the treatment of patients with cervical dystonia to reduce the severity of abnormal head position and neck pain associated with cervical dystonia. | 12902 |
| C5 inhibitor | (Jerini Ophthalmic); (Ophthotech) | Inhibitors of C5 | AMD | |
| Cal101 | Calistoga | PI3Kdelta Inhibitor | AMD, DME | |
| Canstatin | | | | |
| Capromab | ProstaScint ™ (Cytogen Corp) | Imaging Agents | For diagnosis of prostate cancer and detection of intra-pelvic metastases | 84331 |
| Captopril | | ACE Inhibitors | | |
| CCI-779 | (Wyeth) | Limus Immunophilin Binding Compounds | | |
| Cediranib | | Tyrosine Kinase Inhibitors | | 450 |
| Celecoxib | | Cyclooxygenase Inhibitors | | |
| Cetrorelix | Cetrotide ™ | Hormone Antagonists; Infertility Agents | For the inhibition of premature LH surges in women undergoing controlled ovarian stimulation | 78617 |
| Cetuximab | Erbitux ™; Erbitux ™ (ImClone Systems Inc) | Antineoplastic Agents | For treatment of metastatic colorectal cancer. | 42632 |
| Choriogonadotropin alfa | Novarel ™; Ovidrel ™; Pregnyl ™; Profasi ™ | Fertility Agents; Gonadotropins | For the treatment of female infertility | 78617 |
| Cilary neurotrophic factor | (Neurotech) | Cilary neurotrophic factor | AMD | |
| Coagulation Factor IX | Benefix ™ (Genetics Institute) | Coagulants; Thrombotic Agents | For treatment of hemophilia (Christmas disease). | 267012 |
| Coagulation factor VIIa | NovoSeven ™ (Novo Nordisk) | Coagulants; Thrombotic Agents | For treatment of hemorrhagic complications in hemophilia A and B | 54732 |
| Colchicines | | | | |
| Collagenase | Cordase ™; Santyl ™ (Advance Biofactures Corp); Xiaflextm ™ | Anti-Ulcer Agents; Topical | For treatment of chronic dermal ulcers and severe skin burns | 138885 |
| Complement factor H recombinant | (Optherion); (Taligen Therapeutics) | Complement factor H recombinant | AMD, Geographic Atrophy | |
| Compstatin derivative peptide, POT-4 | (Potentia Pharmaceuticals) | Complement Factor C3 Inhibitors; Compstatin Derivative Peptides | AMD | |
| Corticotropin | ACTH ™; Acethropan ™; Acortan ™; Acthar ™; Exacthin ™; H.P. Acthar Gel ™; Isactid ™; Purified cortrophin gel ™; Reactin ™; Solacthyl ™; Tubex | Diagnostic Agents | For use as a diagnostic agent in the screening of patients presumed to have adrenocortical insufficiency. | 33927 |
| Cosyntropin | Cortrosyn ™; Synacthen depot ™ | Diagnostic Agents | For use as a diagnostic agent in the screening of patients presumed to have adrenocortical insufficiency. | 33927 |
| Cyclophilins | | Limus Immunophilin Binding Compounds | | |
| Cyclosporine | Gengraf ™ (Abbott labs); Neoral ™ (Novartis); Restasis ™; Restasis ™ (Allergan Inc); Sandimmune ™ (Novartis); Sangcya ™ | Antifungal Agents; Antirheumatic Agents; Dermatologic Agents; Enzyme Inhibitors; Immunomodulatory | For treatment of transplant rejection, rheumatoid arthritis, severe psoriasis | 32953 |

TABLE 1A-continued

Therapeutic Agent List

| Generic Name | Brands (Companies) | Category | Indication | Molecular Weight |
|---|---|---|---|---|
| Daclizumab | Zenapax ™ (Hoffmann-La Roche Inc) | Agents; Immunosuppressive Agents Immunomodulatory Agents; Immunosuppressive Agents | For prevention of renal transplant rejection; Uveitis | 61118 |
| Darbepoetin alfa | Aranesp ™ (Amgen Inc.) | Antianemic Agents | For the treatment of anemia (from renal transplants or certain HIV treatment) | 55066 |
| Dasatinib | | Tyrosine Kinase Inhibitors | | 488 |
| Defibrotide | Dasovas ™; Noravid ™; Prociclide ™ | Antithrombotic Agents | Defibrotide is used to treat or prevent a failure of normal blood flow (occlusive venous disease, OVD) in the liver of patients who have had bone marrow transplants or received certain drugs such as oral estrogens, mercaptopurine, and many others. | 36512 |
| Denileukin diftitox | Ontak ™ | Antineoplastic Agents | For treatment of cutaneous T-cell lymphoma | 61118 |
| Desmopressin | Adiuretin ™; Concentraid ™; Stimate ™ | Antidiuretic Agents; Hemostatics; Renal Agents | For the management of primary nocturnal enuresis and indicated as antidiuretic replacement therapy in the management of central diabetes insipidus and for the management of the temporary polyuria and polydipsia following head trauma or surgery in the pitu | 46800 |
| Dexamethasone | Ozurdex ™ (Allergan) | Glucocorticoid | DME, inflammation, macular edema following branch retinal vein occlusion (BRVO) or central retinal vein occlusion (CRVO) | 392 |
| Diclofenac Dithiocarbamate | | Cyclooxygenase Inhibitors NFκB Inhibitor | | |
| Dornase Alfa | Dilor ™; Dilor-400 ™; Lufyllin ™; Lufyllin-400 ™; Neothylline ™; Pulmozyme ™ (Genentech Inc) | Enzyme Replacement Agents | For the treatment of cystic fibrosis. | 7656 (double strand) |
| Drotrecogin alfa | Xigris ™; Xigris ™ (Eli Lilly & Co) | Antisepsis Agents | For treatment of severe sepsis | 267012 |
| Eculizumab | Soliris ™; Soliris ™ (Alexion Pharmaceuticals) | Complement Cascade Inhibitor (Factor C5) | AMD | 188333 |
| Efalizumab | Raptiva ™; Raptiva ™ (Genentech Inc) | Immunomodulatory Agents; Immunosuppressive Agents | For the treatment of adult patients with moderate to severe chronic plaque psoriasis, who are candidates for phototherapy or systemic therapy. | 128771 |
| Endostatin | | | | |
| Enfuvirtide | Fuzeon ™; Fuzeon ™ (Roche Pharmaceuticals) | Anti-HIV Agents; HIV Fusion Inhibitors | For treatment of HIV AIDS | 16768 |
| Epoetin alfa | Epogen ™ (Amgen Inc.); Epogin ™ (Chugai); Epomax ™ (Elanex); Eprex ™ (Janssen-Cilag. Ortho Biologics LLC); NeoRecormon ™ (Roche); Procrit ™ (Ortho Biotech); Recormon ™ (Roche) | Antianemic Agents | For treatment of anemia (from renal transplants or certain HIV treatment) | 55066 |
| Eptifibatide | Integrilin ™; Integrilin ™ (Millennium Pharm) | Anticoagulants; Antiplatelet Agents; Platelet Aggregation Inhibitors | For treatment of myocardial infarction and acute coronary syndrome. | 7128 |
| Erlotinib | | Tyrosine Kinase Inhibitors | | 393 |
| Etanercept | Enbrel ™; Enbrel ™ (Immunex Corp) | Antirheumatic Agents; Immunomodulatory Agents | Uveitis, AMD | 25645 |
| Everolimus | Novartis | Limus Immunophilin Binding Compounds, mTOR | AMD | |
| Exenatide | Byetta ™; Byetta ™ (Amylin/Eli Lilly) | | Indicated as adjunctive therapy to improve glycemic control in patients with Type 2 diabetes mellitus who are taking metformin, a sulfonylurea, or a combination of both, but have not achieved adequate glycemic control. | 53060 |
| FCFD4514S | Genentech/Roche | Complement Cascade Inhibitor (Factor D) | AMD, Geographic Atrophy | |
| Felypressin | Felipresina ™ [INN-Spanish]; Felipressina ™ [DCIT]; Felypressin ™ [USAN:BAN:INN]; Felypressine ™ [INN-French]; Felypressinum ™ [INN-Latin]; Octapressin ™ | Renal Agents; Vasoconstrictor Agents | For use as an alternative to adrenaline as a 147ocalizing agent, provided that local ischaemia is not essential. | 46800 |

TABLE 1A-continued

Therapeutic Agent List

| Generic Name | Brands (Companies) | Category | Indication | Molecular Weight |
|---|---|---|---|---|
| Fenretinide | Sirion/reVision Therapeutics | Binding Protein Antagonist for Oral Vitamin A | AMD, Geographic Atrophy | |
| Filgrastim | Neupogen ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| FK605-binding proteins, FKBPs | | Limus Immunophilin Binding Compounds | | |
| Fluocinolone Acetonide | Retisert ™ (Bausch & Lomb); Iluvien ™ (Alimera Sciences, Inc.) | Glucocorticoid | Retinal inflammation, diabetic macular edema | 453 |
| Follitropin beta | Follistim ™ (Organon); Gonal F ™; Gonal-F ™ | Fertility Agents | For treatment of female infertility | 78296 |
| Fumagillin | | | | |
| Galsulfase | Naglazyme ™; Naglazyme ™ (BioMarin Pharmaceuticals) | Enzyme Replacement Agents | For the treatment of adults and children with Mucopolysaccharidosis VI. | 47047 |
| Gefitinib | | Tyrosine Kinase Inhibitors | | 447 |
| Gemtuzumab ozogamicin | Mylotarg ™; Mylotarg ™ (Wyeth) | Antineoplastic Agents | For treatment of acute myeloid leukemia | 39826 |
| Glatiramer Acetate | Copaxone ™ | Adjuvants, Immunologic; Immunosuppressive Agents | For reduction of the frequency of relapses in patients with Relapsing-Remitting Multiple Sclerosis. | 29914 |
| Glucagon recombinant | GlucaGen ™ (Novo Nordisk); Glucagon ™ (Eli Lilly) | Antihypoglycemic Agents | For treatment of severe hypoglycemia, also used in gastrointestinal imaging | 54009 |
| Goserelin | Zoladex ™ | Antineoplastic Agents; Antineoplastic Agents, Hormonal | Breast cancer; Prostate carcinoma; Endometriosis | 78617 |
| Human Serum Albumin | Albutein ™ (Alpha Therapeutic Corp) | Serum substitutes | For treatment of severe blood loss, hypervolemia, hypoproteinemia | 39000 |
| Hyaluronidase | Vitragan ™; Vitrase ™; Vitrase ™ (Ista Pharma) | Anesthetic Adjuvants; Permeabilizing Agents | For increase of absorption and distribution of other injected drugs and for rehydration | 69367 |
| Ibritumomab | Zevalin ™ (IDEC Pharmaceuticals) | Antineoplastic Agents | For treatment of non-Hodgkin's lymphoma | 33078 |
| Idursulfase | Elaprase ™ (Shire Pharmaceuticals) | Enzyme Replacement Agents | For the treatment of Hunter syndrome in adults and children ages 5 and older. | 47047 |
| Imatinib | | Tyrosine Kinase Inhibitors | AMD, DME | 494 |
| Immune globulin | Civacir ™; Flebogamma ™ (Instituto Grifols SA); Gamunex ™ (Talecris Biotherapeutics) | Anti-Infectives; Immunomodulatory Agents | For treatment of immunodeficiencies, thrombocytopenic purpura, Kawasaki disease, gammablobulinemia, leukemia, bone transplant | 42632 |
| Infliximab | Remicade ™ (Centocor Inc) | Immunomodulatory Agents; Immunosuppressive Agents | Uveitis, AMD | 25645 |
| Insulin Glargine recombinant | Lantus ™ | Hypoglycemic Agents | For treatment of diabetes (type I and II) | 156308 |
| Insulin Lyspro recombinant | Humalog ™ (Eli Lily); Insulin Lispro (Eli Lily) | Hypoglycemic Agents | For treatment of diabetes (type I and II) | 154795 |
| Insulin recombinant | Novolin R ™ (Novo Nordisk) | Hypoglycemic Agents | For treatment of diabetes (type I and II) | 156308 |
| Insulin, porcine | Iletin II ™ | Hypoglycemic Agents | For the treatment of diabetes (type I and II) | 156308 |
| Interferon | | | | |
| Interferon Alfa-2a, Recombinant | Roferon A ™ (Hoffmann-La Roche Inc); Veldona ™ (Amarillo Biosciences) | Antineoplastic Agents; Antiviral Agents | For treatment of chronic hepatitis C, hairy cell leukemia, AIDS-related Kaposi's sarcoma, and chronic myelogenous leukemia. Also for the treatment of oral warts arising from HIV infection. | 57759 |
| Interferon Alfa-2b, Recombinant | Intron A ™ (Schering Corp) | Antineoplastic Agents; Antiviral Agents; Immunomodulatory Agents | For the treatment of hairy cell leukemia, malignant melanoma, and AIDS-related Kaposi's sarcoma. | 57759 |
| Interferon alfacon-1 | Advaferon ™; Infergen ™ (InterMune Inc) | Antineoplastic Agents; Antiviral Agents; Immunomodulatory Agents | For treatment of hairy cell leukemia, malignant melanoma, and AIDS-related Kaposi's sarcoma | 57759 |
| Interferon alfa-n1 | Wellferon ™ (GlaxoSmithKline) | Antiviral Agents; Immunomodulatory Agents | For treatment of venereal or genital warts caused by the Human Papiloma Virus | 57759 |
| Interferon alfa-n3 | Alferon ™ (Interferon Sciences Inc.); Alferon LDO ™; Alferon N Injection ™ | Antineoplastic Agents; Antiviral Agents; Immunomodulatory Agents | For the intralesional treatment of refractory or recurring external condylomata 150cuminate. | 57759 |
| Interferon beta-1b | Betaseron ™ (Chiron Corp) | Antiviral Agents; Immunomodulatory Agents | For treatment of relapsing/remitting multiple sclerosis | 57759 |
| Interferon gamma-1b | Actimmune ™; Actimmune ™ (InterMune Inc) | Antiviral Agents; Immunomodulatory Agents | For treatment of Chronic granulomatous disease, Osteopetrosis | 37835 |
| Lapatinib | | Tyrosine Kinase Inhibitors | | 581 |
| Lepirudin | Refludan ™ | Anticoagulants; Antithrombotic Agents; Fibrinolytic Agents | For the treatment of heparin-induced thrombocytopenia | 70037 |

TABLE 1A-continued

Therapeutic Agent List

| Generic Name | Brands (Companies) | Category | Indication | Molecular Weight |
|---|---|---|---|---|
| Lestaurtinib | | Tyrosine Kinase Inhibitors | | 439 |
| Leuprolide | Eligard ™ (Atrix Labs/QLT Inc) | Anti-Estrogen Agents; Antineoplastic Agents | For treatment of prostate cancer, endometriosis, uterine fibroids and premature puberty | 37731 |
| Lutropin alfa | Luveris ™ (Serono) | Fertility Agents | For treatment of female infertility | 78617 |
| Mecasermin | Increlex ™; Increlex ™ (Tercica); Iplex | | For the long-term treatment of growth failure in pediatric patients with Primary IGFD or with GH gene deletion who have developed neutralizing antibodies to GH. It is not indicated to treat Secondary IGFD resulting from GH deficiency, malnutrition, hypoth | 154795 |
| Menotropins | Repronex ™ | Fertility Agents | For treatment of female infertility | 78617 |
| Methotrexate | | Immunomodulatory | Uveitis, DME | |
| mTOR inhibitors | | | | |
| Muromonab | Orthoclone OKT3 ™ (Ortho Biotech) | Immunomodulatory Agents; Immunosuppressive Agents | For treatment of organ transplant recipients, prevention of organ rejection | 23148 |
| Natalizumab | Tysabri ™ | Immunomodulatory Agents | For treatment of multiple sclerosis. | 115334 |
| Nepafenac | | Cyclooxygenase Inhibitors | | |
| Nesiritide | Natrecor ™ | Cardiac drugs | For the intravenous treatment of patients with acutely decompensated congestive heart failure who have dyspnea at rest or with minimal activity. | 118921 |
| Nilotinib | | Tyrosine Kinase Inhibitors | | 530 |
| NS398 | | Cyclooxygenase Inhibitors | | |
| Octreotide | Atrigel ™; Longastatin ™; Sandostatin ™; Sandostatin LAR ™; Sandostatin LAR ™ (Novartis) | Anabolic Agents; Antineoplastic Agents, Hormonal; Gastrointestinal Agents; Hormone Replacement Agents | For treatment of acromegaly and reduction of side effects from cancer chemotherapy | 42687 |
| Omalizumab | Xolair ™ (Genentech Inc) | Anti-Asthmatic Agents; Immunomodulatory Agents | For treatment of asthma caused by allergies | 29596 |
| Oprelvekin | Neumega ™; Neumega ™ (Genetics Institute Inc) | Coagulants; Thrombotics | Increases reduced platelet levels due to chemotherapy | 45223 |
| OspA lipoprotein | LYMErix ™ (SmithKline Beecham) | Vaccines | For prophylactic treatment of Lyme Disease | 95348 |
| OT-551 | (Othera) | Anti-oxidant eyedrop | AMD | |
| Oxytocin | Oxytocin ™ (BAM Biotech); Pitocin ™ (Parke-Davis); Syntocinon ™ (Sandoz) | Anti-tocolytic Agents; Labor Induction Agents; Oxytocics | To assist in labor, elective labor induction, uterine contraction induction | 12722 |
| Palifermin | Kepivance ™ (Amgen Inc) | Antimucositis Agents | For treatment of mucositis (mouth sores) | 138885 |
| Palivizumab | Synagis ™ | Antiviral Agents | For treatment of respiratory diseases casued by respiratory syncytial virus | 63689 |
| Panitumumab | Vectibix ™; Vectibix ™ (Amgen) | Antineoplastic Agents | For the treatment of EGFR-expressing, metastatic colorectal carcinoma with disease progression on or following fluoropyrimidine-, oxaliplatin-, and irinotecan-containing chemotherapy regimens. | 134279 |
| PDGF inhibitor | (Jerini Ophthalmic); (Ophthotech) | Inhibitors of PDGF | AMD | |
| PEDF (pigment epithelium derived factor) | | | | |
| Pegademase bovine | Adagen ™ (Enzon Inc.) | Enzyme Replacement Agents | For treatment of adenosine deaminase deficiency | 36512 |
| Pegaptanib | Macugen ™ | Oligonucleotide | For the treatment of neovascular (wet) age-related macular degeneration. | 103121 |
| Pegaspargase | Oncaspar ™ (Enzon Inc) | Antineoplastic Agents | For treatment of acute lymphoblastic leukemia | 132.118 |
| Pegfilgrastim | Neulasta ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| Peginterferon alfa-2a | Pegasys ™ (Hoffman-La Roche Inc) | Antineoplastic Agents; Antiviral Agents; Immunomodulatory Agents | For treatment of hairy cell leukemia, malignant melanoma, and AIDS-related Kaposi's sarcoma. | 57759 |
| Peginterferon alfa-2b | PEG-Intron (Schering Corp); Unitron PEG ™ | Antineoplastic Agents; Antiviral Agents; Immunomodulatory Agents | For the treatment of chronic hepatitis C in patients not previously treated with interferon alpha who have compensated liver disease and are at least 18 years of age. | 57759 |
| Pegvisomant | Somavert ™ (Pfizer Inc) | Anabolic Agents; Hormone Replacement Agents | For treatment of acromegaly | 71500 |

TABLE 1A-continued

Therapeutic Agent List

| Generic Name | Brands (Companies) | Category | Indication | Molecular Weight |
|---|---|---|---|---|
| Pentoxifylline | | | | |
| Perindozril | | ACE Inhibitors | | |
| Pimecrolimus | | Limus Immunophilin Binding Compounds | | |
| PKC (protein kinase C) inhibitors | | | | |
| POT-4 | Potentia/Alcon | Complement Cascade Inhibitor (Factor C3) | AMD | |
| Pramlintide | Symlin ™; Symlin ™ (Amylin Pharmaceuticals) | | For the mealtime treatment of Type I and Type II diabetes in combination with standard insulin therapy, in patients who have failed to achieve adequate glucose control on insulin monotherapy. | 16988 |
| Proteosome inhibitors | Velcade ™ | | Proteosome inhibitors | |
| Pyrrolidine | | | | |
| Quinopril | | ACE Inhibitors | | |
| Ranibizumab | Lucentis ™ | | For the treatment of patients with neovascular (wet) age-related macular degeneration. | 27043 |
| Rapamycin (siroliums) | (MacuSight) | Limus Immunophilin Binding Compounds | AMD | |
| Rasburicase | Elitek ™; Elitek ™ (Sanofi-Synthelabo Inc); Fasturtec ™ | Antihyperuricemic Agents | For treatment of hyperuricemia, reduces elevated plasma uric acid levels (from chemotherapy) | 168.11 |
| Reteplase | Retavase ™ (Centocor); Retavase ™ (Roche) | Thrombolytic Agents | For lysis of acute pulmonary emboli, intracoronary emboli and management of myocardial infarction | 54732 |
| Retinal stimulant | Neurosolve ™ (Vitreoretinal Technologies) | Retinal stimulants | AMD | |
| Retinoid(s) | | | | |
| Rituximab | MabThera ™; Rituxan ™ | Antineoplastic Agents | For treatment of B-cell non-Hodgkins lymphoma (CD20 positive) | 33078 |
| RNAI (RNA interference of angiogenic factors) | | | | |
| Rofecoxib | Vioxx ™; Ceoxx ™; Ceeoxx ™ (Merck & Co.) | Cyclooxygenase Inhibitors | | |
| Rosiglitazone | | Thiazolidinediones | | |
| Ruboxistaurin | Eli Lilly | Protein Kinase C (PKC)-b Inhibitor | DME, diabetic peripheral retinopathy | 469 |
| Salmon Calcitonin | Calcimar ™; Miacalcin ™ (Novartis) | Antihypocalcemic Agents; Antiosteporotic Agents; Bone Density Conservation Agents | For the treatment of post-menopausal osteoporosis | 57304 |
| Sargramostim | Immunex ™; Leucomax ™ (Novartis); Leukine ™; Leukine ™ (Berlex Laboratories Inc) | Anti-Infective Agents; Antineoplastic Agents; Immunomodulatory Agents | For the treatment of cancer and bone marrow transplant | 46207 |
| SAR 1118 | SARCode | Immunomodulatory Agent | Dry eye, DME, conjunctivitis | |
| SDZ-RAD | | Limus Immunophilin Binding Compounds | | |
| Secretin | SecreFlo ™; Secremax ™, SecreFlo ™ (Repligen Corp) | Diagnostic Agents | For diagnosis of pancreatic exocrine dysfunction and gastrinoma | 50207 |
| Selective inhibitor of the factor 3 complement cascade | | | | |
| Selective inhibitor of the factor 5 complement cascade | | | | |
| Semaxanib | | Tyrosine Kinase Inhibitors | | 238 |
| Sermorelin | Geref ™ (Serono Pharma) | Anabolic Agents; Hormone Replacement Agents | For the treatment of dwarfism, prevention of HIV-induced weight loss | 47402 |
| Serum albumin iodinated | Megatope ™ (IsoTex Diagnostics) | Imaging Agents | For determination of total blood and plasma volumes | 39000 |
| SF1126 | Semafore | PI3k/mTOR Inhibition | AMD, DME | |
| Sirolimus reformulation (rapamycin) | (MacuSight) | Limus Immunophilin Binding Compounds | AMD | |
| siRNA molecule synthetic, FTP-801i-14 | (Quark Pharmaceuticals) | siRNA molecule synthetic | AMD | |

TABLE 1A-continued

Therapeutic Agent List

| Generic Name | Brands (Companies) | Category | Indication | Molecular Weight |
| --- | --- | --- | --- | --- |
| Somatropin recombinant | BioTropin ™ (Biotech General); Genotropin ™ (Pfizer); Humatrope ™ (Eli Lilly); Norditropin ™ (Novo Nordisk); Nutropin ™ (Genentech Inc.); NutropinAQ ™ (Genentech Inc.); Protropin ™ (Genentech Inc.); Saizen ™ (Serono SA); Serostim ™; Serostim ™ (Serono SA); Tev-Tropin ™ (GATE) | Anabolic Agents; Hormone Replacement Agents | For treatment of dwarfism, acromegaly and prevention of HIV-induced weight loss | 71500 |
| Squalamine | | | | |
| Streptokinase | Streptase ™ (Aventis Behringer GmbH) | Thrombolytic Agents | For the treatment of acute evolving transmural myocardial infarction, pulmonary embolism, deep vein thrombosis, arterial thrombosis or embolism and occlusion of arteriovenous cannulae | 90569 |
| Sunitinib | | Tyrosine Kinase Inhibitors | | 398 |
| TA106 | Taligen | Complement Cascade Inhibitor (Factor B) | AMD | |
| Tacrolimus | | Limus Immunophilin Binding Compounds | | |
| Tenecteplase | TNKase ™ (Genentech Inc) | Thrombolytic Agents | For treatment of myocardial infarction and lysis of intracoronary emboli | 54732 |
| Teriparatide | Apthela ™; Forsteo ™; Forteo ™; Fortessa ™; Opthia ™; Optia ™; Optiah ™; Zalectra ™; Zelletra ™ | Bone Density Conservation Agents | For the treatment of osteoporosis in men and postmenopausal women who are at high risk for having a fracture. Also used to increase bone mass in men with primary or hypogonadal osteoporosis who are at high risk for fracture. | 66361 |
| Tetrathiomolybdate | | | | |
| Thalidomide | Celgene | Anti-inflammatory, Anti-proliferative | Uveitis | |
| Thyrotropin Alfa | Thyrogen ™ (Genzyme Inc) | Diagnostic Agents | For detection of residueal or recurrent thyroid cancer | 86831 |
| Tie-1 and Tie-2 kinase inhibitors | | | | |
| Toceranib | | Tyrosine Kinase Inhibitors | | 396 |
| Tositumomab | Bexxar ™ (Corixa Corp) | Antineoplastic Agents | For treatment of non-Hodgkin's lymphoma (CD20 positive, follicular) | 33078 |
| TPN 470 analogue | | | | |
| Trastuzumab | Herceptin ™ (Genentech) | Antineoplastic Agents | For treatment of HER2-positive pulmonary breast cancer | 137912 |
| Triamcinolone acetonide | Triesence ™ | Glucocorticoid | DME, For treatment of inflammation of the retina | 435 |
| Troglitazone | | Thiazolidinediones | | |
| Tumistatin | | | | |
| Urofollitropin | Fertinex ™ (Serono S.A.) | Fertility Agents | For treatment of female infertility | 78296 |
| Urokinase | Abbokinase ™; Abbokinase ™ (Abbott Laboratories) | Thrombolytic Agents | For the treatment of 159ulmonary embolism, coronary artery thrombosis and IV catheter clearance | 90569 |
| Vandetanib | | Tyrosine Kinase Inhibitors | | 475 |
| Vasopressin | Pitressin ™; Pressyn ™ | Antidiuretics; Oxytocics; Vasoconstrictor Agents | For the treatment of enuresis, polyuria, diabetes insipidus, polydipsia and oesophageal varices with bleeding | 46800 |
| Vatalanib | | Tyrosine Kinase Inhibitors | | 347 |
| VEGF receptor kinase inhibitor | | | | |
| VEGF Trap | Aflibercept ™ (Regneron Pharmaceuticals, Bayer HealthCare AG) | Genetically Engineered Antibodies | DME, cancer, retinal vein occlusion, choroidal neovascularization, delay wound healing, cancer treatment | 96600 |
| Visual Cycle Modulator ACU-4229 | (Acucela) | Visual Cycle Modulator | AMD | |
| Vitamin(s) | | | | |
| Vitronectin receptor antagonists | | | | |
| Volociximab | Ophthotech | alpha5beta1 Integrin Inhibitor | AMD | |
| XL765 | Exelixis/Sanofi-Aventis | PI3k/mTOR Inhibition | AMD, DME | |

What is claimed is:

1. A system for injecting a therapeutic agent into an ocular implant, the ocular implant being at least partially implanted in an eye, the system comprising:
a needle defining an internal injection lumen configured to provide a pathway for injecting a therapeutic agent into the ocular implant;
an outlet lumen configured to provide a pathway through which pre-existing fluid in the ocular implant exits the ocular implant as therapeutic agent is injected into the ocular implant through the injection lumen; and
a receiver chamber having a channel fluidly coupled to the outlet lumen and to a first porous structure having a first resistance to flow, the receiver chamber configured to receive the pre-existing fluid that exits the ocular implant via the outlet lumen;
wherein application of a positive pressure into the injection lumen simultaneously injects an amount of the therapeutic agent into the ocular implant via the injection lumen and displaces an amount of pre-existing fluid from the ocular implant into the receiver chamber via the outlet lumen.

2. The system as in claim 1, wherein the outlet lumen and the injection lumen are concentrically positioned relative to one another.

3. The system as in claim 1, further comprising a source chamber configured to be removably attached to the injection lumen.

4. The system as in claim 3, wherein the source chamber is loaded with the therapeutic agent for injecting into the ocular implant via the injection lumen.

5. The system as in claim 3, wherein the source chamber is part of a syringe that attaches to the injection lumen.

6. The system as in claim 1, further comprising a hub configured to removably receive a syringe that is configured to fluidly couple to the injection lumen.

7. The system as in claim 1, further comprising a stop, configured to limit a depth of insertion of the injection lumen into the ocular implant.

8. The system as in claim 1, wherein the outlet lumen surrounds the injection lumen along at least a portion of a length of the injection lumen.

9. The system as in claim 1, wherein the receiver chamber is configured to store in a manner suitable for analysis the amount of pre-existing fluid displaced from the ocular implant.

10. The system as in claim 1, wherein the amount of pre-existing fluid comprises components of the vitreous humor of the eye and a remaining portion of therapeutic agent previously placed in the ocular implant.

11. The system as in claim 1, further comprising the ocular implant, wherein the ocular implant comprises a second porous structure configured to release the therapeutic agent from the ocular implant, the second porous structure having a second resistance to flow.

12. The system as in claim 11, wherein the first resistance to flow of the first porous structure is proportional to or greater than the second resistance to flow of the second porous structure such that a second amount of pre-existing fluid in the ocular implant exits the ocular implant through the second porous structure as the therapeutic agent is injected into the ocular implant through the injection lumen to provide a bolus injection of the pre-existing fluid into the eye.

13. The system as in claim 11, wherein the first resistance to flow is less than the second resistance to flow so as to at least partially separate the amount of pre-existing fluid from the amount of therapeutic agent being injected.

14. The system as in claim 1, wherein the system is configured to inject the therapeutic fluid at a flow rate that inhibits mixing of the amount of the therapeutic fluid with the amount of the pre-existing fluid.

15. The system as in claim 1, wherein the internal injection lumen has a first opening out from the injection lumen and the outlet lumen has a second opening into the outlet lumen, wherein the injection lumen is longer than the outlet lumen such that the first opening from the injection lumen is located distal to the second opening into the outlet lumen.

16. The system as in claim 15, wherein the receiver chamber comprises a container to receive the amount of pre-existing fluid from the ocular implant received through the outlet lumen and wherein the container comprises a vent to pass air displaced from the container and wherein the vent is fluidly coupled to the second opening so as to define a flow path extending from the second opening to the vent and wherein the flow path comprises a resistance to flow so as to encourage at least partial separation between the amount of therapeutic fluid from the amount of pre-existing fluid.

* * * * *